United States Patent
Yang et al.

(10) Patent No.: US 10,125,135 B2
(45) Date of Patent: Nov. 13, 2018

(54) CHEMICAL COMPOUNDS

(71) Applicant: AstraZeneca AB

(72) Inventors: Bin Yang, Waltham, MA (US); Jeffrey Gilbert Varnes, Waltham, MA (US); James Stewart Scott, Cambridge (GB); Thomas Andrew Moss, Cambridge (GB); Daniel Hillebrand O'Donovan, Cambridge (GB); Johannes Wilhelmus Maria Nissink, Cambridge (GB); Samantha Jayne Hughes, Cambridge (GB); Bernard Christophe Barlaam, Cambridge (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 15/491,345

(22) Filed: Apr. 19, 2017

(65) Prior Publication Data

US 2017/0305909 A1    Oct. 26, 2017

Related U.S. Application Data

(60) Provisional application No. 62/429,187, filed on Dec. 2, 2016, provisional application No. 62/325,031, filed on Apr. 20, 2016.

(51) Int. Cl.
*C07D 471/14* (2006.01)
*A61K 31/4745* (2006.01)
*C07D 487/04* (2006.01)

(52) U.S. Cl.
CPC ........ *C07D 471/14* (2013.01); *A61K 31/4745* (2013.01); *C07D 487/04* (2013.01)

(58) Field of Classification Search
CPC .................................................. C07D 471/14
See application file for complete search history.

(56) References Cited

U.S. PATENT DOCUMENTS

| | | |
|---|---|---|
| 2012/0157402 A1 | 6/2012 | Cao et al. |
| 2018/0021316 A1 | 1/2018 | Scott et al. |
| 2018/0111931 A1 | 4/2018 | Barlaam et al. |

FOREIGN PATENT DOCUMENTS

| | | |
|---|---|---|
| CN | 106518768 A | 3/2017 |
| CN | 107814798 A | 3/2018 |
| WO | 2010138695 A1 | 12/2010 |
| WO | 2010138758 A1 | 12/2010 |
| WO | 2011156518 A2 | 12/2011 |
| WO | 2011159769 A2 | 12/2011 |
| WO | 2013090829 A1 | 6/2013 |
| WO | 2013090836 A1 | 6/2013 |
| WO | 2014191726 A1 | 12/2014 |
| WO | 2014205136 A1 | 12/2014 |
| WO | 2014205138 A1 | 12/2014 |
| WO | 2015092634 A1 | 6/2015 |
| WO | 2016097071 A1 | 6/2016 |
| WO | 2016097072 A1 | 6/2016 |
| WO | 2016097073 A1 | 6/2016 |
| WO | 2016174551 A1 | 11/2016 |
| WO | 2016189011 A1 | 12/2016 |
| WO | 2016202161 A1 | 12/2016 |
| WO | 2017059139 A1 | 4/2017 |
| WO | 2017080338 A1 | 5/2017 |
| WO | 2017080966 A1 | 5/2017 |
| WO | 2017107754 A1 | 6/2017 |
| WO | 2017174757 A1 | 10/2017 |
| WO | 2017192991 A1 | 11/2017 |
| WO | 2018001232 A1 | 1/2018 |
| WO | 2018053354 A1 | 3/2018 |

OTHER PUBLICATIONS

Chesworth et al., "Tetrahydroisoquinolines as subtype selective estrogen agonists/antagonists", Bioorg. and Med. Chem. Lett, 2004, 14(11), 2729-2733.

*Primary Examiner* — Paul V Ward

(57) ABSTRACT

The specification relates to compounds of Formula (I):

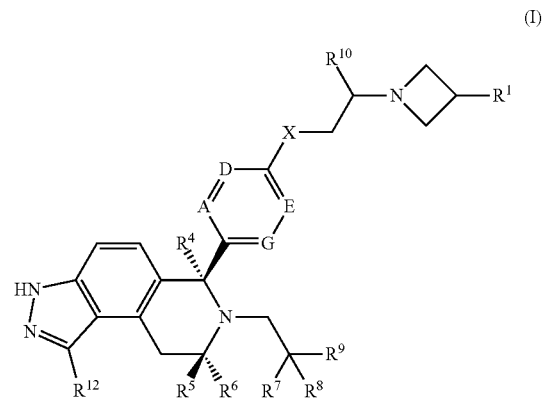

and pharmaceutically acceptable salts thereof. The specification also relates to processes and intermediates used for their preparation, pharmaceutical compositions containing them and their use in the treatment of cell proliferative disorders.

12 Claims, No Drawings

CHEMICAL COMPOUNDS

This application claims benefit under 35 U.S.C. § 119(e) of the following U.S. Provisional Application No. 62/429,187 filed Dec. 2, 2016; and U.S. Provisional Application No. 62/325,031 filed Apr. 20, 2016. Each of the above listed applications is incorporated by reference herein in its entirety for all purposes.

The specification relates to certain indazole compounds and pharmaceutically acceptable salts thereof that selectively down-regulate the estrogen receptor and possess anti-cancer activity. The specification also relates to use of said indazole compounds and pharmaceutically acceptable salts thereof in methods of treatment of the human or animal body, for example in prevention or treatment of cancer. The specification also relates to processes and intermediate compounds involved in the preparation of said indazole compounds and to pharmaceutical compositions containing them.

Estrogen receptor alpha (ERα, ESR1, NR3A) and estrogen receptor beta (ERβ, ESR2, NR3b) are steroid hormone receptors which are members of the large nuclear receptor family. Structured similarly to all nuclear receptors, ERα is composed of six functional domains (named A-F) (Dahlman-Wright, et al., *Pharmacol. Rev.*, 2006, 58:773-781) and is classified as a ligand-dependent transcription factor because after its association with the specific ligand, (the female sex steroid hormone 17b estradiol (E2)), the complex binds to genomic sequences, named Estrogen Receptor Elements (ERE) and interacts with co-regulators to modulate the transcription of target genes. The ERα gene is located on 6q25.1 and encodes a 595AA protein and multiple isoforms can be produced due to alternative splicing and translational start sites. In addition to the DNA binding domain (Domain C) and the ligand binding domain (Domain E) the receptor contains a N-terminal (A/B) domain, a hinge (D) domain that links the C and E domains and a C-terminal extension (F domain). While the C and E domains of ERα and ERβ are quite conserved (96% and 55% amino acid identity respectively) conservation of the A/B, D and F domains is poor (below 30% amino acid identity). Both receptors are involved in the regulation and development of the female reproductive tract and in addition play roles in the central nervous system, cardiovascular system and in bone metabolism. The genomic action of ERs occurs in the nucleus of the cell when the receptor binds EREs directly (direct activation or classical pathway) or indirectly (indirect activation or non-classical pathway). In the absence of ligand, ERs are associated with heat shock proteins, Hsp90 and Hsp70, and the associated chaperone machinery stabilizes the ligand binding domain (LBD) making it accessible to ligand. Liganded ER dissociates from the heat shock proteins leading to a conformational change in the receptor that allows dimerisation, DNA binding, interaction with co-activators or co-repressors and modulation of target gene expression. In the non-classical pathway, AP-1 and Sp-1 are alternative regulatory DNA sequences used by both isoforms of the receptor to modulate gene expression. In this example, ER does not interact directly with DNA but through associations with other DNA bound transcription factors e.g. c-Jun or c-Fos (Kushner et al., *Pure Applied Chemistry* 2003, 75:1757-1769). The precise mechanism whereby ER affects gene transcription is poorly understood but appears to be mediated by numerous nuclear factors that are recruited by the DNA bound receptor. The recruitment of co-regulators is primarily mediated by two protein surfaces, AF2 and AF1 which are located in E-domain and the A/B domain respectively. AF1 is regulated by growth factors and its activity depends on the cellular and promoter environment whereas AF2 is entirely dependent on ligand binding for activity. Although the two domains can act independently, maximal ER transcriptional activity is achieved through synergistic interactions via the two domains (Tzukerman, et al., *Mol. Endocrinology*, 1994, 8:21-30). Although ERs are considered transcription factors they can also act through non-genomic mechanisms as evidenced by rapid ER effects in tissues following E2 administration in a timescale that is considered too fast for a genomic action. It is still unclear if receptors responsible for the rapid actions of estrogen are the same nuclear ERs or distinct G-protein coupled steroid receptors (Warner, et al., *Steroids* 2006 71:91-95) but an increasing number of E2 induced pathways have been identified e.g. MAPK/ERK pathway and activation of endothelial nitric oxide synthase and PI3K/Akt pathway. In addition to ligand dependent pathways, ERα has been shown to have ligand independent activity through AF-1 which has been associated with stimulation of MAPK through growth factor signalling e.g. insulin like growth factor 1 (IGF-1) and epidermal growth factor (EGF). Activity of AF-1 is dependent on phosphorylation of Ser118 and an example of cross-talk between ER and growth factor signalling is the phosphorylation of Ser 118 by MAPK in response to growth factors such as IGF-1 and EGF (Kato, et al., *Science*, 1995, 270:1491-1494).

A large number of structurally distinct compounds have been shown to bind to ER. Some compounds such as endogenous ligand E2, act as receptor agonists whereas others competitively inhibit E2 binding and act as receptor antagonists. These compounds can be divided into 2 classes depending on their functional effects. Selective estrogen receptor modulators (SERMs) such as tamoxifen have the ability to act as both receptor agonists and antagonists depending on the cellular and promoter context as well as the ER isoform targeted. For example tamoxifen acts as an antagonist in breast but acts as a partial agonist in bone, the cardiovascular system and uterus. All SERMs appear to act as AF2 antagonists and derive their partial agonist characteristics through AF1. A second group, fulvestrant being an example, are classified as full antagonists and are capable of blocking estrogen activity via the complete inhibition of AF1 and AF2 domains through induction of a unique conformation change in the ligand binding domain (LBD) on compound binding which results in complete abrogation of the interaction between helix 12 and the remainder of the LBD, blocking co-factor recruitment (Wakeling, et al., *Cancer Res.*, 1991, 51:3867-3873; Pike, et al., *Structure*, 2001, 9:145-153).

Intracellular levels of ERα are down-regulated in the presence of E2 through the ubiquitin/proteosome (Ub/26S) pathway. Polyubiquitinylation of liganded ERα is catalysed by at least three enzymes; the ubiquitin-activating enzyme E1 activated ubiquitin is conjugated by E2 with lysine residues through an isopeptide bond by E3 ubiquitin ligase and polyubiquitinated ERα is then directed to the proteosome for degradation. Although ER-dependent transcription regulation and proteosome-mediated degradation of ER are linked (Lonard, et al., *Mol. Cell*, 2000 5:939-948), transcription in itself is not required for ERα degradation and assembly of the transcription initiation complex is sufficient to target ERα for nuclear proteosomal degradation. This E2 induced degradation process is believed to necessary for its ability to rapidly activate transcription in response to requirements for cell proliferation, differentiation and metabolism (Stenoien, et al., *Mol. Cell Biol.*, 2001, 21:4404-4412). Fulvestrant is also classified as a selective estrogen receptor down-regulator (SERD), a subset of antagonists that can also induce rapid down-regulation of ERα via the 26S proteosomal pathway. In contrast a SERM such as tamoxifen can increase ERα levels although the effect on transcription is similar to that seen for a SERD.

Approximately 70% of breast cancers express ER and/or progesterone receptors implying the hormone dependence of these tumour cells for growth. Other cancers such as ovarian and endometrial are also thought to be dependent on ERα signalling for growth. Therapies for such patients can inhibit ER signalling either by antagonising ligand binding to ER e.g. tamoxifen which is used to treat early and advanced ER positive breast cancer in both pre and post menopausal setting; antagonising and down-regulating ERα e.g. fulvestrant which is used to treat breast cancer in women which have progressed despite therapy with tamoxifen or aromatase inhibitors; or blocking estrogen synthesis e.g. aromatase inhibitors which are used to treat early and advanced ER positive breast cancer. Although these therapies have had an enormously positive impact on breast cancer treatment, a considerable number of patients whose tumours express ER display de novo resistance to existing ER therapies or develop resistance to these therapies over time. Several distinct mechanisms have been described to explain resistance to first-time tamoxifen therapy which mainly involve the switch from tamoxifen acting as an antagonist to an agonist, either through the lower affinity of certain co-factors binding to the tamoxifen-ERα complex being off-set by over-expression of these co-factors, or through the formation of secondary sites that facilitate the interaction of the tamoxifen-ERα complex with co-factors that normally do not bind to the complex. Resistance could therefore arise as a result of the outgrowth of cells expressing specific co-factors that drive the tamoxifen-ERα activity. There is also the possibility that other growth factor signalling pathways directly activate the ER receptor or co-activators to drive cell proliferation independently of ligand signalling.

More recently, mutations in ESR1 have been identified as a possible resistance mechanism in metastatic ER-positive patient derived tumour samples and patient-derived xenograft models (PDX) at frequencies varying from 17-25%. These mutations are predominantly, but not exclusively, in the ligand-binding domain leading to mutated functional proteins; examples of the amino acid changes include Ser463Pro, Val543Glu, Leu536Arg, Tyr537Ser, Tyr537Asn and Asp538Gly, with changes at amino acid 537 and 538 constituting the majority of the changes currently described. These mutations have been undetected previously in the genomes from primary breast samples characterised in the Cancer Genome Atlas database. Of 390 primary breast cancer samples positive for ER expression not a single mutation was detected in ESR1 (Cancer Genome Atlas Network, 2012 Nature 490: 61-70). The ligand binding domain mutations are thought to have developed as a resistance response to aromatase inhibitor endocrine therapies as these mutant receptors show basal transcriptional activity in the absence of estradiol. The crystal structure of ER, mutated at amino acids 537 and 538, showed that both mutants favoured the agonist conformation of ER by shifting the position of helix 12 to allow co-activator recruitment and thereby mimicking agonist activated wild type ER. Published data has shown that endocrine therapies such as tamoxifen and fulvestrant can still bind to ER mutant and inhibit transcriptional activation to some extent and that fulvestrant is capable of degrading Try537Ser but that higher doses may be needed for full receptor inhibition (Toy et al., Nat. Genetics 2013, 45: 1439-1445; Robinson et al., Nat. Genetics 2013, 45: 144601451; Li, S. et al. Cell Rep. 4, 1116-1130 (2013). It is therefore feasible that certain compounds of the Formula (I) or pharmaceutically acceptable salts thereof (as described hereinafter) will be capable of down-regulating and antagonising mutant ER although it is not known at this stage whether ESR1 mutations are associated with an altered clinical outcome.

Regardless of which resistance mechanism or combination of mechanisms takes place, many are still reliant on ER-dependent activities and removal of the receptor through a SERD mechanism offers the best way of removing the ERα receptor from the cell. Fulvestrant is currently the only SERD approved for clinical use, yet despite its mechanistic properties, the pharmacological properties of the drug have limited its efficacy due to the current limitation of a 500mg monthly dose which results in less than 50% turnover of the receptor in patient samples compared to the complete down-regulation of the receptor seen in in vitro breast cell line experiments (Wardell, et al., Biochem. Pharm., 2011, 82:122-130). Hence there is a need for new ER targeting agents that have the required pharmaceutical properties and SERD mechanism to provide enhanced benefit in the early, metastatic and acquired resistance setting.

The compounds of the specification have been found to possess potent anti-tumour activity, being useful in inhibiting the uncontrolled cellular proliferation which arises from malignant disease. The compounds of the specification provide an anti-tumour effect by, as a minimum, acting as SERDs. For example, the compounds of the specification may exhibit anti-tumour activity via the ability to down-regulate the estrogen receptor in a number of different breast cancer cell-lines, for example against the MCF-7, CAMA-1, BT474 and/or MDA-MB-134 breast cancer cell-lines. Such compounds may be expected to be more suitable as therapeutic agents, particularly for the treatment of cancer.

The compounds of the specification may also exhibit advantageous physical properties (for example, lower lipophilicity, higher aqueous solubility, higher permeability, lower plasma protein binding, and/or greater chemical stability), and/or favourable toxicity profiles (for example a decreased activity at hERG), and/or favourable metabolic or pharmacokinetic profiles, in comparison with other known SERDs. Such compounds may therefore be especially suitable as therapeutic agents, particularly for the treatment of cancer.

According to one aspect of the specification there is provided a compound of the Formula (I):

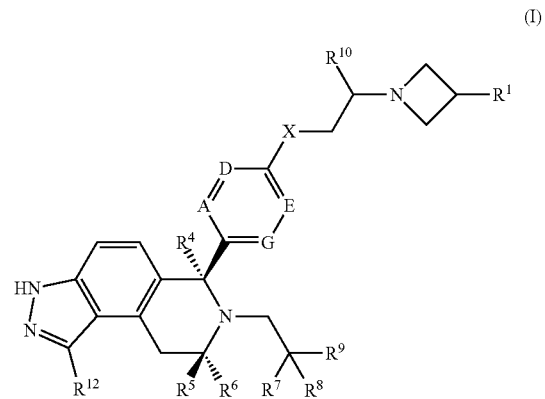

(I)

wherein:
X is O, NH or NMe;
D and E are independently CH or N;
A is $CR^2$ or N;
G is $CR^3$ or N;
$R^1$ is $CH_2F$, $CHF_2$, Me, OMe, F or CN;
$R^2$ is H, F, CN or OMe;
$R^3$ is H or F;
$R^4$ is H or Me;
$R^5$ is H or Me;
$R^6$ is Me, $CHF_2$ or cyclopropyl;
$R^7$ is Me or F;
$R^8$ is Me, F, $CH_2F$, $CH_2OMe$ or $CH_2OH$;
$R^9$ is H or F; or
$R^8$ and $R^9$ taken together with the carbon atom to which they are attached form a cyclopropyl ring or an oxetane ring;
$R^{10}$ is H or Me; and
$R^{12}$ is H or F;
or a pharmaceutically acceptable salt thereof.

In one embodiment there is provided a compound of Formula (I) as defined above.

In one embodiment there is provided a pharmaceutically acceptable salt of a compound of Formula (I).

In one embodiment X is O.
In one embodiment X is NH.
In one embodiment X is NMe.
In one embodiment D is CH.
In one embodiment E is CH.
In one embodiment both D and E are CH.
In one embodiment both D and E are N.
In one embodiment one of D or E is CH and the other of D or E is N.
In one embodiment A is $CR^2$.
In one embodiment G is $CR^3$.
In one embodiment A is $CR^2$ and G is $CR^3$.
In one embodiment A is $CR^2$ and G is N.
In one embodiment A is N and G is $CR^3$.
In one embodiment A is N and G is CH or C—F.
In one embodiment A is N and G is CH.
In one embodiment A is N and G is C—F.
In one embodiment $R^2$ is H, F or OMe.
In one embodiment $R^2$ is H, F or CN.
In one embodiment $R^2$ is F, OMe or CN.
In one embodiment $R^2$ is F.
In one embodiment $R^3$ is H.
In one embodiment $R^3$ is F.
In one embodiment A is $CR^2$ and $R^2$ is H, F or OMe.
In one embodiment G is $CR^3$ and $R^3$ is F.
In one embodiment A is C—F and G is C—F.
In one embodiment A is CH and G is CH.
In one embodiment A is C—F and G is CH.
In one embodiment A is C—OMe and G is CH.
In one embodiment A is C—OMe and G is CF.
In one embodiment $R^1$ is $CH_2F$, $CHF_2$, Me or OMe.
In one embodiment $R^1$ is $CH_2F$, $CHF_2$ or Me.
In one embodiment $R^1$ is $CH_2F$ or $CHF_2$.
In one embodiment $R^1$ is $CH_2F$.
In one embodiment $R^1$ is $CHF_2$.
In one embodiment $R^1$ is $Ch_2F$ and $R^{10}$ is H.
In one embodiment $R^4$ is H.
In one embodiment $R^4$ is Me.
In one embodiment $R^5$ is H.
In one embodiment $R^5$ is Me.
In one embodiment $R^6$ is Me or $CHF_2$.
In one embodiment $R^6$ is Me.
In one embodiment $R^6$ is $CHF_2$.
In one embodiment $R^7$ is Me.

In one embodiment $R^7$ is F.
In one embodiment $R^8$ is Me, $CH_2OMe$ or $CH_2OH$.
In one embodiment $R^8$ is Me, F or $Ch_2F$.
In one embodiment $R^8$ is Me or $CH_2OMe$.
In one embodiment $R^7$ is Me and $R^8$ is Me.
In one embodiment $R^7$ is Me and $R^8$ is $Ch_2F$, $CH_2OMe$ or $CH_2OH$.
In one embodiment $R^7$ is Me and $R^9$ is F.
In one embodiment $R^7$ is F and $R^9$ is F.
In one embodiment $R^8$ is $Ch_2F$, $CH_2OMe$ or $CH_2OH$ and $R^9$ is H.
In one embodiment $R^8$ is $Ch_2F$, $CH_2OMe$ or $CH_2OH$ and $R^9$ is F.
In one embodiment $R^7$ is F and $R^8$ and $R^9$ taken together with the carbon atom to which they are attached form a cyclopropyl ring or an oxetane ring.

In one embodiment the group $—CH_2—C(R^7)(R^8)(R^9)$ in the compound of Formula (I) is selected from the group consisting of:

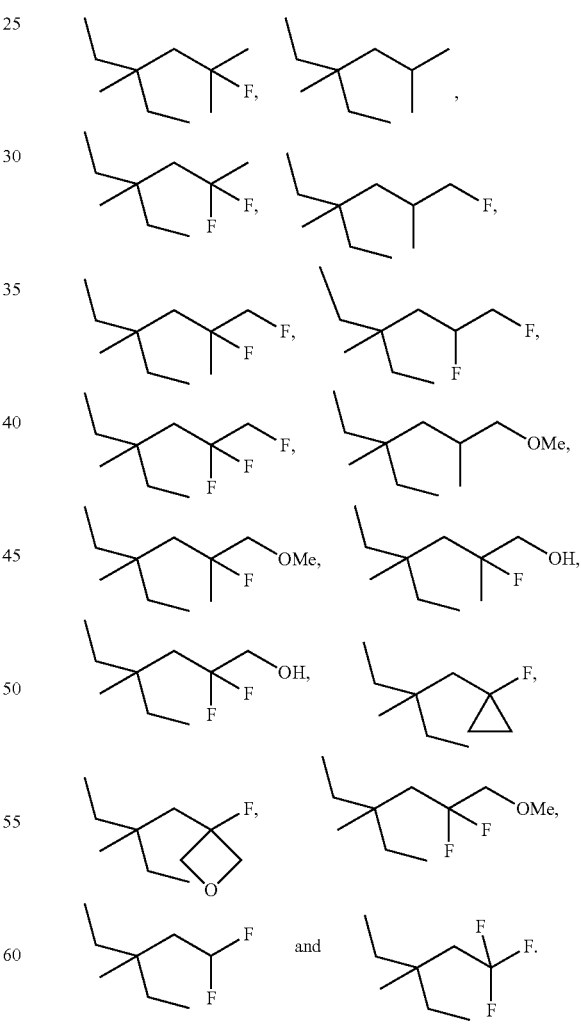

In one embodiment the group $—CH_2—C(R^7)(R^8)(R^9)$ in the compound of Formula (I) is selected from the group consisting of:

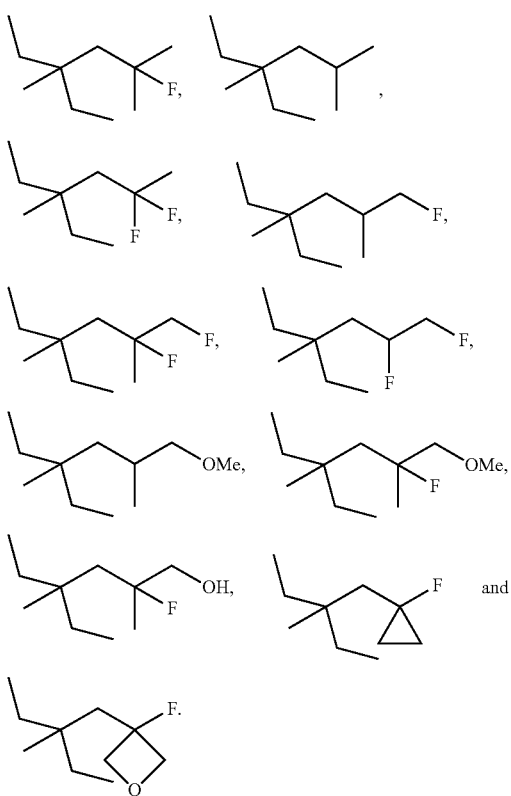
In one embodiment the group —CH$_2$—C(R$^7$)(R$^8$)(R$^9$) in the compound of Formula (I) is selected from the group consisting of:
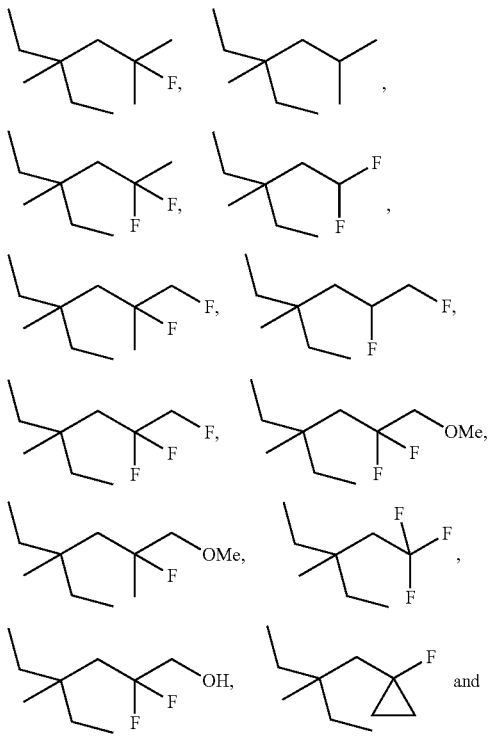
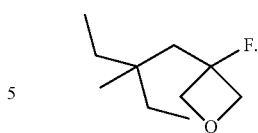
In one embodiment the group —CH$_2$—C(R$^7$)(R$^8$)(R$^9$) in the compound of Formula (I) is selected from the group consisting of:
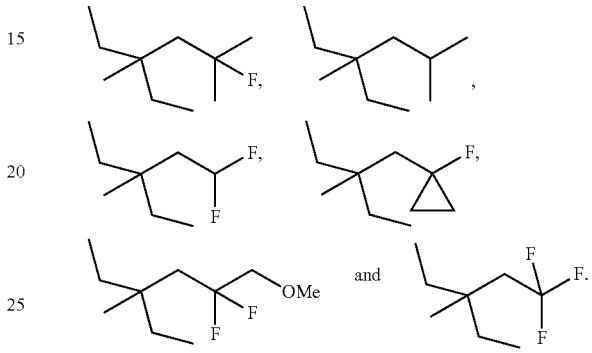
In one embodiment the group —CH$_2$—C(R$^7$)(R$^8$)(R$^9$) in the compound of Formula (I) is selected from the group consisting of:
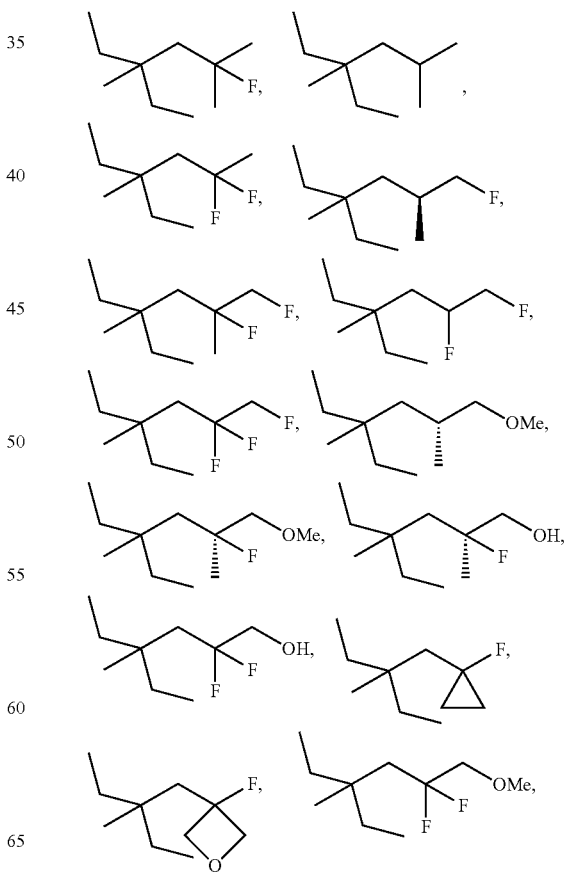

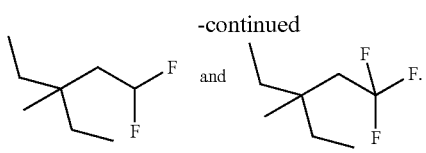

In one embodiment the group —CH$_2$—C(R$^7$)(R$^8$)(R$^9$) in the compound of Formula (I) is selected from the group consisting of:

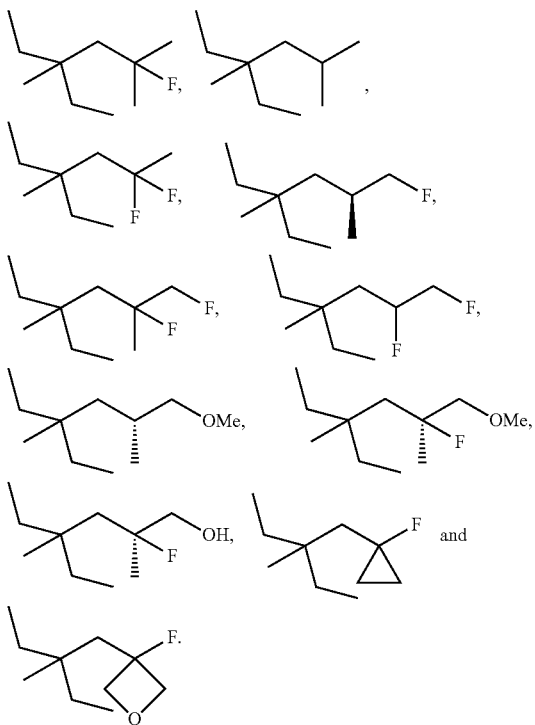

In one embodiment R$^{10}$ is H.
In one embodiment R$^{12}$ is H.
In one embodiment R$^{12}$ is F.
In one embodiment X is O and R$^{12}$ is H.
In one embodiment there is provided a compound of Formula (IA):

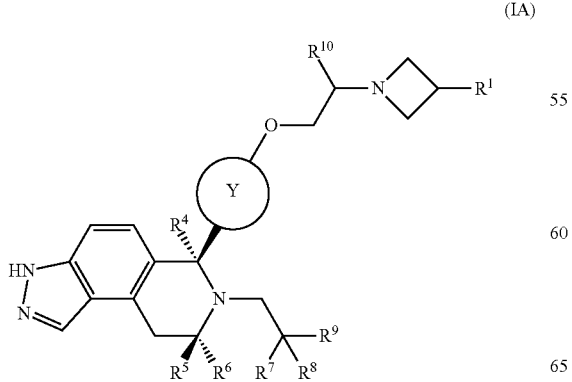

(IA)

wherein:
R$^1$ is Ch$_2$F, CHF$_2$, Me, OMe, F or CN;
R$^4$ is H or Me;
R$^5$ is H or Me;
R$^6$ is Me, CHF$_2$ or cyclopropyl;
R$^7$ is Me or F;
R$^8$ is Me, F, Ch$_2$F, CH$_2$OMe or CH$_2$OH;
R$^9$ is H or F; or
R$^8$ and R$^9$ taken together with the carbon atom to which they are attached form a cyclopropyl ring or an oxetane ring;
R$^{10}$ is H or Me; and
Ring Y is selected from the group consisting of:

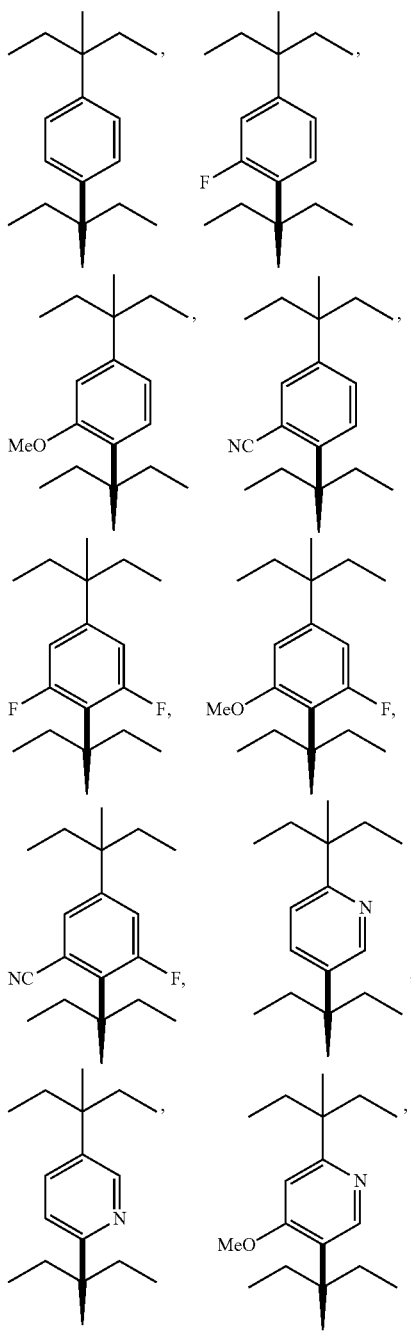

-continued

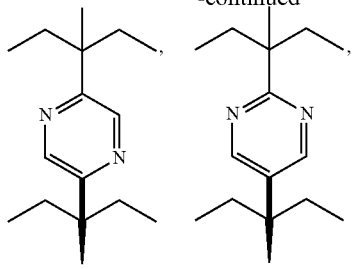

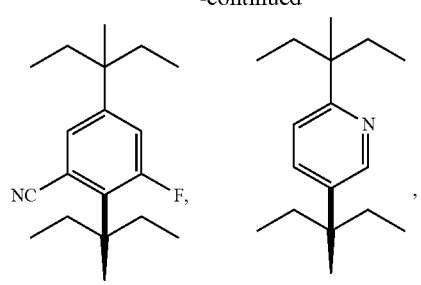

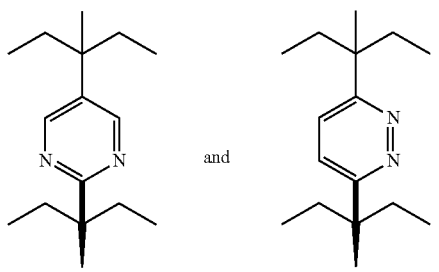 and 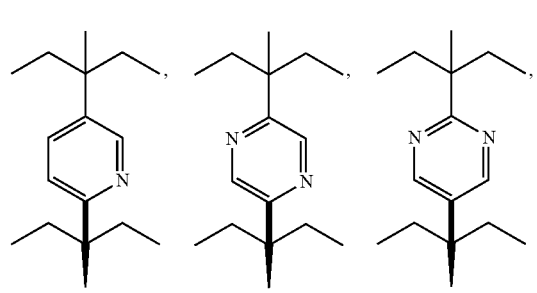;

or a pharmaceutically acceptable salt thereof.

In one embodiment there is provided a compound of Formula (IA), or a pharmaceutically acceptable salt thereof, wherein Ring Y is selected from the group consisting of:

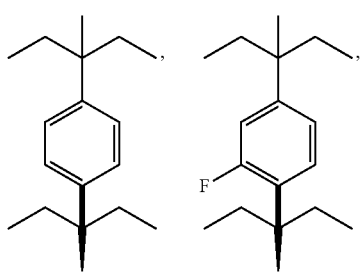

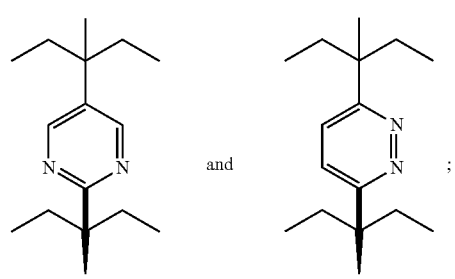

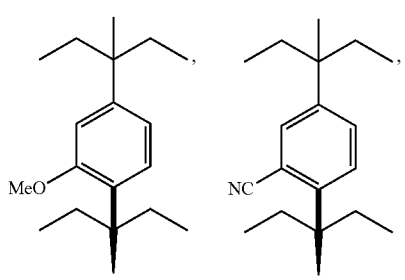 and 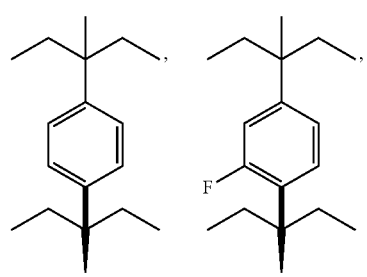;

In one embodiment there is provided a compound of Formula (IA), or a pharmaceutically acceptable salt thereof, wherein Ring Y is selected from the group consisting of:

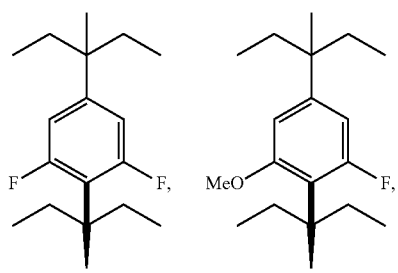

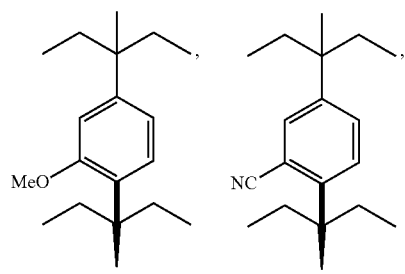

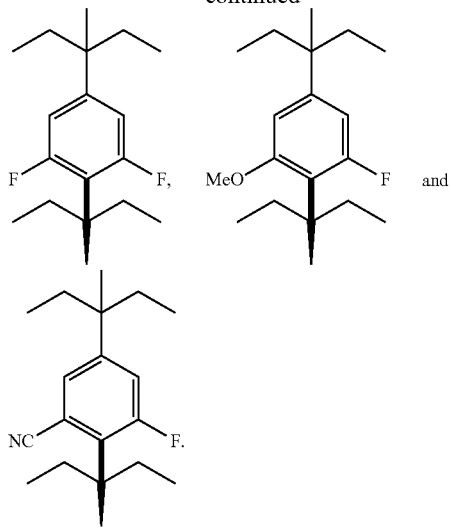

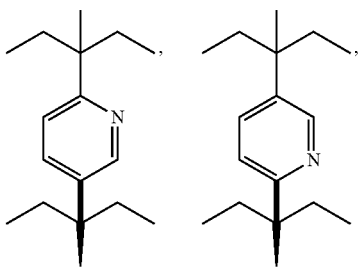

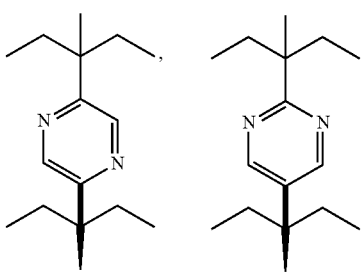

In one embodiment there is provided a compound of Formula (IA), or a pharmaceutically acceptable salt thereof, wherein Ring Y is selected from the group consisting of:

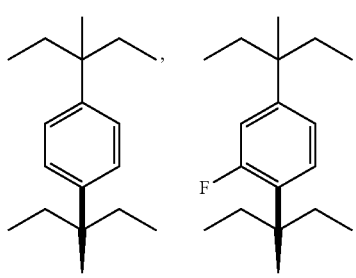

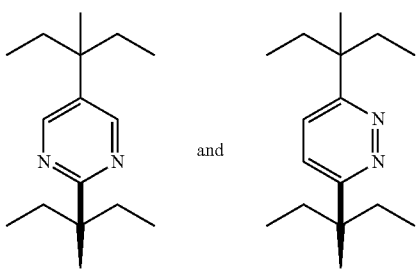

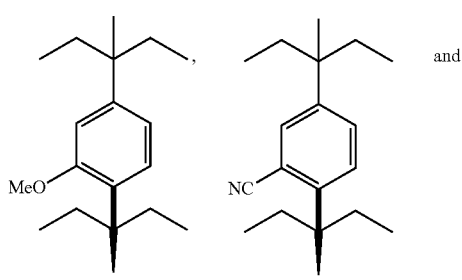

and

In one embodiment there is provided a compound of Formula (IA), or a pharmaceutically acceptable salt thereof, wherein Ring Y is selected from the group consisting of:

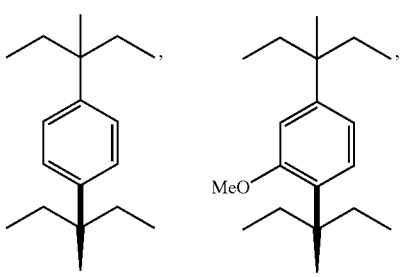

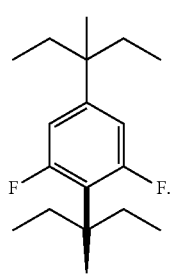

In one embodiment there is provided a compound of Formula (IA), or a pharmaceutically acceptable salt thereof, wherein Ring Y is selected from the group consisting of:

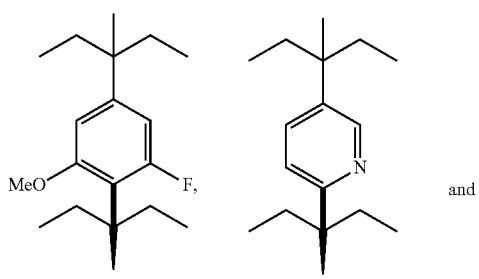

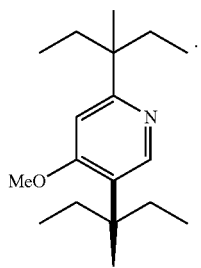

In one embodiment there is provided a compound of Formula (IA), or a pharmaceutically acceptable salt thereof, wherein Ring Y is selected from the group consisting of:

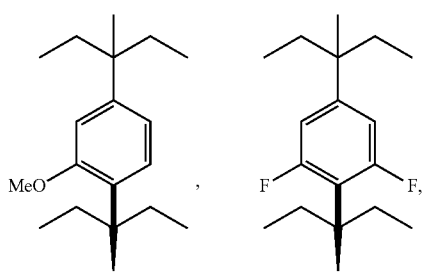

In one embodiment the group —CH$_2$—C(R$^7$)(R$^8$)(R$^9$) in the compound of Formula (IA) is selected from the group consisting of:

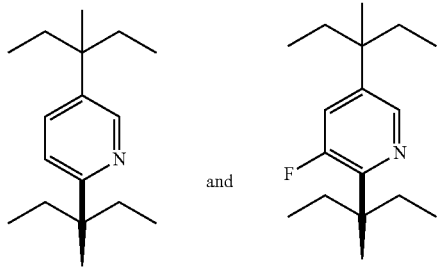

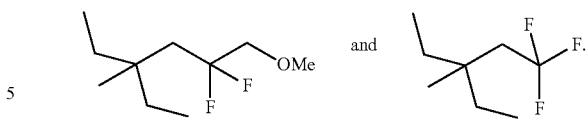

In one embodiment there is provided the compound of Formula (IB):

(IB)

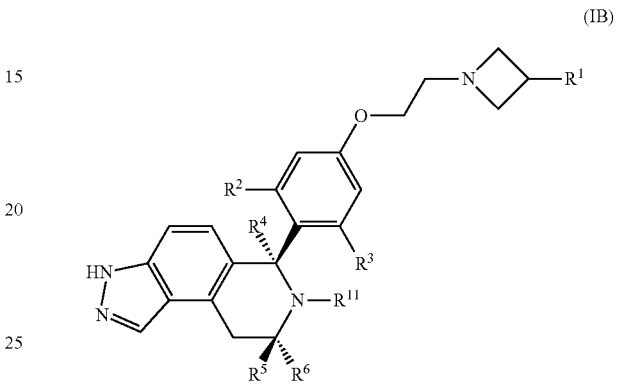

wherein:
R$^1$ is Ch$_2$F, CHF$_2$, Me, OMe, F or CN;
R$^2$ is H, F, CN or OMe;
R$^3$ is H or F;
R$^4$ is H or Me;
R$^5$ is H or Me;
R$^6$ is Me, CHF$_2$ or cyclopropyl; and
R$^{11}$ is selected from the group consisting of:

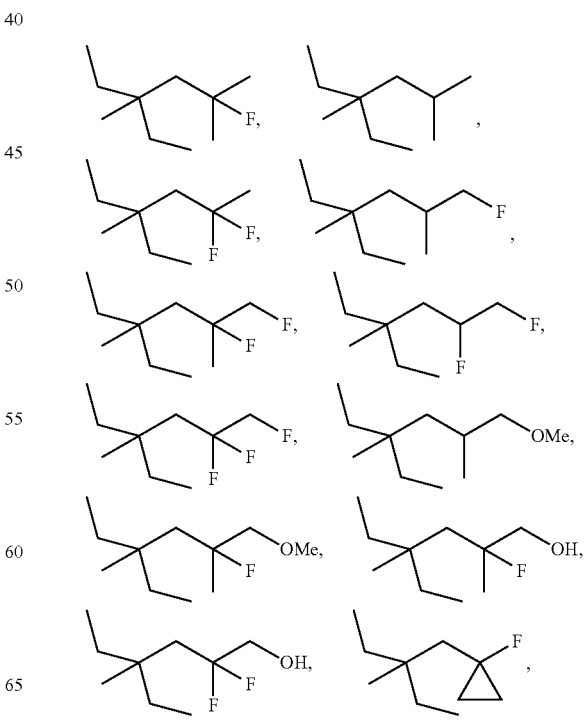

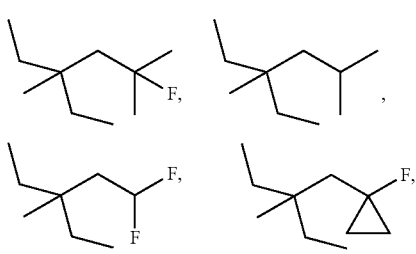

-continued

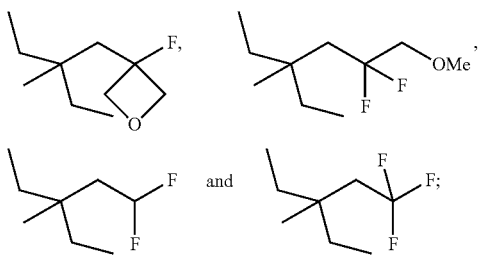

or a pharmaceutically acceptable salt thereof.

In one embodiment there is provided a compound of Formula (IB), or a pharmaceutically acceptable salt thereof, wherein $R^{11}$ is selected from the group consisting of:

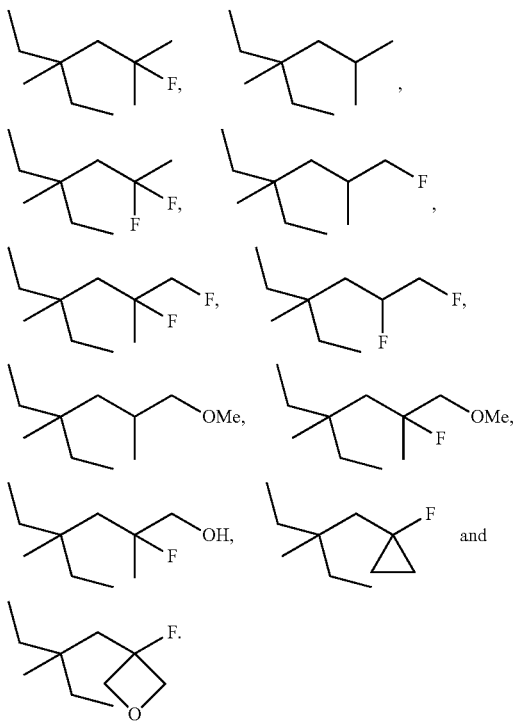

In one embodiment there is provided a compound of Formula (IB), or a pharmaceutically acceptable salt thereof, wherein $R^{11}$ is selected from the group consisting of:

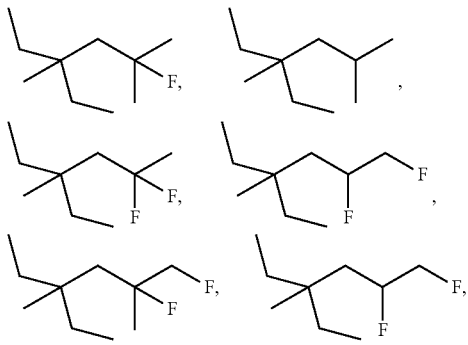

-continued

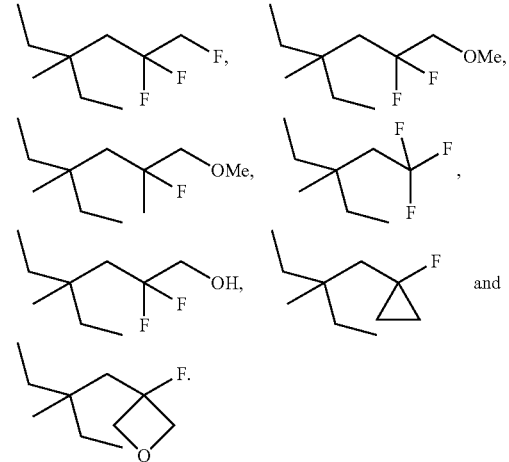

In one embodiment there is provided a compound of Formula (IB), or a pharmaceutically acceptable salt thereof, wherein $R^{11}$ is selected from the group consisting of:

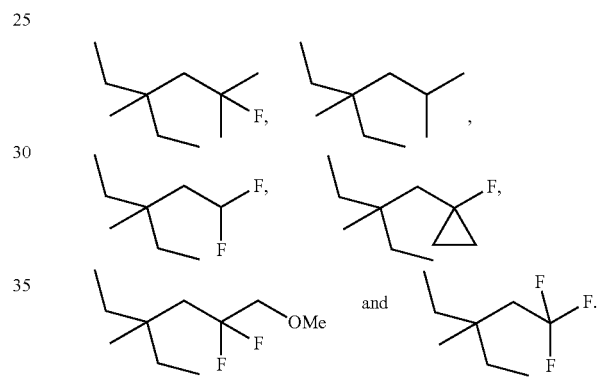

In one embodiment there is provided the compound of Formula (IC):

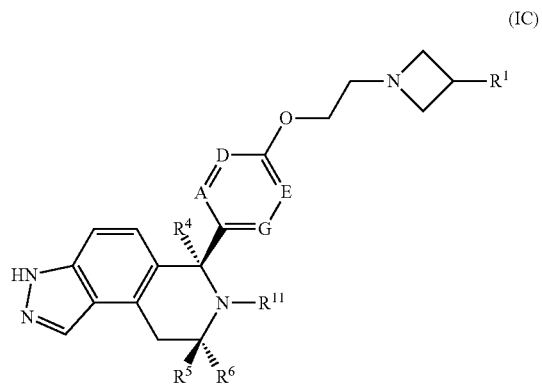

(IC)

wherein:
A, G, D and E are independently selected from CH or N;
$R^1$ is $Ch_2F$, $CHF_2$, Me, OMe, F or CN;
$R^4$ is H or Me;
$R^5$ is H or Me;
$R^6$ is Me, $CHF_2$ or cyclopropyl; and $R^{11}$ is selected from the group consisting of:

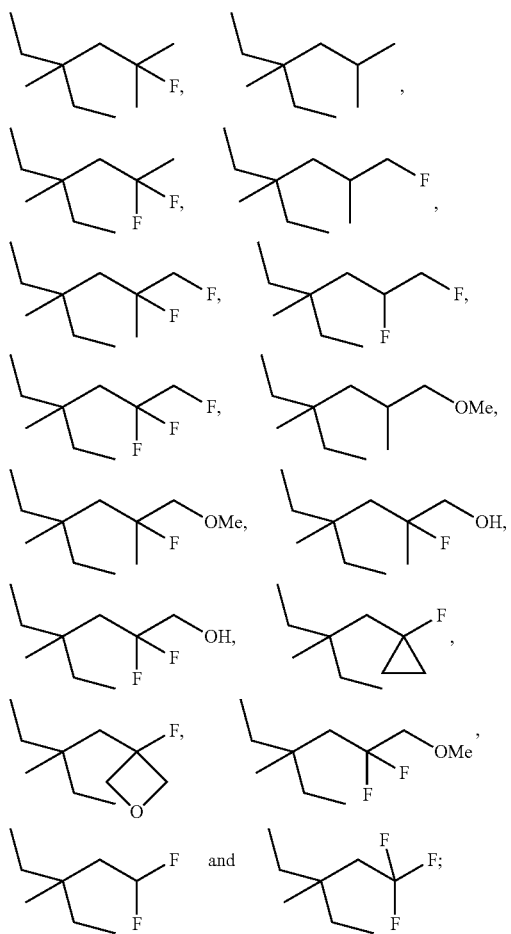

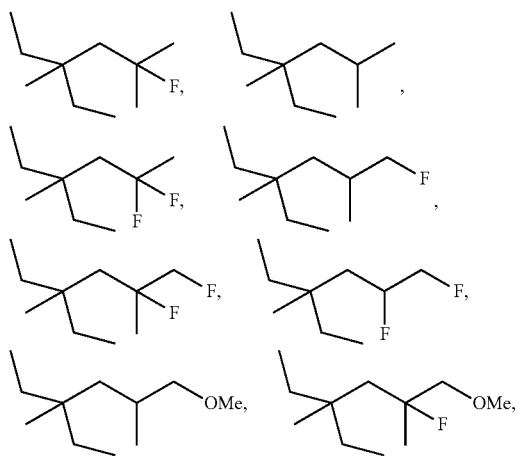

or a pharmaceutically acceptable salt thereof.

In one embodiment, A is N and G is CH.

In one embodiment, A is N and D, E and G are all CH.

In one embodiment there is provided a compound of Formula (IC), or a pharmaceutically acceptable salt thereof, wherein $R^{11}$ is selected from the group consisting of:

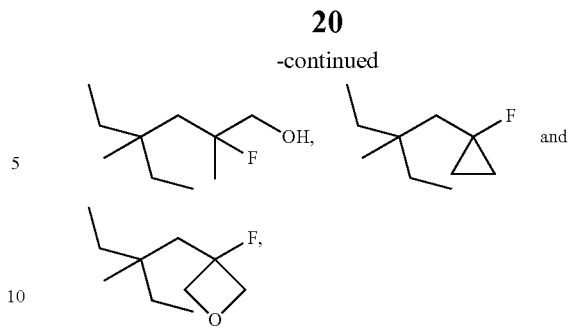

In one embodiment there is provided a compound of Formula (IC), or a pharmaceutically acceptable salt thereof, wherein $R^{11}$ is selected from the group consisting of:

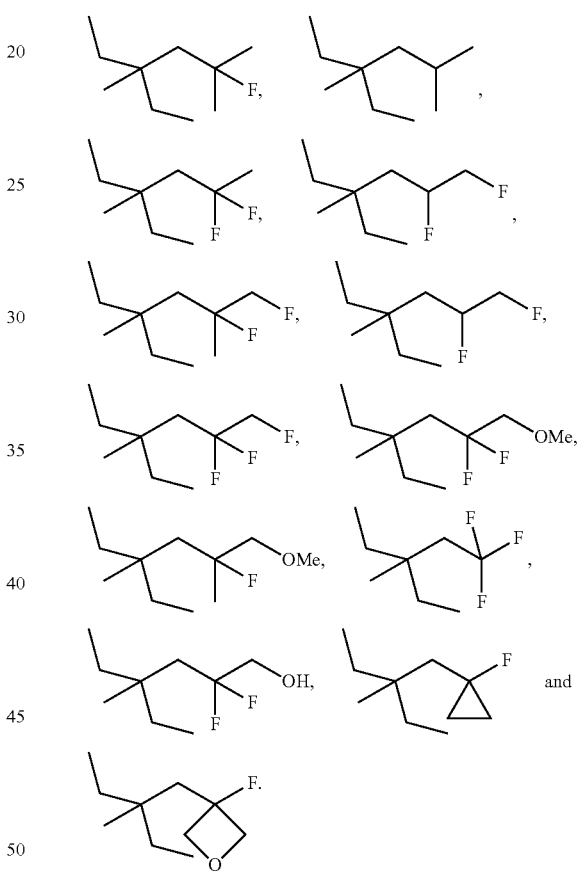

In one embodiment there is provided a compound of Formula (IC), or a pharmaceutically acceptable salt thereof, wherein $R^{11}$ is selected from the group consisting of:

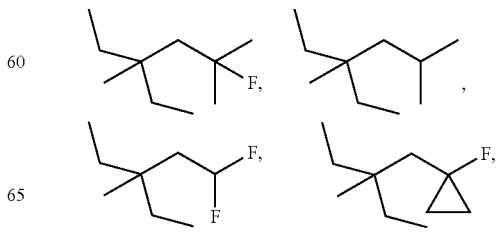

-continued
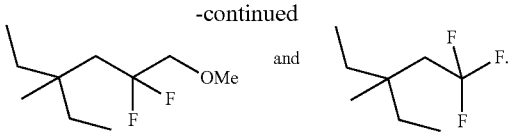 and 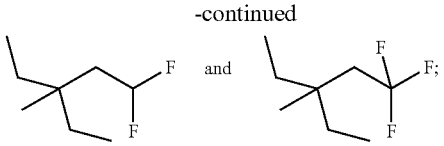
In one embodiment there is provided the compound of Formula (ID):
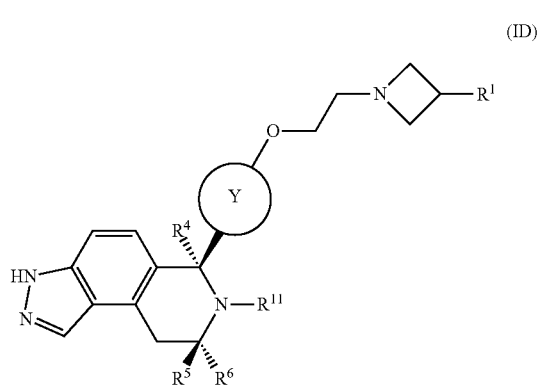
wherein:
R[1] is Ch$_2$F, CHF$_2$, Me, OMe, F or CN;
R[4] is H or Me;
R[5] is H or Me;
R[6] is Me, CHF$_2$ or cyclopropyl;
R[11] is selected from the group consisting of:
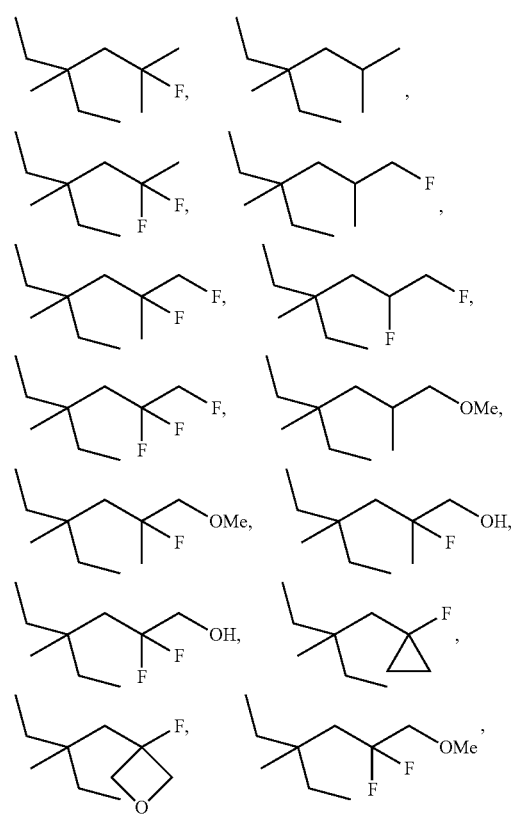
and Ring Y is selected from the group consisting of:
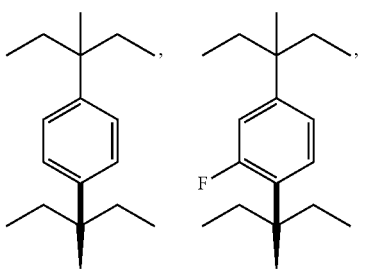
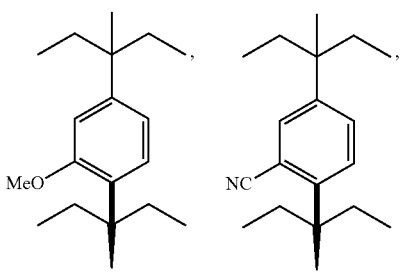
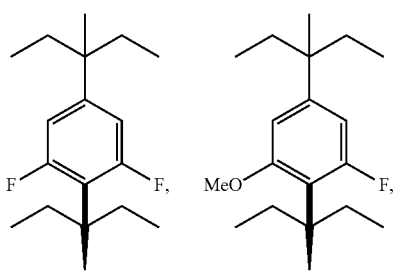
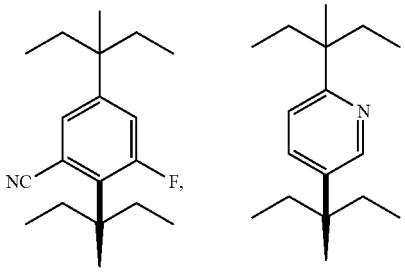
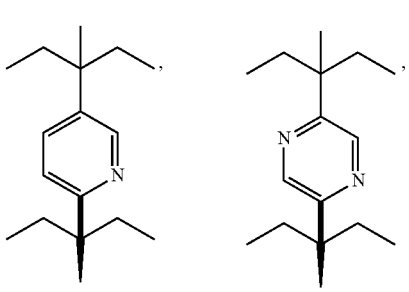

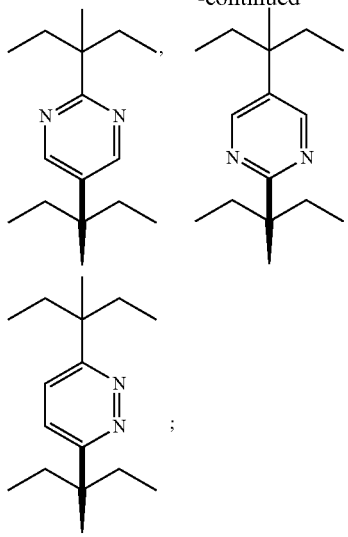

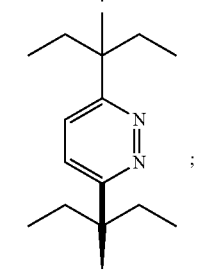

or a pharmaceutically acceptable salt thereof.

In one embodiment there is provided a compound of Formula (ID), or a pharmaceutically acceptable salt thereof, wherein $R^{11}$ is selected from the group consisting of:

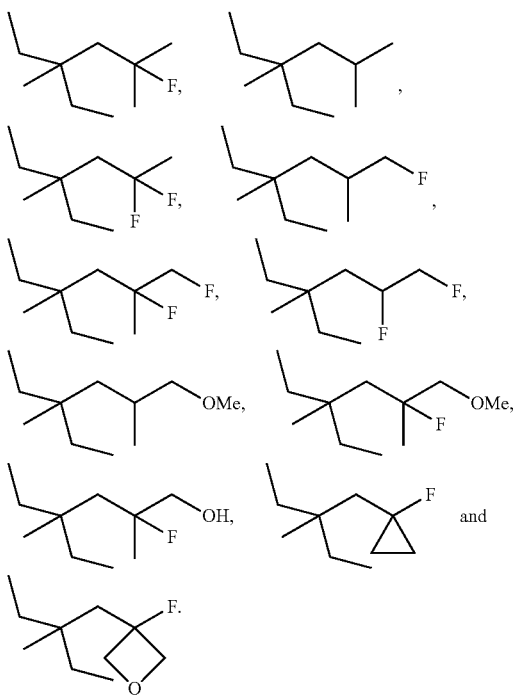

In one embodiment there is provided a compound of Formula (ID), or a pharmaceutically acceptable salt thereof, wherein $R^{11}$ is selected from the group consisting of:

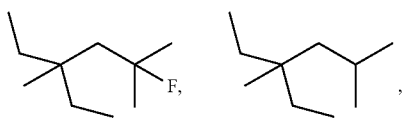

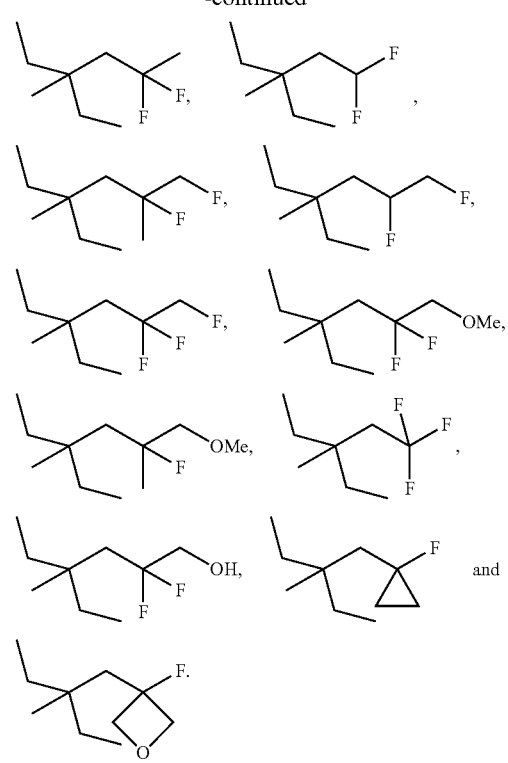

In one embodiment there is provided a compound of Formula (ID), or a pharmaceutically acceptable salt thereof, wherein $R^{11}$ is selected from the group consisting of:

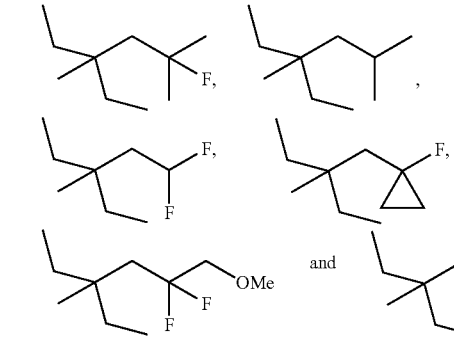

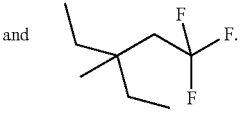

In one embodiment there is provided a compound of Formula (ID) or a pharmaceutically acceptable salt thereof wherein Ring Y is selected from the group consisting of:

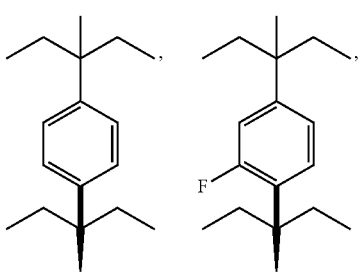

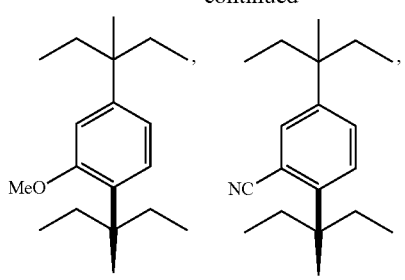

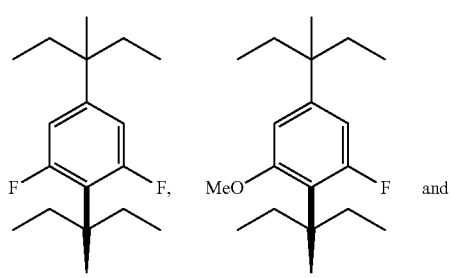 and

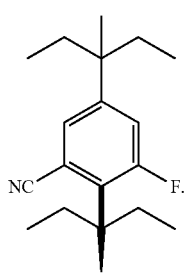

In one embodiment there is provided a compound of Formula (ID) or a pharmaceutically acceptable salt thereof wherein Ring Y is selected from the group consisting of:

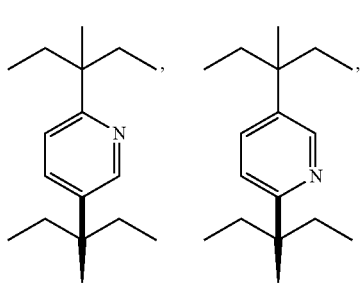

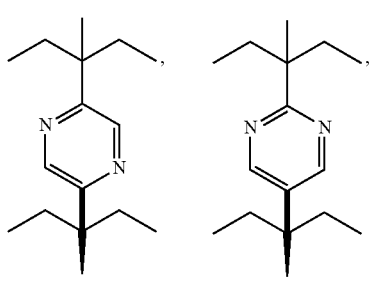

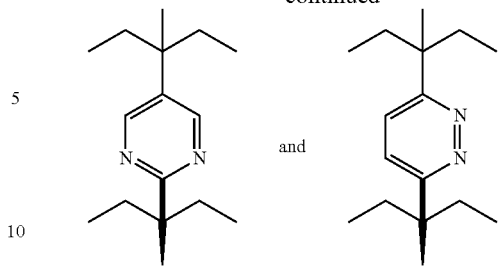

In one embodiment there is provided a compound of Formula (ID), or a pharmaceutically acceptable salt thereof, wherein Ring Y is selected from the group consisting of:

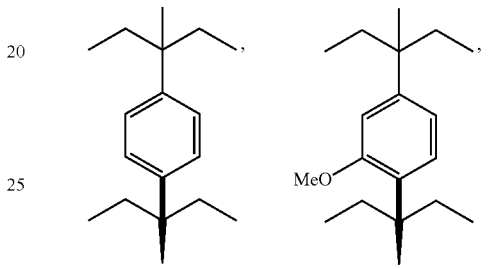

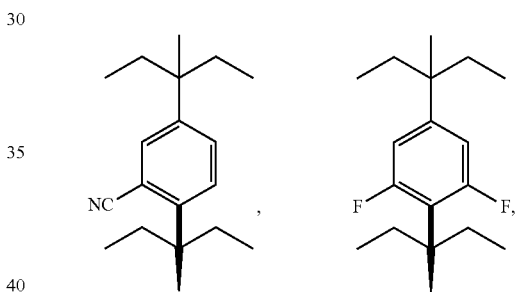

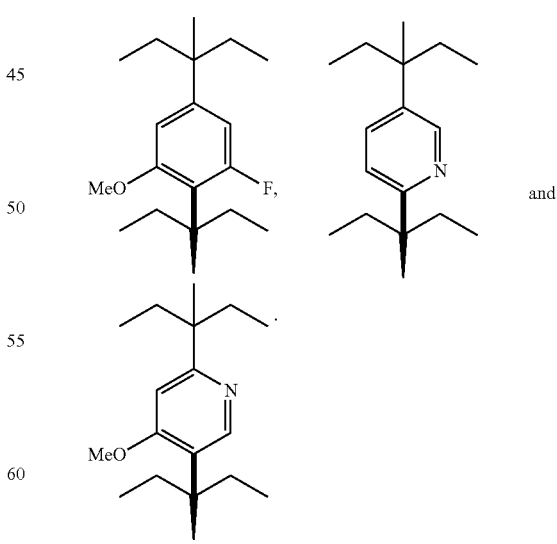

In one embodiment there is provided a compound of Formula (ID), or a pharmaceutically acceptable salt thereof, wherein Ring Y is selected from the group consisting of:

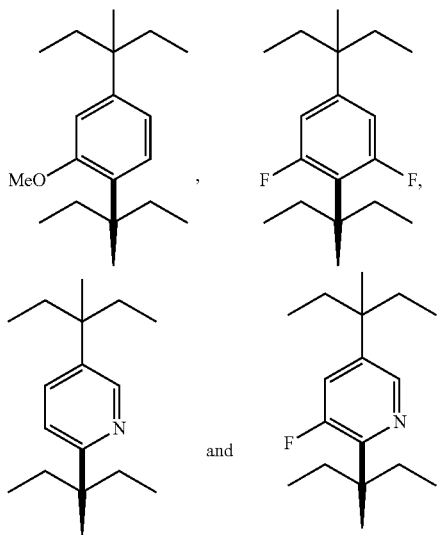

In a further aspect of the specification there is provided the compound of Formula (IE):

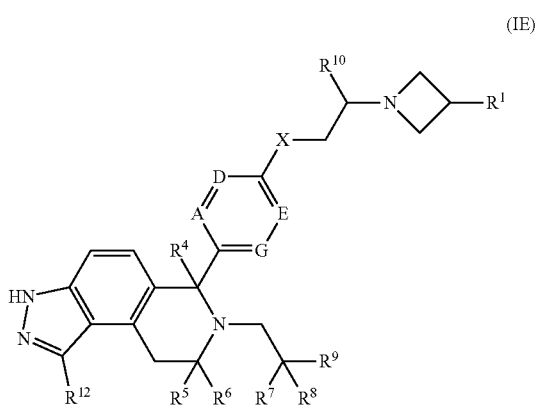

(IE)

wherein:
X is O, NH or NMe;
D and E are independently CH or N;
A is CR² or N;
G is CR³ or N;
R¹ is $CH_2F$, $CHF_2$, Me, OMe, F or CN;
R² is H, F, CN or OMe;
R³ is H or F;
R⁴ is H or Me;
R⁵ is H or Me;
R⁶ is Me, $CHF_2$ or cyclopropyl;
R⁷ is Me or F;
R⁸ is Me, F, $CH_2F$, $CH_2OMe$ or $CH_2OH$;
R⁹ is H or F; or
R⁸ and R⁹ taken together with the carbon atom to which they are attached form a cyclopropyl ring or an oxetane ring;
R¹⁰ is H or Me; and
R¹² is H or F;
or a pharmaceutically acceptable salt thereof.

In a further embodiment there is provided a compound of Formula (IE), or a pharmaceutically acceptable salt thereof, wherein X is O.

In a further embodiment there is provided a compound of Formula (IE), or a pharmaceutically acceptable salt thereof, wherein R¹² is H.

In a further embodiment there is provided a compound of Formula (IE), or a pharmaceutically acceptable salt thereof, wherein X is O and R¹² is H.

In a further embodiment there is provided the compound of Formula (IE) or a pharmaceutically acceptable salt thereof wherein the stereochemistry at the 6-position of the pyrazolo[4,3-f]isoquinoline ring is S.

In a further embodiment there is provided the compound of Formula (IE) or a pharmaceutically acceptable salt thereof wherein the stereochemistry at the 6-position of the pyrazolo[4,3-f]isoquinoline ring is R.

In a further embodiment there is provided the compound of Formula (IE) or a pharmaceutically acceptable salt thereof wherein the stereochemistry at the 8-position of the pyrazolo[4,3-f]isoquinoline ring is S.

In a further embodiment there is provided the compound of Formula (IE) or a pharmaceutically acceptable salt thereof wherein the stereochemistry at the 8-position of the pyrazolo[4,3-f]isoquinoline ring is R.

In one embodiment there is provided a compound of Formula (I), or a pharmaceutically acceptable salt thereof, wherein the compound is selected from the group consisting of:

(6S,8R)-6-(2,6-difluoro-4-(2-(3-(fluoromethyl)azetidin-1-yl)ethoxy)phenyl)-7-(2-fluoro-2-methylpropyl)-8-methyl-6,7,8,9-tetrahydro-3H-pyrazolo[4,3-f]isoquinoline;

(6S,8R)-6-(2,6-difluoro-4-(2-(3-(fluoromethyl)azetidin-1-yl)ethoxy)phenyl)-7-(2-fluoro-2-methylpropyl)-6,8-dimethyl-6,7,8,9-tetrahydro-3H-pyrazolo[4,3-f]isoquinoline;

(6S,8S)-6-(2,6-difluoro-4-(2-(3-(fluoromethyl)azetidin-1-yl)ethoxy)phenyl)-8-(difluoromethyl)-7-(2-fluoro-2-methylpropyl)-6,7,8,9-tetrahydro-3H-pyrazolo[4,3-f]isoquinoline;

(6S,8S)-6-(2,6-difluoro-4-(2-(3-(fluoromethyl)azetidin-1-yl)ethoxy)phenyl)-8-(difluoromethyl)-7-(2-fluoro-2-methylpropyl)-6-methyl-6,7,8,9-tetrahydro-3H-pyrazolo[4,3-f]isoquinoline;

(6S,8R)-7-(2-fluoro-2-methylpropyl)-6-(4-(2-(3-(fluoromethyl)azetidin-1-yl)ethoxy)-2-methoxyphenyl)-8-methyl-6,7,8,9-tetrahydro-3H-pyrazolo[4,3-f]isoquinoline;

(6S,8R)-7-((1-fluorocyclopropyl)methyl)-6-(4-(2-(3-(fluoromethyl)azetidin-1-yl)ethoxy)-2-methoxyphenyl)-8-methyl-6,7,8,9-tetrahydro-3H-pyrazolo[4,3-f]isoquinoline;

(6S,8R)-7-(2,2-difluoroethyl)-6-(4-(2-(3-(fluoromethyl)azetidin-1-yl)ethoxy)-2-methoxyphenyl)-8-methyl-6,7,8,9-tetrahydro-3H-pyrazolo[4,3-f]isoquinoline;

(6S,8R)-7-((1-fluorocyclopropyl)methyl)-6-(5-(2-(3-(fluoromethyl)azetidin-1-yl)ethoxy)pyridin-2-yl)-8-methyl-6,7,8,9-tetrahydro-3H-pyrazolo[4,3-f]isoquinoline;

(6S,8R)-6-(4-(2-(3-(fluoromethyl)azetidin-1-yl)ethoxy)-2-methoxyphenyl)-7-isobutyl-8-methyl-6,7,8,9-tetrahydro-3H-pyrazolo[4,3-f]isoquinoline; and (6S,8R)-7-(2,2-difluoro-3-methoxypropyl)-6-(5-(2-(3-(fluoromethyl)azetidin-1-yl)ethoxy)pyridin-2-yl)-8-methyl-6,7,8,9-tetrahydro-3H-pyrazolo[4,3-f]isoquinoline.

(6S,8R)-7-(2,2-difluoropropyl)-6-(4-(2-(3-(fluoromethyl)azetidin-1-yl)ethoxy)-2-methoxyphenyl)-8-methyl-6,7,8,9-tetrahydro-3H-pyrazolo[4,3-f]isoquinoline;

(6S,8R)-6-(4-(2-(3-(fluoromethyl)azetidin-1-yl)ethoxy)-2-methoxyphenyl)-8-methyl-7-(2,2,2-trifluoroethyl)-6,7,8,9-tetrahydro-3H-pyrazolo[4,3-f]isoquinoline;

2,2-difluoro-3-((6S,8R)-6-(4-(2-(3-(fluoromethyl)azetidin-1-yl)ethoxy)-2-methoxyphenyl)-8-methyl-3,6,8,9-tetrahydro-7H-pyrazolo[4,3-f] isoquinolin-7-yl)propan-1-ol;

(6S,8R)-7-(2,2-difluoro-3-methoxypropyl)-6-(4-(2-(3-(fluoromethyl)azetidin-1-yl)ethoxy)-2-methoxyphenyl)-8-methyl-6,7,8,9-tetrahydro-3H-pyrazolo[4,3-f]isoquinoline;

(6S,8R)-7-(2-fluoro-3-methoxy-2-methylpropyl)-6-(4-(2-(3-(fluoromethyl)azetidin-1-yl)ethoxy)-2-methoxyphenyl)-8-methyl-6,7,8,9-tetrahydro-3H-pyrazolo[4,3-f]isoquinoline;

(6S,8R)-7-(2,3-difluoropropyl)-6-(4-(2-(3-(fluoromethyl)azetidin-1-yl)ethoxy)-2-methoxyphenyl)-8-methyl-6,7,8,9-tetrahydro-3H-pyrazolo[4,3-f]isoquinoline;

(6S,8R)-7-(2,3-difluoro-2-methylpropyl)-6-(4-(2-(3-(fluoromethyl)azetidin-1-yl)ethoxy)-2-methoxyphenyl)-8-methyl-6,7,8,9-tetrahydro-3H-pyrazolo[4,3-f]isoquinoline;

(6S,8R)-6-(4-(2-(3-(fluoromethyl)azetidin-1-yl)ethoxy)-2-methoxyphenyl)-8-methyl-7-(2,2,3-trifluoropropyl)-6,7,8,9-tetrahydro-3H-pyrazolo[4,3-f]isoquinoline;

(6S,8R)-7-(2-fluoro-2-methylpropyl)-6-(2-methoxy-4-(2-(3-methylazetidin-1-yl)ethoxy)phenyl)-8-methyl-6,7,8,9-tetrahydro-3H-pyrazolo[4,3-f]isoquinoline;

(6S,8R)-7-(2-fluoro-2-methylpropyl)-6-(2-methoxy-4-(2-(3-methoxyazetidin-1-yl)ethoxy)phenyl)-8-methyl-6,7,8,9-tetrahydro-3H-pyrazolo[4,3-f]isoquinoline;

(6S,8R)-7-(2,2-difluoropropyl)-6-(2-fluoro-4-(2-(3-(fluoromethyl)azetidin-1-yl)ethoxy)-6-methoxyphenyl)-8-methyl-6,7,8,9-tetrahydro-3H-pyrazolo[4,3-f]isoquinoline;

2,2-difluoro-3-((6S,8R)-6-(2-fluoro-4-(2-(3-(fluoromethyl)azetidin-1-yl)ethoxy)-6-methoxyphenyl)-8-methyl-8,9-dihydro-3H-pyrazolo[4,3-f]isoquinolin-7(6H)-yl)propan-1-ol;

(6S,8R)-6-(2-fluoro-4-(2-(3-(fluoromethyl)azetidin-1-yl)ethoxy)-6-methoxyphenyl)-8-methyl-7-(2,2,3-trifluoropropyl)-6,7,8,9-tetrahydro-3H-pyrazolo[4,3-f]isoquinoline;

(6R,8R)-6-(4-(2-(3-(fluoromethyl)azetidin-1-yl)ethoxy)phenyl)-7-isobutyl-8-methyl-6,7,8,9-tetrahydro-3H-pyrazolo[4,3-f]isoquinoline;

(6R,8R)-7-((1-fluorocyclopropyl)methyl)-6-(4-(2-(3-(fluoromethyl)azetidin-1-yl)ethoxy)phenyl)-8-methyl-6,7,8,9-tetrahydro-3H-pyrazolo[4,3-f]isoquinoline;

(6R,8R)-7-((1-fluorocyclopropyl)methyl)-6-(4-(2-(3-(fluoromethyl)azetidin-1-yl)ethoxy)phenyl)-6,8-dimethyl-6,7,8,9-tetrahydro-3H-pyrazolo[4,3-f]isoquinoline;

(6R,8R)-6-(4-(2-(3-(fluoromethyl)azetidin-1-yl)ethoxy)phenyl)-7-((3-fluorooxetan-3-yl)methyl)-8-methyl-6,7,8,9-tetrahydro-3H-pyrazolo[4,3-f]isoquinoline;

(6R,8R)-6-(4-(2-(3-(fluoromethyl)azetidin-1-yl)ethoxy)phenyl)-7-((3-fluorooxetan-3-yl)methyl)-6,8-dimethyl-6,7,8,9-tetrahydro-3H-pyrazolo[4,3-f]isoquinoline;

(6S,8R)-6-(2,6-difluoro-4-(2-(3-(fluoromethyl)azetidin-1-yl)ethoxy)phenyl)-7-isobutyl-8-methyl-6,7,8,9-tetrahydro-3H-pyrazolo[4,3-f]isoquinoline;

(6S,8R)-6-(2,6-difluoro-4-(2-(3-(fluoromethyl)azetidin-1-yl)ethoxy)phenyl)-7-(2,3-difluoropropyl)-8-methyl-6,7,8,9-tetrahydro-3H-pyrazolo[4,3-f]isoquinoline;

6-(2,6-difluoro-4-(2-(3-(fluoromethyl)azetidin-1-yl)ethoxy)phenyl)-7-isobutyl-8,8-dimethyl-6,7,8,9-tetrahydro-3H-pyrazolo[4,3-f]isoquinoline;

6-(2,6-difluoro-4-(2-(3-(fluoromethyl)azetidin-1-yl)ethoxy)phenyl)-7-(2-fluoro-2-methylpropyl)-8,8-dimethyl-6,7,8,9-tetrahydro-3H-pyrazolo[4,3-f]isoquinoline;

(6S,8R)-6-(4-(2-(3-(difluoromethyl)azetidin-1-yl)ethoxy)-2,6-difluorophenyl)-7-(2-fluoro-2-methylpropyl)-8-methyl-6,7,8,9-tetrahydro-3H-pyrazolo[4,3-f]isoquinoline;

2-((6S,8R)-7-((1-fluorocyclopropyl)methyl)-8-methyl-6,7,8,9-tetrahydro-3H-pyrazolo[4,3-f]isoquinolin-6-yl)-5-(2-(3-(fluoromethyl)azetidin-1yl)ethoxy)benzonitrile;

(6S,8R)-6-(5-(2-(3-(fluoromethyl)azetidin-1-yl)ethoxy)pyridin-2-yl)-7-isobutyl-8-methyl-6,7,8,9-tetrahydro-3H-pyrazolo[4,3-f]isoquinoline;

(6S,8R)-7-(2,2-difluoropropyl)-6-(5-(2-(3-(fluoromethyl)azetidin-1-yl)ethoxy)pyridin-2-yl)-8-methyl-6,7,8,9-tetrahydro-3H-pyrazolo[4,3-f]isoquinoline; and (6S,8R)-7-((1-fluorocyclopropyl)methyl)-6-(6-(2-(3-(fluoromethyl)azetidin-1-yl)ethoxy)-4-methoxypyridin-3-yl)-8-methyl-6,7,8,9-tetrahydro-3H-pyrazolo[4,3-f]isoquinoline.

In one embodiment there is provided a compound of Formula (I), or a pharmaceutically acceptable salt thereof, wherein the compound is selected from the group consisting of:

(6S,8R)-6-(2,6-difluoro-4-(2-(3-(fluoromethyl)azetidin-1-yl)ethoxy)phenyl)-7-(2-fluoro-2-methylpropyl)-8-methyl-6,7,8,9-tetrahydro-3H-pyrazolo[4,3-f]isoquinoline;

(6S,8R)-6-(2,6-difluoro-4-(2-(3-(fluoromethyl)azetidin-1-yl)ethoxy)phenyl)-7-(2-fluoro-2-methylpropyl)-6,8-dimethyl-6,7,8,9-tetrahydro-3H-pyrazolo[4,3-f]isoquinoline;

(6S,8S)-6-(2,6-difluoro-4-(2-(3-(fluoromethyl)azetidin-1-yl)ethoxy)phenyl)-8-(difluoromethyl)-7-(2-fluoro-2-methylpropyl)-6,7,8,9-tetrahydro-3H-pyrazolo[4,3-f]isoquinoline;

(6S,8S)-6-(2,6-difluoro-4-(2-(3-(fluoromethyl)azetidin-1-yl)ethoxy)phenyl)-8-(difluoromethyl)-7-(2-fluoro-2-methylpropyl)-6-methyl-6,7,8,9-tetrahydro-3H-pyrazolo[4,3-f]isoquinoline;

(6S,8R)-7-(2-fluoro-2-methylpropyl)-6-(4-(2-(3-(fluoromethyl)azetidin-1-yl)ethoxy)-2-methoxyphenyl)-8-methyl-6,7,8,9-tetrahydro-3H-pyrazolo[4,3-f]isoquinoline;

(6S,8R)-7-((1-fluorocyclopropyl)methyl)-6-(4-(2-(3-(fluoromethyl)azetidin-1-yl)ethoxy)-2-methoxyphenyl)-8-methyl-6,7,8,9-tetrahydro-3H-pyrazolo[4,3-f]isoquinoline;

(6S,8R)-7-(2,2-difluoroethyl)-6-(4-(2-(3-(fluoromethyl)azetidin-1-yl)ethoxy)-2-methoxyphenyl)-8-methyl-6,7,8,9-tetrahydro-3H-pyrazolo[4,3-f]isoquinoline;

(6S,8R)-7-((1-fluorocyclopropyl)methyl)-6-(5-(2-(3-(fluoromethyl)azetidin-1-yl)ethoxy)pyridin-2-yl)-8-methyl-6,7,8,9-tetrahydro-3H-pyrazolo[4,3-f]isoquinoline;

(6S,8R)-6-(4-(2-(3-(fluoromethyl)azetidin-1-yl)ethoxy)-2-methoxyphenyl)-7-isobutyl-8-methyl-6,7,8,9-tetrahydro-3H-pyrazolo[4,3-f]isoquinoline; and (6S,8R)-7-(2,2-difluoro-3-methoxypropyl)-6-(5-(2-(3-(fluoromethyl)azetidin-1-yl)ethoxy)pyridin-2-yl)-8-methyl-6,7,8,9-tetrahydro-3H-pyrazolo[4,3-f]isoquinoline.

In one embodiment there is provided a compound of Formula (I), or a pharmaceutically acceptable salt thereof, wherein the compound is selected from the group consisting of:

(6S,8R)-6-(2,6-difluoro-4-(2-(3-(fluoromethyl)azetidin-1-yl)ethoxy)phenyl)-7-(2-fluoro-2-methylpropyl)-8-methyl-6,7,8,9-tetrahydro-3H-pyrazolo[4,3-f]isoquinoline;

(6S,8R)-6-(2,6-difluoro-4-(2-(3-(fluoromethyl)azetidin-1-yl)ethoxy)phenyl)-7-(2-fluoro-2-methylpropyl)-6,8-dimethyl-6,7,8,9-tetrahydro-3H-pyrazolo[4,3-f]isoquinoline;

(6S,8S)-6-(2,6-difluoro-4-(2-(3-(fluoromethyl)azetidin-1-yl)ethoxy)phenyl)-8-(difluoromethyl)-7-(2-fluoro-2-methylpropyl)-6,7,8,9-tetrahydro-3H-pyrazolo[4,3-f]isoquinoline; and (6S,8S)-6-(2,6-difluoro-4-(2-(3-(fluoromethyl)azetidin-1-yl)ethoxy)phenyl)-8-(difluoromethyl)-7-(2-fluoro-2-methylpropyl)-6-methyl-6,7,8,9-tetrahydro-3H-pyrazolo[4,3-f]isoquinoline.

In one embodiment there is provided a compound of Formula (I), or a pharmaceutically acceptable salt thereof, wherein the compound is selected from the group consisting of:

(6S,8R)-6-(5-(2-(3-(fluoromethyl)azetidin-1-yl)ethoxy)pyridin-2-yl)-8-methyl-7-(2,2,2-trifluoroethyl)-6,7,8,9-tetrahydro-3H-pyrazolo[4,3-f]isoquinoline;

(6S,8R)-6-(3-fluoro-5-(2-(3-(fluoromethyl)azetidin-1-yl)ethoxy)pyridin-2-yl)-8-methyl-7-(2,2,2-trifluoroethyl)-6,7,8,9-tetrahydro-3H-pyrazolo[4,3-f]isoquinoline;

(6S,8R)-6-(5-bromo-3-fluoropyridin-2-yl)-8-methyl-7-(2,2,2-trifluoroethyl)-6,7,8,9tetrahydro-3H-pyrazolo[4,3-f]isoquinoline; and (6S,8R)-7-(2,2-difluoroethyl)-6-(5-(2-(3-(fluoromethyl)azetidin-1-yl)ethoxy)pyridin-2-yl)-8-methyl-6,7,8,9-tetrahydro-3H-pyrazolo[4,3-f]isoquinoline.

In one embodiment there is provided a compound of Formula (I), or a pharmaceutically acceptable salt thereof, wherein the compound is selected from the group consisting of:

(6S,8R)-6-(2,6-difluoro-4-(2-(3-(fluoromethyl)azetidin-1-yl)ethoxy)phenyl)-1-fluoro-7-((3-fluorooxetan-3-yl)methyl)-8-methyl-6,7,8,9-tetrahydro-3H-pyrazolo[4,3-f]isoquinoline;

(6S,8R)-6-(2,6-difluoro-4-(2-(3-(fluoromethyl)azetidin-1-yl)ethoxy)phenyl)-1-fluoro-7-isobutyl-8-methyl-6,7,8,9-tetrahydro-3H-pyrazolo[4,3-f]isoquinoline;

7-(2-difluoroethyl)-6-(5-(2-(3-(fluoromethyl)azetidin-1-yl)ethoxy)pyridin-2-yl)-8,8-dimethyl-6,7,8,9-tetrahydro-3H-pyrazolo[4,3-f]isoquinoline;

(6S,8R)-7-((1-fluorocyclopropyl)methyl)-6-(6-(2-(3-(fluoromethyl)azetidin-1-yl)ethoxy)-2-methoxypyridin-3-yl)-8-methyl-6,7,8,9-tetrahydro-3H-pyrazolo[4,3-f]isoquinoline;

3,5-difluoro-4-((6S,8R)-7-(2-fluoro-2-methylpropyl)-8-methyl-6,7,8,9-tetrahydro-3H-pyrazolo[4,3-f]isoquinolin-6-yl)-N-(2-(3-(fluoromethyl)azetidin-1-yl)ethyl)aniline; and (6S,8R)-7-(2,2-difluoroethyl)-6-(3-fluoro-5-(2-(3(fluoromethyl)azetidin-1-yl)ethoxy)pyridin-2-yl)-8-methyl-6,7,8,9-tetrahydro-3H-pyrazolo[4,3-f]isoquinoline.

A further embodiment provides any of the embodiments defined herein (for example the embodiment of claim 1) with the proviso that one or more specific Examples (for instance one, two, three or more specific Examples) selected from the group consisting of Examples 1 to 51 is individually disclaimed.

For the avoidance of doubt, the use of " $\sim$ " in formulas of this specification denotes the point of attachment between different groups.

For the further avoidance of doubt, where multiple substituents are independently selected from a given group, the selected substituents may comprise the same substituents or different substituents from within the given group.

The compounds of Formula (I), (IA), (IB), (IC), (ID) or (IE) have two or more chiral centres and it will be recognised that the compound of Formula (I), (IA), (IB), (IC), (ID) or (IE) may be prepared, isolated and/or supplied with or without the presence, in addition, of one or more of the other possible enantiomeric and/or diastereomeric isomers of the compound of Formula (I), (IA), (IB), (IC), (ID) or (IE) in any relative proportions. The preparation of enantioenriched/enantiopure and/or diastereoenriched/diastereopure compounds may be carried out by standard techniques of organic chemistry that are well known in the art, for example by synthesis from enantioenriched or enantiopure starting materials, use of an appropriate enantioenriched or enantiopure catalyst during synthesis, and/or by resolution of a racemic or partially enriched mixture of stereoisomers, for example via chiral chromatography.

For use in a pharmaceutical context it may be preferable to provide a compound of Formula (I), (IA), (IB), (IC), (ID) or (IE) or a pharmaceutically acceptable salt thereof without large amounts of the other stereoisomeric forms being present.

Accordingly, in one embodiment there is provided a composition comprising a compound of Formula (I), (IA), (IB), (IC), (ID) or (IE) or a pharmaceutically acceptable salt thereof, optionally together with one or more of the other stereoisomeric forms of the compound of Formula (I), (IA), (IB), (IC), (ID) or (IE) or pharmaceutically acceptable salt thereof, wherein the compound of Formula (I), (IA), (IB), (IC), (ID) or (IE) or pharmaceutically acceptable salt thereof is present within the composition with a diastereomeric excess (% de) of ≥90%.

In a further embodiment the % de in the above-mentioned composition is ≥95%.

In a further embodiment the % de in the above-mentioned composition is ≥98%.

In a further embodiment the % de in the above-mentioned composition is ≥99%.

In a further embodiment there is provided a composition comprising a compound of Formula (I), (IA), (IB), (IC), (ID) or (IE) or a pharmaceutically acceptable salt thereof, optionally together with one or more of the other stereoisomeric forms of the compound of Formula (I), (IA), (IB), (IC), (ID) or (IE) or pharmaceutically acceptable salt thereof, wherein the compound of Formula (I), (IA), (IB), (IC), (ID) or (IE) or pharmaceutically acceptable salt thereof is present within the composition with an enantiomeric excess (% ee) of ≥90%.

In a further embodiment the % ee in the above-mentioned composition is ≥95%.

In a further embodiment the % ee in the above-mentioned composition is ≥98%.

In a further embodiment the % ee in the above-mentioned composition is ≥99%.

In a further embodiment there is provided a composition comprising a compound of Formula (I), (IA), (IB), (IC), (ID) or (IE) or a pharmaceutically acceptable salt thereof, optionally together with one or more of the other stereoisomeric forms of the compound of Formula (I), (IA), (IB), (IC), (ID) or (IE) or pharmaceutically acceptable salt thereof, wherein the compound of Formula (I), (IA), (IB), (IC), (ID) or (IE) or pharmaceutically acceptable salt thereof is present within the composition with an enantiomeric excess (% ee) of ≥90% and a diastereomeric excess (% de) of ≥90%.

In further embodiments of the above-mentioned composition the % ee and % de may take any combination of values as listed below:

The % ee is ≤5% and the % de is ≥80%.
The % ee is ≤5% and the % de is ≥90%.
The % ee is ≤5% and the % de is ≥95%.
The % ee is ≤5% and the % de is ≥98%.
The % ee is ≥95% and the % de is ≥95%.
The % ee is ≥98% and the % de is ≥98%.
The % ee is ≥99% and the % de is ≥99%.

In a further embodiment there is provided a pharmaceutical composition which comprises a compound of the Formula (I), (IA), (IB), (IC), (ID) or (IE) or a pharmaceutically acceptable salt thereof, in association with a pharmaceutically acceptable excipient.

In one embodiment there is provided a pharmaceutical composition which comprises a compound of the Formula (I), (IA), (IB), (IC), (ID) or (IE) or a pharmaceutically acceptable salt thereof, in association with a pharmaceutically acceptable excipient, optionally further comprising one or more of the other stereoisomeric forms of the compound of Formula (I), (IA), (IB), (IC), (ID) or (IE) or pharmaceutically acceptable salt thereof, wherein the compound of Formula (I), (IA), (IB), (IC), (ID) or (IE) or pharmaceutically acceptable salt thereof is present within the composition with an enantiomeric excess (% ee) of ≥90%.

In a further embodiment the % ee in the above-mentioned composition is ≥95%.

In a further embodiment the % ee in the above-mentioned composition is ≥98%.

In a further embodiment the % ee in the above-mentioned composition is ≥99%.

In one embodiment there is provided a pharmaceutical composition which comprises a compound of the Formula (I), (IA), (IB), (IC), (ID) or (IE) or a pharmaceutically acceptable salt thereof, in association with a pharmaceutically acceptable excipient, optionally further comprising one or more of the other stereoisomeric forms of the compound of Formula (I), (IA), (IB), (IC), (ID) or (IE) or pharmaceutically acceptable salt thereof, wherein the compound of Formula (I), (IA), (IB), (IC), (ID) or (IE) or pharmaceutically acceptable salt thereof is present within the composition with a diastereomeric excess (% de) of ≥90%.

In a further embodiment the % de in the above-mentioned composition is ≥95%.

In a further embodiment the % de in the above-mentioned composition is ≥98%.

In a further embodiment the % de in the above-mentioned composition is ≥99%.

In one embodiment there is provided a pharmaceutical composition which comprises a compound of the Formula (I), (IA), (IB), (IC), (ID) or (IE) or a pharmaceutically acceptable salt thereof, in association with a pharmaceutically acceptable excipient, optionally further comprising one or more of the other stereoisomeric forms of the compound of Formula (I), (IA), (IB), (IC), (ID) or (IE) or pharmaceutically acceptable salt thereof, wherein the compound of Formula (I), (IA), (IB), (IC), (ID) or (IE) or pharmaceutically acceptable salt thereof is present within the composition with an enantiomeric excess (% ee) of ≥90% and a diastereomeric excess (% de) of ≥90%.

In further embodiments of the above-mentioned pharmaceutical composition the % ee and % de may take any combination of values as listed below:

The % ee is ≥95% and the % de is ≥95%.
The % ee is ≥98% and the % de is ≥98%.
The % ee is ≥99% and the % de is ≥99%.

The compounds of Formula (I), (IA), (IB), (IC), (ID) or (IE) and pharmaceutically acceptable salts thereof may be prepared, used or supplied in amorphous form, crystalline form, or semicrystalline form and any given compound of Formula (I), (IA), (IB), (IC), (ID) or (IE) or pharmaceutically acceptable salt thereof may be capable of being formed into more than one crystalline/polymorphic form, including hydrated (e.g. hemi-hydrate, a mono-hydrate, a di-hydrate, a tri-hydrate or other stoichiometry of hydrate) and/or solvated forms. It is to be understood that the present specification encompasses any and all such solid forms of the compound of Formula (I), (IA), (IB), (IC), (ID) or (IE) and pharmaceutically acceptable salts thereof.

In further embodiments there is provided a compound of Formula (I), (IA), (IB), (IC), (ID) or (IE), which is obtainable by the methods described in the 'Examples' section hereinafter.

The present specification is intended to include all isotopes of atoms occurring in the present compounds. Isotopes will be understood to include those atoms having the same atomic number but different mass numbers. For example, isotopes of hydrogen include tritium and deuterium. Isotopes of carbon include $^{13}C$ and $^{14}C$. In a particular embodiment there is provided a compound of Formula (I), (IA), (IB), (IC), (ID) or (IE) wherein $R^4$ is deuterium.

A suitable pharmaceutically acceptable salt of a compound of the Formula (I), (IA), (IB), (IC), (ID) or (IE) is, for example, an acid addition salt. A suitable pharmaceutically acceptable salt of a compound of the Formula (I), (IA), (IB), (IC), (ID) or (IE) may be, for example, an acid-addition salt of a compound of the Formula (I), (IA), (IB), (IC), (ID) or (IE), for example an acid-addition salt with an inorganic or organic acid such as hydrochloric acid, hydrobromic acid, sulphuric acid or trifluoroacetic acid. Pharmaceutically acceptable salts of a compound of the Formula (I), (IA), (IB), (IC), (ID) or (IE) may also be an acid-addition salt with an acid such as one of the following: acetic acid, adipic acid, benzene sulfonic acid, benzoic acid, cinnamic acid, citric acid, D,L-lactic acid, ethane disulfonic acid, ethane sulfonic acid, fumaric acid, L-tartaric acid, maleic acid, malic acid, malonic acid, methane sulfonic acid, napadisylic acid, phosphoric acid, saccharin, succinic acid, p-toluenesulfonic acid or toluene sulfonic acid.

A further suitable pharmaceutically acceptable salt of a compound of the Formula (I), (IA), (IB), (IC), (ID) or (IE) is, for example, a salt formed within the human or animal body after administration of a compound of the Formula (I), (IA), (IB), (IC), (ID) or (IE) to said human or animal body.

The compound of Formula (I), (IA), (IB), (IC), (ID) or (IE) or pharmaceutically acceptable salt thereof may be prepared as a co-crystal solid form. It is to be understood that a pharmaceutically acceptable co-crystal of a compound of the Formula (I), (IA), (IB), (IC), (ID) or (IE) or pharmaceutically acceptable salts thereof, form an aspect of the present specification.

It is to be understood that a suitable pharmaceutically acceptable pro-drug of a compound of the Formula (I), (IA), (IB), (IC), (ID) or (IE) also forms an aspect of the present specification. Accordingly, the compounds of the specification may be administered in the form of a pro-drug, which is a compound that is broken down in the human or animal body to release a compound of the specification. A pro-drug may be used to alter the physical properties and/or the pharmacokinetic properties of a compound of the specification. A pro-drug can be formed when the compound of the specification contains a suitable group or substituent to which a property-modifying group can be attached. Examples of pro-drugs include in-vivo cleavable ester or amide derivatives of the compound of the Formula (I), (IA), (IB), (IC), (ID) or (IE).

Accordingly, one aspect of the present specification includes those compounds of Formula (I), (IA), (IB), (IC), (ID) or (IE) as defined hereinbefore when made available by organic synthesis and when made available within the human or animal body by way of cleavage of a pro-drug thereof. Accordingly, the present specification includes those compounds of the Formula (I), (IA), (IB), (IC), (ID) or (IE) that are produced by organic synthetic means and also such compounds that are produced in the human or animal body by way of metabolism of a precursor compound, that is a compound of the Formula (I), (IA), (IB), (IC), (ID) or (IE) may be a synthetically-produced compound or a metabolically-produced compound.

A suitable pharmaceutically acceptable pro-drug of a compound of the Formula (I), (IA), (IB), (IC), (ID) or (IE) is one that is based on reasonable medical judgement as being suitable for administration to the human or animal body without undesirable pharmacological activities and without undue toxicity.

Various forms of pro-drug have been described, for example in the following documents:

a) *Methods in Enzymology*, Vol. 42, p. 309-396, edited by K. Widder, et al. (Academic Press, 1985);

b) Design of Pro-drugs, edited by H. Bundgaard, (Elsevier, 1985);

c) A Textbook of Drug Design and Development, edited by Krogsgaard-Larsen and H. Bundgaard, Chapter 5 "Design and Application of Pro-drugs", by H. Bundgaard p. 113-191 (1991);

d) H. Bundgaard, *Advanced Drug Delivery Reviews*, 8, 1-38 (1992);

e) H. Bundgaard, et al., *Journal of Pharmaceutical Sciences*, 77, 285 (1988);

f) N. Kakeya, et al., *Chem. Pharm. Bull.*, 32, 692 (1984);

g) T. Higuchi and V. Stella, "Pro-Drugs as Novel Delivery Systems", A.C.S. Symposium Series, Volume 14; and h) E. Roche (editor), "Bioreversible Carriers in Drug Design", Pergamon Press, 1987.

The in-vivo effects of a compound of the Formula (I), (IA), (IB), (IC), (ID) or (IE) may be exerted in part by one or more metabolites that are formed within the human or animal body after administration of a compound of the Formula (I), (IA), (IB), (IC), (ID) or (IE). As stated hereinbefore, the in-vivo effects of a compound of the Formula (I), (IA), (IB), (IC), (ID) or (IE) may also be exerted by way of metabolism of a precursor compound (a pro-drug).

For the avoidance of doubt it is to be understood that where in this specification a group is qualified by 'hereinbefore defined' or 'defined herein' the said group encompasses the first occurring and broadest definition as well as each and all of the alternative definitions for that group.

Another aspect of the present specification provides a process for preparing a compound of the Formula (I), (IA), (IB), (IC), (ID) or (IE), or a pharmaceutically acceptable salt thereof. A suitable process is illustrated by the following representative process variants in which, unless otherwise stated, A, D, E, G, X and $R^1$ to $R^{12}$ have any of the meanings defined hereinbefore. Necessary starting materials may be obtained by standard procedures of organic chemistry. The preparation of such starting materials is described in conjunction with the following representative process variants and within the accompanying Examples. Alternatively, necessary starting materials are obtainable by analogous procedures to those illustrated which are within the ordinary skill of an organic chemist.

Compounds of Formula (I), (IA), (IB), (IC), (ID) or (IE) may be made by, for example, etherification or amination of a suitable compound of formula (II), where L is for example a halogen (such as Br) or a trifluoromethanesulfonyl (triflate) group or a boronic acid or boronate ester, with an alcohol or amine of formula (III) using a suitable metal catalyst (for example RockPhos 3rd Generation Precatalyst) in a suitable solvent (for example toluene or DME) in the presence of a suitable base (for example cesium carbonate) and a suitable temperature (such as 90-120° C.) where P is optionally an appropriate protecting group (for example THP that may be subsequently removed by treatment with acid).

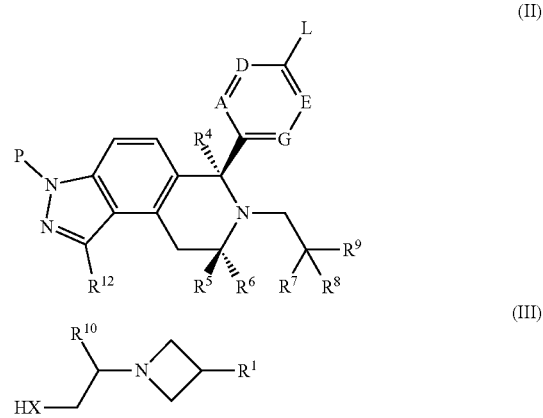

Compounds of formula (II) where $R^4$ is not equal to hydrogen may be made, for example, from compounds of formula (IV) by oxidation with a suitable reagent (for example bis(trifluoracetoxy)-iodobenzene) and treatment with an organometallic reagent (for example methyl magnesium bromide when $R^4$ is methyl) in a suitable solvent (for example THF) at low temperature (typically −80 to −60° C.).

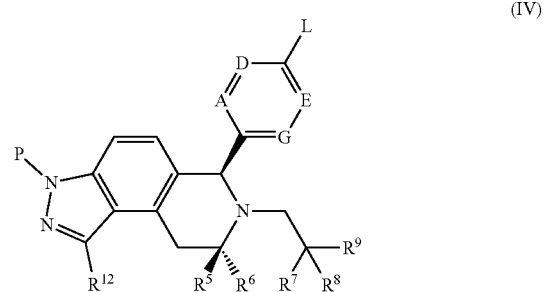

Compounds of formula (IV), where $R^{12}$ is hydrogen, may be prepared by, for example, reaction of an aniline of Formula (V) with suitable reagents to effect the construction of an indazole such as inorganic nitrite (such as sodium nitrite) in organic acid (such as propionic acid) at low temperature (typically −20 to 0° C.) or alternatively an acid anhydride (such as acetic anhydride) in the presence of a suitable base (such as potassium acetate) together with organic nitrite (such as isopentyl nitrite) optionally in the presence of a crown ether (such as 18-crown-6) in a suitable solvent (such as chloroform) at a suitable temperature (such as 70° C.).

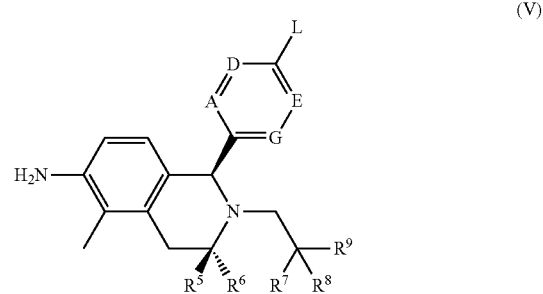

Compounds of formula (V) may be made by reaction of a compound of formula (VI) with a compound of formula (VII) under conditions known in the art as suitable for Pictet-Spengler reactions, such as in the presence of acid (such as acetic acid) and in a suitable solvent (for example toluene or water) and a suitable temperature (such as 60-100° C.).

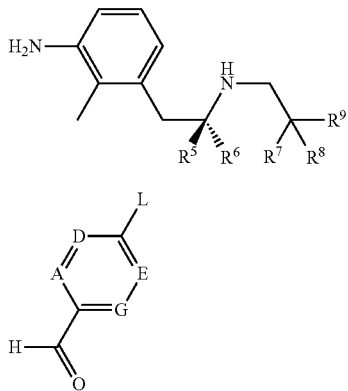

(VI)

(VII)

Compounds of formula (VI) may be prepared by functional group interconversions known to the art, for example aminations of halides of formula (VIII) from aryl halides (such as bromo) using a protected amine (such as diphenylmethanimine) in the presence of a suitable catalyst and ligand (such as bis(dibenzylideneacetone)palladium(0) and rac-2,2'-bis(diphenylphosphino)-1,1'-binaphthyl) in the presence of a suitable base (such as sodium tert-butoxide) in a suitable solvent (such as toluene) at a suitable temperature (such as 80-100° C.).

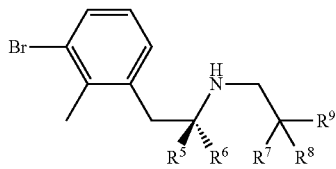

(VIII)

Compounds of formula (VIII) may be prepared by:
a) reaction of a compound of formula (IX) with an aldehyde of formula (X), in a suitable solvent (for example THF) in the presence of a suitable reducing agent (such as sodium triacetoxyborohydride) and at a suitable temperature (such as 20-30° C.);
b) (i) reaction of a compound of formula (IX) with an acid of formula (XI) under standard amide bond forming conditions (for example in the presence of an amide coupling reagent (such as HATU) and a suitable base (such as triethylamine) in a suitable solvent (such as DMF)), followed by (ii) reduction of the resultant amide bond using a suitable reducing agent (such as borane) in a suitable solvent (such as THF) at a suitable temperature (such as 60-70° C.);
c) reaction of a compound of formula (IX) with a compound of formula (XII), wherein LG is a suitable leaving group (for example a halogen atom (such as bromo or chloro) or trifluoromethanesulfone), in the presence of a suitable base (such as diisopropylethylamine) in a suitable solvent (for example DCM or dioxane) and at a suitable temperature (such as 20-85° C.).

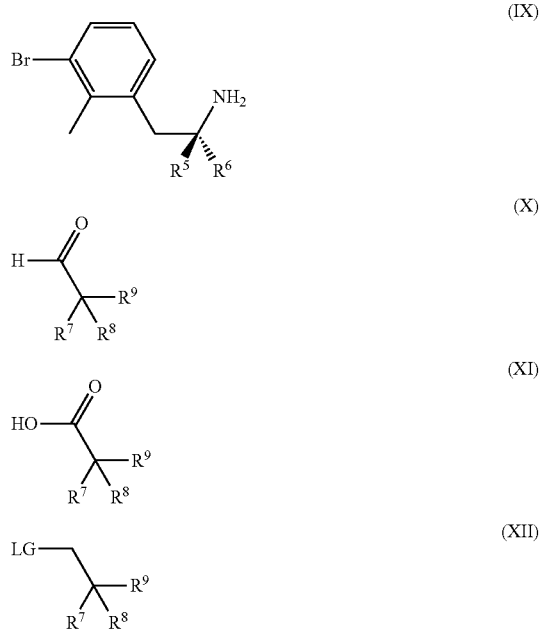

(IX)

(X)

(XI)

(XII)

Compounds of formula (IX) may be prepared by a number of methods known to the art for the synthesis of chiral amines notably;

a) Ring opening of sulfamidates of formula (XIII) according to the scheme shown below.

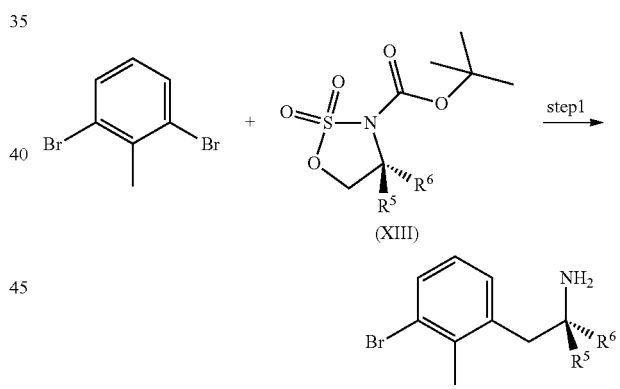

(XIII)

Step 1: Alkylation, e.g. n-butyllithium/THF/−78° C. to 0° C.

b) Phase transfer alklyation in the presence of a chiral catalyst (such as (1S,2S,4S,5R)-2-((R)-(allyloxy)(quinolin-4-yl)methyl)-1-(anthracen-9-ylmethyl)-5-vinylquinuclidin-1-ium bromide) followed by functional group manipulation

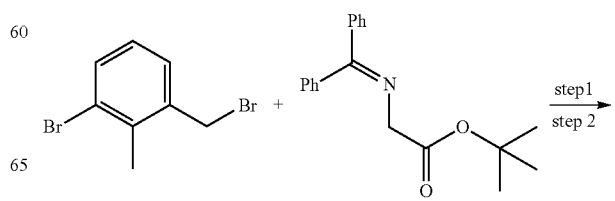

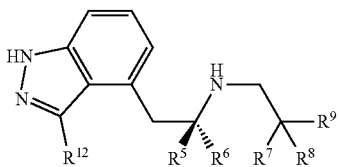

Step 1: Alkylation, e.g. chiral catalyst, toluene/KOH, 0° C.

Step 2: Functional Group Interconversion

Certain compounds of formula (II) (with P═H) may alternatively be made by cyclisation of compounds containing a preformed indazole of formula (XIV) with a compound of formula (VII) under conditions known in the art as suitable for Pictet-Spengler reactions, such as in the presence of acid (such as trifluoroacetic acid) and in a suitable solvent (for example toluene or water) and a suitable temperature (such as 60-100° C.).

(XIV)

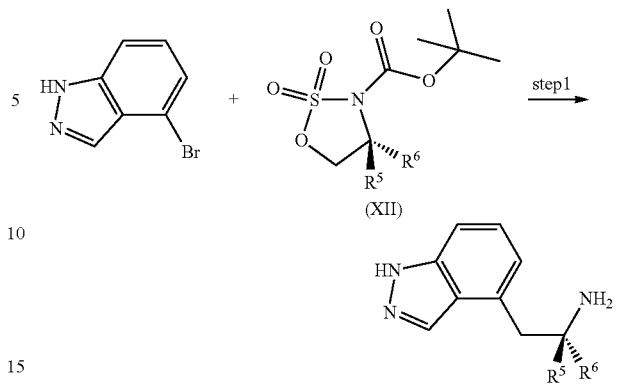

Compounds of formula (XIV) may be prepared by:

a) reaction of a compound of formula (XV) with an aldehyde of formula (X), in a suitable solvent (for example THF) in the presence of a suitable reducing agent (such as sodium triacetoxyborohydride) and at a suitable temperature (such as 20-30° C.);

b) (i) reaction of a compound of formula (XV) with an acid of formula (XI) under standard amide bond forming conditions (for example in the presence of an amide coupling reagent (such as HATU) and a suitable base (such as triethylamine) in a suitable solvent (such as DMF)), followed by (ii) reduction of the resultant amide bond using a suitable reducing agent (such as borane) in a suitable solvent (such as THF) at a suitable temperature (such as 60-70° C.);

c) reaction of a compound of formula (XV) with a compound of formula (XII), wherein LG is a suitable leaving group (for example a halogen atom (such as bromo or chloro) or trifluoromethanesulfone), in the presence of a suitable base (such as diisopropylethylamine) in a suitable solvent (for example DCM or dioxane) and at a suitable temperature (such as 20-85° C.).

(XV)

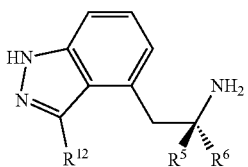

Compounds of formula (XV) may be prepared by a number of methods known to the art for the synthesis of chiral amines notably; Ring opening of sulfamidates of formula (XII) according to the scheme shown

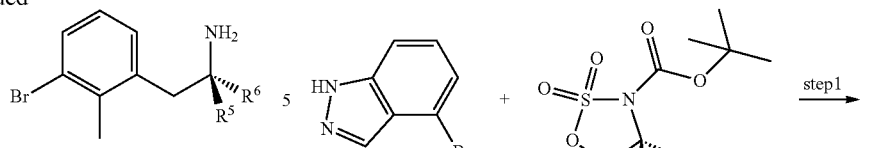

Step 1: Alkylation, e.g. n-butyllithium/THF/−78° C. to 0° C.

Step 2: Removal of protecting groups, e.g. anhydrous HCl in dioxane/MeOH/DCM etc It is to be understood that other permutations of the process steps in the process variants described above are also possible.

When a pharmaceutically acceptable salt of a compound of the Formula (I), (IA), (IB), (IC), (ID) or (IE) is required it may be obtained by, for example, reaction of said compound with a suitable acid or suitable base. When a pharmaceutically acceptable pro-drug of a compound of the Formula (I), (IA), (IB), (IC), (ID) or (IE) is required, it may be obtained using a conventional procedure.

It will also be appreciated that, in some of the reactions mentioned hereinbefore, it may be necessary or desirable to protect any sensitive groups in the compounds. The instances where protection is necessary or desirable, and suitable methods for protection, are known to those skilled in the art. Conventional protecting groups may be used in accordance with standard practice (for illustration see T.W. Green, Protective Groups in Organic Synthesis, John Wiley and Sons, 1991). Thus, if reactants include groups such as amino, carboxy or hydroxy, it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

Certain of the intermediates defined herein are novel and these are provided as further features of the specification.

Biological Assays

The following assays were used to measure the effects of the compounds of the present specification.

ERα binding assay

The ability of compounds to bind to isolated Estrogen Receptor Alpha Ligand binding domain (ER alpha—LBD (GST)) was assessed in competition assays using a LanthaScreen™ Time-Resolved Fluorescence Resonance Energy Transfer (TR-FRET) detection end-point. For the LanthaScreen TR-FRET endpoint, a suitable fluorophore (Fluormone ES2, ThermoFisher, Product code P2645) and recombinant human Estrogen Receptor alpha ligand binding domain, residues 307-554 (expressed and purified in-house) were used to measure compound binding. The assay principle is that ER alpha -LBD (GST) is added to a fluorescent ligand to form a receptor/fluorophore complex. A terbium-labelled anti-GST antibody (Product code PV3551) is used to indirectly label the receptor by binding to its GST tag, and competitive binding is detected by a test compounds' ability to displace the fluorescent ligand resulting in a loss of TR-FRET signal between the Tb-anti-GST antibody and the tracer. The assay was performed as follows with all reagent additions carried out using the Beckman Coulter BioRAPTR FRD microfluidic workstation:

1. Acoustic dispense 120 nL of the test compound into a black low volume 384 well assay plates.
2. Prepare 1× ER alpha —LBD/Tb-antiGST Ab in ES2 screening buffer and incubate for 15 minutes.
3. Dispense 6µL of the 1× AR-LBD/Tb-anti-GST Ab reagent into each well of the assay plate followed by 6µL Fluorophore reagent into each well of the assay plate
4. Cover the assay plate to protect the reagents from light and evaporation, and incubate at room temperature for 4 hours.
5. Excite at 337 nm and measure the fluorescent emission signal of each well at 490 nm and 520 nm using the BMG PheraSTAR.

Compounds were dosed directly from a compound source microplate containing serially diluted compound (4 wells containing 10 mM, 0.1 mM, 1 mM and 10 nM final compound respectively) to an assay microplate using the Labcyte Echo 550. The Echo 550 is a liquid handler that uses acoustic technology to perform direct microplate-to-microplate transfers of DMSO compound solutions and the system can be programmed to transfer multiple small nL volumes of compound from the different source plate wells to give the desired serial dilution of compound in the assay which is then back-filled to normalise the DMSO concentration across the dilution range. In total 120 nL of compound plus DMSO is added to each well and compounds were tested in a 12-point concentration response format over a final compound concentration range of 10, 2.917, 1.042, 0.2083, 0.1, 0.0292, 0.0104, 0.002083, 0.001, 0.0002917, 0.0001042, 0.00001 µM respectively. TR-FRET dose response data obtained with each compound was exported into a suitable software package (such as Origin or Genedata) to perform curve fitting analysis. Competitive ER alpha binding was expressed as an $IC_{50}$ value. This was determined by calculation of the concentration of compound that was required to give a 50% reduction in tracer compound binding to ER alpha-LBD.

MCF-7 ER Down Regulation Assay

The ability of compounds to down-regulate Estrogen Receptor (ER) numbers was assessed in a cell based immuno-fluorescence assay using the MCF-7 human ductal carcinoma breast cell line. MCF-7 cells were revived directly from a cryovial (approx $5 \times 10^6$ cells) in Assay Medium (phenol red free Dulbecco's Modified Eagle's medium (DMEM) (Sigma D5921) containing 2mM L-Glutamine and 5% (v/v) Charcoal/Dextran treated foetal calf serum. Cells were syringed once using a sterile 18 G×1.5 inch (1.2×40 mm) broad gauge needle and cell density was measured using a Coulter Counter (Beckman). Cells were further diluted in Assay Medium to a density of $3.75 \times 10^4$ cells per mL and 40 µL per well added to transparent bottomed, black, tissue culture treated 384 well plates (Costar, No. 3712) using a Thermo Scientific Matrix WellMate or Thermo Multidrop. Following cell seeding, plates were incubated overnight at 37° C., 5% $CO_2$ (Liconic carousel incubator). Test data was generated using the LabCyte Echo™ model 555 compound reformatter which is part of an automated workcell (Integrated Echo 2 workcell). 10 mM compound stock solutions of the test compounds were used to generate a 384 well compound dosing plate (Labcyte P-05525-CV1). 40 µΛ of each of the 10 mM compound stock solutions was dispensed into the first quadrant well and then 1:100 step-wise serial dilutions in DMSO were performed using a Hydra II (MATRIX UK) liquid handling unit to give 40 µL of diluted compound into quadrant wells 2 (0.1 mM), 3 (1 µM) and 4 (0.01 µM), respectively. 40 µΛ of DMSO added to wells in row P on the source plate allow for DMSO normalisation across the dose range. To dose the control wells 40 µL of DMSO was added to row O1 and 40 µL of 100 µM fulvestrant in DMSO was added to row O3 on the compound source plate. The Echo uses acoustic technology to perform direct microplate-to-microplate transfers of DMSO compound solutions to assay plates. The system can be programmed to transfer volumes as low as 2.5 nL in multiple increments between microplates and in so doing generates a serial dilution of compound in the assay plate which is then back-filled to normalise the DMSO concentration across the dilution range. Compounds were dispensed onto the cell plates with a compound source plate prepared as above producing a 12 pt duplicate 3 µM to 3 pM dose range with 3 fold dilutions and one final 10 fold dilution using the Integrated Echo 2 workcell. The maximum signal control wells were dosed with DMSO to give a final concentration of 0.3% and the minimum signal control wells were dosed with fulvestrant to give a final concentration of 100 nM accordingly. Plates were further incubated for 18-22 hours at 37° C., 5% $CO_2$ and then fixed by the addition of 20 μL of 11.1% (v/v) formaldehyde solution (in phosphate buffered saline (PBS)) giving a final formaldehyde concentration of 3.7% (v/v). Cells were fixed at room temperature for 20 mins before being washed two times with 250 μL PBS/Proclin (PBS with a Biocide preservative) using a BioTek platewasher, 40 μL of PBS/Proclin was then added to all wells and the plates stored at 4° C. The fixing method described above was carried out on the Integrated Echo 2 workcell. Immunostaining was performed using an automated AutoElisa workcell. The PBS/Proclin was aspirated from all wells and the cells permeabilised with 40 μL PBS containing 0.5% Tween™ 20 (v/v) for 1 hour at room temperature. The plates were washed three times in 250 μL of PBS/0.05% (v/v) Tween 20 with Proclin (PBST with a Biocide preservative) and then 20 μL of ERα (SP1) Rabbit monoclonal antibody (Thermofisher) 1:1000 in PBS/Tween™/3% (w/v) Bovine Serum Albumin was added. The plates were incubated overnight at 4° C. (Liconic carousel incubator) and then washed three times in 250 μL of PBS/0.05% (v/v) Tween™ 20 with Proclin (PBST). The plates were then incubated with 20 μL/well of a goat anti-rabbit IgG AlexaFluor 594 or goat anti-rabbit AlexaFluor 488 antibody (Molecular Probes) with Hoechst at 1:5000 in PBS/Tween™/3% (w/v) Bovine Serum Albumin for 1hour at room temperature. The plates were then washed three times in 250 μL of PBS/0.05% (v/v) Tween™ 20 with Proclin (PBST with a Biocide preservative). 20 μL of PBS was added to each well and the plates covered with a black plate seal and stored at 4° C. before being read. Plates were read using a Cellomics Arrayscan reading the 594 nm (24 hr time point) or 488 nm (5 hr timepoint) fluorescence to measure the ERα receptor level in each well. The mean total intensity was normalized for cell number giving the total intensity per cell. The data was exported into a suitable software package (such as Origin) to perform curve fitting analysis. Down-regulation of the ERα receptor was expressed as an $IC_{50}$ value and was determined by calculation of the concentration of compound that was required to give a 50% reduction of the average maximum Total Intensity signal.

The data shown in Table A were generated for the Examples (the data below may be a result from a single experiment or an average of two or more experiments):

TABLE A

| Example | ER binding IC50 value (nM) | ER down regulation IC50 value (nM)[1] |
|---|---|---|
| 1 | 1.2 | 0.097 |
| 2 | 1.5 | 0.088 |
| 3 | 0.52 | 0.16 |
| 4 | 0.50 | 0.16 (80%) |
| 5 | 3.3 | 0.16 |
| 6 | 10 | 0.13 |
| 7 | 2.0 | 0.085 |
| 8 | 1.3 | 0.39 |
| 9 | 5.8 | 0.50 |
| 10 | 7.9 | 0.51 |
| 11 | 1.3 | 0.036 |
| 12 | 2.9 | 0.051 |
| 13 | 3.7 | 0.23 |
| 14 | 3.5 | 0.15 |
| 15 | 5.2 | 0.091 |
| 16 | 4.1 | 0.44 (56%) |
| 17 | 9.7 | 0.24 |
| 18 | 2.4 | 0.19 |
| 19 | 2.4 | 0.28 |
| 20 | 1.1 | 0.13 |
| 21 | 2.0 | 0.13 |
| 22 | 1.9 | 0.15 |
| 23 | 2.8 | 0.24 (67%) |
| 24 | 3.7 | <50% |
| 25 | 1.3 | 0.11 |
| 26 | 3.8 | 0.13 |
| 27 | 2.6 | 0.059 |
| 28 | 1.9 | 0.14 |
| 29 | 9.2 | 0.35 |
| 30 | 0.98 | 0.087 |
| 31 | 1.4 | 0.2 |
| 32 | 0.67 | 0.076 |
| 33 | 0.9 | 0.21 |
| 34 | 3.8 | 0.28 |
| 35 | 2.7 | 0.26 |
| 36 | 1.9 | 0.25 |
| 37 | 1 | 0.16 |
| 38 | 0.58 | 0.26 |
| 39 | 2.8 | 0.17 |
| 40 | 9.4 | 0.36 |
| 41 | 1.8 | 0.29 |
| 42 | 6.6 | 0.59 |
| 43 | 2.2 | 0.59 |
| 44 | 2.5 | 0.42 |
| 45 | 7.1 | 3.1 |
| 46 | 4.9 | 0.14 |
| 47 | 1.1 | 0.28 (86%) |
| 48 | 4.1 | 1.9 |
| 49 | 2.2 | 0.21 |
| 50 | 2.1 | 0.5 |
| 51 | 5.9 | 0.54 |

[1]Compounds tested in the ER down regulation assay show downregulation values (>90%) in the assay unless otherwise stated, in which case the % downregulation is shown in brackets.

Western Blotting Assay

The ability of compounds to down-regulate estrogen receptor (ER) was assessed by western blotting using human breast cancer cell lines (MCF-7 and CAMA-1). Cells were plated into 12-well tissue culture-treated plates at $0.5 \times 10^6$/well in phenol red-free RPMI containing 2 mM L-glutamine and 5% (v/v) charcoal treated foetal calf serum (F6765, Sigma). Cells were incubated with compounds (100 nM) or vehicle control (0.1% DMSO) for 48 h at 37° C., 5% $CO_2$ before washing once with PBS and lysing with 80 μl lysis buffer (25 mM Tris/HCl, 3 mM EDTA, 3 mM EGTA, 50 mM NaF, 2 mM sodium orthovanadate, 0.27 M sucrose, 10 mM β-glycerophosphate, 5 mM sodium pyrophosphate, 0.5% TritonX-100, pH 6.8) on ice.

Cells were scraped, sonicated and centrifuged prior to performing a protein assay (DC Bio-Rad Protein kit, 500-0116) and making samples to a protein concentration of 1-2 mg/ml in lysis buffer containing 1× LDS Sample Buffer (NP0007, Invitrogen) and 1× NuPAGE sample reducing agent (NP0009, Invitrogen). Samples were boiled for 10 min at 95° C. and then frozen at −20° C. until ready for use.

10-20 μg protein was loaded onto 26-well Criterion gels (BioRad 345-0034). Gels were run at 125 V for 1 hr 25 min in running buffer (24 mM Tris Base Sigma, 192 mM Glycine, 3.5 mM SDS, made up in distilled water). Gels were then transferred at 30V for 2 hr in transfer buffer (25 mM Tris, 192 mM Glycine, 20% (v/v) methanol, pH 8.3, made up in distilled water) onto nitrocellulose membrane. The blot was stained with Ponceau S (P7170, Sigma) and cut according to appropriate molecular weight markers.

Membranes were blocked for 1 hour at room temp in 5% Marvel (w/v) in phosphate-buffered saline containing 0.05%

Tween™ 20 (PBS/Tween). Blots were then incubated with anti-ERα (SP1) rabbit monoclonal antibody (Thermofisher) diluted 1:1000 at 4° C. overnight (with gentle shaking) followed by several washes with PBS/Tween. Secondary anti-rabbit HRP antibody (7074, CST) diluted 1:2000 dilution was incubated for 2 h at room temperature (with gentle shaking) followed by several washes with PBS/Tween. All antibodies were made up in 5% Marvel (w/v) in PBS/Tween.

The immunoblots were developed using Pierce WestDura chemiluminescent reagents (Thermo Scientific 34076) and developed/quantified on the G-box using Syngene software. Down-regulation of the ERα receptor was normalised to the vehicle control (0% down-regulation) and the 100 nM fulvestrant control (100% down-regulation) run within the same gel.

Table B shows the data generated for selected Examples (the data below may be a result from a single experiment or an average of two or more experiments):

TABLE B

| Example | CAMA1 Western % ER deg vs Fv | MCF7 Western % ER deg vs Fv |
|---|---|---|
| 5 | 74 | 69 |
| 6 | 87 | 77 |
| 7 | 95 | 100 |
| 8 | 86 | 80 |
| 9 | 81 | 97 |
| 10 | 66 | 87 |
| 49 | 77 | 98 |
| 51 | 82 | 97 |

Human Hepatocyte Assay

The metabolic stability of compounds in human hepatocytes was assessed using the following protocol:

1. Prepare 10 mM stock solutions of compound and control compounds in appropriate solvent (DMSO). Place incubation medium (L-15Medium) in a 37° C. water bath, and allow warming for at least 15 minutes prior to use.
2. Add 80 μL of acetonitrile to each well of the 96-well deep well plate (quenching plate).
3. In a new 96-well plate, dilute the 10 mM test compounds and the control compounds to 100 μM by combining 198 μL of acetonitrile and 2 μL of 10 mM stock.
4. Remove a vial of cryopreserved (less than −150° C.) human hepatocytes (LiverPool™ 10 Donor Human hepatocytes obtained from Celsis IVT. Chicago, Ill. (Product No. S01205)) from storage, ensuring that vials remain at cryogenic temperatures until thawing process ensues. As quickly as possible, thaw the cells by placing the vial in a 37° C. water bath and gently shaking the vials. Vials should remain in water bath until all ice crystals have dissolved and are no longer visible. After thawing is completed, spray vial with 70% ethanol, transfer the vial to a bio-safety cabinet.
5. Open the vial and pour the contents into the 50 mL conical tube containing thawing medium. Place the 50 mL conical tube into a centrifuge and spin at 100 g for 10 minutes. Upon completion of spin, aspirate thawing medium and resuspend hepatocytes in enough incubation medium to yield ~1.5×10$^6$ cells/mL.
6. Using Cellometer® Vision, count cells and determine the viable cell density. Cells with poor viability (<80% viability) are not acceptable for use. Dilute cells with incubation medium to a working cell density of 1.0×10$^6$ viable cells/mL.
7. Transfer 247.5 μL of hepatocytes into each well of a 96-well cell culture plate. Place the plate on Eppendorf Thermomixer Comfort plate shaker to allow the hepatocytes to warm for 10 minutes.
8. Add 2.5 μL of 100 μM test compound or control compounds into an incubation well containing cells, mix to achieve a homogenous suspension at 0.5 min, which when achieved, will define the 0.5 min time point. At the 0.5 min time, transfer 20 μL incubated mixture to wells in a "Quenching plate" followed by vortexing.
9. Incubate the plate at 37° C. at 900 rpm on an Eppendorf Thermomixer Comfort plate shaker. At 5, 15, 30, 45, 60, 80, 100 and 120 min, mix the incubation system and transfer samples of 20 μL incubated mixture at each time point to wells in a separate "Quenching plate" followed by vortexing.
10. Centrifuge the quenching plates for 20 minutes at 4,000 rpm. 4 different compounds are pooled into one cassette and used for LC/MS/MS analysis.

All calculations are carried out using Microsoft Excel. Peak areas are determined from extracted ion chromatograms. In vitro intrinsic clearance (in vitro $Cl_{int}$, in μL/min/10$^6$ cells) of parent compound is determined by regression analysis of the Ln percent parent disappearance vs. time curve. The in vitro intrinsic clearance (in vitro $Cl_{int}$, in μL/min/10$^6$ cells) is determined from the slope value using the following equation and is shown in Table C:

in vitro $Cl_{int}$=kV/N
V=incubation volume (0.25 mL);
N=number of hepatocytes per well (0.25×10$^6$ cells).

TABLE C

| Example | $Cl_{int}$ (μL/min/10$^6$ cells) |
|---|---|
| 1 | 8 |
| 2 | 8 |
| 3 | 16 |
| 4 | 10 |
| 5 | 12 |
| 6 | 7 |
| 8 | 8 |
| 9 | 3 |
| 28 | 8 |
| 29 | 12 |
| 30 | 13 |
| 31 | 38 |
| 32 | 29 |
| 33 | 9 |
| 38 | 15 |
| 40 | 8 |
| 47 | 8 |
| 49 | 3 |
| 51 | 5 |

Physical Properties
logD

The lipophilicity of a drug is an important physical property which may influence many biological and metabolic properties of a compound. The distribution coefficient between 1-octanol and aqueous buffer, Log DO/W, at pH 7.4, is the most commonly used measurement of the lipophilicity of a compound. The current method for measurement of Log DO/W is based on the traditional shake flask technique, but with the modification of measuring compounds in mixtures of ten at a time using UPLC with quantitative mass spectrometry (MS) as a method to measure the relative octanol and aqueous concentrations. The maximum capacity is 379 project compounds (48 pools with 10 compounds incl. three QC compounds) per experiment.

2 quality control (QC) samples, Cyclobenzaprine with moderate Log D and Nicardipine high Log D is used in all pools to ensure good quality. An additional QC sample Caffeine, with low Log D, are used and randomly placed in all runs. The method has been thoroughly validated against the previous shake flask methodologies.

Solubility

The thermodynamic solubility of a research compound is measured under standard conditions. It is a shake-flask approach that uses 10 mM DMSO solutions which are supplied from the Compound Managements liquid store and is a high throughput method. The dried compounds are equilibrated in an aqueous phosphate buffer (pH 7.4) for 24 hours at 25° C., the portion with the dissolved compound is then separated from the remains. The solutions are analyzed and quantified using UPLC/MS/MS, QC-samples are incorporated in each assay-run to ensure the quality of the assay.

Human Plasma Protein Binding

The automated equilibrium dialysis assay in human plasma uses the RED (Rapid Equilibrium Dialysis) Device and sample handling. The assay generally runs over two to three days including delivery of results. After dialysis for 18 hours, plasma and buffer samples are prepared for analysis by liquid chromatography and mass spectrometry. Samples are generally tested in singlicates and quantified by LC/MSMS by using a 7-point calibration curve in plasma. The compounds are pooled together in plasma pools up to 10 compounds. Three reference compounds are used in each run, Propranolol, Metoprolol and Warfarin. Warfarin is used as a control in each pool and Propranolol and Metoprolol are placed randomly in each run. An in-house Excel macro is used for preparation of files for the robot and the mass spectrometer and also used for the calculations of fraction unbound (fu %) in plasma.

Table D shows the data for log D, solubility and plasma protein binding generated for selected Examples (the data below may be a result from a single experiment or an average of two or more experiments):

TABLE D

| Example | LogD pH 7.4 | Solubility (μM) | Human plasma protein binding (% free) |
| --- | --- | --- | --- |
| 5 | 3.5 | 263 | 6.2 |
| 6 | 2.8 | 957 | 21 |
| 7 | 3.4 | 364 | 11 |
| 8 | 2.6 | >1000 | 34 |
| 9 | 2.4 | >1000 | 52 |
| 10 | 2.4 | 811 | 27 |
| 49 | 3.0 | >1000 | 23 |
| 50 | 2.8 | 1000 | 20 |
| 51 | 2.4 | 974 | 49 |

According to a further aspect of the specification there is provided a pharmaceutical composition, which comprises a compound of the Formula (I), (IA), (IB), (IC), (ID) or (IE), or a pharmaceutically acceptable salt thereof, as defined hereinbefore in association with a pharmaceutically acceptable excipient.

Suitable pharmaceutically acceptable excipients for a tablet formulation include, for example, inert diluents, granulating and disintegrating agents, binding agents, lubricating agents, preservative agents and antioxidants. A further suitable pharmaceutically acceptable excipient may be a chelating agent. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may alternatively be in the form of hard gelatin capsules in which the active ingredient is mixed with an inert solid diluent, or as soft gelatin capsules in which the active ingredient is mixed with water or an oil.

Aqueous suspensions generally contain the active ingredient in finely powdered form together with one or more suspending agents, dispersing or wetting agents. The aqueous suspensions may also contain one or more preservatives, anti-oxidants, colouring agents, flavouring agents, and/or sweetening agents.

Oily suspensions may be formulated by suspending the active ingredient in a vegetable oil or in a mineral oil. The oily suspensions may also contain a thickening agent. Sweetening agents such as those set out above, and flavouring agents may be added to provide a palatable oral preparation. These compositions may be preserved by the addition of an anti-oxidant.

Dispersible powders and granules suitable for preparation of an aqueous suspension by the addition of water generally contain the active ingredient together with a dispersing or wetting agent, suspending agent and one or more preservatives. Additional excipients such as sweetening, flavouring and colouring agents, may also be present.

The pharmaceutical compositions of the specification may also be in the form of oil-in-water emulsions. The oily phase may be a vegetable oil or a mineral oil or a mixture of any of these. The emulsions may also contain sweetening, flavouring and preservative agents.

Syrups and elixirs may be formulated with sweetening agents, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent system.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient. Dry powder inhalers may also be suitable.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, oral administration to humans will generally require, for example, from 1 mg to 2 g of active agent (more suitably from 100 mg to 2 g, for example from 250 mg to 1.8 g, such as from 500 mg to 1.8 g, particularly from 500 mg to 1.5 g, conveniently from 500 mg to 1 g) to be administered compounded with an appropriate and convenient amount of excipients which may vary from about 3 to about 98 percent by weight of the total composition. It will be understood that, if a large dosage is required, multiple dosage forms may be required, for example two or more tablets or capsules, with the dose of active ingredient divided conveniently between them. Typically, unit dosage forms will contain about 10 mg to 0.5 g of a compound of this specification, although a unit dosage form may contain up to 1 g. Conveniently, a single solid dosage form may contain between 1 and 300 mg of active ingredient.

The size of the dose for therapeutic or prophylactic purposes of compounds of the present specification will naturally vary according to the nature and severity of the disease state, the age and sex of the animal or patient and the route of administration, according to well-known principles of medicine.

In using compounds of the present specification for therapeutic or prophylactic purposes it will generally be administered so that a daily dose in the range, for example, 1 mg/kg to 100 mg/kg body weight is received, given if required in divided doses. In general, lower doses will be administered when a parenteral route is employed. Thus, for example, for intravenous administration, a dose in the range, for example, 1 mg/kg to 25 mg/kg body weight will generally be used. Similarly, for administration by inhalation, a dose in the range, for example, 1 mg/kg to 25 mg/kg body weight will be used. Oral administration is however preferred, particularly in tablet form.

In one aspect of the specification, compounds of the present specification or pharmaceutically acceptable salts thereof, are administered as tablets comprising 10 mg to 100 mg of the compound of Formula (I), (IA), (IB), (IC), (ID) or (IE) (or a pharmaceutically acceptable salt thereof), wherein one or more tablets are administered as required to achieve the desired dose.

As stated above, it is known that signalling through ERα causes tumourigenesis by one or more of the effects of mediating proliferation of cancer and other cells, mediating angiogenic events and mediating the motility, migration and invasiveness of cancer cells. We have found that the compounds of the present specification possess potent anti-tumour activity which it is believed is obtained by way of antagonism and down-regulation of ERα that is involved in the signal transduction steps which lead to the proliferation and survival of tumour cells and the invasiveness and migratory ability of metastasising tumour cells.

Accordingly, the compounds of the present specification may be of value as anti-tumour agents, in particular as selective inhibitors of the proliferation, survival, motility, dissemination and invasiveness of mammalian cancer cells leading to inhibition of tumour growth and survival and to inhibition of metastatic tumour growth. Particularly, the compounds of the present specification may be of value as anti-proliferative and anti-invasive agents in the containment and/or treatment of solid tumour disease. Particularly, the compounds of the present specification may be useful in the prevention or treatment of those tumours which are sensitive to inhibition of ERα and that are involved in the signal transduction steps which lead to the proliferation and survival of tumour cells and the migratory ability and invasiveness of metastasising tumour cells. Further, the compounds of the present specification may be useful in the prevention or treatment of those tumours which are mediated alone or in part by antagonism and down-regulation of ERα, i.e. the compounds may be used to produce an ERα inhibitory effect in a warm-blooded animal in need of such treatment.

According to a further aspect of the specification there is provided a compound of the Formula (I), (IA), (IB), (IC), (ID) or (IE), or a pharmaceutically acceptable salt thereof, as defined hereinbefore for use as a medicament in a warm-blooded animal such as man.

According to a further aspect of the specification, there is provided a compound of the Formula (I), (IA), (IB), (IC), (ID) or (IE), or a pharmaceutically acceptable salt thereof, as defined hereinbefore for use in the production of an anti-proliferative effect in a warm-blooded animal such as man.

According to a further aspect of the specification there is provided a compound of the Formula (I), (IA), (IB), (IC), (ID) or (IE), or a pharmaceutically acceptable salt thereof, as defined hereinbefore for use in a warm-blooded animal such as man as an anti-invasive agent in the containment and/or treatment of solid tumour disease.

According to a further aspect of the specification, there is provided the use of a compound of the Formula (I), (IA), (IB), (IC), (ID) or (IE), or a pharmaceutically acceptable salt thereof, as defined hereinbefore, for the production of an anti-proliferative effect in a warm-blooded animal such as man.

According to a further aspect of the specification there is provided the use of a compound of the Formula (I), (IA), (IB), (IC), (ID) or (IE), or a pharmaceutically acceptable salt thereof, as defined hereinbefore, in the manufacture of a medicament for use in the production of an anti-proliferative effect in a warm-blooded animal such as man.

According to a further aspect of the specification there is provided the use of a compound of the Formula (I), (IA), (IB), (IC), (ID) or (IE), or a pharmaceutically acceptable salt thereof, as defined hereinbefore, in the manufacture of a medicament for use in a warm-blooded animal such as man as an anti-invasive agent in the containment and/or treatment of solid tumour disease.

According to a further aspect of the specification there is provided a method for producing an anti-proliferative effect in a warm-blooded animal, such as man, in need of such treatment which comprises administering to said animal an effective amount of a compound of the Formula (I), (IA), (IB), (IC), (ID) or (IE), or a pharmaceutically acceptable salt thereof, as defined hereinbefore.

According to a further aspect of the specification there is provided a method for producing an anti-invasive effect by the containment and/or treatment of solid tumour disease in a warm-blooded animal, such as man, in need of such treatment which comprises administering to said animal an effective amount of a compound of the Formula (I), (IA), (IB), (IC), (ID) or (IE), or a pharmaceutically acceptable salt thereof, as defined hereinbefore.

According to a further aspect of the specification, there is provided a compound of the Formula (I), (IA), (IB), (IC), (ID) or (IE), or a pharmaceutically acceptable salt thereof, as defined hereinbefore, for use in the prevention or treatment of cancer in a warm-blooded animal such as man.

According to a further aspect of the specification there is provided the use of a compound of the Formula (I), (IA), (IB), (IC), (ID) or (IE), or a pharmaceutically acceptable salt thereof, as defined hereinbefore in the manufacture of a medicament for use in the prevention or treatment of cancer in a warm-blooded animal such as man.

According to a further aspect of the specification there is provided a method for the prevention or treatment of cancer in a warm-blooded animal, such as man, in need of such treatment which comprises administering to said animal an effective amount of a compound of the Formula (I), (IA), (IB), (IC), (ID) or (IE), or a pharmaceutically acceptable salt thereof, as defined hereinbefore.

According to a further aspect of the specification, there is provided a compound of the Formula (I), (IA), (IB), (IC), (ID) or (IE), or a pharmaceutically acceptable salt thereof, as defined hereinbefore for use in the prevention or treatment of solid tumour disease in a warm-blooded animal such as man.

According to a further aspect of the specification there is provided the use of a compound of the Formula (I), (IA), (IB), (IC), (ID) or (IE), or a pharmaceutically acceptable salt thereof, as defined hereinbefore, in the manufacture of a medicament for use in the prevention or treatment of solid tumour disease in a warm-blooded animal such as man.

According to a further aspect of the specification there is provided a method for the prevention or treatment of solid tumour disease in a warm-blooded animal, such as man, in need of such treatment which comprises administering to said animal an effective amount of a compound of the Formula (I), (IA), (IB), (IC), (ID) or (IE), or a pharmaceutically acceptable salt thereof, as defined hereinbefore.

According to a further aspect of the specification there is provided a compound of the Formula (I), (IA), (IB), (IC), (ID) or (IE), or a pharmaceutically acceptable salt thereof, as defined hereinbefore, for use in the prevention or treatment of those tumours which are sensitive to inhibition of ERα that are involved in the signal transduction steps which lead to the proliferation, survival, invasiveness and migratory ability of tumour cells.

According to a further aspect of the specification there is provided the use of a compound of the Formula (I), (IA), (IB), (IC), (ID) or (IE), or a pharmaceutically acceptable salt thereof, as defined hereinbefore, in the manufacture of a medicament for use in the prevention or treatment of those tumours which are sensitive to inhibition of ERα that are involved in the signal transduction steps which lead to the proliferation, survival, invasiveness and migratory ability of tumour cells.

According to a further aspect of the specification there is provided a method for the prevention or treatment of those tumours which are sensitive to inhibition of ERα that are involved in the signal transduction steps which lead to the proliferation, survival, invasiveness and migratory ability of tumour cells which comprises administering to said animal an effective amount of a compound of the Formula (I), (IA), (IB), (IC), (ID) or (IE), or a pharmaceutically acceptable salt thereof, as defined hereinbefore.

According to a further aspect of the specification there is provided a compound of the Formula (I), (IA), (IB), (IC), (ID) or (IE), or a pharmaceutically acceptable salt thereof, as defined hereinbefore for use in providing an inhibitory effect on ERα.

According to a further aspect of the specification there is provided the use of a compound of the Formula (I), (IA), (IB), (IC), (ID) or (IE), or a pharmaceutically acceptable salt thereof, as defined hereinbefore in the manufacture of a medicament for use in providing an inhibitory effect on ERα.

According to a further aspect of the specification there is also provided a method for providing an inhibitory effect on ERα which comprises administering an effective amount of a compound of the Formula (I), (IA), (IB), (IC), (ID) or (IE), or a pharmaceutically acceptable salt thereof, as defined hereinbefore.

According to a further aspect of the specification there is provided a compound of the Formula (I), (IA), (IB), (IC), (ID) or (IE), or a pharmaceutically acceptable salt thereof, as defined hereinbefore, for use in providing a selective inhibitory effect on ERα.

According to a further aspect of the specification there is provided the use of a compound of the Formula (I), (IA), (IB), (IC), (ID) or (IE), or a pharmaceutically acceptable salt thereof, as defined hereinbefore, in the manufacture of a medicament for use in providing a selective inhibitory effect on ERα.

According to a further aspect of the specification there is also provided a method for providing a selective inhibitory effect on ERα which comprises administering an effective amount of a compound of the Formula (I), (IA), (IB), (IC), (ID) or (IE), or a pharmaceutically acceptable salt thereof, as defined hereinbefore.

Described herein are compounds that can bind to ERα ligand binding domain and are selective estrogen receptor degraders. In biochemical and cell based assays the compounds of the present specification are shown to be potent estrogen receptor binders and reduce cellular levels of ERα and may therefore be useful in the treatment of estrogen sensitive diseases or conditions (including diseases that have developed resistance to endocrine therapies), i.e. for use in the treatment of cancer of the breast and gynaecological cancers (including endometrial, ovarian and cervical) and cancers expressing ERα mutated proteins which may be de novo mutations or have arisen as a result of treatment with a prior endocrine therapy such as an aromatase inhibitor.

According to a further aspect of the specification there is provided a compound of the Formula (I), (IA), (IB), (IC), (ID) or (IE), or a pharmaceutically acceptable salt thereof, as defined hereinbefore, for use in the treatment of breast or gynaecological cancers.

According to a further aspect of the specification there is provided a compound of the Formula (I), (IA), (IB), (IC), (ID) or (IE), or a pharmaceutically acceptable salt thereof, as defined hereinbefore, for use in the treatment of cancer of the breast, endometrium, ovary or cervix.

According to a further aspect of the specification there is provided a compound of the Formula (I), (IA), (IB), (IC), (ID) or (IE), or a pharmaceutically acceptable salt thereof, as defined hereinbefore, for use in the treatment of cancer of the breast.

According to a further aspect of the specification there is provided a compound of the Formula (I), (IA), (IB), (IC), (ID) or (IE), or a pharmaceutically acceptable salt thereof, as defined hereinbefore, for use in the treatment of cancer of the breast, wherein the cancer has developed resistance to one or more other endocrine therapies.

According to a further aspect of the specification there is provided a method for treating breast or gynaecological cancers, which comprises administering an effective amount of a compound of the Formula (I), (IA), (IB), (IC), (ID) or (IE), or a pharmaceutically acceptable salt thereof, as defined hereinbefore.

According to a further aspect of the specification there is provided a method for treating cancer of the breast, endometrium, ovary or cervix, which comprises administering an effective amount of a compound of the Formula (I), (IA), (IB), (IC), (ID) or (IE), or a pharmaceutically acceptable salt thereof, as defined hereinbefore.

According to a further aspect of the specification there is provided a method for treating breast cancer, which comprises administering an effective amount of a compound of the Formula (I), (IA), (IB), (IC), (ID) or (IE), or a pharmaceutically acceptable salt thereof, as defined hereinbefore.

According to a further aspect of the specification there is provided a method for treating breast cancer, wherein the cancer has developed resistance to one or more other endocrine therapies, which comprises administering an effective amount of a compound of the Formula (I), (IA), (IB), (IC), (ID) or (IE), or a pharmaceutically acceptable salt thereof, as defined hereinbefore.

According to a further aspect of the specification there is provided the use of a compound of the Formula (I), (IA), (IB), (IC), (ID) or (IE), or a pharmaceutically acceptable salt thereof, as defined hereinbefore, in the manufacture of a medicament for use in the treatment of breast or gynaecological cancers.

According to a further aspect of the specification there is provided the use of a compound of the Formula (I), (IA), (IB), (IC), (ID) or (IE), or a pharmaceutically acceptable salt thereof, as defined hereinbefore, in the manufacture of a medicament for use in the treatment of cancer of the breast, endometrium, ovary or cervix.

According to a further aspect of the specification there is provided the use of a compound of the Formula (I), (IA), (IB), (IC), (ID) or (IE), or a pharmaceutically acceptable salt thereof, as defined hereinbefore, in the manufacture of a medicament for use in the treatment of breast cancer.

According to a further aspect of the specification there is provided the use of a compound of the Formula (I), (IA), (IB), (IC), (ID) or (IE), or a pharmaceutically acceptable salt thereof, as defined hereinbefore, in the manufacture of a medicament for use in the treatment of breast cancer, wherein the cancer has developed resistance to one or more other endocrine therapies.

In one feature of the specification, the cancer to be treated is breast cancer. In a further aspect of this feature, the breast cancer is Estrogen Receptor+ve (ER+ve). In one embodiment of this aspect, the compound of Formula (I), (IA), (IB), (IC), (ID) or (IE) is dosed in combination with another anticancer agent, such as an anti-hormonal agent as defined herein.

According to a further aspect of the specification there is provided a compound of the Formula (I), (IA), (IB), (IC), (ID) or (IE), or a pharmaceutically acceptable salt thereof, as defined hereinbefore, for use in the treatment of ER+ve breast cancer.

According to a further aspect of the specification there is provided a method for treating ER+ve breast cancer, which comprises administering an effective amount of a compound of the Formula (I), (IA), (IB), (IC), (ID) or (IE), or a pharmaceutically acceptable salt thereof, as defined hereinbefore.

According to a further aspect of the specification there is provided the use of a compound of the Formula (I), (IA), (IB), (IC), (ID) or (IE), or a pharmaceutically acceptable salt thereof, as defined herein before in the manufacture of a medicament for use in the treatment of ER+ve breast cancer.

As stated hereinbefore, the in-vivo effects of a compound of the Formula (I), (IA), (IB), (IC), (ID) or (IE) may be exerted in part by one or more metabolites that are formed within the human or animal body after administration of a compound of the Formula (I), (IA), (IB), (IC), (ID) or (IE).

The present specification therefore also contemplates a method for inhibiting ER-α in a patient, comprising administering to a patient an amount of a compound of Formula (I), (IA), (IB), (IC), (ID) or (IE), or a pharmaceutically acceptable salt thereof, effective in inhibiting ER-α in the patient.

The present specification therefore also contemplates a method for inhibiting ER-α in a patient, comprising administering to a patient an amount of a compound of Formula (I), (IA), (IB), (IC), (ID) or (IE), or a pharmaceutically acceptable salt thereof, effective in inhibiting ER-α in the patient.

The anti-cancer treatment defined herein may be applied as a sole therapy or may involve, in addition to the compounds of the specification, conventional surgery or radiotherapy or chemotherapy. Such chemotherapy may include one or more of the following categories of anti-tumour agents:

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) antihormonal agents such as antioestrogens (for example tamoxifen, fulvestrant, toremifene, raloxifene, droloxifene and iodoxyfene), progestogens (for example megestrol acetate), aromatase inhibitors (for example as anastrozole, letrozole, vorazole and exemestane);

(iii) inhibitors of growth factor function and their downstream signalling pathways: included are Ab modulators of any growth factor or growth factor receptor targets, reviewed by Stern et al. *Critical Reviews in Oncology/Haematology*, 2005, 54, pp11-29); also included are small molecule inhibitors of such targets, for example kinase inhibitors—examples include the anti-erbB2 antibody trastuzumab [Herceptin™], the anti-EGFR antibody panitumumab, the anti-EGFR antibody cetuximab [Erbitux, C225] and tyrosine kinase inhibitors including inhibitors of the erbB receptor family, such as epidermal growth factor family receptor (EGFR/erbB1) tyrosine kinase inhibitors such as gefitinib or erlotinib, erbB2 tyrosine kinase inhibitors such as lapatinib, and mixed erb1/2 inhibitors such as afatanib; similar strategies are available for other classes of growth factors and their receptors, for example inhibitors of the hepatocyte growth factor family or their receptors including c-met and ron; inhibitors of the insulin and insulin growth factor family or their receptors (IGFR, IR) inhibitors of the platelet-derived growth factor family or their receptors (PDGFR), and inhibitors of signalling mediated by other receptor tyrosine kinases such as c-kit, AnLK, and CSF-1R; also included are modulators which target signalling proteins in the PI3-kinase signalling pathway, for example, inhibitors of PI3-kinase isoforms such as PI3K-α/β/γ and ser/thr kinases such as AKT, mTOR (such as AZD2014), PDK, SGK, PI4K or PIP5K; also included are inhibitors of serine/threonine kinases not listed above, for example raf inhibitors such as vemurafenib, MEK inhibitors such as selumetinib (AZD6244), Abl inhibitors such as imatinib or nilotinib, Btk inhibitors such as ibrutinib, Syk inhibitors such as fostamatinib, aurora kinase inhibitors (for example AZD1152), inhibitors of other ser/thr kinases such as JAKs, STATs and IRAK4, and cyclin dependent kinase inhibitors for example inhibitors of CDK1, CDK7, CDK9 and CDK4/6 such as palbociclib;

iv) modulators of DNA damage signalling pathways, for example PARP inhibitors (e.g. Olaparib), ATR inhibitors or ATM inhibitors;
v) modulators of apoptotic and cell death pathways such as Bcl family modulators (e.g. ABT-263/Navitoclax, ABT-199);
(vi) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as sorafenib, axitinib, pazopanib, sunitinib and vandetanib (and compounds that work by other mechanisms (for example linomide, inhibitors of integrin αvβ3 function and angiostatin)];
(vii) vascular damaging agents, such as Combretastatin A4;
(viii) anti-invasion agents, for example c-Src kinase family inhibitors like (dasatinib, *J. Med. Chem.*, 2004, 47, 6658-6661) and bosutinib (SKI-606), and metalloproteinase inhibitors like marimastat, inhibitors of urokinase plasminogen activator receptor function or antibodies to Heparanase];
(ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies. Specific examples include monoclonal antibodies targeting PD-1 (e.g. BMS-936558) or CTLA4 (e.g. *ipilimumab* and tremelimumab);
(x) Antisense or RNAi based therapies, for example those which are directed to the targets listed.
(xi) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy.

Accordingly, in one embodiment there is provided a compound of Formula (I), (IA), (IB), (IC), (ID) or (IE), or a pharmaceutically acceptable salt thereof, and an additional anti-tumour substance for the conjoint treatment of cancer.

According to this aspect of the specification there is provided a combination suitable for use in the treatment of cancer comprising a compound of the Formula (I), (IA), (IB), (IC), (ID) or (IE) or a pharmaceutically acceptable salt thereof and another anti-tumour agent, in particular any one of the anti tumour agents listed under (i)-(xi) above. In particular, the anti-tumour agent listed under (i)-(xi) above is the standard of care for the specific cancer to be treated; the person skilled in the art will understand the meaning of "standard of care".

Therefore in a further aspect of the specification there is provided a compound of the Formula (I), (IA), (IB), (IC), (ID) or (IE), or a pharmaceutically acceptable salt thereof, in combination with another anti-tumour agent, in particular an anti-tumour agent selected from one listed under (i)-(xi) herein above.

In a further aspect of the specification there is provided a compound of the Formula (I), (IA), (IB), (IC), (ID) or (IE), or a pharmaceutically acceptable salt thereof, in combination with another anti-tumour agent, in particular an anti-tumour agent selected from one listed under (i) above.

In a further aspect of the specification there is provided a compound of the Formula (I), (IA), (IB), (IC), (ID) or (IE), or a pharmaceutically acceptable salt thereof, and any one of the anti-tumour agents listed under (i) above.

In a further aspect of the specification there is provided a combination suitable for use in the treatment of cancer comprising a compound of the Formula (I), (IA), (IB), (IC), (ID) or (IE), or a pharmaceutically acceptable salt thereof, and a taxoid, such as for example taxol or taxotere, conveniently taxotere.

In a further aspect of the specification there is provided a compound of the Formula (I), (IA), (IB), (IC), (ID) or (IE), or a pharmaceutically acceptable salt thereof, in combination with another anti-tumour agent, in particular an anti-tumour agent selected from one listed under (ii) herein above.

In a further aspect of the specification there is provided a combination suitable for use in the treatment of cancer comprising a compound of the Formula (I), (IA), (IB), (IC), (ID) or (IE), or a pharmaceutically acceptable salt thereof, and any one of the antihormonal agents listed under (ii) above, for example any one of the anti-oestrogens listed in (ii) above, or for example an aromatase inhibitor listed in (ii) above.

In a further aspect of the specification there is provided a combination suitable for use in the treatment of cancer comprising a compound of the Formula (I), (IA), (IB), (IC), (ID) or (IE), or a pharmaceutically acceptable salt thereof, and an mTOR inhibitor, such as AZD2014 (see for example WO2008/023161).

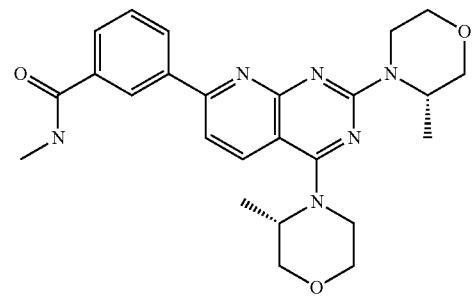

AZD2014

In a further aspect of the specification there is provided a combination suitable for use in the treatment of cancer comprising a compound of the Formula (I), (IA), (IB), (IC), (ID) or (IE), or a pharmaceutically acceptable salt thereof, and a PI3Kα-inhibitor, such as the compound 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one, or a pharmaceutically-acceptable salt thereof.

In a further aspect of the specification there is provided a combination suitable for use in the treatment of cancer comprising a compound of the Formula (I), (IA), (IB), (IC), (ID) or (IE), or a pharmaceutically acceptable salt thereof, and palbociclib.

In one aspect the above combination of a compound of the Formula (I), (IA), (IB), (IC), (ID) or (IE), or a pharmaceutically acceptable salt thereof, with an anti-tumour agent listed in (ii) above, or an mTOR inhibitor (such as AZD2014), or a PI3K-α inhibitor (such as the compound 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one) or palbociclib, is suitable for use in the treatment of breast or gynaecological cancers, such as cancer of the breast, endometrium, ovary or cervix, particularly breast cancer, such as ER+ve breast cancer.

Herein, where the term "combination" is used it is to be understood that this refers to simultaneous, separate or sequential administration. In one aspect of the specification "combination" refers to simultaneous administration. In another aspect of the specification "combination" refers to separate administration. In a further aspect of the specification "combination" refers to sequential administration. Where the administration is sequential or separate, the delay in administering the second component should not be such as to lose the beneficial effect of the combination. Where a combination of two or more components is administered separately or sequential, it will be understood that the dosage regime for each component may be different to and independent of the other components. Conveniently, the compounds of the present specification are dosed once daily.

According to a further aspect of the specification there is provided a pharmaceutical composition which comprises a compound of Formula (I), (IA), (IB), (IC), (ID) or (IE) or a pharmaceutically acceptable salt thereof in combination with an anti-tumour agent selected from one listed under (i)-(xi) herein above, in association with a pharmaceutically acceptable excipient.

According to a further aspect of the specification there is provided a pharmaceutical composition which comprises a compound of Formula (I), (IA), (IB), (IC), (ID) or (IE) or a pharmaceutically acceptable salt thereof in combination with any one of antihormonal agents listed under (ii) above, for example any one of the anti-oestrogens listed in (ii) above, or for example an aromatase inhibitor listed in (ii) above in association with a pharmaceutically acceptable excipient.

In a further aspect of the specification there is provided a pharmaceutical composition comprising a compound of the Formula (I), (IA), (IB), (IC), (ID) or (IE), or a pharmaceutically acceptable salt thereof, and an mTOR inhibitor, such as AZD2014 (see for example WO2008/023161); in association with a pharmaceutically acceptable excipient.

In a further aspect of the specification there is provided a pharmaceutical composition comprising a compound of the Formula (I), (IA), (IB), (IC), (ID) or (IE), or a pharmaceutically acceptable salt thereof, and a PI3Kα-inhibitor, such as the compound 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one, in association with a pharmaceutically acceptable excipient.

In a further aspect of the specification there is provided a pharmaceutical composition comprising a compound of the Formula (I), (IA), (IB), (IC), (ID) or (IE), or a pharmaceutically acceptable salt thereof, and palbociclib in association with a pharmaceutically acceptable excipient.

According to a further aspect of the specification there is provided a pharmaceutical composition which comprises a compound of the Formula (I), (IA), (IB), (IC), (ID) or (IE), or a pharmaceutically acceptable salt thereof, in combination with an anti-tumour agent selected from one listed under (i)-(xi) herein above, in association with a pharmaceutically acceptable excipient for use in treating cancer.

According to a further aspect of the specification there is provided a pharmaceutical composition which comprises a compound of the Formula (I), (IA), (IB), (IC), (ID) or (IE), or a pharmaceutically acceptable salt thereof, in combination with any one of antihormonal agents listed under (ii) above, for example any one of the anti-oestrogens listed in (ii) above, or for example an aromatase inhibitor listed in (ii) above in association with a pharmaceutically acceptable excipient for use in treating cancer.

In a further aspect of the specification there is provided a pharmaceutical composition comprising a compound of the Formula (I), (IA), (IB), (IC), (ID) or (IE), or a pharmaceutically acceptable salt thereof, and an mTOR inhibitor, such as AZD2014 (see for example WO2008/023161); in association with a pharmaceutically acceptable excipient for use in treating cancer.

In a further aspect of the specification there is provided a pharmaceutical composition comprising a compound of the Formula (I), (IA), (IB), (IC), (ID) or (IE), or a pharmaceutically acceptable salt thereof, and a PI3Kα-inhibitor, such as the compound 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one, in association with a pharmaceutically acceptable excipient for use in treating cancer.

In a further aspect of the specification there is provided a pharmaceutical composition comprising a compound of the Formula (I), (IA), (IB), (IC), (ID) or (IE), or a pharmaceutically acceptable salt thereof, and palbociclib in association with a pharmaceutically acceptable excipient for use in treating cancer.

In one aspect the above pharmaceutical compositions of a compound of the Formula (I), (IA), (IB), (IC), (ID) or (IE), or a pharmaceutically acceptable salt thereof, with an anti-tumour agent listed in (ii) above, or an mTOR inhibitor (such as AZD2014), or a PI3K-α inhibitor (such as the compound 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one) or palbociclib, is suitable for use in the treatment of breast or gynaecological cancers, such as cancer of the breast, endometrium, ovary or cervix, particularly breast cancer, such as ER+ve breast cancer.

According to another feature of the specification there is provided the use of a compound of the Formula (I), (IA), (IB), (IC), (ID) or (IE) or a pharmaceutically acceptable salt thereof in combination with an anti-tumour agent selected from one listed under (i)-(xi) herein above, in the manufacture of a medicament for use in the treatment of cancer in a warm-blooded animal, such as man.

According to a further aspect of the specification there is provided the use of a compound of Formula (I), (IA), (IB), (IC), (ID) or (IE) or a pharmaceutically acceptable salt thereof in combination with any one of antihormonal agents listed under (ii) above, for example any one of the anti-oestrogens listed in (ii) above, or for example an aromatase inhibitor listed in (ii) above in the manufacture of a medicament for use in the treatment of cancer in a warm-blooded animal, such as man.

In a further aspect of the specification there is provided the use of a compound of the Formula (I), (IA), (IB), (IC), (ID) or (IE), or a pharmaceutically acceptable salt thereof, in combination with an mTOR inhibitor, such as AZD2014 (see for example WO2008/023161); in the manufacture of a medicament for use in the treatment of cancer in a warm-blooded animal, such as man.

In a further aspect of the specification there is provided the use of a compound of the Formula (I), (IA), (IB), (IC), (ID) or (IE), or a pharmaceutically acceptable salt thereof, in combination with a PI3Kα-inhibitor, such as the compound 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-

3-hydroxypropan-1-one, in the manufacture of a medicament for use in the treatment of cancer in a warm-blooded animal, such as man.

In a further aspect of the specification there is provided the use a compound of the Formula (I), (IA), (IB), (IC), (ID) or (IE), or a pharmaceutically acceptable salt thereof, in combination with palbociclib in the manufacture of a medicament for use in the treatment of cancer in a warm-blooded animal, such as man.

In one aspect the above uses of a compound of the Formula (I), (IA), (IB), (IC), (ID) or (IE), or a pharmaceutically acceptable salt thereof, in combination with an anti-tumour agent listed in (ii) above, or an mTOR inhibitor (such as AZD2014), or a PI3K-α inhibitor (such as the compound 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one) or palbociclib, is suitable for use in the manufacture of a medicament for the treatment of breast or gynaecological cancers, such as cancer of the breast, endometrium, ovary or cervix, particularly breast cancer, such as ER+ve breast cancer.

Therefore in an additional feature of the specification, there is provided a method of treating cancer in a warm-blooded animal, such as man, in need of such treatment which comprises administering to said animal an effective amount of a compound of the Formula (I), (IA), (IB), (IC), (ID) or (IE), or a pharmaceutically acceptable salt thereof, in combination with an anti-tumour agent selected from one listed under (i)-(xi) herein above.

According to a further aspect of the specification there is provided a method of treating cancer in a warm-blooded animal, such as man, in need of such treatment which comprises administering to said animal an effective amount of a compound of Formula (I), (IA), (IB), (IC), (ID) or (IE) or a pharmaceutically acceptable salt thereof in combination with any one of antihormonal agents listed under (ii) above, for example any one of the anti-oestrogens listed in (ii) above, or for example an aromatase inhibitor listed in (ii) above.

In a further aspect of the specification there is provided a method of treating cancer in a warm-blooded animal, such as man, in need of such treatment which comprises administering to said animal an effective amount of a compound of the Formula (I), (IA), (IB), (IC), (ID) or (IE), or a pharmaceutically acceptable salt thereof, in combination with an mTOR inhibitor, such as AZD2014 (see for example WO2008/023161).

In a further aspect of the specification there provided a method of treating cancer in a warm-blooded animal, such as man, in need of such treatment which comprises administering to said animal an effective amount of a compound of the Formula (I), (IA), (IB), (IC), (ID) or (IE), or a pharmaceutically acceptable salt thereof, in combination with a PI3Kα-inhibitor, such as the compound 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one.

In a further aspect of the specification there is provided a method of treating cancer in a warm-blooded animal, such as man, in need of such treatment which comprises administering to said animal an effective amount of a compound of the Formula (I), (IA), (IB), (IC), (ID) or (IE), or a pharmaceutically acceptable salt thereof, in combination with palbociclib.

In one aspect the above combinations, pharmaceutical compositions, uses and methods of treating cancer, are methods for the treatment of breast or gynaecological cancers, such as cancer of the breast, endometrium, ovary or cervix, particularly breast cancer, such as ER+ve breast cancer.

According to a further aspect of the present specification there is provided a kit comprising a compound of Formula (I), (IA), (IB), (IC), (ID) or (IE) or a pharmaceutically acceptable salt thereof in combination with an anti-tumour agent selected from one listed under (i)-(xi) herein above.

According to a further aspect of the present specification there is provided a kit comprising a compound of Formula (I), (IA), (IB), (IC), (ID) or (IE) or a pharmaceutically acceptable salt thereof in combination with an anti-tumour agent selected from one listed under (i) or (ii) herein above.

According to a further aspect of the present specification there is provided a kit comprising:
a) a compound of Formula (I), (IA), (IB), (IC), (ID) or (IE) or a pharmaceutically acceptable salt thereof in a first unit dosage form;
b) an anti-tumour agent selected from one listed under (i)-(xi) herein above in a second unit dosage form; and
c) container means for containing said first and second dosage forms.

According to a further aspect of the present specification there is provided a kit comprising:
a) a compound of Formula (I), (IA), (IB), (IC), (ID) or (IE) or a pharmaceutically acceptable salt thereof in a first unit dosage form;
b) an anti-tumour agent selected from one listed under (i)-(ii) herein above in a second unit dosage form; and
c) container means for containing said first and second dosage forms.

According to a further aspect of the present specification there is provided a kit comprising:
a) a compound of the Formula (I), (IA), (IB), (IC), (ID) or (IE), or a pharmaceutically acceptable salt thereof, in a first unit dosage form;
b) an anti-tumour agent selected from an anti-tumour agent listed in (ii) above, an mTOR inhibitor (such as AZD2014), a PI3Kα-inhibitor, such as the compound 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one, and palbociclib, in a second unit dosage form; and
c) container means for containing said first and second dosage forms.

Combination therapy as described above may be added on top of standard of care therapy typically carried out according to its usual prescribing schedule.

Although the compounds of the Formula (I), (IA), (IB), (IC), (ID) or (IE) are primarily of value as therapeutic agents for use in warm-blooded animals (including man), they are also useful whenever it is required to inhibit ER-α. Thus, they are useful as pharmacological standards for use in the development of new biological tests and in the search for new pharmacological agents.

Personalised Healthcare

Another aspect of the present specification is based on identifying a link between the status of the gene encoding ERα and potential susceptibility to treatment with a compound of Formula (I), (IA), (IB), (IC), (ID) or (IE). In particular, ERα gene status may indicate that a patient is less likely to respond to exisiting hormone therapy (such as aromatase inhibitors), in part at least because some ERα mutations are though to arise as resistance mechanisms to existing treatments. A SERD, particularly a SERD which can be administered orally in potentially larger doses without excessive inconvenince, may then advantageously be used to treat patentients with ERα mutations who may be resistant to other therapies. This therefore provides opportunities, methods and tools for selecting patients for treatment with a compound of Formula (I), (IA), (IB), (IC), (ID) or (IE), particularly cancer patients. The present specification relates to patient selection tools and methods (including personalised medicine). The selection is based on whether the tumour cells to be treated possess wild-type or mutant ERα gene. The ERα gene status could therefore be used as a biomarker to indicate that selecting treatment with a SERD may be advantageous. For the avoidance of doubt, compounds of the Formula (I), (IA), (IB), (IC), (ID) or (IE) as described herein are thought to be similarly active against wild-type and mutant ERα genes, at least those mutations in ERα gene identified at the date of filing this application.

There is a clear need for biomarkers that will enrich for or select patients whose tumours will respond to treatment with a SERD, such as a compound of Formula (I), (IA), (IB), (IC), (ID) or (IE). Patient selection biomarkers that identify the patients most likely to respond to one agent over another are ideal in the treatment of cancer, since they reduce the unnecessary treatment of patients with non-responding tumours to the potential side effects of such agents.

A biomarker can be described as "a characteristic that is objectively measured and evaluated as an indicator of normal biologic processes, pathogenic processes, or pharmacologic responses to a therapeutic intervention". A biomarker is any identifiable and measurable indicator associated with a particular condition or disease where there is a correlation between the presence or level of the biomarker and some aspect of the condition or disease (including the presence of, the level or changing level of, the type of, the stage of, the susceptibility to the condition or disease, or the responsiveness to a drug used for treating the condition or disease). The correlation may be qualitative, quantitative, or both qualitative and quantitative. Typically a biomarker is a compound, compound fragment or group of compounds. Such compounds may be any compounds found in or produced by an organism, including proteins (and peptides), nucleic acids and other compounds.

Biomarkers may have a predictive power, and as such may be used to predict or detect the presence, level, type or stage of particular conditions or diseases (including the presence or level of particular microorganisms or toxins), the susceptibility (including genetic susceptibility) to particular conditions or diseases, or the response to particular treatments (including drug treatments). It is thought that biomarkers will play an increasingly important role in the future of drug discovery and development, by improving the efficiency of research and development programs. Biomarkers can be used as diagnostic agents, monitors of disease progression, monitors of treatment and predictors of clinical outcome. For example, various biomarker research projects are attempting to identify markers of specific cancers and of specific cardiovascular and immunological diseases. It is believed that the development of new validated biomarkers will lead both to significant reductions in healthcare and drug development costs and to significant improvements in treatment for a wide variety of diseases and conditions.

In order to optimally design clinical trials and to gain the most information from these trials, a biomarker may be required. The marker may be measurable in surrogate and tumour tissues. Ideally these markers will also correlate with efficacy and thus could ultimately be used for patient selection.

Thus, the technical problem underlying this aspect of the present specification is the identification of means for stratification of patients for treatment with a compound of Formula (I), (IA), (IB), (IC), (ID) or (IE). The technical problem is solved by provision of the embodiments characterized in the claims and/or description herein.

Tumours which contain wild type ERα are believed to be susceptible to treatment with a compound of Formula (I), (IA), (IB), (IC), (ID) or (IE), for example as a first-line treatment. Tumours may also respond to treatment with a compound of Formula (I), (IA), (IB), (IC), (ID) or (IE) as a second-line, third-line or subsequent therapy and this may be useful, in particular, where the tumours contain mutant ERα and may thus be resistant to existing therapies such as AIs. A higher dosage of a compound of Formula (I), (IA), (IB), (IC), (ID) or (IE) may be required in the resistant setting than in wild type tumours).

The specification provides a method of determining sensitivity of cells to a compound of Formula (I), (IA), (IB), (IC), (ID) or (IE). The method comprises determining the status of ERα gene in said cells. A cell is defined as sensitive to a compound of Formula (I), (IA), (IB), (IC), (ID) or (IE) if it inhibits the increase in cell number in a cell growth assay (either through inhibition of cell proliferation and/or through increased cell death). Methods of the specification are useful for predicting which cells are more likely to respond to a compound of Formula (I), (IA), (IB), (IC), (ID) or (IE) by growth inhibition.

A sample "representative of the tumour" can be the actual tumour sample isolated, or may be a sample that has been further processed, e.g. a sample of PCR amplified nucleic acid from the tumour sample.

Definitions:

In this Personalised Healthcare section:

"Allele" refers to a particular form of a genetic locus, distinguished from other forms by its particular nucleotide or amino acid sequence.

"Amplification reactions" are nucleic acid reactions which result in specific amplification of target nucleic acids over non-target nucleic acids. The polymerase chain reaction (PCR) is a well-known amplification reaction.

"Cancer" is used herein to refer to neoplastic growth arising from cellular transformation to a neoplastic phenotype. Such cellular transformation often involves genetic mutation.

"Gene" is a segment of DNA that contains all the information for the regulated biosynthesis of an RNA product, including a promoter, exons, introns, and other sequence elements which may be located within 5' or 3' flanking regions (not within the transcribed portions of the gene) that control expression.

"Gene status" refers to whether the gene is wild type or not (i.e. mutant).

"Label" refers to a composition capable of producing a detectable signal indicative of the presence of the target polynucleotide in an assay sample. Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical or chemical means.

"Non-synonymous variation" refers to a variation (variance) in or overlapping the coding sequence of a gene that result in the production of a distinct (altered) polypeptide sequence. These variations may or may not affect protein function and include missense variants (resulting in substitution of one amino acid for another), nonsense variants (resulting in a truncated polypeptide due to generation of a premature stop codon) and insertion/deletion variants.

"Synonymous variation" refers to a variation (variance) in the coding sequence of a gene that does not affect sequence of the encoded polypeptide. These variations may affect protein function indirectly (for example by altering expression of the gene), but, in the absence of evidence to the contrary, are generally assumed to be innocuous.

"Nucleic acid" refers to single stranded or double stranded DNA and RNA molecules including natural nucleic acids found in nature and/or modified, artificial nucleic acids having modified backbones or bases, as are known in the art.

"Primer" refers to a single stranded DNA oligonucleotide sequence capable of acting as a point of initiation for synthesis of a primer extension product which is complementary to the nucleic acid strand to be copied. The length and sequence of the primer must be such that they are able to prime the synthesis of extension products. A typical primer contains at least about 7 nucleotides in length of a sequence substantially complementary to the target sequence, but somewhat longer primers are preferred. Usually primers contain about 15-26 nucleotides, but longer or shorter primers may also be employed.

"Polymorphic site" is a position within a locus at which at least two alternative sequences are found in a population.

"Polymorphism" refers to the sequence variation observed in an individual at a polymorphic site. Polymorphisms include nucleotide substitutions, insertions, deletions and microsatellites and may, but need not, result in detectable differences in gene expression or protein function. In the absence of evidence of an effect on expression or protein function, common polymorphisms, including non-synonymous variants, are generally considered to be included in the definition of wild-type gene sequence. A catalog of human polymorphisms and associated annotation, including validation, observed frequencies, and disease association, is maintained by NCBI (dbSNP: http://www.ncbi.nlm.nih.gov/projects/SNP/). Please note that the term "polymorphism" when used in the context of gene sequences should not be confused with the term "polymorphism" when used in the context of solid state form of a compound, which is the crystalline or amorphous nature of a compound. The skilled person will understand the intended meaning by its context.

"Probe" refers to single stranded sequence-specific oligonucleotides which have a sequence that is exactly complementary to the target sequence of the allele to be detected.

"Response" is defined by measurements taken according to Response Evaluation Criteria in Solid Tumours (RECIST) involving the classification of patients into two main groups: those that show a partial response or stable disease and those that show signs of progressive disease.

"Stringent hybridisation conditions" refers to an overnight incubation at 42° C. in a solution comprising 50% formamide, 5× SSC (750 mM NaCl, 75 mM trisodium citrate), 50 mM sodium phosphate (pH 7.6), 5× Denhardt's solution, 10% dextran sulphate, and 20 pg/ml denatured, sheared salmon sperm DNA, followed by washing the filters in 0.1× SSC at about 65° C.

"Survival" encompasses a patients' overall survival and progression-free survival.

"Overall survival" (OS) is defined as the time from the initiation of drug administration to death from any cause. "Progression-free survival" (PFS) is defined as the time from the initiation of drug administration to first appearance of progressive disease or death from any cause.

According to one aspect of the specification there is provided a method for selecting a patient for treatment with a compound of Formula (I), (IA), (IB), (IC), (ID) or (IE), the method comprising providing a tumour cell containing sample from a patient; determining whether the ERα gene in the patient's tumour cell containing sample is wild type or mutant; and selecting a patient for treatment with a compound of Formula (I), (IA), (IB), (IC), (ID) or (IE) based thereon.

The method may include or exclude the actual patient sample isolation step. Thus, according to one aspect of the specification there is provided a method for selecting a patient for treatment with a compound of Formula (I), (IA), (IB), (IC), (ID) or (IE), the method comprising determining whether the ERα gene in a tumour cell containing sample previously isolated from the patient is wild type or mutant; and selecting a patient for treatment with a compound of Formula (I), (IA), (IB), (IC), (ID) or (IE) based thereon.

In one embodiment, the patient is selected for treatment with a compound of Formula (I), (IA), (IB), (IC), (ID) or (IE) if the tumour cell DNA has a mutant ERα gene. In other embodiments, a patient whose tumour cell DNA possesses a wild type ERα gene is selected for treatment with a compound of Formula (I), (IA), (IB), (IC), (ID) or (IE).

For the purpose of this specification, a gene status of wild-type is meant to indicate normal or appropriate expression of the gene and normal function of the encoded protein. In contrast, mutant status is meant to indicate expression of a protein with altered function, consistent with the known roles of mutant ERα genes in cancer (as described herein). Any number of genetic or epigenetic alterations, including but not limited to mutation, amplification, deletion, genomic rearrangement, or changes in methylation profile, may result in a mutant status. However, if such alterations nevertheless result in appropriate expression of the normal protein, or a functionally equivalent variant, then the gene status is regarded as wild-type. Examples of variants that typically would not result in a functional mutant gene status include synonymous coding variants and common polymorphisms (synonymous or non-synonymous). As discussed below, gene status can be assessed by a functional assay, or it may be inferred from the nature of detected deviations from a reference sequence.

In certain embodiments the wild-type or mutant status of the ERα gene is determined by the presence or absence of non-synonymous nucleic acid variations in the genes. Observed non-synonymous variations corresponding to known common polymorphisms with no annotated functional effects do not contribute to a gene status of mutant.

Other variations in the ERα gene that signify mutant status include splice site variations that decrease recognition of an intron/exon junction during processing of pre-mRNA to mRNA. This can result in exon skipping or the inclusion of normally intronic sequence in spliced mRNA (intron retention or utilization of cryptic splice junctions). This can, in turn, result in the production of aberrant protein with insertions and/or deletions relative to the normal protein. Thus, in other embodiments, the gene has a mutant status if there is a variant that alters splice site recognition sequence at an intron/exon junction.

For ESR1, reference sequences are available for the gene (GenBank accession number: NG_008493), mRNA (GenBank accession number: NM_000125), and protein (GenBank accession number: NP_000116 or Swiss-Prot accession: P03372). A person of skill in the art will be able to determine the ESR1 gene status, i.e. whether a particular ESR1gene is wild type or mutant, based on comparison of DNA or protein sequence with wild type.

It will be apparent that the gene and mRNA sequences disclosed for ERα gene are representative sequences. In normal individuals there are two copies of each gene, a maternal and paternal copy, which will likely have some sequence differences, moreover within a population there will exist numerous allelic variants of the gene sequence. Other sequences regarded as wild type include those that possess one or more synonymous changes to the nucleic acid sequence (which changes do not alter the encoded protein sequence), non-synonymous common polymorphisms (e.g. germ-line polymorphisms) which alter the protein sequence but do not affect protein function, and intronic non-splice-site sequence changes.

There are numerous techniques available to the person skilled in the art to determine the gene status of ERα. The gene status can be determined by determination of the nucleic acid sequence. This could be via direct sequencing of the full-length gene or analysis of specific sites within the gene, e.g. commonly mutated sites.

Samples

The patient's sample to be tested for the gene status can be any tumour tissue or tumour-cell containing sample obtained or obtainable from the individual. The test sample is conveniently a sample of blood, mouth swab, biopsy, or other body fluid or tissue obtained from an individual. Particular examples include: circulating tumour cells, circulating DNA in the plasma or serum, cells isolated from the ascites fluid of ovarian cancer patients, lung sputum for patients with tumours within the lung, a fine needle aspirate from a breast cancer patient, urine, peripheral blood, a cell scraping, a hair follicle, a skin punch or a buccal sample.

It will be appreciated that the test sample may equally be a nucleic acid sequence corresponding to the sequence in the test sample, that is to say that all or a part of the region in the sample nucleic acid may firstly be amplified using any convenient technique e.g. polymerase chain reaction (PCR), before analysis. The nucleic acid may be genomic DNA or fractionated or whole cell RNA. In particular embodiments the RNA is whole cell RNA and is used directly as the template for labelling a first strand cDNA using random primers or poly A primers. The nucleic acid or protein in the test sample may be extracted from the sample according to standard methodologies (see Green & Sambrook, Eds., Molecular Cloning: A Laboratory Manual, (2012, 4th edition, Vol. 1-3, ISBN 9781936113422), Cold Spring Harbor Laboratory Press, Cold Spring Harbor, N.Y.)

The diagnostic methods of the specification can be undertaken using a sample previously taken from the individual or patient. Such samples may be preserved by freezing or fixed and embedded in formalin-paraffin or other media. Alternatively, a fresh tumour cell containing sample may be obtained and used.

The methods of the specification can be applied using cells from any tumour. Suitable tumours for treatment with a compound of Formula (I), (IA), (IB), (IC), (ID) or (IE) have been described hereinbefore.

Methods for Detection of Nucleic Acids

The detection of mutant ERα nucleic acids can be employed, in the context of the present specification, to select drug treatment. Since mutations in these genes occur at the DNA level, the methods of the specification can be based on detection of mutations or variances in genomic DNA, as well as transcripts and proteins themselves. It can be desirable to confirm mutations in genomic DNA by analysis of transcripts and/or polypeptides, in order to ensure that the detected mutation is indeed expressed in the subject.

It will be apparent to the person skilled in the art that there are a large number of analytical procedures which may be used to detect the presence or absence of variant nucleotides at one or more positions in a gene. In general, the detection of allelic variation requires a mutation discrimination technique, optionally an amplification reaction (such as one based on polymerase chain reaction) and optionally a signal generation system. There are a multitude of mutation detection techniques available in the art and these may be used in combination with a signal generation system, of which there are numerous available in the art. Many methods for the detection of allelic variation are reviewed by Nollau et al., *Clin. Chem.*, 1997, 43, 1114-1120; Anderson SM. *Expert Rev Mol Diagn.*, 2011, 11, 635-642; Meyerson M. et al., *Nat Rev Genet.*, 2010, 11, 685-696; and in standard textbooks, for example "*Laboratory Protocols for Mutation Detection*", Ed. by U. Landegren, Oxford University Press, 1996 and "PCR", $2^{nd}$ Edition by Newton & Graham, BIOS Scientific Publishers Limited, 1997.

As noted above, determining the presence or absence of a particular variance or plurality of variances in the ERα gene in a patient with cancer can be performed in a variety of ways. Such tests are commonly performed using DNA or RNA collected from biological samples, e.g., tissue biopsies, urine, stool, sputum, blood, cells, tissue scrapings, breast aspirates or other cellular materials, and can be performed by a variety of methods including, but not limited to, PCR, hybridization with allele-specific probes, enzymatic mutation detection, chemical cleavage of mismatches, mass spectrometry or DNA sequencing, including minisequencing.

Suitable mutation detection techniques include amplification refractory mutation system (ARMS™), amplification refractory mutation system linear extension (ALEX™) competitive oligonucleotide priming system (COPS), Taqman, Molecular Beacons, restriction fragment length polymorphism (RFLP), and restriction site based PCR and fluorescence resonance energy transfer (FRET) techniques.

In particular embodiments the method employed for determining the nucleotide(s) within a biomarker gene is selected from: allele-specific amplification (allele specific PCR)-such as amplification refractory mutation system (ARMS), sequencing, allelic discrimination assay, hybridisation, restriction fragment length polymorphism (RFLP) or oligonucleotide ligation assay (OLA).

In particular embodiments, hybridization with allele specific probes can be conducted by: (1) allele specific oligonucleotides bound to a solid phase (e.g. glass, silicon, nylon membranes) with the labelled sample in solution, for example as in many DNA chip applications; or, (2) bound sample (often cloned DNA or PCR amplified DNA) and labelled oligonucleotides in solution (either allele specific or short so as to allow sequencing by hybridization). Diagnostic tests may involve a panel of variances, often on a solid support, which enables the simultaneous determination of more than one variance. Such hybridization probes are well known in the art (see, e.g., Green & Sambrook, Eds., Molecular Cloning: A Laboratory Manual, (2012, 4th edition, Vol. 1-3, ISBN 9781936113422), Cold Spring Harbor Laboratory Press, Cold Spring Harbor, N.Y.) and may span two or more variance sites.

Thus, in one embodiment, the detection of the presence or absence of at least one mutation provides for contacting ERα nucleic acid containing a putative mutation site with at least one nucleic acid probe. The probe preferentially hybridizes with a nucleic acid sequence including a variance site and containing complementary nucleotide bases at the variance site under selective hybridization conditions.

Hybridization can be detected with a detectable label using labels known to one skilled in the art. Such labels include, but are not limited to radioactive, fluorescent, dye, and enzymatic labels.

In another embodiment, the detection of the presence or absence of at least one mutation provides for contacting ERα nucleic acid containing a putative mutation site with at least one nucleic acid primer. The primer preferentially hybridizes with a nucleic acid sequence including a variance site and containing complementary nucleotide bases at the variance site under selective hybridization conditions.

Oligonucleotides used as primers for specific amplification may carry the complementary nucleotide base to the mutation of interest in the centre of the molecule (so that amplification depends on differential hybridization; see, e.g., Gibbs, et al., 1989. *Nucl. Acids Res.*, 17, 2437-248) or at the extreme 3'-terminus of one primer where, under appropriate conditions, mismatch can prevent, or reduce polymerase extension (see, e.g., Prossner, 1993, Tibtech, 11 238).

In yet another embodiment, the detection of the presence or absence of at least one mutation comprises sequencing at least one nucleic acid sequence and comparing the obtained sequence with the known wild type nucleic acid sequence.

Alternatively, the presence or absence of at least one mutation comprises mass spectrometric determination of at least one nucleic acid sequence.

In one embodiment, the detection of the presence or absence of at least one nucleic acid variance comprises performing a polymerase chain reaction (PCR). The target nucleic acid sequence containing the hypothetical variance is amplified and the nucleotide sequence of the amplified nucleic acid is determined. Determining the nucleotide sequence of the amplified nucleic acid comprises sequencing at least one nucleic acid segment. Alternatively, amplification products can be analysed using any method capable of separating the amplification products according to their size, including automated and manual gel electrophoresis, and the like.

Mutations in genomic nucleic acid are advantageously detected by techniques based on mobility shift in amplified nucleic acid fragments. For instance, Chen et al., *Anal Biochem* 1996, 239, 61-9, describe the detection of single-base mutations by a competitive mobility shift assay. Moreover, assays based on the technique of Marcelino et al., *BioTechniques* 1999, 26, 1134-1148 are available commercially.

In a particular example, capillary heteroduplex analysis may be used to detect the presence of mutations based on mobility shift of duplex nucleic acids in capillary systems as a result of the presence of mismatches.

Generation of nucleic acids for analysis from samples generally requires nucleic acid amplification. Many amplification methods rely on an enzymatic chain reaction (such as a polymerase chain reaction, a ligase chain reaction, or a self-sustained sequence replication) or from the replication of all or part of the vector into which it has been cloned. Preferably, the amplification according to the specification is an exponential amplification, as exhibited by for example the polymerase chain reaction.

Many target and signal amplification methods have been described in the literature, for example, general reviews of these methods in Landegren, U., et al., *Science*, 1988 242, 229-237 and Lewis, R., *Genetic Engineering News* 1990, 10, 54-55. These amplification methods can be used in the methods of our specification, and include polymerase chain reaction (PCR), PCR in situ, ligase amplification reaction (LAR), ligase hybridisation, Qβ bacteriophage replicase, transcription-based amplification system (TAS), genomic amplification with transcript sequencing (GAWTS), nucleic acid sequence-based amplification (NASBA) and in situ hybridisation. Primers suitable for use in various amplification techniques can be prepared according to methods known in the art.

Polymerase Chain Reaction (PCR) PCR is a nucleic acid amplification method described inter alia in U.S. Pat. Nos. 4,683,195 and 4,683,202. PCR consists of repeated cycles of DNA polymerase generated primer extension reactions. The target DNA is heat denatured and two oligonucleotides, which bracket the target sequence on opposite strands of the DNA to be amplified, are hybridised. These oligonucleotides become primers for use with DNA polymerase. The DNA is copied by primer extension to make a second copy of both strands. By repeating the cycle of heat denaturation, primer hybridisation and extension, the target DNA can be amplified a million fold or more in about two to four hours. PCR is a molecular biology tool, which must be used in conjunction with a detection technique to determine the results of amplification. An advantage of PCR is that it increases sensitivity by amplifying the amount of target DNA by 1 million to 1 billion fold in approximately 4 hours. PCR can be used to amplify any known nucleic acid in a diagnostic context (Mok et al., *Gynaecologic Oncology*, 1994, 52: 247-252,).

An allele specific amplification technique such as Amplification Refractory Mutation System (ARMS™) (Newton et al., *Nucleic Acids Res.*, 1989, 17, 2503-2516) can also be used to detect single base mutations. Under the appropriate PCR amplification conditions a single base mismatch located at the 3'-end of the primer is sufficient for preferential amplification of the perfectly matched allele (Newton et al., 1989, supra), allowing the discrimination of closely related species. The basis of an amplification system using the primers described above is that oligonucleotides with a mismatched 3'-residue will not function as primers in the PCR under appropriate conditions. This amplification system allows genotyping solely by inspection of reaction mixtures after agarose gel electrophoresis.

Analysis of amplification products can be performed using any method capable of separating the amplification products according to their size, including automated and manual gel electrophoresis, mass spectrometry, and the like.

The methods of nucleic acid isolation, amplification and analysis are routine for one skilled in the art and examples of protocols can be found, for example, Green & Sambrook, Eds., Molecular Cloning: A Laboratory Manual, (2012, 4th edition, Vol. 1-3, ISBN 9781936113422), Cold Spring Harbor Laboratory Press, Cold Spring Harbor, N.Y.) Particularly useful protocol source for methods used in PCR amplification is *PCR* (*Basics: From Background to Bench*) by M. J. McPherson, S. G. Mailer, R. Beynon, C. Howe, Springer Verlag; 1st edition (Oct. 15, 2000), ISBN: 0387916008.

The present specification also provides predictive and diagnostic kits comprising degenerate primers to amplify a target nucleic acid in the ERα gene and instructions comprising; amplification protocol and analysis of the results. The kit may alternatively also comprise buffers, enzymes, and containers for performing the amplification and analysis of the amplification products. The kit may also be a component of a screening, or diagnostic kit comprising other tools such as DNA microarrays, or other supports. Preferably, the kit also provides one or more control templates, such as nucleic acids isolated from normal tissue sample, and/or a series of samples representing different variances in the reference genes.

In one embodiment, the kit provides two or more primer pairs, each pair capable of amplifying a different region of the reference (ERα) gene (each region a site of potential variance) thereby providing a kit for analysis of expression of several gene variances in a biological sample in one reaction or several parallel reactions.

Primers in the kits may be labelled, for example fluorescently labelled, to facilitate detection of the amplification products and consequent analysis of the nucleic acid variances. The kit may also allow for more than one variance to be detected in one analysis. A combination kit will therefore comprise of primers capable of amplifying different segments of the reference gene. The primers may be differentially labelled, for example using different fluorescent labels, so as to differentiate between the variances.

In another aspect, the specification provides a method of treating a patient suffering from cancer comprising: determining the mutant or wild type status of the ERα gene in the patient's tumour cells and if the ERα gene is mutant, administering to the patient an effective amount of a compound of Formula (I), (IA), (IB), (IC), (ID) or (IE).

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. "Less effective" means that the treatment results in a therapeutically significant lower level of pharmacological effectiveness and/or a therapeutically greater level of adverse physiological effects.

According to another aspect of the specification there is provided the use of a compound of Formula (I), (IA), (IB), (IC), (ID) or (IE) or a pharmaceutically acceptable salt thereof to treat a cancer patient whose tumour cells have been identified as possessing a mutant ERα gene.

According to another aspect of the specification there is provided a compound of Formula (I), (IA), (IB), (IC), (ID) or (IE) or a pharmaceutically acceptable salt thereof for treating cancers with tumour cells identified as harbouring mutant ERα gene.

According to another aspect of the specification there is provided a method of treating cancers with tumour cells identified as harbouring mutant ERα gene comprising administering an effective amount of a compound of Formula (I), (IA), (IB), (IC), (ID) or (IE) or a pharmaceutically acceptable salt thereof.

In still further embodiments, the specification relates to a pharmaceutical composition comprising a compound of Formula (I), (IA), (IB), (IC), (ID) or (IE) for use in the prevention and treatment of cancer with tumour cells identified as harbouring a mutant ERα gene.

For all the aspects above, mutant forms of ERα determined/identified are at all positions across the gene.

For all the aspects above, using tumours such as breast cancer as an example, particular mutant forms of ERα determined/identified are those at positions Ser463Pro, Val543Glu, Leu536Arg, Tyr537Ser, Tyr537Asn and Asp538Gly.

EXAMPLES

The specification will now be illustrated in the following Examples in which, generally:

(i) operations were carried out at ambient temperature, i.e. in the range 17 to 25° C. and under an atmosphere of an inert gas such as nitrogen unless otherwise stated;

(ii) evaporations were carried out by rotary evaporation or utilising Genevac equipment or Biotage v10 evaporator in vacuo and work-up procedures were carried out after removal of residual solids by filtration;

(iii) flash chromatography purifications were performed on an automated Teledyne Isco CombiFlash® Rf or Teledyne Isco CombiFlash® Companion® using prepacked RediSep Rf Gold™ Silica Columns (20-40 μm, spherical particles), GraceResolv™ Cartridges (Davisil® silica) or Silicycle cartridges (40-63 μm).

(iv) preparative chromatography was performed on a Gilson prep HPLC instrument with UV collection or via supercritical fluid chromatography performed on a Waters Prep 100 SFC-MS instrument with MS- and UV- triggered collection or a Thar MultiGram III SFC instrument with UV collection;

(v) chiral preparative chromatography was performed on a Gilson instrument with UV collection (233 injector/fraction collector, 333 & 334 pumps, 155 UV detector) or a Varian Prep Star instrument (2× SD1 pumps, 325 UV detector, 701 fraction collector) pump running with Gilson 305 injection;

(vi) yields, where present, are not necessarily the maximum attainable;

(vii) in general, the structures of end-products of the Formula I were confirmed by nuclear magnetic resonance (NMR) spectroscopy; NMR chemical shift values were measured on the delta scale [proton magnetic resonance spectra were determined using a Bruker Avance 500 (500 MHz) or Bruker Avance 400 (400 MHz) instrument]; measurements were taken at ambient temperature unless otherwise specified; the following abbreviations have been used: s, singlet; d, doublet; t, triplet; q, quartet; m, multiplet; dd, doublet of doublets; ddd, doublet of doublet of doublet; dt, doublet of triplets; bs, broad signal (viii) in general, end-products of the Formula I were also characterised by mass spectroscopy following liquid chromatography (LCMS or UPLC); UPLC was carried out using a Waters UPLC fitted with Waters SQ mass spectrometer (Column temp 40, UV=220-300 nm, Mass Spec=ESI with positive/negative switching) at a flow rate of 1 ml/min using a solvent system of 97% A+3% B to 3% A to 97% B over 1.50 mins (total runtime with equilibration back to starting conditions etc 1.70 min), where A=0.1% formic acid in water (for acid work) or 0.1% ammonia in water (for base work) B=acetonitrile. For acid analysis the column used was Waters Acquity HSS T3 1.8 μm 2.1×50 mm, for base analysis the column used was Waters Acquity BEH 1.7 μm 2.1×50mm; LCMS was carried out using a Waters Alliance HT (2795) fitted with a Waters ZQ ESCi mass spectrometer and a Phenomenex Gemini —NX (50×2.1mm 5μm) column at a flow rate of 1.1 ml/min 95% A to 95% B over 4 min with a 0.5 min hold. The modifier is kept at a constant 5% C (50:50 acetonitrile:water 0.1% formic acid) or D (50:50 acetonitrile:water 0.1% ammonium hydroxide (0.88 SG) depending on whether it is an acidic or basic method.

(ix) ion exchange purification was generally performed using a SCX-2 (Biotage, Propylsulfonic acid functionalized silica. Manufactured using a trifunctional silane. Non end-capped) cartridge.

(x) intermediate purity was assessed by thin layer chromatographic, mass spectral, HPLC (high performance liquid chromatography) and/or NMR analysis;

(xi) RockPhos 3rd Generation Precatalyst was sourced from Strem Chemicals Inc. and from Sigma-Aldrich.

(xii) the following abbreviations have been used:
AcOH acetic acid
aq. aqueous
BINAP 2,2'-Bis(diphenylphosphino)-1,1'-binaphthalene
n-BuLi n-butyl lithium
tBuOH tert-butanol
$CDCl_3$ deutero-chloroform
Conc. concentrated
DCM dichloromethane
DEAD diethylazodicarboxylate
DIPEA diisopropylethylamine
DMA N,N-dimethylacetamide
DMAP dimethylaminopyridine
DME dimethoxyethane
DMF N,N-dimethylformamide
DMSO dimethyl sulphoxide
EtOH ethanol
EtOAc ethyl acetate
HATU  1-[Bis(dimethylamino)methylene]-1H-1,2,3-triazolo[4,5-b]pyridinium 3-oxid hexafluorophosphate,
HPLC high performance liquid chromatography
IPA isopropyl alcohol
MeCN acetonitrile
MeOH methanol
RockPhos 3rd Generation [(2-Di-tert-butylphosphino-3-methoxy-6-methyl-2',4',6'-triisopropyl-1,1'-biphenyl)-2-(2-aminobiphenyl)]palladium(II)
Precatalyst methanesulfonate
rt/RT room temperature
sat. saturated
SFC supercritical fluid chromatography
sol. solution
TBME tert-butyl methyl ether
THF tetrahydrofuran Example 1

Preparation of (6S,8R)-6-(2,6-difluoro-4-(2-(3-(fluoromethyl)azetidin-1-yl)ethoxy)phenyl)-7-(2-fluoro-2-methylpropyl)-8-methyl-6,7,8,9-tetrahydro-3H-pyrazolo[4,3-f]isoquinoline

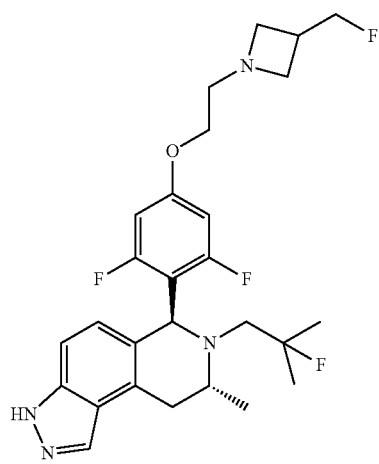 [SMILES: C[C@@H]1Cc2c(ccc3[nH]ncc23)[C@@H](c2c(F)cc(OCCN3CC(CF)C3)cc2F)N1CC(C)(C)F]

HCl in dioxane (4N; 0.42 mL) was added to a solution of (6S,8R)-6-(2,6-difluoro-4-(2-(3-(fluoromethyl)azetidin-1-yl)ethoxy)phenyl)-7-(2-fluoro-2-methylpropyl)-8-methyl 3-(tetrahydro-2H-pyran-2-yl)-6,7,8,9-tetrahydro-3H-pyrazolo[4,3-f]isoquinoline (120 mg, 0.20 mmol) in MeOH (0.51 mL) and the reaction was stirred at room temperature for 30 minutes. The solvents were evaporated, and the resulting residue was dissolved in DCM and washed with saturated aqueous $NaHCO_3$. The aqueous layer was extracted with DCM, and the combined organic layers were dried over sodium sulfate, filtered, and concentrated to dryness. The resulting residue was purified by flash silica chromatography, elution gradient 0 to 20% MeOH in DCM. Product fractions were concentrated under reduced pressure and lyophilized to afford (6S,8R)-6-(2,6-difluoro-4-(2-(3-(fluoromethyl)azetidin-1-yl)ethoxy)phenyl)-7-(2-fluoro-2-methylpropyl)-8-methyl-6,7,8,9-tetrahydro-3H-pyrazolo[4,3-f]isoquinoline (80 mg, 78%) as a beige solid. $^1$H NMR (500 MHz DMSO-$d_6$, 27° C.) 0.91 (3H, d), 1.02 (3H, d), 1.07 (3H, d), 2.20 (1H, dd), 2.63 (3H, m), 2.82 (2H, q), 2.92 (2H, m), 3.18 (3H, m), 3.55 (1H, m), 3.84 (2H, m), 4.37 (1H, d), 4.47 (1H, d), 5.06 (1H, s), 6.53 (1H, d), 6.57 (2H, d), 7.13 (1H, d), 7.99 (1H, s), 12.9 (1H, s). m/z: ES+ [M+H]+ 505.

The (6S,8R)-6-(2,6-difluoro-4-(2-(3-(fluoromethyl)azetidin-1-yl)ethoxy)phenyl)-7-(2-fluoro-2-methylpropyl)-8-methyl-3-(tetrahydro-2H-pyran-2-yl)-6,7,8,9-tetrahydro-3H-pyrazolo[4,3-f]isoquinoline was prepared as follows;

Preparation of 2-fluoro-2-methylpropyl trifluoromethanesulfonate

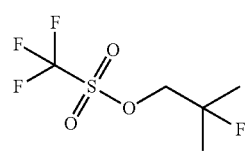

Trifluoromethanesulfonic anhydride (10.11 mL, 59.71 mmol) was added dropwise to a solution of 2-fluoro-2-methylpropan-1-ol (5.00 g, 54.3 mmol) and 2,6-dimethylpyridine (7.6 mL, 65.1 mmol) in DCM (118 mL) at −10° C. The reaction was stirred for 90 minutes, then washed successively with water, 2N HCl and saturated $NaHCO_3$ solution, dried over $Na_2SO_4$, filtered and concentrated under reduced pressure to afford 2-fluoro-2-methylpropyl trifluoromethanesulfonate as a red oil (11.0 g, 90%). $^1$H NMR (500 MHz, $CDCl_3$, 27° C.) 1.47 (6H, d) 4.42 (2H, d).

Preparation of (R)-1-(3-bromo-2-methylphenyl)propan-2-amine

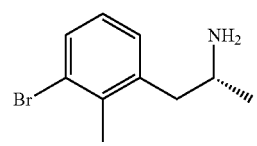

n-BuLi in hexanes (2.5 M; 8.1 mL, 20 mmol) was added dropwise to a solution of 1,3-dibromo-2-methylbenzene (4.8 g, 19 mmol) in THF (50 mL) at −78° C. at such a rate as to keep the internal reaction temperature below -60° C. After stirring for 30 minutes, tert-butyl (R)-4-methyl-1,2,3-oxathiazolidine-3-carboxylate 2,2-dioxide (5.01 g, 21.1 mmol) was added in portions, and the reaction was stirred for a further 30 minutes before being allowed to warm to 0° C. over 2 hours. Aqueous citric acid (1N; 40 mL) was added at 0° C., and the mixture was stirred for 15 min before it was extracted with EtOAc (2×100 mL). The combined organic layers were concentrated under reduced pressure. The residue was stirred in HCl in dioxane (4N; 30 mL) at room temperature for 1 hour and then concentrated. The resulting residue was dissolved in water (100 mL) and extracted with diethyl ether (2×60 mL). The aqueous layer was then basified by addition of Na$_2$CO$_3$ and extracted with DCM (3×100 mL). The combined DCM extracts were dried over Na$_2$SO$_4$, filtered and concentrated to dryness. The crude product was purified by flash silica chromatography, elution gradient 0 to 10% MeOH in DCM. Product fractions were concentrated to dryness to afford (R)-1-(3-bromo-2-methylphenyl)propan-2-amine (2.6 g, 60%) as a brown oil. $^1$H NMR (500 MHz, DMSO-d$_6$, 27 ° C.) 1.1 (3H, d) 2.34 (3H, s) 2.64 (1H, dd) 2.77 (1H, dd) 3.08 (1H, ddd) 7.05 (1H, t) 7.15 (1H, d) 7.45 (1H, d). NH2 was not observed. m/z: ES+ [M+H]+ 228.

Preparation of (R)-N-(1-(3-bromo-2-methylphenyl)propan-2-yl)-2-fluoro-2-methylpropan-1-amine

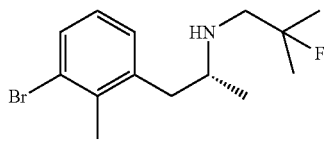 [SMILES: Cc1c(Br)cccc1C[C@@H](C)NCC(C)(C)F]

2-Fluoro-2-methylpropyl trifluoromethanesulfonate (4.73 g, 21.1 mmol) was added to a solution of (R)-1-(3-bromo-2-methylphenyl)propan-2-amine (3.7 g, 16 mmol) and diisopropylethylamine (3.97 mL, 22.7 mmol) in dioxane (77 mL) and stirred at 85° C. for 16 hours. After cooling, the reaction mixture was diluted with EtOAc (100 mL) and washed with water (100 mL). The aqueous layer was extracted with EtOAc (2×100 mL) and the combined EtOAc extracts were dried over Na$_2$SO$_4$, filtered and concentrated to dryness. The crude product was purified by flash silica chromatography, elution gradient 0 to 10% MeOH in DCM. Product fractions were concentrated to dryness to afford (R)—N-(1-(3-bromo-2-methylphenyl)propan-2-yl)-2-fluoro-2-methylpropan-1-amine (3.1 g, 63%) as a brown oil. $^1$H NMR (500 MHz, DMSO-d$_6$, 27° C.) 0.93 (3H, d) 1.23 (3H, d) 1.27 (3H, d) 1.49 (1H, s) 2.34 (3H, s) 2.51-2.78 (4H, m) 2.86 (1H, dd) 7.03 (1H, t) 7.15 (1H, d) 7.43 (1H, d). m/z: ES+ [M+H]+ 302.

Preparation of (R)-3-(24(2-fluoro-2-methylpropyl)amino)propyl)-2-methylaniline

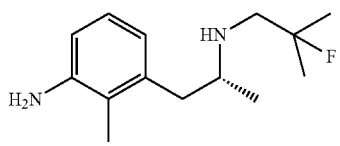 [SMILES: Cc1c(N)cccc1C[C@@H](C)NCC(C)(C)F]

A solution of (R)—N -(1-(3-bromo-2-methylphenyl)propan-2-yl)-2-fluoro-2-methylpropan-1-amine (3.1 g, 10 mmol) in toluene (50 mL) was degassed and backfilled with nitrogen (3×). Bis(dibenzylideneacetone)palladium(0) (0.18 g, 0.31 mmol), rac-2,2'-bis(diphenylphosphino)-1,1'-binaphthyl (0.19 g, 0.31 mmol), sodium tert-butoxide (1.48 g, 15.4 mmol), and diphenylmethanimine (1.72 mL, 10.3 mmol) were added. The reaction mixture was degassed and backfilled with nitrogen (3×), then heated at 90° C. for 2.5 hours. After cooling, the volatiles were removed under vacuum, and the resulting residue was dissolved in EtOAc (30 mL). Aqueous HCl (1N; 30 mL) was added, and the biphasic mixture was stirred vigorously for 30 minutes. The layers were separated and the aqueous layer was extracted with DCM (30 mL). The aqueous layer was then basified by addition of aqueous NaOH (1N; 30 mL) and extracted with DCM (3×50 mL). The combined basic DCM extracts were dried over Na$_2$SO$_4$, filtered, and concentrated under reduced pressure. The resulting residue was purified by flash silica chromatography, elution gradient 50 to 100% EtOAc in hexane. Product fractions were concentrated to dryness to afford (R)-3-(2-((2-fluoro-2-methylpropyl)amino)propyl)-2-methylaniline (2.07 g, 85%) as a yellow oil. $^1$H NMR (500 MHz, DMSO-d$_6$, 27° C.) 0.91 (3H, d), 1.24 (3H, s), 1.29 (3H, s), 1.43 (1H, s), 1.97 (3H, s), 2.37 (1H, q), 2.57-2.72 (4H, m), 4.68 (2H, s), 6.34 (1H, s), 6.47 (1H, s), 6.77 (1H, t). m/z: ES+ [M+H]+ 239.

Preparation of (1S,3R)-1-(4-bromo-2,6-difluorophenyl)-2-(2-fluoro-2-methylpropyl)-3,5-dimethyl-1,2,3,4-tetrahydroisoauinolin-6-amine

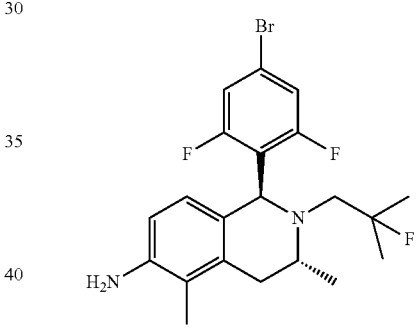

(R)-3-(2-((2-fluoro-2-methylpropyl)amino)propyl)-2-methylaniline (0.65 g, 2.7 mmol) and 4-bromo-2,6-difluorobenzaldehyde (1.2 g, 5.5 mmol) were heated in a mixture of acetic acid (8 mL) and water (0.25 mL) at 60° C. for 48 hours. After cooling, the solvent was evaporated and the resulting residue was dissolved in DCM (20 mL). Aqueous HCl (1N; 20 mL) was added, and the biphasic mixture was stirred vigourously for 30 minutes. The layers were separated is and the organic layer was extracted with aqueous HCl (1N; 2x). The combined aqueous acidic layers were basified by addition of aqueous NaOH (1N) and then extracted with DCM (2×). The combined organic layers were dried over sodium sulfate, filtered, and concentrated to dryness. The resulting residue was purified by flash silica chromatography, elution gradient 0 to 70% EtOAc in hexane. Product fractions were concentrated to dryness to afford (1S,3R)-1-(4-bromo-2,6-difluorophenyl)-2-(2-fluoro-2-methylpropyl)-3,5-dimethyl-1,2,3,4-tetrahydroisoquinolin-6-amine (650 mg, 54%) as a pale syrup. $^1$H NMR (500 MHz, DMSO-d$_6$, 27° C.) 0.94 (3H, d), 1.12 (3H, d), 1.19 (3H, d), 1.95 (3H, s), 2.19 (1H, dd), 2.55 (1H, dd), 2.84 (1H, dd), 2.87 (1H, dd), 3.48 (1H, q), 4.65 (2H, s), 5.02 (1H, s), 6.25 (1H, d), 6.37 (1H, d), 7.34 (2H, d). m/z: ES+ [M+H]+ 441.

Preparation of (6S,8R)-6-(4-bromo-2,6-difluorophenyl)-7-(2-fluoro-2-methylpropyl)-8-methyl-6,7,8,9-tetrahydro-3H-pyrazolo[4,3-f]isoquinoline

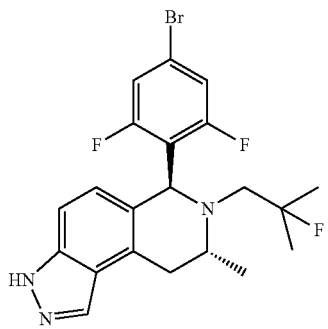 [SMILES: C[C@@H]1Cc2c(ccc3[nH]ncc23)[C@@H](c2c(F)cc(Br)cc2F)N1CC(C)(C)F]

A solution of sodium nitrite (112 mg, 1.62 mmol) in water (0.3 mL) at −17° C. was added dropwise to a solution of (1S,3R)-1-(4-bromo-2,6-difluorophenyl)-2-(2-fluoro-2-methylpropyl)-3,5-dimethyl-1,2,3,4-tetrahydroisoquinolin-6-amine (650 mg, 1.47 mmol) in propionic acid (3 mL, 40.09 mmol) at the same temperature, and the reaction was maintained under these conditions for 90 minutes. Cold EtOAc (30 mL) and saturated aqueous NaHCO₃ (100 mL) were added, and the layers were separated. The aqueous layer was extracted with EtOAc (3×30 mL), and the combined organic layers were washed with saturated aqueous sodium chloride, dried over sodium sulfate, filtered and concentrated to dryness. The rsulting residue was purified by flash silica chromatography, elution gradient 0 to 70% EtOAc in hexane. Product fractions were concentrated to dryness to afford (6S,8R)-6-(4-bromo-2,6-difluorophenyl)-7-(2-fluoro-2-methylpropyl)-8-methyl-6,7,8,9-tetrahydro-3H-pyrazolo[4,3-f]isoquinoline (350 mg, 53%) as a pale syrup. $^1$H NMR (500 MHz, DMSO-$d_6$, 27° C.) 1.0 (3H, d), 1.13 (3H, d), 1.22 (3H, d), 1.28 (1H, dd), 2.92 (1H, t), 2.96 (1H, dd), 3.30 (1H, dd), 3.61(1H, m), 5.21 (1H, s), 6.68 (1H, d), 7.23 (1H, d), 7.39 (2H, d), 8.08 (1H, s), 13.01 (s, 1H). m/z: ES+ [M+H]+ 452.

Preparation of (6S,8R)-6-(4-bromo-2,6-difluorophenyl)-7-(2-fluoro-2-methylpropyl)-8-methyl-3-(tetrahydro-2H-pyran-2-yl)-6,7,8,9-tetrahydro-3H-pyrazolo[4,3-f]isoquinoline

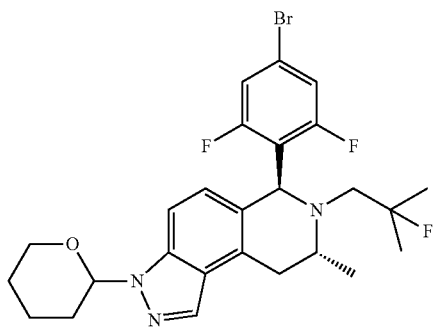 [SMILES: C[C@@H]1Cc2c(ccc3c2cnn3C2CCCCO2)[C@@H](c2c(F)cc(Br)cc2F)N1CC(C)(C)F]

3,4-Dihydro-2H-pyran (103 μl, 1.13 mmol) and p-toluenesulfonic acid monohydrate (14 mg, 0.08 mmol) were added to a solution of (6S,8R)-6-(4-bromo-2,6-difluorophenyl)-7-(2-fluoro-2-methylpropyl)-8-methyl-6,7,8,9-tetrahydro-3H-pyrazolo[4,3-f]isoquinoline (340 mg, 0.75 mmol) in DCM (3.7 mL), and the reaction was stirred at room temperature for 30 minutes. The reaction was then warmed to reflux conditions and maintained under these conditions for 3 hours. After cooling, the reaction was diluted with DCM (25 mL) and washed with saturated aqueous NaHCO₃ (25 mL). The organic layer was dried over sodium sulfate, filtered, and concentrated under reduced pressure. The resulting residue was purified by flash silica chromatography, elution gradient 0 to 70% EtOAc in hexane. Product fractions were concentrated to dryness to afford (6S,8R)-6-(4-bromo-2,6-difluorophenyl)-7-(2-fluoro-2-methylpropyl)-8-methyl-3-(tetrahydro-2H-pyran-2-yl)-6,7,8,9-tetrahydro-3H-pyrazolo[4,3-f]isoquinoline (300 mg, 74%) as a pale yellow solid. $^1$H NMR (500 MHz, DMSO-$d_6$, 27° C.) 0.99 (3H, d), 1.12 (3H, d), 1.21 (3H, d), 1.61 (2H, t), 1.75 (1H, m), 1.98 (1H, dd), 2.07 (1H, dd), 2.20 (1H, m), 2.27 (1H, dd), 2.84 (1H, dt), 2.94 (1H, dd), 3.23 (1H, dt), 3.60 (1H, m), 3.73 (1H, m), 4.02 (1H, dd), 5.13 (1H, s), 5.72 (1H, d), 6.58 (1H, d), 7.31 (1H, d), 7.40 (2H, d), 8.51 (1H, s). m/z: ES+ [M+H]+ 536.

Preparation of (6S,8R)-6-(2,6-difluoro-4-(2-(3-(fluoromethyl)azetidin-1-yl)ethoxy)phenyl)-7-(2-fluoro-2-methylpropyl)-8-methyl-3-(tetrahydro-2H-pyran-2-yl)-6,7,8,9-tetrahydro-3H-pyrazolo[4,3-f]isoquinoline

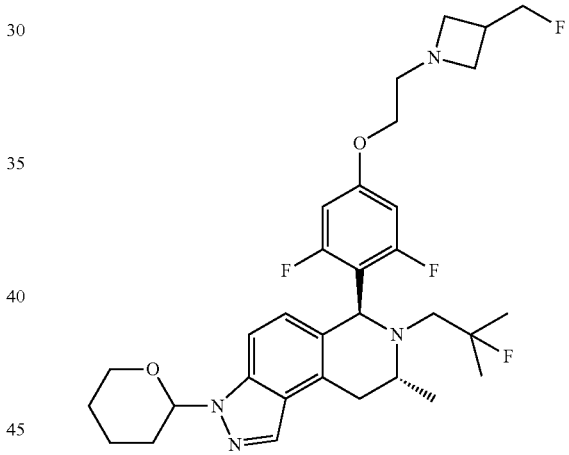

2-(3-(Fluoromethyl)azetidin-1-yl)ethan-1-ol (75 mg, 0.56 mmol) was added to a degassed suspension of of (6S,8R)-6-(4-bromo-2,6-difluorophenyl)-7-(2-fluoro-2-methylpropyl)-8-methyl-3-(tetrahydro-2H-pyran-2-yl)-6,7,8,9-tetrahydro-3H-pyrazolo[4,3-f]isoquinoline (150 mg, 0.28 mmol), RockPhos 3rd Generation Precatalyst (12 mg, 0.01 mmol) and cesium carbonate (228 mg, 0.70 mmol) in toluene (2.3 mL). The reaction was heated to 90° C. and maintained under these conditions for 30 minutes. After cooling, the reaction was diluted with EtOAc and washed with water. The aqueous layer was extracted with EtOAc, and the combined organic layers were dried over sodium sulfate, filtered, and concentrated to dryness. The resulting residue was purified by flash silica chromatography, elution gradient 0 to 10% MeOH in DCM. Product fractions were concentrated to dryness to afford (6S,8R)-6-(2,6-difluoro-4-(2-(3-(fluoromethyl)azetidin-1-yl)ethoxy)phenyl)-7-(2-fluoro-2-methylpropyl)-8-methyl-3-(tetrahydro-2H-pyran-2-yl)-6,7,8,9-tetrahydro-3H-pyrazolo[4,3-f]isoquinoline (128 mg, 78%) as a pale yellow gum. $^1$H NMR (500 MHz DMSO-d$_6$, 27° C.) 0.99 (3H, d), 1.13 (3H, d), 1.14 (3H, d), 1.20 (1H, m), 1.61 (2H, m), 1.74 (1H, m), 1.97 (1H, dd), 2.04 (1H, dd), 2.23 (1H, t), 2.28 (1H, dd), 2.70 (3H, m), 2.78 (1H, dd), 2.99 (2H, t), 3.18 (1H, dd), 3.31 (2H, t), 3.61 (1H, dd), 3.73 (1H, m), 3.92 (2H, t), 3.99 (1H, dd), 4.45 (1H, d), 4.54 (1H, d), 5.05 (1H, s), 5.69 (1H, d), 6.55 (1H, d), 6.61 (2H, d), 7.28 (1H, d), 8.49 (1H, s). m/z: ES+ [M+H]+ 589.

Example 2

Preparation of (6S,8R)-6-(2,6-difluoro-4-(2-(3-(fluoromethyl)azetidin-1-yl)ethoxy)phenyl)-7-(2-fluoro-2-methylpropyl)-6,8-dimethyl-6,7,8,9-tetrahydro-3H-pyrazolo[4,3-f]isoquinoline

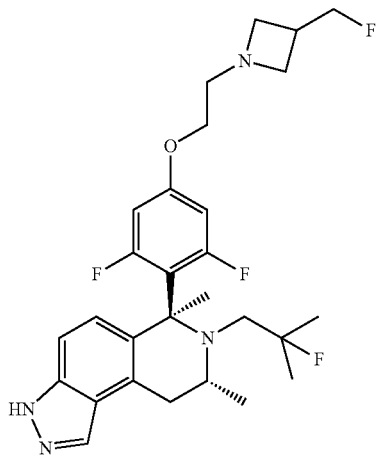 [SMILES: C[C@@H]1Cc2c(ccc3[nH]ncc23)[C@@](C)(c2c(F)cc(OCCN3CC(CF)C3)cc2F)N1CC(C)(C)F]

2-(3-(Fluoromethyl)azetidin-1-yl)ethan-1-ol (27 mg, 0.20 mmol) was added to a degassed suspension of (6S,8R)-6-(4-bromo-2,6-difluorophenyl)-7-(2-fluoro-2-methylpropyl)-6,8-dimethyl-3-(tetrahydro-2H-pyran-2-yl)-6,7,8,9-tetrahydro-3H-pyrazolo[4,3-f]isoquinoline (55 mg, 0.10 mmol), RockPhos 3rd Generation Precatalyst (4 mg, 0.005 mmol) and cesium carbonate (81 mg, 0.25 mmol) in toluene (0.7 mL). The reaction was heated to 90° C. and maintained under these conditions for 90 minutes. After cooling, the reaction was diluted with EtOAc and washed with water. The aqueous layer was extracted with EtOAc, then the combined organic layers were dried over sodium sulfate and concentrated under reduced pressure to dryness. The resulting residue was taken up in MeOH (0.5 mL) and HCl in dioxane (4N; 0.25 mL) was added. Stirring was continued for 10 minutes. The solvents were evaporated, and the resulting residue was dissolved in DCM and washed with saturated aqueous NaHCO$_3$. The aqueous layer was extracted with DCM, and then the combined organic layers were dried over sodium sulfate and concentrated under reduced pressure to dryness. The resulting residue was purified by flash silica chromatography, elution gradient 0 to 20% MeOH in DCM. Product fractions were concentrated and lyophilized to afford (6S,8R)-6-(2,6-difluoro-4-(2-(3-(fluoromethyl)azetidin-1-yl)ethoxy)phenyl)-7-(2-fluoro-2-methylpropyl)-6,8-dimethyl-6,7,8,9-tetrahydro-3H-pyrazolo[4,3-f]isoquinoline (30 mg, 58%) as a beige solid. $^1$H NMR (500 MHz DMSO-d$_6$, 27° C.) 0.93 (3H, d), 1.07 (3H, d), 1.11 (3H, d), 1.79 (3H, s), 2.67 (4H, m), 2.97 (3H, m), 3.11 (2H, q), 3.30 (2H, m), 3.80 (1H, m), 3.87 (2H, m), 4.44 (1H, d), 4.54 (1H, d), 6.46 (2H, d), 6.85 (1H, d), 7.19 (1H, d), 8.09 (1H, s), 12.94 (1H, s)). m/z: ES+ [M+H]+ 519.

The (6S,8R)-6-(4-bromo-2,6-difluorophenyl)-7-(2-fluoro-2-methylpropyl)-6,8-dimethyl-3-(tetrahydro-2H-pyran-2-yl)-6,7,8,9-tetrahydro-3H-pyrazolo [4,3-f]isoquinoline was prepared as follows;

Preparation of (6S,8R)-6-(4-bromo-2,6-difluorophenyl)-7-(2-fluoro-2-methylpropyl)-6,8-dimethyl-3-(tetrahydro-2H-pyran-2-yl)-6,7,8,9-tetrahydro-3H-pyrazolo[4,3-f]isoquinoline

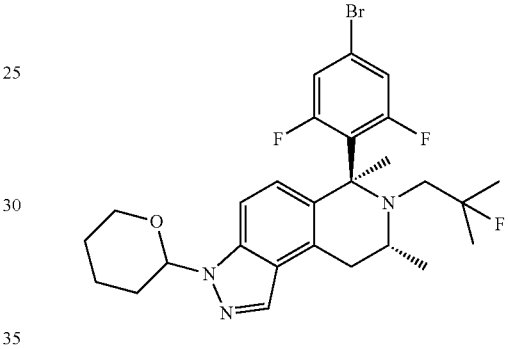

Bis(trifluoracetoxy)-iodobenzene (144 mg, 0.34 mmol) was added to a solution of (6S,8R)-6-(4-bromo-2,6-difluorophenyl)-7-(2-fluoro-2-methylpropyl)-8-methyl-3-(tetrahydro-2H-pyran-2-yl)-6,7,8,9-tetrahydro-3H-pyrazolo[4,3-f]isoquinoline (120 mg, 0.22 mmol) in THF (1.5 mL) at room temperature. The reaction was stirred for 1 hour and then cooled to −78° C. Methylmagnesium bromide in ether (3 M; 0.597 mL, 1.79 mmol) was added dropwise, and stifling was continued under these conditions for 45 minutes. The reaction was quenched by a slow addition of saturated aqueous ammonium chloride at 4° C. and then extracted with DCM (3×30 mL). The combined organic layers were washed with saturated aqueous sodium chloride, dried over Na$_2$SO$_4$, filtered and concentrated to dryness. The resulting residue was purified by flash silica chromatography, elution gradient 0 to 70% EtOAc in hexane. Product fractions were concentrated to dryness to afford (6S,8R)-6-(4-bromo-2,6-difluorophenyl)-7-(2-fluoro-2-methylpropyl)-6,8-dimethyl-3-(tetrahydro-2H-pyran-2-yl)-6,7,8,9-tetrahydro-3H-pyrazolo[4,3-f]isoquinoline as a pale foam (62 mg, 50%). $^1$H NMR (500 MHz DMSO-d$_6$, 27° C.) 0.94 (3H, d), 1.08 (3H, q), 1.18 (3H, d), 1.61 (2H, m), 1.75 (1H, m), 1.81 (3H, s), 1.97 (1H, m), 2.07 (1H, dt), 2.22 (1H, m), 2.43 (1H, dd), 2.91 (1H, dd), 3.13 (1H, t), 3.26 (1H, dt), 3.76 (2H, m), 4.02 (1H, dd), 5.71 (1H, dt), 6.79 (1H, d), 7.26 (2H, d), 7.31 (1H, d), 8.54 (1H, s). m/z: ES+ [M+H] 550.

Example 3

Preparation of (6S,8S)-6-(2,6-difluoro-4-(2-(3-(fluoromethyl)azetidin-1-yl)ethoxy)phenyl)-8-(difluoromethyl)-7-(2-fluoro-2-methylpropyl)-6,7,8,9-tetrahydro-3H-pyrazolo[4,3-f]isoquinoline

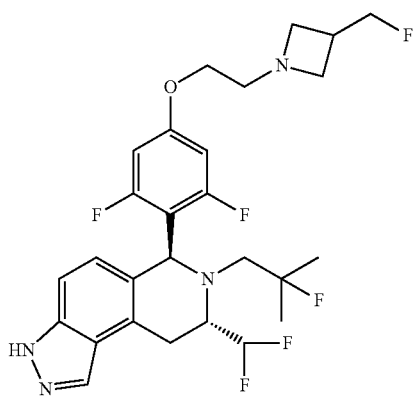 [SMILES: CC(C)(F)CN1[C@H](c2c(F)cc(OCCN3CC(CF)C3)cc2F)c2ccc3[nH]ncc3c2C[C@H]1C(F)F]

4N HCl in dioxane (0.44 mL) was added to a solution of (6S,8S)-6-(2,6-difluoro-4-(2-(3-(fluoromethyl)azetidin-1-yl)ethoxy)phenyl)-8-(difluoromethyl)-7-(2-fluoro-2-methylpropyl)-3-(tetrahydro-2H-pyran-2-yl)-6,7,8,9-tetrahydro-3H-pyrazolo[4,3-f]isoquinoline (110 mg, 0.18 mmol) in methanol (0.44 mL) and the reaction was stirred at room temperature for 2 hours. The crude product was purified by ion exchange chromatography, using an SCX column. The desired product was eluted from the column using 1M NH$_3$/MeOH and product fractions were concentrated to dryness to afford (6S,8S)-6-(2,6-difluoro-4-(2-(3-(fluoromethyl)azetidin-1-yl)ethoxy)phenyl)-8-(difluoromethyl)-7-(2-fluoro-2-methylpropyl)-6,7,8,9-tetrahydro-3H-pyrazolo[4,3-f]isoquinoline (81 mg, 85%) as a pale yellow solid. $^1$H NMR (500 MHz, CDCl$_3$, 27° C.) 1.15 (3H, d), 1.24 (3H, d), 2.51 (1H, dd), 2.79-2.98 (3H, m), 3.16-3.29 (3H, m), 3.32-3.50 (2H, m), 3.56 (2H, d), 3.90-3.94 (3H, m), 4.45 (1H, d), 4.54 (1H, d), 5.53 (1H, s), 5.87 (1H, td), 6.34 (2H, d), 6.80 (1H, d), 7.20 (1H, d), 8.09 (1H, d), 10.55 (1H, s). m/z: ES+ [M+H]+ 541.

The (6S,8S)-6-(2,6-difluoro-4-(2-(3-(fluoromethyl)azetidin-1-yl)ethoxy)phenyl)-8-(difluoromethyl)-7-(2-fluoro-2-methylpropyl)-3-(tetrahydro-2H-pyran-2-yl)-6,7,8,9-tetrahydro-3H-pyrazolo[4,3-f]isoquinoline was prepared as follows;

Preparation of 3-bromo-2-methylbenzaldehyde

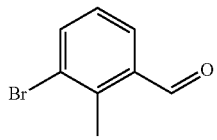

n-BuLi (1.6M in hexanes, 28.5 mL, 45.6 mmol) was added dropwise to a solution of 1,3-dibromo-2-methylbenzene (9.50 g, 38.0 mmol) in THF (119 mL) at −78° C. and the reaction was maintained at this temperature for 30 minutes. N,N-Dimethylformamide (4.41 mL, 57.0 mmol) was added and the reaction was stirred for a further 30 min, before being allowed to warm to 0° C. over 1 hour. The reaction was quenched by addition of water, then was extracted with EtOAc. The organic phase was dried over magnesium sulfate and concentrated to dryness to afford 3-bromo-2-methylbenzaldehyde (7.19 g, 95%) as a straw coloured oil. $^1$H NMR (500 MHz, CDCl$_3$, 27° C.) 2.75 (3H, s), 7.18-7.37 (1H, m), 7.78 (2H, ddd), 10.26 (1H, s).

Preparation of (3-bromo-2-methylphenyl)methanol

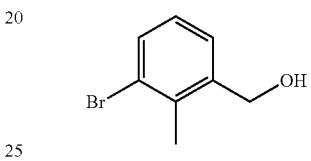

Sodium borohydride (1.78 g, 47.1 mmol) was added to a solution of 3-bromo-2-methylbenzaldehyde (7.50 g, 37.7 mmol) in THF (151 mL) and the reaction was stirred at room temperature for 2 hours. The reaction was cooled in an ice-bath and quenched by addition of 2N HCl solution, then extracted with EtOAc (×2). The combined organics were washed with saturated aqueous sodium chloride, dried over magnesium sulfate and concentrated to dryness to afford (3-bromo-2-methylphenyl)methanol (7.73 g,>100%) as a pale yellow solid. $^1$H NMR (500 MHz, CDCl$_3$, 27° C.) 1.99 (1H, br s), 2.41 (3H, s), 4.70 (2H, s), 7.05 (1H, t), 7.30 (1H, d), 7.49-7.53 (1H, m).

Preparation of 1-bromo-3-(bromomethyl)-2-methylbenzene

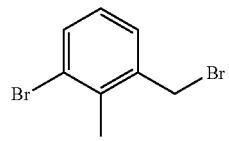

Perbromomethane (14.35 g, 43.3 mmol) was added portionwise to a solution of (3-bromo-2-methylphenyl)methanol (7.25 g, 36.1 mmol) and triphenylphosphine (11.35 g, 43.27 mmol) in DCM (120 mL) (reaction exotherms to ~40° C.) and the reaction was stirred at room temperature for 2 hours. The residue was passed through a pad of silica, eluting with DCM. The filtrate was concentrated to dryness, then the crude product was purified by flash silica chromatography, elution gradient 0 to 25% EtOAc in heptane. Product fractions were concentrated to dryness to afford 1-bromo-3-(bromomethyl)-2-methylbenzene (8.52 g, 90%) as a colourless oil. $^1$H NMR (500 MHz, CDCl$_3$, 27° C.) 2.48 (3H, s), 4.52 (2H, s), 6.99-7.05 (1H, m), 7.22-7.27 (1H, m), 7.52 (1H, dd).

Preparation of tert-butyl (S)-3-(3-bromo-2-methylphenyl)-2-((diphenylmethylene) amino)propanoate

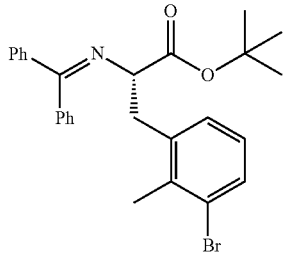 [SMILES: Cc1c(Br)cccc1C[C@H](N=C(c1ccccc1)c1ccccc1)C(=O)OC(C)(C)C]

1-Bromo-3-(bromomethyl)-2-methylbenzene (6.86 g, 26.0 mmol) was added to a solution of tert-butyl 2-((diphenylmethylene)amino)acetate (7.68 g, 26 mmol) and (1S,2S,4S,5R)-2-((R)-(allyloxy)(quinolin-4-yl)methyl)-1-(anthracen-9-ylmethyl)-5-vinylquinuclidin-1-ium bromide (1.58 g, 2.60 mmol) in toluene (130 mL) and 50% aq. KOH solution (15.08 g, 130.0 mmol). The biphasic mixture was stirred vigourously at 0° C. (ice-bath) for 4 hours. The reaction was diluted by addition of water (100 mL), then extracted with EtOAc (×2). The combined organics were washed with saturated aqueous sodium chloride, dried over magnesium sulfate and concentrated to dryness. The crude product was purified by flash silica chromatography, elution gradient 0 to 50% EtOAc in heptane. Product fractions were concentrated to dryness to afford tert-butyl (S)-3-(3-bromo-2-methylphenyl)-2-((diphenylmethylene)amino)propanoate (9.96 g, 80%) as a pale yellow liquid. $^1$H NMR (500 MHz, CDCl$_3$, 27° C.) 1.46 (9H, s), 1.99 (3H, s), 3.17 (1H, dd), 3.34 (1H, dd), 4.12 (1H, dd), 6.48 (2H, s), 6.82-6.89 (1H, m), 7.01 (1H, dd), 7.25-7.41 (7H, m), 7.53-7.59 (2H, m). m/z: ES+ [M+H]+ 478. Chiral analysis using analytical HPLC (Regis (R,R)Whelk-O1 column, 5µm silica, 4.6 mm diameter, 250 mm length), using a 95/05 mixture of Heptane/EtOH as eluents at 2 mL/min showed the product existed in a 98.3:1.7 ratio of isomers.

Preparation of tert-butyl (S)-2-amino-3-(3-bromo-2-methylphenyl)propanoate

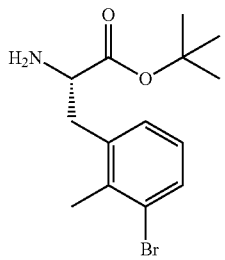 [SMILES: Cc1c(Br)cccc1C[C@H](N)C(=O)OC(C)(C)C]

Tert-butyl (S)-3-(3-bromo-2-methylphenyl)-2-((diphenylmethylene)amino)propanoate (9.0 g, 18.8 mmol) was stirred in EtOAc (63 mL) and 2N HCl (31.5 mL) at room temperature for 1 hour. The aqueous layer was basified by addition of 2N NaOH solution, then extracted with EtOAc (×2). The combined organics were dried over magnesium sulfate and concentrated to dryness. The crude product was purified by flash silica chromatography, elution gradient 0 to 100% EtOAc in heptane. Product fractions were concentrated to dryness to afford tert-butyl (S)-2-amino-3-(3-bromo-2-methylphenyl)propanoate (4.98 g, 84%) as a pale yellow oil. $^1$H NMR (500 MHz, CDCl$_3$, 27° C.) 1.40 (9H, s), 2.44 (3H, s), 2.80 (1H, dd), 3.12 (1H, dd), 3.55 (1H, dd), 6.94-7.00 (1H, m), 7.07-7.12 (1H, m), 7.45 (1H, dd). m/z: ES+ [M+H]+ 314.

Preparation of (S)-2-amino-3-(3-bromo-2-methylphenyl)propan-1-ol

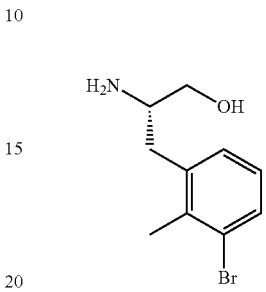

Lithium borohydride solution (2M in THF; 14.38 mL, 28.75 mmol) was added to a solution of tert-butyl (S)-2-amino-3-(3-bromo-2-methylphenyl)propanoate (7.23 g, 23.0 mmol) in THF (78 mL). The reaction was heated to 50° C. and maintained under these conditions for 1 hour. After cooling in an ice-bath, the reaction was quenched by addition of 1N HCl solution. The aqueous layer was then basified by addition of 2N NaOH and extracted with EtOAc (×3). The combined organics were dried over magnesium sulfate and concentrated to dryness to afford (S)-2-amino-3-(3-bromo-2-methylphenyl)propan-1-ol (5.93 g, >100%) as a straw coloured oil. $^1$H NMR (500 MHz, CDCl$_3$, 27° C.) 1.91-2.04 (2H, m), 2.41 (3H, s), 2.60 (1H, dd), 2.88 (1H, dd), 3.01-3.14 (1H, m), 3.40 (1H, dd), 3.63 (1H, dd), 6.94-7.01 (1H, m), 7.08 (1H, dd), 7.13 (1H, dd), 7.45 (1H, dd). m/z: ES+ [M+H]+ 244.

Preparation of (S)-3-(3-bromo-2-methylphenyl)-2-((2-fluoro-2-methylpropyl)amino)propan-1-ol

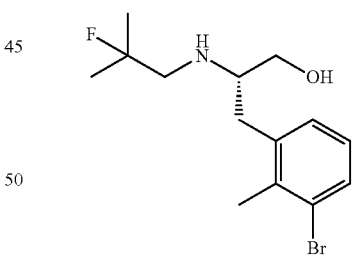

2-Fluoro-2-methylpropyl trifluoromethanesulfonate (6.08 g, 27.1 mmol) was added to a solution of (S)-2-amino-3-(3-bromo-2-methylphenyl)propan-1-ol (5.30 g, 21.7 mmol) and DIPEA (5.63 mL, 32.6 mmol) in 1,4-dioxane (56.4 mL). The reaction was heated to 90° C. and maintained under these conditions overnight. The volatiles were concentrated to dryness, then the residue was dissolved in EtOAc and washed with water. The aqueous layer was extracted with EtOAc, then the combined organics were dried over sodium sulfate and concentrated to dryness. The crude product was purified by flash silica chromatography, elution gradient 0 to 100% EtOAc in heptane. Product fractions were concentrated to dryness to afford (S)-3-(3-bromo-2-methylphenyl)-

2-((2-fluoro-2-methylpropyl)amino)propan-1-ol (5.65 g, 82%) as a light brown oil. $^1$H NMR (500 MHz, CDCl$_3$, 27° C.) 1.34 (3H, d), 1.38 (3H, d), 2.42 (3H, s), 2.61 (1H, dd), 2.74-2.91 (4H, m), 3.30 (1H, dd), 3.54-3.59 (1H, m), 6.95-7.01 (1H, m), 7.08 (1H, dd), 7.44 (1H, dd). m/z: ES+ [M+H]+ 318.

Preparation of (S)-3-(3-amino-2-methylphenyl)-2-((2-fluoro-2-methylpropyl)amino)propan-1-ol

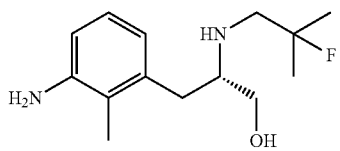 [SMILES: Cc1c(N)cccc1C[C@@H](CO)NCC(C)(C)F]

Sodium tert-butoxide (2.64 g, 27.4 mmol) and Pd$_2$(dba)'$_3$ (0.373 g, 0.46 mmol) were added to a degassed solution of (S)-3-(3-bromo-2-methylphenyl)-2-((2-fluoro-2-methylpropyl)amino)propan-1-ol (5.82 g, 18.3 mmol), diphenylmethanimine (3.22 mL, 19.2 mmol) and rac-BINAP (0.569 g, 0.91 mmol) in toluene (70 mL). The reaction was heated to 90° C. and maintained under these conditions for 2 hours. After cooling, EtOAc and saturated aqueous NH4Cl solution were added and the layers were separated. The aqueous layer was extracted with EtOAc, then the combined organics were concentrated to dryness. The residue was dissolved in EtOAc (50 mL) and 2N HCl (50 mL) was added. The biphasic mixture was stirred vigorously for 1 hour, then the layers were separated. The aqueous layer was extracted with EtOAc, then the organics were extracted with 2N HCl. The combined aqueous layers were bascified by addition of solid K$_2$CO$_3$, then extracted with DCM (×3). The combined DCM extracts were dried over sodium sulfate and concentrated to dryness to afford (S)-3-(3-amino-2-methylphenyl)-2-((2-fluoro-2-methylpropyl)amino)propan-1-ol (4.27 g, 92%) as a light brown oil, which was used directly. $^1$H NMR (500 MHz, CDCl$_3$, 27° C.) 1.33 (3H, d), 1.37 (3H, d), 2.12 (3H, s), 2.58 (1H, dd), 2.66-2.76 (1H, m), 2.78-2.81 (1H, m), 2.82 (1H, d), 2.84-2.89 (1H, m), 3.31 (1H, dd), 3.58 (1H, dd), 3.60 (2H, s), 6.59 (2H, d), 6.90-7.01 (1H, m). m/z: ES+ [M+H]+ 255.

Preparation of ((lS,3S)-6-amino-1-(4-bromo-2,6-difluorophenyl)-2-(2-fluoro-2-methylpropyl)-5-methyl-1,2,3,4-tetrahydroisoauinolin-3-yl)methanol

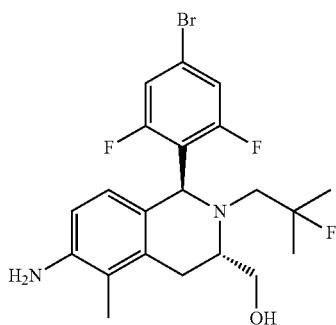 [SMILES: Cc1c(N)ccc2c1C[C@@H](CO)N(CC(C)(C)F)[C@@H]2c1c(F)cc(Br)cc1F]

(S)-3-(3-Amino-2-methylphenyl)-2-((2-fluoro-2-methylpropyl)amino)propan-1-ol (4.20 g, 16.5 mmol) and 4-bromo-2,6-difluorobenzaldehyde (7.85 g, 35.5 mmol) were heated in a mixture of acetic acid (72 mL) and water (1.5 mL) to 65° C. and the reaction was maintained under these conditions overnight. After cooling, the solvent was evaporated, then the residue was dissolved in DCM (60 mL) and washed with saturated aqueous NaHCO$_3$ solution. To the organic phase was then added 2N HCl solution (60 mL) and the biphasic mixture was stirred vigourously for 30 min. The layers were separated and the organic layer was extracted with 2N HCl (×2). The aqueous layer was basified by addition of 2N NaOH solution, then extracted with DCM (×2). The combined organics were dried over magnesium sulfate and concentrated to dryness. The crude mixture was dissolved in THF (20 mL) and MeOH (10 mL), then 2N NaOH solution (10 mL) was added, and the reaction was stirred at room temperature for 1 hour. The reaction was extracted with EtOAc (×2), then the combined organics were dried over magnesium sulfate and concentrated to dryness. The crude product was purified by flash silica chromatography, elution gradient 0 to 100% EtOAc in heptane. Product fractions were concentrated to dryness to afford ((lS,3S)-6-amino-1-(4-bromo-2,6-difluorophenyl)-2-(2-fluoro-2-methylpropyl)-5-methyl-1,2,3,4-tetrahydroisoquinolin-3-yl)methanol (4.15 g, 55%) as a pale yellow solid. $^1$H NMR (500 MHz, CDCl$_3$, 27° C.) 1.32 (3H, d), 1.37 (3H, d), 2.07 (3H, s), 2.46 (1H, dd), 2.57 (1H, dd), 2.65 (1H, dd), 2.80 (1H, dd), 3.38-3.52 (1H, m), 3.56 (1H, dd), 3.66 (1H, dd), 5.33 (1H, s), 6.50 (1H, d), 6.58 (1H, d), 6.94-7.02 (2H, m). m/z: ES+ [M+H]+ 457.

Preparation of ((6S,8S)-6-(4-bromo-2,6-difluorophenyl)-7-(2-fluoro-2-methylpropyl)-6,7,8,9-tetrahydro-3H-pyrazolo[4,3-f]isoquinline-8-yl)methanol

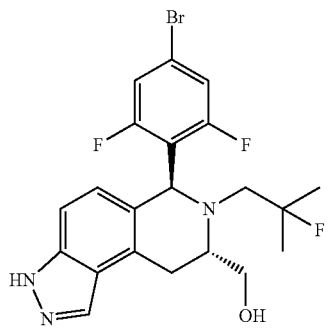 [SMILES: CC(C)(F)CN1[C@H](CO)Cc2c(ccc3[nH]ncc23)[C@H]1c1c(F)cc(Br)cc1F]

Sodium nitrite (145 mg, 2.10 mmol) was added to a cooled solution of ((lS,3S)-6-amino-1-(4-bromo-2,6-difluorophenyl)-2-(2-fluoro-2-methylpropyl)-5-methyl-1,2,3,4-tetrahydroisoquinolin-3-yl)methanol (915 mg, 2.00 mmol) in propionic acid (5 mL)/water (1 mL) at −10° C. and the reaction was maintained under these conditions for 1 hour. Water (20 mL) and DCM (40 mL) were added and the layers were separated. The aqueous layer was extracted with DCM (×2), then the combined organics were washed with saturated aqueous NaHCO$_3$ solution, dried over sodium sulfate and concentrated to dryness. The crude product was purified by flash silica chromatography, elution gradient 0 to 100% EtOAc in heptane. Product fractions were concentrated to dryness to afford ((6S,8S)-6-(4-bromo-2,6-difluorophenyl)-7-(2-fluoro-2-methylpropyl)-6,7,8,9-tetrahydro-3H-pyrazolo[4,3-f]isoquinolin-8-yl)methanol (424 mg, 45%) as a beige solid. $^1$H NMR (500 MHz, CDCl$_3$, 27 ° C.) 1.31 (3H, d), 1.36 (3H, d), 2.52 (1H, dd), 2.95 (1H, dd), 3.05 (1H, dd), 3.12 (1H, dd), 3.62 (2H, dd), 3.70-3.90 (1H, m), 5.50 (1H, s), 6.87 (1H, d), 7.01 (2H, d), 7.19-7.25 (1H, m), 8.08 (1H, d). m/z: ES+ [M+H]+ 468.

Preparation of (6S,8S)-6-(4-bromo-2,6-difluorophenyl)-7-(2-fluoro-2-methylpropyl)-6,7,8,9-tetrahydro-3H-pyrazolo[4,3-f]isoquinoline-8-carbaldehyde

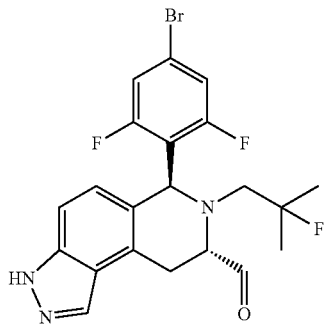 [SMILES: CC(C)(F)CN1[C@H](c2c(F)cc(Br)cc2F)c2ccc3[nH]ncc3c2C[C@H]1C=O]

Sufur trioxide pyridine complex (477 mg, 3.00 mmol) was added dropwise in DMSO (5.7 mL) to a cooled solution of ((6S,8S)-6-(4-bromo-2,6-difluorophenyl)-7-(2-fluoro-2-methylpropyl)-6,7,8,9-tetrahydro-3H-pyrazolo[4,3-f]isoquinolin-8-yl)methanol (702 mg, 1.50 mmol) and triethylamine (0.5 mL, 3.75 mmol) in a mixture of DCM (5.7 mL)/DMSO (5.7 mL) at 0° C. and the reaction was allowed to warm to room temperature over 2 hours. The reaction was diluted with DCM (50 mL) and water (50 mL), and the layers were separated. The aqueous layer was extracted with DCM (×2), then the combined organics were washed with saturated aqueous sodium chloride, dried over magnesium sulfate and concentrated to dryness. The crude product was purified by flash silica chromatography, elution gradient 0 to 100% EtOAc in heptane. Product fractions were concentrated to dryness to afford (6S,8S)-6-(4-bromo-2,6-difluorophenyl)-7-(2-fluoro-2-methylpropyl)-6,7,8,9-tetrahydro-3H-pyrazolo[4,3-f]isoquinoline-8-carbaldehyde (512 mg, 73%) as a beige solid. $^1$H NMR (500 MHz, CDCl$_3$, 27° C.) 1.10 (3H, d), 1.23 (3H, d), 2.56 (1H, dd), 3.35 (1H, t), 3.50 (1H, dd), 3.58 (1H, dd), 4.41 (1H, dt), 5.90 (1H, s), 6.78 (1H, d), 6.92-7.1 (2H, m), 7.20 (1H, d), 8.11 (1H, d), 9.75 (1H, s), 10.12 (1H, s). m/z: ES+ [M+H]+ 466.

Preparation of (6S,8S)-6-(4-bromo-2,6-difluorophenyl)-7-(2-fluoro-2-methylpropyl)-3-(tetrahydro-2H-pyran-2-yl)-6,7,8,9-tetrahydro-3H-pyrazolo[4,3-f]isoquinoline-8-carbaldehyde

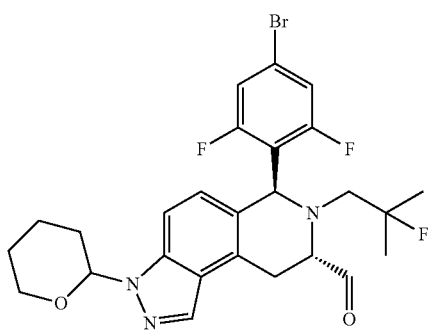 [SMILES: CC(C)(F)CN1[C@H](c2c(F)cc(Br)cc2F)c2ccc3c(cnn3C3CCCCO3)c2C[C@H]1C=O]

3,4-Dihydro-2H-pyran (0.24 mL, 2.57 mmol) and p-toluenesulphonic acid hydrate (32.8 mg, 0.17 mmol) were added to a solution of (6S,8S)-6-(4-bromo-2,6-difluorophenyl)-7-(2-fluoro-2-methylpropyl)-6,7,8,9-tetrahydro-3H-pyrazolo[4,3-f]isoquinoline-8-carbaldehyde (800 mg, 1.72 mmol) in DCM (8.3 mL) and the reaction was stirred at room temperature for 1 hour, followed by heating to reflux and maintaining under these conditions for 3 hours. After cooling, the reaction was diluted with DCM (25 mL) and washed with saturated aqueous NaHCO$_3$ solution (25 mL), then dried over sodium sulfate and concentrated to dryness. The crude product was purified by flash silica chromatography, elution gradient 0 to 50% EtOAc in heptane. Product fractions were concentrated to dryness to afford (6S,8S)-6-(4-bromo-2,6-difluorophenyl)-7-(2-fluoro-2-methylpropyl)-3-(tetrahydro-2H-pyran-2-yl)-6,7,8,9-tetrahydro-3H-pyrazolo[4,3-f]isoquinoline-8-carbaldehyde (772 mg, 82%) as a pale yellow solid. $^1$H NMR (500 MHz, CDCl$_3$, 27° C.) 1.09 (3H, d), 1.23 (3H, dd), 1.59-1.68 (1H, m), 1.69-1.81 (2H, m), 2.00-2.09 (1H, m), 2.09-2.20 (1H, m), 2.43-2.65 (2H, m), 3.27-3.44 (1H, m), 3.48 (1H, dt), 3.51-3.60 (1H, m), 3.66-3.74 (1H, m), 3.94-4.07 (1H, m), 4.38 (1H, ddt), 5.64 (1H, ddd), 5.89 (1H, s), 6.77 (1H, d), 7.01 (2H, d), 7.27-7.33 (1H, m), 8.05 (1H, d), 9.72 (1H, d). m/z: ES+ [M+H]+ 550.

Preparation of (6S,8S)-6-(4-bromo-2,6-difluorophenyl)-8-(difluoromethyl)-7-(2-fluoro-2-methylpropyl)-3-(tetrahydro-2H-pyran-2-yl)-6,7,8,9-tetrahydro-3H-pyrazolo[4,3-f]isoquinoline

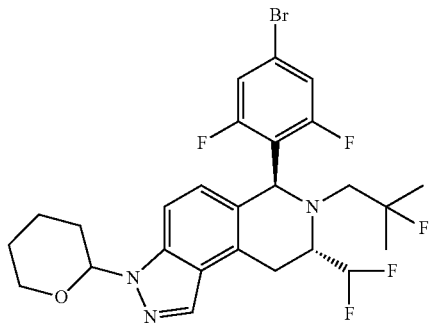 [SMILES: CC(C)(F)CN1[C@H](c2c(F)cc(Br)cc2F)c2ccc3c(cnn3C3CCCCO3)c2C[C@H]1C(F)F]

Diethylaminosulfur trifluoride (0.384 mL, 2.91 mmol) was added to a cooled solution of (6S,8S)-6-(4-bromo-2,6-difluorophenyl)-7-(2-fluoro-2-methylpropyl)-3-(tetrahydro-2H-pyran-2-yl)-6,7,8,9-tetrahydro-3H-pyrazolo[4,3-f]isoquinoline-8-carbaldehyde (800 mg, 1.45 mmol) in DCM (13.3 mL) at 0° C. The reaction was allowed to warm to room temperature and stirred for 5 hours. After dilution with DCM (20 mL), the reaction was quenched by addition of saturated aqueous NaHCO$_3$ solution. The layers were separated, then the aqueous layer was extracted with DCM. The combined organics were dried over sodium sulfate and concentrated to dryness. The crude product was purified by flash silica chromatography, elution gradient 0 to 25% EtOAc in heptane. Product fractions were concentrated to dryness to afford (6S,8S)-6-(4-bromo-2,6-difluorophenyl)-8-(difluoromethyl)-7-(2-fluoro-2-methylpropyl)-3-(tetrahydro-2H-pyran-2-yl)-6,7,8,9-tetrahydro-3H-pyrazolo[4,3-f]isoquinoline (753 mg, 91%) as a beige solid. ¹H NMR (500 MHz, CDCl₃, 27° C.) 1.15 (3H, d), 1.26 (3H, dd), 1.59-1.83 (3H, m), 2.04-2.11 (1H, m), 2.14 (1H, dd), 2.41-2.51 (1H, m), 2.51-2.64 (1H, m), 3.25 (1H, dt), 3.34-3.52 (2H, m), 3.72 (1H, ddd), 3.91 (1H, s), 3.97-4.05 (1H, m), 5.59 (1H, s), 5.66 (1H, dt), 5.83 (1H, tdd), 6.78 (1H, dd), 7.01 (2H, d), 7.31 (1H, dd), 8.04 (1H, d). m/z: ES+ [M+H]+ 572.

Preparation of (6S,8S)-6-(2,6-difluoro-4-(2-(3-(fluoromethyl)azetidin-1-yl)ethoxy)phenyl)-8-(difluoromethyl)-7-(2-fluoro-2-methylpropyl)-3-(tetrahydro-2H-pyran-2-yl)-6,7,8,9-tetrahydro-3H-pyrazolo[4,3-f]isoquinoline

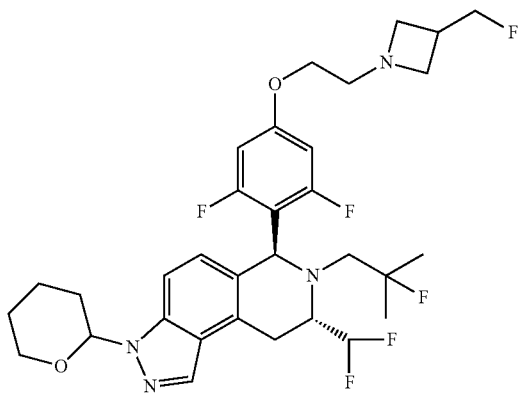 [SMILES: CC(C)(F)CN1[C@H](c2c(F)cc(OCCN3CC(CF)C3)cc2F)c2ccc3c(cnn3C3CCCCO3)c2C[C@H]1C(F)F]

2-(3-(Fluoromethyl)azetidin-1-yl)ethan-1-ol (64 mg, 0.48 mmol) was added to a degassed suspension of (6S,8S)-6-(4-bromo-2,6-difluorophenyl)-8-(difluoromethyl)-7-(2-fluoro-2-methylpropyl)-3-(tetrahydro-2H-pyran-2-yl)-6,7,8,9-tetrahydro-3H-pyrazolo[4,3-f]isoquinoline (137 mg, 0.24 mmol), RockPhos 3rd Generation Precatalyst (8 mg, 0.01 mmol) and cesium carbonate (195 mg, 0.60 mmol) in degassed toluene (2.0 mL). The reaction was heated to 90° C. and maintained under these conditions overnight. After cooling, the reaction was diluted with EtOAc and washed with water. The aqueous layer was extracted with EtOAc, then the combined organics were dried over sodium sulfate and concentrated to dryness. The crude product was purified by flash silica chromatography, elution gradient 0 to 10% MeOH in EtOAc. Product fractions were concentrated to dryness to afford (6S,8S)-6-(2,6-difluoro-4-(2-(3-(fluoromethyl)azetidin-1-yl)ethoxy)phenyl)-8-(difluoromethyl)-7-(2-fluoro-2-methylpropyl)-3-(tetrahydro-2H-pyran-2-yl)-6,7,8,9-tetrahydro-3H-pyrazolo[4,3-f]isoquinoline (116 mg, 77%) as a pale yellow gum. ¹H NMR (500 MHz, CDCl₃, 27° C.) 1.14 (3H, d), 1.23 (3H, d), 1.59-1.79 (3H, m), 2.05-2.19 (2H, m), 2.43-2.62 (2H, m), 2.80 (2H, t), 2.81-2.92 (1H, m), 3.08-3.17 (2H, m), 3.23 (1H, dt), 3.33-3.45 (2H, m), 3.44-3.52 (2H, m), 3.71 (1H, ddd), 3.85-3.90 (2H, m), 3.90-3.97 (1H, m), 3.97-4.04 (2H, m), 4.33-4.50 (1H, m), 4.51-4.58 (1H, m), 5.52 (1H, s), 5.65 (1H, dt), 5.84 (1H, tdd), 6.30-6.40 (2H, m), 6.81 (1H, d), 7.29 (1H, dd), 8.03 (1H, s). m/z: ES+ [M+H]+ 625.

Example 4

Preparation of (6S,8S)-6-(2,6-difluoro-4-(2-(3-(fluoromethyl)azetidin-1-yl)ethoxy)phenyl)-8-(difluoromethyl)-7-(2-fluoro-2-methylpropyl)-6-methyl-6,7,8,9-tetrahydro-3H-pyrazolo[4,3-f]isoquinoline

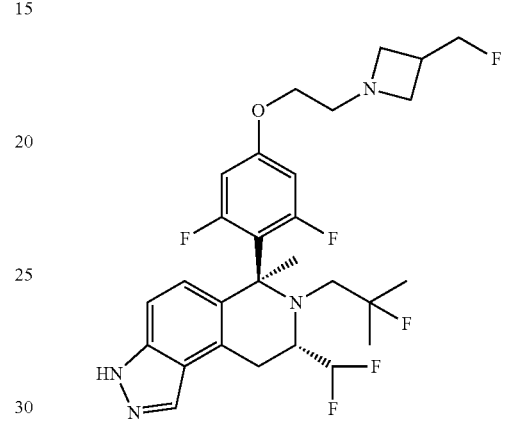

HCl-dioxane (0.42 mL) was added to a solution of (6S,8S)-6-(2,6-difluoro-4-(2-(3-(fluoromethyl)azetidin-1-yl)ethoxy)phenyl)-8-(difluoromethyl)-7-(2-fluoro-2-methylpropyl)-6-methyl-3-(tetrahydro-2H-pyran-2-yl)-6,7,8,9-tetrahydro-3H-pyrazolo[4,3-f]isoquinoline (106 mg, 0.17 mmol) in methanol (0.42 mL) and the reaction was stirred at room temperature for 3 hours. The solvents were evaporated, then the residue was dissolved in DCM and washed with saturated aqueous NaHCO₃ solution. The aqueous was extracted with DCM, then the combined organics were dried over sodium sulfate and concentrated to dryness. The crude product was purified by flash silica chromatography, elution gradient 0 to 20% MeOH in EtOAc. Product fractions were concentrated to dryness to afford (6S,8S)-6-(2,6-difluoro-4-(2-(3-(fluoromethyl)azetidin-1-yl)ethoxy)phenyl)-8-(difluoromethyl)-7-(2-fluoro-2-methylpropyl)-6-methyl-6,7,8,9-tetrahydro-3H-pyrazolo[4,3-f]isoquinoline (82 mg, 89%) as a beige solid. ¹H NMR (500 MHz, CDCl₃, 27° C.) 0.98 (3H, d), 1.18 (3H, d), 1.90 (3H, t), 2.55 (1H, dd), 2.79-2.95 (3H, m), 3.18 (2H, ddd), 3.23 (1H, d), 3.44-3.56 (3H, m), 3.62 (1H, dd), 3.83-3.92 (2H, m), 4.09 (1H, d), 4.43 (1H, d), 4.52 (1H, d), 5.90 (1H, td), 6.21 (2H, d), 6.92 (1H, d), 7.17 (1H, d), 8.10 (1H, d). m/z: ES+ [M+H]+ 555.

The (6S,8S)-6-(2,6-difluoro-4-(2-(3-(fluoromethyl)azetidin-1-yl)ethoxy)phenyl)-8-(difluoromethyl)-7-(2-fluoro-2-methylpropyl)-6-methyl-3-(tetrahydro-2H-pyran-2-yl)-6,7,8,9-tetrahydro-3H-pyrazolo[4,3-f]isoquinoline was prepared as follows;

Preparation of (6S,8S)-6-(2,6-difluoro-4-(2-(3-(fluoromethyl)azetidin-1-yl)ethoxy)phenyl)-8-(difluoromethyl)-7-(2-fluoro-2-methylpropyl)-6-methyl-3-(tetrahydro-2H-pyran-2-yl)-6,7,8,9-tetrahydro-3H-pyrazolo[4,3-f]isoquinoline

Example 5

Preparation of (6S,8R)-7-(2-fluoro-2-methylpropyl)-6-(4-(2-(3-(fluoromethyl)azetidin-1-yl)ethoxy)-2-methoxyphenyl)-8-methyl-6,7,8,9-tetrahydro-3H-pyrazolo[4,3-f]isoquinoline

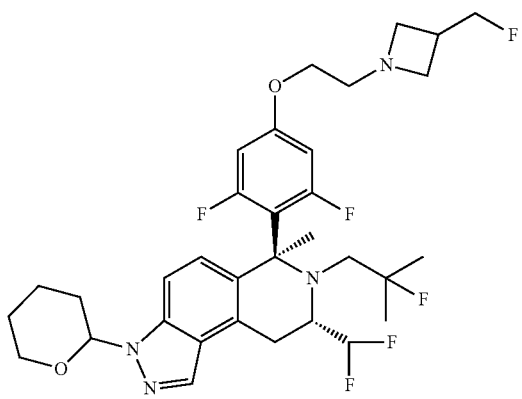 [SMILES: CC(C)(F)CN1[C@H](C(F)F)Cc2c(ccc3c2cnn3C2CCCCO2)[C@@]1(C)c1c(F)cc(OCCN2CC(CF)C2)cc1F]

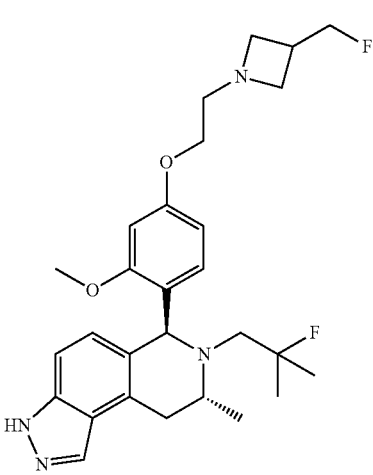 [SMILES: COc1cc(OCCN2CC(CF)C2)ccc1[C@@H]1c2ccc3[nH]ncc3c2C[C@@H](C)N1CC(C)(C)F]

2-(3-(Fluoromethyl)azetidin-1-yl)ethan-1-ol (64 mg, 0.48 mmol) was added to a degassed suspension of (6S,8S)-6-(4-bromo-2,6-difluorophenyl)-8-(difluoromethyl)-7-(2-fluoro-2-methylpropyl)-6-methyl-3-(tetrahydro-2H-pyran-2-yl)-6,7,8,9-tetrahydro-3H-pyrazolo[4,3-f]isoquinoline (141 mg, 0.24 mmol), RockPhos 3rd Generation Precatalyst (8 mg, 0.01 mmol) and cesium carbonate (195 mg, 0.60 mmol) in degassed toluene (2.0 mL). The reaction was heated to 90° C. and maintained under these conditions overnight. After cooling, the reaction was diluted with EtOAc and washed with water. The aqueous layer was extracted with EtOAc, then the combined organics were dried over sodium sulfate and concentrated to dryness. The crude product was purified by flash silica chromatography, elution gradient 0 to 10% MeOH in EtOAc. Product fractions were concentrated to dryness to afford (6S,8S)-6-(2,6-difluoro-4-(2-(3-(fluoromethyl)azetidin-1-yl)ethoxy)phenyl)-8-(difluoromethyl)-7-(2-fluoro-2-methylpropyl)-6-methyl-3-(tetrahydro-2H-pyran-2-yl)-6,7,8,9-tetrahydro-3H-pyrazolo[4,3-f]isoquinoline (111 mg, 72%) as a pale yellow gum. $^1$H NMR (500 MHz, CDCl$_3$, 27° C.) 0.98 (3H, dd), 1.18 (3H, d), 1.59-1.68 (1H, m), 1.68-1.80 (2H, m), 1.89 (3H, s), 2.05-2.10 (1H, m), 2.10-2.22 (1H, m), 2.45-2.63 (2H, m), 2.78 (2H, d), 2.80-2.92 (1H, m), 3.12 (2H, t), 3.21 (1H, d), 3.38-3.55 (3H, m), 3.55-3.67 (1H, m), 3.71 (1H, td), 3.85 (2H, t), 3.96-4.10 (2H, m), 4.43 (1H, dd), 4.53 (1H, dd), 5.65 (1H, ddd), 5.87 (1H, tdd), 6.26 (2H, d), 6.95 (1H, d), 7.29 (1H, dd), 8.04 (1H, dd). m/z: ES+ [M+H]+ 639.

To a solution of (6S,8R)-7-(2-fluoro-2-methylpropyl)-6-(4-(2-(3-(fluoromethyl)azetidin-1-yl)ethoxy)-2-methoxyphenyl)-8-methyl-2-(tetrahydro-2H-pyran-2-yl)-6,7,8,9-tetrahydro-2H-pyrazolo[4,3-f]isoquinoline and (6S,8R)-7-(2-fluoro-2-methylpropyl)-6-(4-(2-(3-(fluoromethyl)azetidin-1-yl)ethoxy)-2-methoxyphenyl)-8-methyl-3-(tetrahydro-2H-pyran-2-yl)-6,7,8,9-tetrahydro-3H-pyrazolo[4,3-f]isoquinoline (1.08 g, 1.85 mmol) in dichloromethane (6 mL) was added hydrogen chloride in dioxane, (4.0 M, 4.63 mL, 18.53 mmol) slowly. The sticky suspension was stirred vigorously for 30 minutes. The reaction mixture was evaporated to a solid, co-evaporated with toluene and dissolved in DMSO. The crude product was purified by preparative HPLC (Waters X-select, CSH, Prep C-18, 5 micron particle size) column, (30×100 mm), using decreasingly polar mixtures of water (containing 1% NH3) and MeCN as eluents. Fractions containing the desired compound were evaporated to dryness to afford (6S,8R)-7-(2-fluoro-2-methylpropyl)-6-(4-(2-(3-(fluoromethyl)azetidin-1-yl)ethoxy)-2-methoxyphenyl)-8-methyl-6,7,8,9-tetrahydro-3H-pyrazolo[4,3-f]isoquinoline (0.460 g, 50%) as an off-white foam. $^1$H NMR (500 MHz, CDCl$_3$, 27° C.) 1.05 (3H, d), 1.21-1.28 (6H, m), 2.34 (1H, dd), 2.79-2.89 (4H, m), 3.09-3.19 (2H, m), 3.24-3.36 (1H, m), 3.43-3.54 (3H, m), 3.68-3.77 (1H, m), 3.86 (3H, s), 3.87-3.95 (2H, m), 4.45 (1H, d), 4.55 (1H, d), 5.33 (1H, s), 6.27 (1H, dd), 6.48 (1H, d), 6.79 (2H, dd), 7.12 (1H, d), 8.05 (1H, d); m/z (ES+), [M+H]+=499.

The (6S,8R)-7-(2-fluoro-2-methylpropyl)-6-(4-(2-(3-(fluoromethyl)azetidin-1-yl)ethoxy)-2-methoxyphenyl)-8-methyl-2-(tetrahydro-2H-pyran-2-yl)-6,7 ,8,9-tetrahydro-2H-pyrazolo[4,3-f]isoquinoline and (6S,8R)-7-(2-fluoro-2-methylpropyl)-6-(4-(2-(3-(fluoromethyl)azetidin-1-yl)ethoxy)-2-methoxyphenyl)-8-methyl-3-(tetrahydro-2H-pyran-2-yl)-6,7,8,9-tetrahydro-3H-pyrazolo[4,3-f]isoquinoline were prepared as follows;

Preparation of (1S,3R)-1-(4-bromo-2-methoxyphenyl)-2-(2-fluoro-2-methylpropyl)-3,5-dimethyl-1,2,3,4-tetrahydroisoauinolin-6-amine

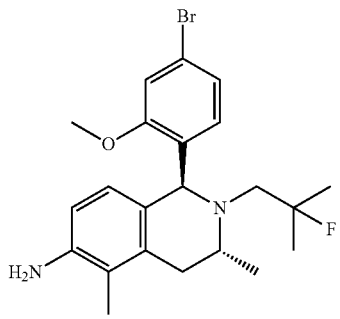 [SMILES: COc1cc(Br)ccc1[C@@H]1c2ccc(N)c(C)c2C[C@@H](C)N1CC(C)(C)F]

4-Bromo-2-methoxybenzaldehyde (3.61 g, 16.8 mmol) was added to a solution of (R)-3-(2-((2-fluoro-2-methylpropyl)amino)propyl)-2-methylaniline (2.00 g, 8.39 mmol) in acetic acid (45 mL) and water (0.756 mL, 42.0 mmol). The reaction mixture was stirred at 60° C. overnight and then the reaction mixture was evaporated to a dark brown oil. The residue was neutralised by dissolving in EtOAc (50 mL) and washing with saturated aqueous sodium bicarbonate (3×50 mL). The combined aqueous layers were extracted with EtOAc (2×50 mL), the combined organic layers were dried over magnesium sulfate, filtered and the filtrate concentrated. The residue was dissolved in DCM (60 mL), 1M HCl (50 mL) was added and the biphasic mixture was stirred vigorously for 1 hour. The layers were separated and the aqueous was extracted with DCM (2×30 mL). The aqueous layer was then basified by addition of 2M aqueous $Na_2CO_3$ and extracted with EtOAc (3×35 mL). The combined EtOAc extracts were washed with brine (1×50 mL), dried over magnesium sulfate and concentrated. The crude material was purified by flash silica chromatography, elution gradient 0-50% EtOAc in Heptane. Pure fractions were combined and concentrated to afford (1S,3R)-1-(4-bromo-2-methoxyphenyl)-2-(2-fluoro-2-methylpropyl)-3,5-dimethyl-1,2,3,4-tetrahydroisoquinolin-6-amine (2.90 g, 79%) as an off-white foam. $^1H$ NMR (500 MHz, $CDCl_3$, 27° C.) 0.99 (3H, d), 1.21-1.32 (6H, m), 2.06 (3H, s), 2.26 (1H, dd), 2.49 (1H, dd), 2.72 (1H, dd), 2.85 (1H, dd), 3.48 (2H, d), 3.54 (1H, dt), 3.87 (3H, s), 5.23 (1H, s), 6.43 (2H, s), 6.80 (1H, d), 6.89 (1H, dd), 7.00 (1H, d); m/z: ES+ [M+H]+ 435.

Preparation of (6S,8R)-6-(4-bromo-2-methoxyphenyl)-7-(2-fluoro-2-methylpropyl)-8-methyl-6,7,8,9-tetrahydro-3H-pyrazolo[4,3-f]isoquinoline

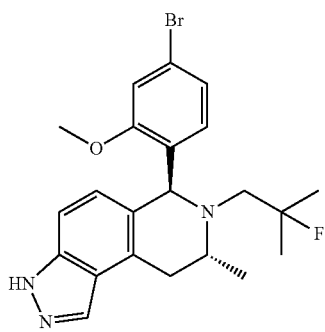 [SMILES: COc1cc(Br)ccc1[C@@H]1c2ccc3[nH]ncc3c2C[C@@H](C)N1CC(C)(C)F]

(1S,3R)-1-(4-Bromo-2-methoxyphenyl)-2-(2-fluoro-2-methylpropyl)-3,5-dimethyl-1,2,3,4-tetrahydroisoquinolin-6-amine (2.40 g, 5.51 mmol) in propionic acid (25 mL) was cooled to −17° C. (dry ice/acetone; internal temperature via thermometer) in a 3-necked flask. Sodium nitrite (0.380 g, 5.51 mmol) in water (5 mL) was added dropwise over ~5 mins. The reaction mixture was stirred at −17° C. for 30 mins. The reaction mixture was diluted with ice-cold TBME (150 mL) (temperature rise to −4° C.). The reaction mixture was stirred vigorously and neutralised by addition of 2M aqueous NaOH (300 mL, dropping funnel over ~15 mins) (temp ~5-10° C.; ice/water bath, internal temperature via thermometer) and stirred for 30 min. The organics were washed with further 2M aqueous NaOH solution (200 mL), the combined aqueous phases were washed with TBME (2×100 mL) and the combined organics were washed with saturated aqueous sodium chloride (1×100 mL), dried over magnesium sulfate, filtered and the filtrate was evaporated to a brown oil. The crude material was purified by flash silica chromatography, elution gradient 0-35% EtOAc in Heptane to afford (6S,8R)-6-(4-bromo-2-methoxyphenyl)-7-(2-fluoro-2-methylpropyl)-8-methyl-6,7,8,9-tetrahydro-3H-pyrazolo[4,3-f]isoquinoline (1.660 g, 68%) as a straw-coloured foam. $^1H$ NMR (500 MHz, $CDCl_3$, 27° C.) 1.05 (3H, d), 1.23 (3H, d), 1.27 (3H, d), 2.30 (1H, dd), 2.76-2.92 (2H, m), 3.31 (1H, dd), 3.66-3.77 (1H, m), 3.90 (3H, s), 5.37 (1H, s), 6.75 (1H, d), 6.83 (1H, d), 6.90 (1H, dd), 7.04 (1H, d), 7.14 (1H, d), 8.06 (1H, d), 10.01 (1H, s); m/z: ES+ [M+H]+ 448 (Br isotope pattern)

Preparation of (6S,8R)-6-(4-bromo-2-methoxyphenyl)-7-(2-fluoro-2-methylpropyl)-8-methyl-3-(tetrahydro-2H-pyran-2-yl)-6,7,8,9-tetrahydro-3H-pyrazolo[4,3-f]isoquinoline and (6S,8R)-6-(4-bromo-2-methoxyphenyl)-7-(2-fluoro-2-methylpropyl)-8-methyl-2-(tetrahydro-2H-pyran-2-yl)-6,7,8,9-tetrahydro-2H-pyrazolo[4,3-f]isoquinoline

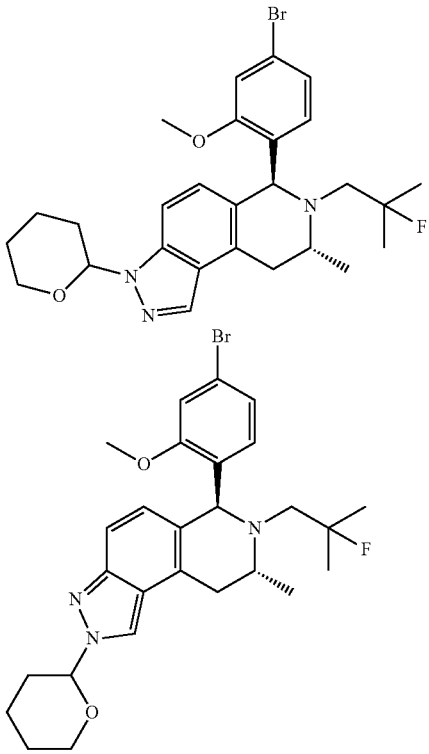

4-Methylbenzenesulfonic acid hydrate (0.163 g, 0.86 mmol) was added to a solution of (6S,8R)-6-(4-bromo-2-methoxyphenyl)-7-(2-fluoro-2-methylpropyl)-8-methyl-6,7,8,9-tetrahydro-3H-pyrazolo[4,3-f]isoquinoline (1.91 g, 4.28 mmol) and 3,4-dihydro-2H-pyran (3.90 mL, 42.79 mmol) in DCM (15 mL) and the mixture heated at 45° C. for 5 hours and then stirred at room temperature for 4 days. The reaction mixture was diluted with DCM, washed with saturated aqueous sodium bicarbonate, saturated aqueous sodium chloride, then dried over magnesium sulfate, filtered and the filtrate concentrated. The crude material was purified by flash silica chromatography, elution gradient 0-25% EtOAc in heptane. Fractions were combined and concentrated to afford a mixture of (6S,8R)-6-(4-bromo-2-methoxyphenyl)-7-(2-fluoro-2-methylpropyl)-8-methyl-2-(tetrahydro-2H-pyran-2-yl)-6,7,8,9-tetrahydro-2H-pyrazolo[4,3-f]isoquinoline and (6S,8R)-6-(4-bromo-2-methoxyphenyl)-7-(2-fluoro-2-methylpropyl)-8-methyl-3-(tetrahydro-2H-pyran-2-yl)-6,7,8,9-tetrahydro-3H-pyrazolo[4,3-f]isoquinoline (2.25 g, 99%) as an orange-brown glassy solid. m/z: ES+ [M+H]+ 530 (appears to be a 1:1 mix of isomers).

Preparation of (6S,8R)-7-(2-fluoro-2-methylpropyl)-6-(4-(2-(3-(fluoromethyl)azetidin-1-yl)ethoxy)-2-methoxyphenyl)-8-methyl-3-(tetrahydro-2H-pyran-2-yl)-6,7,8,9-tetrahydro-3H-pyrazolo[4,3-f]isoquinoline/(6S,8R)-7-(2-fluoro-2-methylpropyl)-6-(4-(2-(3-(fluoromethyl)azetidin-1-yl)ethoxy)-2-methoxyphenyl)-8-methyl-2-(tetrahydro-2H-pyran-2-yl)-6,7,8,9-tetrahydro-2H-pyrazolo[4,3-f]isoquinoline

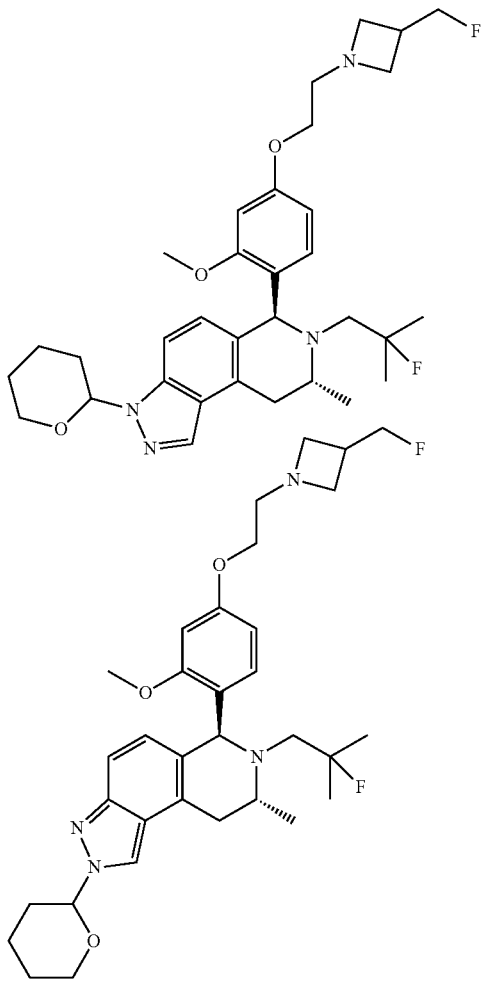

A round bottomed flask equipped with a stirrer bar was charged with a mixture of (6S,8R)-6-(4-bromo-2-methoxyphenyl)-7-(2-fluoro-2-methylpropyl)-8-methyl-2-(tetrahydro-2H-pyran-2-yl)-6,7,8,9-tetrahydro-2H-pyrazolo[4,3-f]isoquinoline and (6S,8R)-6-(4-bromo-2-methoxyphenyl)-7-(2-fluoro-2-methylpropyl)-8-methyl-3-(tetrahydro-2H-pyran-2-yl)-6,7,8,9-tetrahydro-3H-pyrazolo[4,3-f]isoquinoline (1.75 g, 3.30 mmol), 2-(3-(fluoromethyl)azetidin-1-yl)ethan-1-ol (0.879 g, 6.60 mmol), cesium carbonate (2.150 g, 6.60 mmol), RockPhos 3$^{rd}$ Generation Precatalyst (0.277 g, 0.33 mmol) and molecular sieves, (4Å activated powder, 0.5 g, 3.30 mmol). The flask was evacuated and back-filled with nitrogen (×3). Toluene (15 mL) was added and the mixture stirred at 90° C. for 16 hours. The cooled reaction mixture was diluted with EtOAc and filtered through Celite™ to remove insoluble material. The filtrate was washed with water, saturated aqueous sodium chloride and then dried over magnesium sulfate, filtered and the filtrate concentrated. The crude material was purified by flash silica chromatography, elution gradient 0-8% MeOH in DCM. Pure fractions were combined and concentrated to afford a mixture of (6S,8R)-7-(2-fluoro-2-methylpropyl)-6-(4-(2-(3-(fluoromethyl)azetidin-1-yl)ethoxy)-2-methoxyphenyl)-8-methyl-2-(tetrahydro-2H-pyran-2-yl)-6,7,8,9-tetrahydro-2H-pyrazolo[4,3-f]isoquinoline and (6S,8R)-7-(2-fluoro-2-methylpropyl)-6-(4-(2-(3-(fluoromethyl)azetidin-1-yl)ethoxy)-2-methoxyphenyl)-8-methyl-3-(tetrahydro-2H-pyran-2-yl)-6,7,8,9-tetrahydro-3H-pyrazolo[4,3-f]isoquinoline (1.080 g, 56%). The material was isolated as an orange-brown foam. m/z: ES+ [M+H]+ 583 (appears to be a 1:1 mix of isomers).

Example 6

Preparation of (6S,8R)-7-((1-fluorocyclopropyl)methyl)-6-(4-(2-(3-(fluoromethyl)azetidin-1-yl)ethoxy)-2-methoxyphenyl)-8-methyl-6,7,8,9-tetrahydro-3H-is pyrazolo[4,3-f]isoquinoline

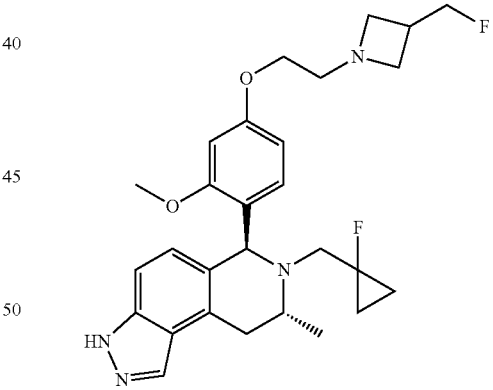

Hydrochloric acid in dioxane (4 M; 0.5 mL, 2 mmol) was added to a solution of (6S,8R)-7-((1-fluorocyclopropyl)methyl)-6-(4-(2-(3-(fluoromethyl)azetidin-1-yl)ethoxy)-2-methoxyphenyl)-8-methyl-3-(tetrahydro-2H-pyran-2-yl)-6,7,8,9-tetrahydro-3H-p yrazolo [4,3-f]isoquinoline (0.052 g, 0.09 mmol) and (6S,8R)-74(1-fluorocyclopropyl)methyl)-6-(4-(2-(3-(fluoromethyl)azetidin-1-yl)ethoxy)-2-methoxyphenyl)-8-methyl-2-(tetrahydro-2H-pyran-2-yl)-6,7,8,9-tetrahydro-2H-pyrazolo[4,3-f]isoquinoline (0.065 g, 0.11 mmol) in MeOH (1 mL). The resulting solution was stirred at room temperature for 2 hours and then concentrated under reduced pressure. The resulting residue was purified directly by reverse phase HPLC (Waters XBridge Phenyl column, 19 mm diameter, 100 mm length, 5μm silica), elution gradient 50 to 80% MeCN in water containing 0.2% ammonium hydroxide (pH 10) as a modifier, to give (6S,8R)-7-((1-fluorocyclopropyl)methyl)-6-(4-(2-(3-(fluoromethyl)azetidin-1-yl)ethoxy)-2-methoxyphenyl)-8-methyl-6,7,8,9-tetrahydro-3H-pyrazolo[4,3-f]isoquinoline (0.037 g, 37%) as a white solid. ¹H NMR (300 MHz, DMSO-d₆) 0.34-0.63 (2H, m), 0.76-0.92 (2H, m), 1.00 (1H, d), 2.52-2.78 (4H, m), 2.83-3.01 (4H, m), 3.60-3.77 (1H, m), 3.79-3.92 (5H, m), 4.42 (1H, d), 4.58 (1H, d), 5.25 (1H, s), 6.32 (1H, dd), 6.56 (1H, d), 6.64 (1H, d), 6.78(1H, d), 7.16 (1H, d), 8.03 (1H, s) 12.9 (1H, s). m/z: ES+ [M+H]+ 497.

The starting materials (6S,8R)-7-((1-fluorocyclopropyl)methyl)-6-(4-(2-(3-(fluoromethyl)azetidin-1-yl)ethoxy)-2-methoxyphenyl)-8-methyl-3-(tetrahydro-2H-pyran-2-yl)-6,7,8,9-tetrahydro-3H-pyrazolo[4,3-f]isoquinoline and (6S,8R)-7-((1-fluorocyclopropyl)methyl)-6-(4-(2-(3-(fluoromethyl)azetidin-1-yl)ethoxy)-2-methoxyphenyl)-8-methyl-2-(tetrahydro-2H-pyran-2-yl)-6,7,8,9-tetrahydro-2H-pyrazolo[4,3-f]isoquinoline were prepared as follows;

Preparation of 1-(3-bromo-2-methylphenyl)-2,5-dimethyl-1H-pyrrole

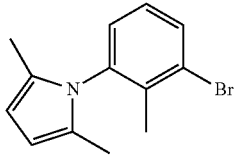

A mixture of 3-bromo-2-methylaniline (40 g, 215 mmol), hexane-2,5-dione (25.3 mL, 215 mmol) and p-toluenesulfonic acid monohydrate (0.409 g, 2.15 mmol) in toluene (300 mL) was heated at reflux conditions for 2 hours in a flask equipped with a condensor and Dean-Stark trap. The mixture was then cooled to room temperature and washed sequentially with saturated aqueous sodium bicarbonate, aqueous HCl (1N), and saturated aqueous sodium chloride. The organic layer was dried over sodium sulfate, filtered and concentrated under reduced pressure to give crude 1-(3-bromo-2-methylphenyl)-2,5-dimethyl-1H-pyrrole (57.9 g, 102%) as a pale yellow oil. ¹H NMR (300 MHz, DMSO-d₆, 27° C.) 1.80 (6H, s), 1.90 (3H, s), 5.80 (2H, s), 7.20-7.40 (2H, m), 7.70 (1H, dd). m/z: ES+ [M+H]+ 264.

Preparation of tent-butyl (R)-(1-(3-(2,5-dimethyl-1H-pyrrol-1-yl)-2-methylphenyl)propan-2-yl)carbamate

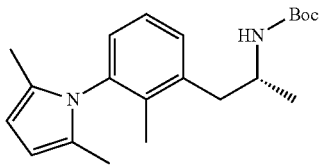 [SMILES: Cc1c(C[C@@H](C)NC(=O)OC(C)(C)C)cccc1-n1c(C)ccc1C]

n-Butyllithium in hexane (2.5M; 89 mL, 221 mmol) was added over 15 minutes to a solution of crude 1-(3-bromo-2-methylphenyl)-2,5-dimethyl-1H-pyrrole (55.7 g, 211 mmol) in THF (400 mL) at −78° C. After 30 minutes, tert-butyl (R)-4-methyl-1,2,3-oxathiazolidine-3-carboxylate 2,2-dioxide (50 g, 211 mmol) was added. The resulting mixture was stirred at −78 ° C. for 15 minutes and allowed to warm to room temperature over 2 hours. Aqueous citric acid (1N; 250 mL) was added, and stirring was continued for 30 minutes. The mixture was extracted with hexanes, and the combined organic layers were washed with saturated aqueous sodium carbonate, dried over sodium sulfate, filtered, and concentrated under reduced pressure. The resulting brown solid, crude tert-butyl (R)-(1-(3-(2,5-dimethyl-1H-pyrrol-1-yl)-2-methylphenyl)propan-2-yl)carbamate was used in the next step without further purification. m/z: ES+ [M+H]+ 343.

Preparation of (R)-1-(3-(2,5-dimethyl-1H-pyrrol-1-yl)-2-methylphenyl)propan-2-amine

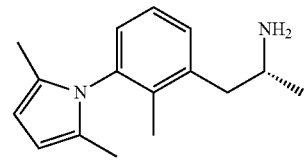 [SMILES: Cc1c(C[C@@H](C)N)cccc1-n1c(C)ccc1C]

Hydrochloric acid in dioxane (4 M; 100 mL, 400 mmol) was added to a suspension of crude tert-butyl (R)-(1-(3-(2,5-dimethyl-1H-pyrrol-1-yl)-2-methylphenyl)prop an-2-yl)carbamatein MeOH (200 mL) and DCM (50 mL). The resulting red solution was stirred at room temperature for 4 hours and then concentrated under reduced pressure. The resulting brown solid was used in the next step without further purification. m/z: ES+ [M+H]+ 243.

Preparation of (R)-3-(2-aminopropyl)-2-methylaniline

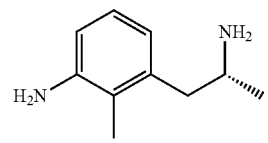

A mixture of crude (R)-1-(3-(2,5-dimethyl-1H-pyrrol-1-yl)-2-methylphenyl)propan-2-amine dihydrochloride, aqueous hydroxylamine (50 wt %; 107 mL, 1.74 mol), and hydroxylamine hydrochloride (97 g, 1.39 mol) in ethanol (400 mL) was warmed to reflux conditions. After 18 hours, the reaction was cooled to 0° C., basified with aqueous sodium hydroxide (50 wt %, 153 g, 1.92 mol) and extracted with DCM. The organic layer was dried over sodium sulfate, filtered and concentrated under reduced pressure. The resulting residue was purified by SFC (Princeton Chromatography DEAP column, 100 mm length, 30 mm diameter, 5 μm, 40° C. column temperature, 100 bar column pressure, 100 mg/mL flow rate), eluting with 25% methanol containing 0.2% NH₄OH in CO₂, to afford (R)-3-(2-aminopropyl)-2-methylaniline (24 g, 84%) as a light amber solid. ¹H NMR (300 MHz, DMSO-d₆, 27° C.) 1H NMR (500 MHz, DMSO, 27° C.) 1.05 (3H, d), 1.99 (3H, s), 2.55 (1H, dd), 2.93 (1H, dd), 3.11-3.25 (1H, m), 4.77 (2H, s), 6.35 (1H, dd), 6.52 (1H, dd), 6.81 (1H, t). Two exchangeable protons not observed. m/z: ES+ [M+H]+ 165.

Preparation of (R)—N-(1-(3-amino-2-methylphenyl)propan-2-yl)-1-fluorocyclopropane-1-carboxamide

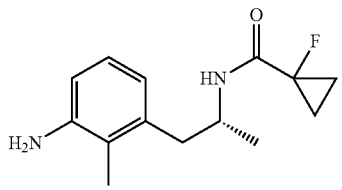 [SMILES: Cc1c(N)cccc1C[C@@H](C)NC(=O)C1(F)CC1]

(R)-3-(2-aminopropyl)-2-methylaniline (1.70 g, 10.4 mmol) was dissolved in DMF (29.9 mL) and treated with 1-fluorocyclopropane-1-carboxylic acid (1.00 g, 9.61 mmol), HATU (4.02 g, 10.6 mmol), and Et3N (2.68 mL, 19.22 mmol). The reaction was stirred at room temperature for 3 hours and then quenched with water and extracted with EtOAc. The organic layer was washed with saturated aqueous sodium chloride, dried over sodium sulfate, and filtered. The filtrate was concentrated under reduced pressure, and the resulting residue was dried under vacuum overnight to remove residual DMF. The residue was then adsorbed onto silica and purified by flash column silica chromatography, elution gradient 0 to 80% ethyl acetate in hexanes to afford (R)—N-(1-(3-amino-2-methylphenyl)propan-2-yl)-1-fluorocyclopropane-1-carboxamide (1.47 g, 61%) as a light yellow solid. $^1$H NMR (300 MHz, DMSO-$d_6$, 27° C.) 1.01-1.28 (7H, m), 2.02 (3H, s), 2.54-2.62 (1H, m), 2.83 (1H, dd), 3.89-4.16 (1H, m), 4.68 (2H, s), 6.38 (1H, d), 6.49 (1H, d), 6.78 (1H, t), 8.14 (1H, d) m/z: ES+ [M+H]+ 251.

Preparation of (R)-3-(2-(((1-fluorocyclopropyl)methyl)amino)propyl)-2-methylaniline

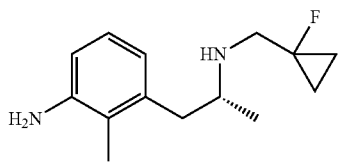 [SMILES: Cc1c(N)cccc1C[C@@H](C)NCC1(F)CC1]

Borane tetrahydrofuran complex in THF (1 M; 35.2 ml, 35.2 mmol) was added to a solution of (R)-N-(1-(3-amino-2-methylphenyl)propan-2-yl)-1-fluorocyclopropane-1-carboxamide (1.47 g, 5.87 mmol) in THF (13.7 mL) at room temperature under nitrogen. The reaction was then heated at 65° C. for 6 hrs. The reaction was cooled to 0° C. and quenched cautiously with MeOH (gas evolution). The solution was then concentrated under reduced pressure and stored in the freezer for 18 hours. The residue was dissolved in MeOH (6 mL) and heated at 65° C. for 3 hrs. The solution was cooled to room temperature and then concentrated under reduced pressure. The residue obtained was purified by flash silica chromatography, elution gradient 0 to 16% methanol in DCM, to afford (R)-3-(2-(((1-fluorocyclopropyl)methyl)amino)propyl)-2-methylaniline (1.14 g, 82%) as colorless oil. $^1$H NMR (300 MHz, DMSO-$d_6$, 27° C.) 0.54-0.70 (2H, m), 0.79-1.02 (5H, m), 1.64 (1H, br. s.), 1.99 (3H, s), 2.36 (1H, dd), 2.69-2.97 (4H, m), 4.68 (2H, s), 6.36 (1H, d), 6.49 (1H, d), 6.79 (1H, t). m/z: ES+ [M+H]+ 237.

Preparation of (1S,3R)-1-(4-bromo-2-methoxyphenyl)-2-((1-fluorocyclopropyl)methyl)-3,5-dimethyl-1,2,3,4-tetrahydroisoauinolin-6-amine and N-((1S,3R)-1-(4-bromo-2-methoxyphenyl)-2-((1-fluorocyclopropyl)methyl)-3,5-dimethyl-1,2,3,4-tetrahydroisoauinolin-6-yl)acetamide

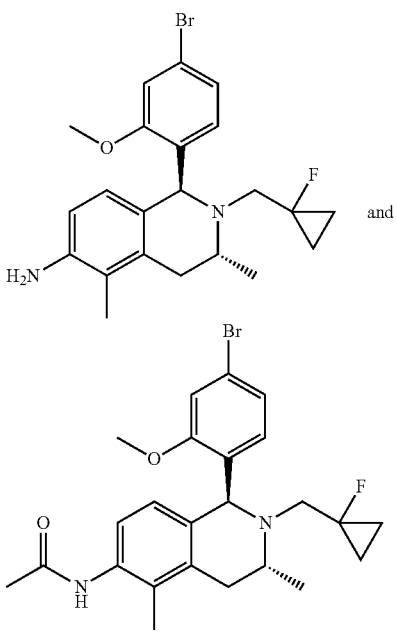

A mixture of (R)-3-(2-(((1-fluorocyclopropyl)methyl)amino)propyl)-2-methylaniline (0.63 g, 2.7 mmol), 4-bromo-2-methoxybenzaldehyde (1.15 g, 5.33 mmol) and water (0.240 mL, 13.3 mmol) in acetic acid (10 mL) was stirred at 80° C. for 20 hours before being cooled to room temperature and then concentrated under reduced pressure. The residue was treated with aqueous HCl (1N; 10 mL) for 30 minutes and then extracted with EtOAc. This organic layer was set aside. The aqueous layer was basified with solid potassium carbonate and extracted with EtOAc. This extract was dried over sodium sulfate, filtered and concentrated under reduced pressure. The resulting residue was purified by flash silica chromatography, elution gradient 0 to 100% ethyl acetate in hexanes, to afford (1S,3R)-1-(4-bromo-2-methoxyphenyl)-2-((1-fluorocyclopropyl)methyl)-3,5-dimethyl-1,2,3,4-tetrahydroisoquinolin-6-amine (0.71 g, 62%) as a light yellow foam solid. m/z: ES+ [M+H]+ 433.

Also isolated was N-((1S,3R)-1-(4-bromo-2-methoxyphenyl)-2-((1-fluorocyclopropyl)methyl)-3,5-dimethyl-1,2,3,4-tetrahydroisoquinolin-6-yl)acetamide (0.27 g, 21%) as a light yellow foam solid. m/z: ES+ [M+H]+ 475. This could be converted to (1S,3R)-1-(4-bromo-2-methoxyphenyl)-2-((1-fluorocyclopropyl)methyl)-3,5-dimethyl-1,2,3,4-tetrahydroisoquinolin-6-amine according to the procedure detailed below.

Preparation of (1S,3R)-1-(4-bromo-2-methoxyphenyl)-2-((1-fluorocyclopropyl)methyl)-3,5-dimethyl-1,2,3,4-tetrahydroisoauinolin-6-amine

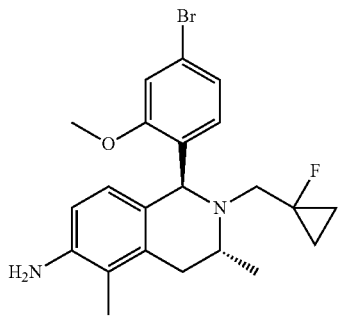 [SMILES: COc1cc(Br)ccc1[C@@H]1c2ccc(N)c(C)c2C[C@@H](C)N1CC1(F)CC1]

A mixture of N -((1S,3R)-1-(4-bromo-2-methoxyphenyl)-2-((1-fluorocyclopropyl)methyl)-3,5-dimethyl-1,2,3,4-tetrahydroisoquinolin-6-yl)acetamide (0.27 g, 0.57 mmol) and aqueous hydrochloric acid (1N; 2 mL, 2 mmol) was stirred under reflux conditions for 18 hours and then cooled to room temperature. The reaction was basified to pH 10 with aqueous NaOH (1N), and the mixture was extracted with EtOAc. The organic layer was dried over magnesium sulfate, filtered, and concentrated under reduced pressure to afford additional (1S,3R)-1-(4-bromo-2-methoxyphenyl)-24 (1-fluorocyclopropyl)methyl)-3,5-dimethyl-1,2,3,4-tetrahydroisoquinolin-6-amine (0.23 g, 92%) as a light yellow foam. m/z: ES+ [M+H]+ 433.

Preparation of (6S,8R)-6-(4-bromo-2-methoxyphenyl)-7-((1-fluorocyclopropyl)methyl)-8-methyl-6,7,8,9-tetrahydro-3H-pyrazolo[4,3-f]isoquinoline

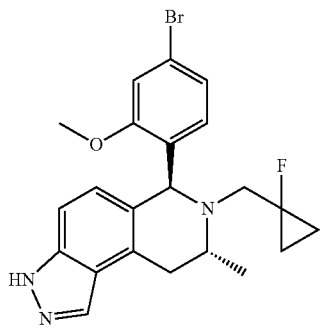 [SMILES: COc1cc(Br)ccc1[C@@H]1c2ccc3[nH]ncc3c2C[C@@H](C)N1CC1(F)CC1]

A solution of sodium nitrite (0.095 g, 1.4 mmol) in water (0.600 mL) was added dropwise to a solution of (1S,3R)-1-(4-bromo-2-methoxyphenyl)-2-((1-fluoroc yclopropyl)methyl)-3 ,5-dimethyl-1,2,3,4-tetrahydroisoquinolin-6-amine (0.60 g, 1.4 mmol) in propionic acid (6 mL) at −10° C., and the mixture was stirred under these conditions for 20 minutes. The reaction was then diluted with EtOAc (20 mL, precooled to 0° C.) and treated with saturated aqueous NaHCO₃ (25 mL, precooled to 0° C.) dropwise followed by portion-wise addition of solid NaHCO₃ (7 g). The mixture was stirred for 18 hours, and, during this time, the reaction was allowed to warm to room temperature. The mixture was extracted with EtOAc, and the extract was dried over MgSO₄, filtered, and concentrated under reduced pressure.

The resulting residue was purified by flash silica chromatography, elution gradient 0 to 80% EtOAc in hexanes to afford (6S,8R)-6-(4-bromo-2-methoxyphenyl)-7-((1-fluorocyclopropyl)methyl)-8-methyl-6,7,8,9-tetrahydro-3H-pyrazolo[4,3-f]isoquinoline (0.46 g, 75%) as an amber foam solid. m/z: ES+ [M+H]+ 444.

Preparation of (6S,8R)-6-(4-bromo-2-methoxyphenyl)-7-((1-fluorocyclopropyl)methyl)-8-methyl-3-(tetrahydro-2H-pyran-2-yl)-6,7,8,9-tetrahydro-3H-pyrazolo[4,3-f]isoquinoline and (6S,8R)-6-(4-bromo-2-methoxyphenyl)-7-((1fluorocyclopropyl)methyl)-8-methyl-2-(tetrahydro-2H-pyran-2-yl)-6,7,8,9-tetrahydro-2H-pyrazolo[4,3-f]isoquinoline

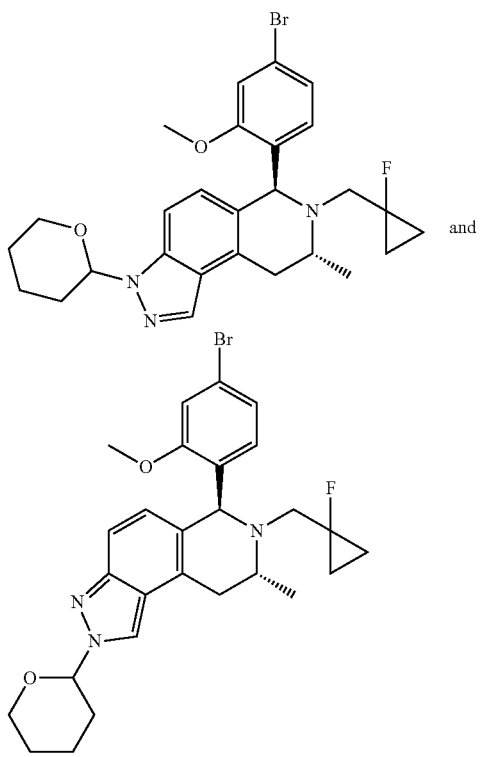

3,4-Dihydro-2H-pyran (0.52 mL, 5.7 mmol) was added to a solution of (6S,8R)-6-(4-bromo-2-methoxyphenyl)-7-((1-fluorocyclopropyl)methyl)-8-methyl-6,7,8,9-tetrahydro-3H-pyrazolo[4,3-f]isoquinoline (0.63 g, 1.4 mmol) and 4-methylbenzenesulfonic acid monohydrate (0.01 g, 0.05 mmol) in DCM (6 mL), and the resulting mixture was subject to microwave conditions (100° C., 300W) for 1.5 hours. The mixture was cooled to room temperature, and solid potassium carbonate was added. After stirring vigorously for 5 minutes the mixture was filtered. The filtrate was concentrated under reduced pressure, and the resulting residue was purified by flash silica chromatography, elution gradient 0 to 60% ethyl acetate in hexanes, to afford the major isomer, presumed to be (6S,8R)-6-(4-bromo-2-methoxyphenyl)-7-((1-fluorocyclopropyl)methyl)-8-methyl-3-(tetrahydro-2H-pyran-2-yl)-6,7,8,9-tetrahydro-3H-pyrazolo[4,3-f]isoquinoline (0.51 g, 67%) as a light yellow foam solid. m/z: ES+ [M+H]+ 528.

Also isolated was the minor isomer, presumed to be (6S,8R)-6-(4-bromo-2-methoxyphenyl)-7-((1-fluorocyclopropyl)methyl)-8-methyl-2-(tetrahydro-2H-pyran-2-yl )-6,7 ,8,9-tetrahydro-2H-pyrazolo[4,3-f]isoquinoline (0.15 g, 19%) as a light yellow oil. m/z: ES+ [M+H]+ 528.

Preparation of (6S,8R)-7-((1-fluorocyclopropyl)methyl)-6-(4-(2-(3-(fluoromethyl)azetidin-1-yl)ethoxy)-2-methoxyphenyl)-8-methyl-3-(tetrahydro-2H-pyran-2-yl)-6,7,8,9-tetrahydro-3H-pyrazolo[4,3-f]isoquinoline

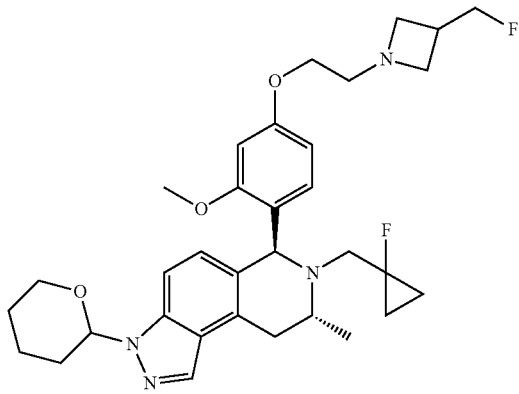 [SMILES: COc1cc(OCCN2CC(CF)C2)ccc1[C@@H]1c2ccc3c(cnn3C3CCCCO3)c2C[C@@H](C)N1CC1(F)CC1]

A mixture of presumed (6S,8R)-6-(4-bromo-2-methoxyphenyl)-7-((1-fluorocyclopropyl)methyl)-8-methyl-3-(tetrahydro-2H-pyran-2-yl)-6,7,8,9-tetrahydro-3H-pyrazolo[4,3 f]isoquinoline (0.096 g, 0.18 mmol), 2-(3-(fluoromethyl)azetidin-1-yl)ethan-1-ol (0.048 g, 0.36 mmol), RockPhos 3$^{rd}$ Generation Precatalyst (8 mg, 0.009 mmol) and cesium carbonate (0.15 g, 0.45 mmol) was evacuated and back filled with nitrogen (3×). Toluene (2 mL) was added, and the mixture was again evacuated and back filled with nitrogen (2×). The suspension was stirred at 80° C. for 1 hour and then cooled to room temperature. The mixture was filtered, and the filtrate was purified by flash silica chromatography, elution gradient 0 to 8% methanol in DCM, to give (6S,8R)-7-((1-fluorocyclopropyl)methyl)-6-(4-(2-(3-(fluoromethyl)azetidin-1-yl)ethoxy)-2-methoxyphenyl)-8-methyl-3-(tetrahydro-2H-pyran-2-yl)-6,7,8,9-tetrahydro-3H-pyrazolo[4,3 f]isoquinoline (0.052 g, 49%) as an amber solid. m/z: ES+ [M+H]+ 581.

Preparation of (6S,8R)-7-((1-fluorocyclopropyl)methyl)-6-(4-(2-(3-(fluoromethyl)azetidin-1-yl)ethoxy)-2-methoxyphenyl)-8-methyl-2-(tetrahydro-2H-pyran-2-yl)-6,7,8,9-tetrahydro-2H-pyrazolo[4,3-f]isoquinoline

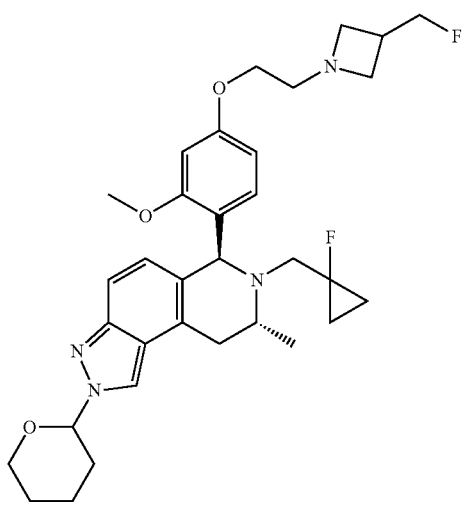 [SMILES: COc1cc(OCCN2CC(CF)C2)ccc1[C@@H]1c2ccc3nn(C4CCCCO4)cc3c2C[C@@H](C)N1CC1(F)CC1]

A mixture of (6S,8R)-6-(4-bromo-2-methoxyphenyl)-7-((1-fluorocyclopropyl)methyl)-8-methyl-2-(tetrahydro-2H-pyran-2-yl)-6,7,8,9-tetrahydro-2H-pyrazolo[4,3-f]isoquinoline (0.14 g, 0.26 mmol), 2-(3-(fluoromethyl)azetidin-1-yl)ethan-1-ol (0.071 g, 0.53 mmol), RockPhos 3$^{rd}$ Generation Precatalyst (0.011 g, 0.010 mmol), and cesium carbonate (0.22 g, 0.66 mmol) was evacuated and back filled with nitrogen (3×). Toluene (3 mL) was added, and the mixture was again evacuated and back filled with nitrogen (2×). The suspension was stirred at 90° C. for 1 hour, cooled to room temperature, and filtered. The filtrate was purified by flash silica chromatography, elution gradient 0 to 8% methanol in DCM, to afford (6S,8R)-7-((1-fluorocyclopropyl)methyl)-6-(4-(2-(3-(fluoromethyl)azetidin-1-yl)ethoxy)-2-methoxyphenyl)-8-methyl-2-(tetrahydro-2H-pyran-2-yl)-6,7,8,9-tetrahydro-2H-pyrazolo[4,3-f]isoquinoline (0.065 g, 42%) as an amber solid. m/z: ES+ [M+H]+ 581.

Example 7

(6S,8R)-7-(2,2-difluoroethyl)-6-(4-(2-(3-(fluoromethyl)azetidin-1-yl)ethoxy)-2-methoxyphenyl)-8-methyl-6,7,8,9-tetrahydro-3H-pyrazolo[4,3-f]isoquinoline

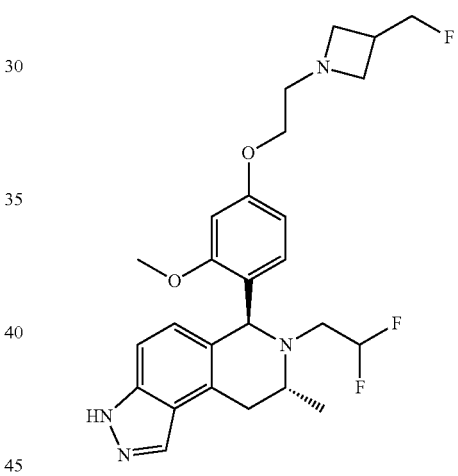

MeOH (0.5 mL) followed by HCl in dioxane (4 M; 0.400 mL, 1.60 mmol) was added to a flask charged with (6S,8R)-7-(2,2-difluoroethyl)-6-(4-(2-(3-(fluoromethyl)azetidin-1-yl)ethoxy)-2-methoxyphenyl)-8-methyl-3-(tetrahydro-2H-pyran-2-yl)-6,7,8,9-tetrahydro-3H-PYrazolo[4,3-f]isoquinoline (87 mg, 0.15 mmol), and the reaction was stirred at room temperature for 1 hour. The reaction was concentrated under reduced pressure and treated with saturated aqueous sodium hydrogen carbonate before being extracted with ethyl acetate (×3). The combined organic layers were dried over sodium sulfate, filtered and concentrated under reduced pressure. The resulting residue was purified by flash silica chromatography, elution gradient 5 to 10% methanol in DCM, to give (6S,8R)-7-(2,2-difluoroethyl)-6-(4-(2-(3-(fluoromethyl)azetidin-1-yl)ethoxy)-2-methoxyphenyl)-8-methyl-6,7,8,9-tetrahydro-3H-pyrazolo[4,3-f]isoquinoline (46.2 mg, 62%) as a white solid. $^1$H NMR (500 MHz, DMSO-$d_6$, 27° C.) 1.04 (3H, d), 2.55-2.63 (1H, m), 2.66-2.76 (3H, m), 2.82 (1H, dd), 2.95-3.05 (3H, m), 3.12 (1H, dd), 3.29-3.33 (2H, m), 3.36-3.43 (1H, m), 3.85-3.92 (5H, m), 4.51 (2H, dd), 5.29 (1H, s), 5.77-6.09

(1H, m), 6.31 (1H, dd), 6.55 (1H, d), 6.59 (1H, d), 6.68 (1H, d), 7.22 (1H, d), 8.07 (1H, s), 12.99 (1H, s). m/z: ES+ [M+H]+ 489.

The starting material (6S,8R)-7-(2,2-difluoroethyl)-6-(4-(2-(3-(fluoromethyl)azetidin-1-yl)ethoxy)-2-methoxyphenyl)-8-methyl-6,7,8,9-tetrahydro-3H-pyrazolo[4,3-f]isoquinoline was prepared as follows;

Preparation of 2,2-difluoroethyl trifluoromethanesulfonate

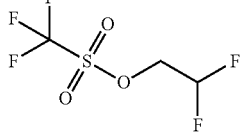

Trifluoromethanesulfonic anhydride (3.97 ml, 23.5 mmol) was added dropwise to a solution of 2,2-difluoroethan-1-ol (1.75 g, 21.3 mmol) in DCM (40 mL at) at −10° C. (salt/ice bath). Lutidine (2.98 ml, 25.6 mmol) was then added, and the reaction was stirred for 1 hour at −10° C. The reaction was then quenched with water, and the layers were separated. The organic layer was washed with water and then dried over sodium sulfate, filtered and concentrated under reduced pressure to afford 2,2-difluoroethyl trifluoromethanesulfonate (3.10 g, 67.9%) as a colorless liquid. $^1$H NMR (500 MHz, CDCl$_3$, 27° C.) 4.57 (2H, td), 6.03 (1H, tt).

Preparation of (R)-3-(2-((2,2-difluoroethyl)amino)propyl)-2-methylaniline

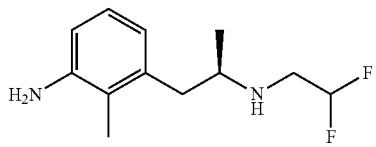 [SMILES: Cc1c(N)cccc1C[C@@H](C)NCC(F)F]

2,2-Difluoroethyl trifluoromethanesulfonate (0.789 g, 3.68 mmol) was added to a stirred solution of (R)-3-(2-aminopropyl)-2-methylaniline (0.55 g, 3.4 mmol) and DIPEA (0.760 ml, 4.35 mmol) in 1,4-dioxane (10 mL). The reaction was heated at 65° C. for 3 hours and then cooled to room temperature. The reaction was concentrated under reduced pressure, and the resulting residue was dissolved in EtOAc (30 mL) and washed with saturated aqueous sodium hydrogen carbonate. The layers were separated, and the aqueous layer was extracted with EtOAc (20 mL). The combined organic layers were dried over sodium sulfate, filtered and concentrated under reduced pressure to give a red liquid. This oil was purified by flash silica chromatography, elution gradient 30 to 90% ethyl acetate in hexanes to give (R)-3-(2-((2,2-difluoroethyl)amino)propyl)-2-methylaniline (0.52 g, 68%) as a gum. $^1$H NMR (400 MHz, CDCl$_3$, 27° C.) 1.06 (3H, d), 2.09 (3H, s), 2.60 (1H, dd), 2.77 (1H, dd), 2.81-2.99 (3H, m), 3.56 (2H, br s) 5.78 (1H, tt), 6.58 (2H, d), 6.94 (1H, t). m/z: ES+ [M+H]+ 229.

Preparation of (6S,8R)-6-(4-bromo-2-methoxyphenyl)-7-(2,2-difluoroethyl)-8-methyl-6,7,8,9-tetrahydro-3H-pyrazolo[4,3-f]isoquinoline

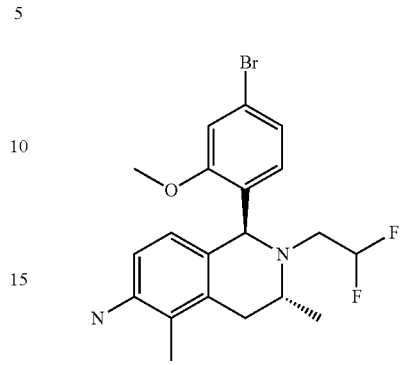

4-Bromo-2-methoxybenzaldehyde (0.942 g, 4.38 mmol) was added to a solution of (R)-3-(2-((2,2-difluoroethyl)amino)propyl)-2-methylaniline (0.50 g, 2.2 mmol) in AcOH (15 mL) and water (0.197 g, 11.0 mmol), and the reaction was heated at 80° C. overnight. After cooling, the reaction was concentrated under reduced pressure, and the resulting residue was dissolved in EtOAc and neutralised by washing with saturated aqueous NaHCO$_3$. The organic layer was treated with aqueous HCl (1N), and the biphasic mixture was stirred at room temperature for 30 minutes. The layers were separated, and the organic layer was was washed with aqueous HCl (1N). The combined aqueous layers were also extracted with ethyl acetate. The combined aqueous layers were then basified by addition of solid K$_2$CO$_3$ extracted with ethyl acetate (×2). The combined organic layers obtained after basification were dried over sodium sulfate, filtered, and concentrated under reduced pressure. The resulting residue was purified by flash silica chromatography, elution gradient 10 to 60% ethyl acetate in hexanes to afford (1S,3R)-1-(4-bromo-2-methoxyphenyl)-2-(2,2-difluoroethyl)-3,5-dimethyl-1,2,3,4-tetrahydroisoquinolin-6-amine (0.55 g, 59%) as the desired product. $^1$H NMR (400 MHz, CDCl$_3$, 27° C.) 0.92-1.12 (3H, m), 2.05 (3H, s), 2.40 (1 H, br. dd), 2.50-2.81 (3H, m), 2.81-2.92 (1H, m), 3.18-3.34 (1H, m), 3.40-3.69 (2H, m), 3.89 (3H, s), 5.21 (1H, s), 5.80 (1H, t), 6.42-6.47 (2H, m), 6.63 (1H, d), 6.89 (1H, d), 7.02 (1H, s). m/z: ES+ [M+H]+ 425.

Preparation of (6S,8R)-6-(4-bromo-2-methoxyphenyl)-7-(2,2-difluoroethyl)-8-methyl-6,7,8,9-tetrahydro-3H-pyrazolo[4,3-f]isoquinoline

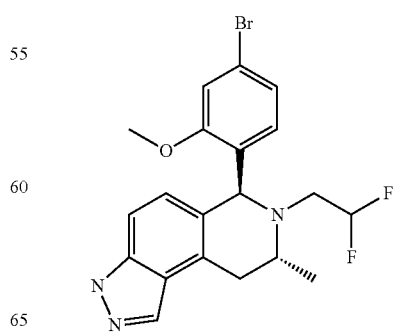

Sodium nitrite (0.039 g, 0.57 mmol) as a solution in water (0.500 mL) was added dropwise to a solution of (1S,3R)-1-(4-bromo-2-methoxyphenyl)-2-(2,2-difluoroethyl)-3,5-dimethyl-1,2,3,4-tetrahydroisoquinolin-6-amine (0.23 g, 0.54 mmol) in propionic acid (2.0 mL) at −15° C., and the reaction was stirred under these conditions for 1 hour. Ice-cold EtOAc (10 mL) was added to the flask, followed by saturated aqueous NaHCO$_3$ (10 mL) in portions. The layers were separated, and then the organic layer was washed with saturated aqueous NaHCO$_3$. The combined aqueous layers were extracted with EtOAc, and then the combined organic layers were dried over sodium sulfate, filtered, and concentrated under reduced pressure. The crude product was purified by flash silica chromatography, elution gradient 10 to 50% ethyl acetate in hexanes to give (6S,8R)-6-(4-bromo-2-methoxyphenyl)-7-(2,2-difluoroethyl)-8-methyl-6,7,8,9-tetrahydro-3H-pyrazolo[4,3-f]isoquinoline (0.20 g, 85%) as a gum. $^1$H NMR (500 MHz, CDCl$_3$, 27° C.) 1.00-1.31 (3H, m), 2.58-2.75 (1H, m), 2.83 (1 H, dd), 2.90-3.04 (1H, m), 3.13-3.24 (1H, m), 3.38-3.47 (1H, m), 3.92 (3H, s), 5.38 (1H, br s), 5.79 (1 H, t), 6.65 (1H, d), 6.77 (1H, d), 6.89 (1H, dd), 7.06 (1H, d), 7.18 (1H, d), 8.05 (1H, s). Indazole NH not observed. m/z: ES+ [M+H]+ 436.

Preparation of (6S,8R)-6-(4-bromo-2-methoxyphenyl)-7-(2,2-difluoroethyl)-8-methyl-3-(tetrahydro-2H-pyran-2-yl)-6,7,8,9-tetrahydro-3H-pyrazolo[4,3-f]isoquinoline

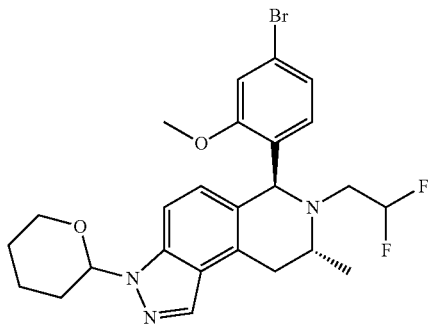 [SMILES: COc1cc(Br)ccc1[C@@H]1c2ccc3c(cnn3C3CCCCO3)c2C[C@@H](C)N1CC(F)F]

DCM (5 mL) was added to a flask charged with (6S,8R)-6-(4-bromo-2-methoxyphenyl)-7-(2,2-difluoroethyl)-8-methyl-6,7,8,9-tetrahydro-3H-pyrazolo[4,3-f]isoquinoline (0.18 g, 0.41 mmol) and para-toluenesulfonic acid monohydrate (8 mg, 0.04 mmol). 3,4-Dihydro-2H-pyran (0.052 g, 0.62 mmol) was added, and the reaction was stirred at room temperature overnight. The reaction was washed with saturated aqueous sodium hydrogen carbonate, and the organic layer was dried over sodium sulfate, filtered, and concentrated under reduced pressure to give a brown gum. This gum was purified by flash silica chromatography, elution gradient 5 to 40% ethyl acetate in hexanes to afford (6S,8R)-6-(4-bromo-2-methoxyphenyl)-7-(2,2-difluoroethyl)-8-methyl-3-(tetrahydro-2H-pyran-2-yl)-6,7,8,9-tetrahydro-3H-pyrazolo[4,3-f]isoquinoline (0.17 g, 77%). $^1$H NMR (500 MHz, CDCl$_3$, 27° C.) 1.11 (3H, br. s), 1.63-1.83 (4H, m), 2.06-2.13 (1H, m), 2.21-2.27 (2H, m), 2.61-2.81 (2H, m), 2.87-3.14 (2H, m), 3.42 (1H, br. s), 3.80 (1H, td), 3.95 (2H, br. s), 4.14-4.19 (1H, m), 5.30 (1H, br. s), 5.62-5.97 (2H, m), 6.61-6.76 (2H, m), 6.86-6.95 (1H, m), 7.01-7.16 (1H, m), 7.39-7.45 (1H, m), 8.13 (1H, br. s). m/z: ES+ [M+H]+ 521.

Preparation of (6S,8R)-7-(2,2-difluoroethyl)-6-(4-(2-(3-(fluoromethyl)azetidin-1-yl)ethoxy)-2-methoxyphenyl)-8-methyl-3-(tetrahydro-2H-pyran-2-yl)-6,7,8,9-tetrahydro-3H-pyrazolo[4,3-f]isoquinoline

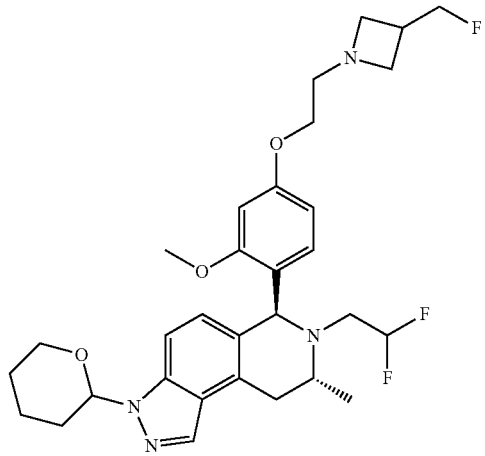 [SMILES: COc1cc(OCCN2CC(CF)C2)ccc1[C@@H]1c2ccc3c(cnn3C3CCCCO3)c2C[C@@H](C)N1CC(F)F]

Toluene (2 mL) was added to a flask charged with 2-(3-(fluoromethyl)azetidin-1-yl)ethan-1-ol (0.079 g, 0.60 mmol) and (6S,8R)-6-(4-bromo-2-methoxyphenyl)-7-(2,2-difluoroethyl)-8-methyl-3-(tetrahydro-2H-pyran-2-yl)-6,7,8,9-tetrahydro-3H-pyrazolo[4,3-f]isoquinoline (0.155 g, 0.30 mmol). The reaction flask was evacuated and filled with nitrogen (3×). Cesium carbonate (0.243 g, 0.74 mmol) and RockPhos 3$^{rd}$ Generation Precatalyst (0.025 g, 0.030 mmol) were added, and again the reaction flask was evacuated and filled with nitrogen (3×). The reaction was heated at 90° C. for 2 hours. The reaction was stopped, cooled to room temperature, filtered through Celite® with a 10% methanol in DCM wash, and the filtrate was concentrated under reduced pressure. The resulting residue was purified by flash silica chromatography, elution gradient 2 to 10% MeOH in DCM, to give (6S,8R)-7-(2,2-difluoroethyl)-6-(4-(2-(3-(fluoromethyl)azetidin-1-yl)ethoxy)-2-methoxyphenyl)-8-methyl-3-(tetrahydro-2H-pyran-2-yl)-6,7,8,9-tetrahydro-3H-pyrazolo[4,3-f]isoquinoline (0.091 g, 53%) as a dry film. $^1$H NMR (500 MHz, CDCl$_3$, 27° C.) 1.08 (3H, dd), 1.65 (1H, m), 1.74 (2 H, m), 2.05 (1H, m), 2.21 (2H, m), 2.66 (2H, br dd), 2.82 (2H, m), 2.90 (2H, m), 3.04 (1H, m), 3.15 (2H, br s), 3.42 (1H, m), 3.50 (2H, br s), 3.77 (1H, td), 3.87 (3H, s), 3.90 (2H, br t), 4.12 (1 H, m), 4.44 (1H, d), 4.53 (1H, d), 5.25 (1H, s), 5.64 (1H, m), 6.24 (1H, dt), 6.67 (2 H, m), 7.37 (1H, d), 8.08 (1H, s). m/z: ES+ [M+H]+ 573.

Example 8

Preparation of (6S,8R)-7-((1-fluorocyclopropyl)methyl)-6-(5-(2-(3-(fluoromethyl)azetidin-1-yl)ethoxy)pyridin-2-yl)-8-methyl-6,7,8,9-tetrahydro-3H-pyrazolo[4,3-f]isoquinoline

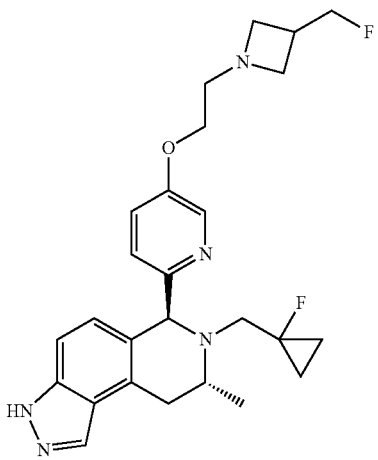 [SMILES: C[C@@H]1Cc2c(ccc3[nH]ncc23)[C@@H](c2ccc(OCCN3CC(CF)C3)cn2)N1CC1(F)CC1]

(6S,8R)-7-((1-Fluorocyclopropyl)methyl)-6-(5-(2-(3-(fluoromethyl)azetidin-1-yl)ethoxy)pyridin-2-yl)-8-methyl-3-(tetrahydro-2H-pyran-2-yl)-6,7,8,9-tetrahydro-3H-PYrazolo[4,3-f]isoquinoline (69 mg, 0.12 mmol) was dissolved in MeOH (1.13 mL) and cooled to 0° C. The solution was then treated slowly with HCl in dioxane (4 M; 0.16 mL, 0.62 mmol). The reaction was stirred at room temperature for 30 minutes. The reaction mixture was then concentrated under reduced pressure, and the resulting residue was purified by preparative HPLC (Waters Xbridge C18 column, 5 μm silica, 19 mm diameter, 150 mm length, 20 mL/min), eluting with 40 to 70% acetonitrile in water containing 0.2% NH$_4$OH (pH 10) over 5 minutes. Product fractions were combined and concentrated under reduced pressure to afford (6S,8R)-7-((1-fluorocyclopropyl)methyl)-6-(5-(2-(3-(fluoromethyl)azetidin-1-yl)ethoxy)pyridin-2-yl)-8-methyl-6,7,8,9-tetrahydro-3H-pyrazolo[4,3-f]isoquinoline (27 mg, 45%) as a light yellow solid. $^1$H NMR (300 MHz, DMSO-d$_6$, 27° C.) 0.47 (1H, m), 0.67 (1H, m), 0.79-0.99 (2H, m), 1.03 (3H, d), 2.63-2.77 (4H, m), 2.87-3.08 (4H, m), 3.17-3.35 (3H, m), 3.63-3.73 (1H, m), 3.95 (2H, t), 4.50 (2H, dd), 4.92 (1H, s), 6.78 (1H, d), 7.16-7.29 (3H, m), 8.05 (1H, s), 8.14 (1H, d), 12.87 (1 H, br. s). m/z: ES+ [M+H]+ 468. The starting material (6S,8R)-7-((1-fluorocyclopropyl)methyl)-6-(5-(2-(3-(fluoromethyl)azetidin-1-yl)ethoxy)p yridin-2-yl)-8-methyl-3-(tetrahydro-2H-pyran-2-yl)-6,7,8,9-tetrahydro-3H-pyrazolo[4,3-f]isoquinoline was prepared as follows;

Preparation of (1S,3R)-1-(5-bromopyridin-2-0)-2-((1-fluorocyclopropyl)methyl)-3,5-dimethyl-1,2,3,4-tetrahydroisoauinolin-6-amine

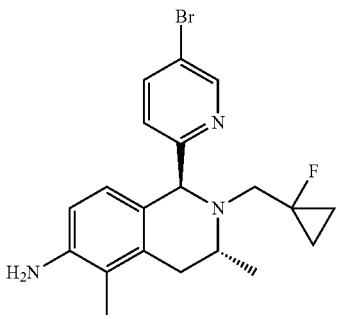 [SMILES: Cc1c(N)ccc2c1C[C@@H](C)N(CC1(F)CC1)[C@@H]2c1ccc(Br)cn1]

(R)-3-(2-(((1-Fluorocyclopropyl)methyl)amino)propyl)-2-methylaniline (185 mg, 0.78 mmol) and 5-bromopicolinaldehyde (291 mg, 1.57 mmol) were suspended in acetic acid (4 mL) and water (0.082 mL). The reaction was heated at 80° C. under nitrogen for 3 hours. The reaction was concentrated under reduced pressure, and the resulting residue was redissolved in EtOAc (12 mL) and neutralized with saturated aqueous NaHCO$_3$. The aqueous layer was extracted with EtOAc (10 mL), and the combined organic layers were dried over sodium sulfate, filtered, and concentrated under reduced pressure to a brown residue. The residue was dissolved in EtOAc (11 mL) and treated with aqueous HCl (1N; 7 mL). The biphasic mixture was stirred vigorously for 30 minutes, the layers were separated, and organic layer was extracted with aqueous HCl (1N; 2×4 mL). The combined acidic aqueous layers were extracted with DCM (10 mL). The aqueous layer was then basified with saturated aqueous potassium carbonate and extracted with DCM (3×11 mL). The combined DCM extracts were dried over sodium sulfate, filtered, and concentrated at reduced pressure. The resulting residue was purified by flash silica chromatography, elution gradient 0 to 60% EtOAc in hexanes. Product were combined and concentrated under reduced pressure to afford (1S,3R)-1-(5-bromopyridin-2-yl)-2-((1-fluorocyclopropyl)methyl)-3,5-dimethyl-1,2,3,4-tetrahydroisoquinolin-6-amine (138 mg, 44%) as an off-white foam. $^1$H NMR (300 MHz, DMSO-d$_6$, 27° C.) 0.38-0.51 (1H, m), 0.59-0.75 (1H, m), 0.77-1.01 (2H, m), 0.96 (3H, d), 1.94 (3H, s), 2.52-2.62 (2H, m), 2.76-2.85 (1H, m), 2.87-3.07 (1H, m), 3.41-3.65 (1H, m), 4.63 (2H, s), 4.75 (1H, s), 6.28-6.46 (2H, m), 7.24 (1H, d), 7.75-7.97 (1H, m), 8.42-8.66 (1H, m). m/z: ES+ [M+H]+ 404.

Preparation of (6S,8R)-6-(5-bromopyridin-2-0)-7-((1-fluorocyclopropyl)methyl)-8-methyl-6,7,8,9-tetrahydro-3H-pyrazolo[4,3-f]isoquinoline

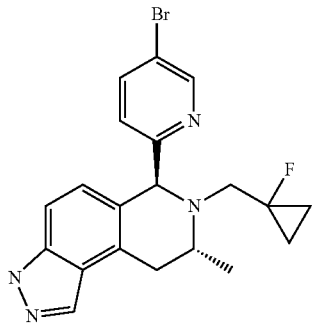 [SMILES: C[C@@H]1Cc2c(ccc3[nH]ncc23)[C@@H](c2ccc(Br)cn2)N1CC1(F)CC1]

A solution of sodium nitrite (23.55 mg, 0.34 mmol) in water (0.14 mL) was added dropwise over 1 minute to a stirred solution of (1S,3R)-1-(5-bromopyridin-2-yl)-2-((1-fluorocyclopropyl)methyl)-3,5-dimethyl-1,2,3,4-tetrahydroisoquinolin-6-amine (138 mg, 0.34 mmol) in propionic acid (1.39 ml) at −20° C. (salt/ice bath). After 20 minutes the reaction was diluted with ice-cold EtOAc (13 mL). The biphasic mixture was stirred vigorously and neutralised by slow addition of cold saturated aqueous NaHCO₃ (12 mL), resulting in gas evolution. The reaction was allowed to slowly warm to room temperature over 2 hours. The phases were separated, and the organic layer was washed with saturated aqueous NaHCO₃ solution (12 mL) saturated aqueous sodium chloride (10 mL), dried over magnesium sulfate, filtered, and concentrated under reduced pressure. The resulting residue was purified by flash silica chromatography, elution gradient 0 to 80% EtOAc in hexanes. Product fractions were concentrated under reduced pressure to give (6S,8R)-6-(5-bromopyridin-2-yl)-7-((1-fluorocyclopropyl)methyl)-8-methyl-6,7,8,9-tetrahydro-3H-pyrazolo[4,3-f]isoquinoline (82 mg, 58%) as a yellow-orange film. $^1$H NMR (300 MHz, DMSO-d₆, 27° C.) 0.39-0.56 (1H, m), 0.60-0.76 (1H, m), 0.77-1.00 (2H, m), 1.03 (3H, d) 2.60-2.72 (1H, m) 2.83-3.27 (3H, m) 3.48-3.80 (1H, m) 4.98 (1H, s) 6.85 (1H, d) 7.22 (1H, d) 7.35 (1H, d) 7.93 (1H, dd) 8.07 (1H, s) 8.59 (1H, d) 12.97 (1H, s). m/z: ES+ [M+H]+ 415.

Preparation of (6S,8R)-6-(5-bromopyridin-2-yl)-7-((1-fluorocyclopropyl)methyl)-8-methyl-3-(tetrahydro-2H-pyran-2-yl)-6,7,8,9-tetrahydro-3H-pyrazolo[4,3-f]isoquinoline

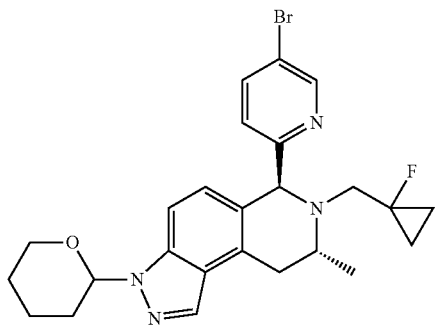 [SMILES: C[C@@H]1Cc2c(ccc3c2cnn3C2CCCCO2)[C@@H](c2ccc(Br)cn2)N1CC1(F)CC1]

To a solution of (6S,8R)-6-(5-bromopyridin-2-yl)-74(1-fluorocyclopropyl)methyl)-8-methyl-6,7,8,9-tetrahydro-3H-pyrazolo[4,3-f]isoquinoline (82 mg, 0.20 mmol) in DCM (1.46 mL) was added successively 3,4-dihydro-2H-pyran (0.027 ml, 0.30 mmol) and para-toluenesulfonic acid monohydrate (4 mg, 0.02 mmol) at room temperature. The reaction was stirred at room temperature for 30 minutes and then heated at 40° C. for 3 hours. More p-toluenesulfonic acid monohydrate (4 mg, 0.02 mmol) and 3,4-dihydro-2H-pyran (0.027 ml, 0.30 mmol) were added, and the reaction was transferred to a sealed microwave vessel and heated at 40° C. (behind a blast shield) in an oil bath overnight. The reaction was diluted with DCM and washed with saturated aqueous NaHCO₃, dried over sodium sulfate, filtered, and concentrated under reduced pressure. The resulting residue was purified by flash silica chromatography, elution gradient 0 to 70% EtOAc in hexanes. Product fractions were combined and concentrated under reduced pressure to give (6S,8R)-6-(5-bromopyridin-2-yl)-7-((1-fluorocyclopropyl)methyl)-8-methyl-3-(tetrahydro-2H-pyran-2-yl)-6,7,8,9-tetrahydro-3H-pyrazolo[4,3-f]isoquinoline (63 mg, 64%) as a light-yellow foam. $^1$H NMR (300 MHz, DMSO-d₆, 27° C.) 0.42-0.54 (1H, m), 0.62-0.73 (1H, m), 0.78-0.99 (2H, m), 1.00-1.06 (3H, m), 1.55-1.64 (2H, m), 1.67-1.81 (1H, m), 1.92-2.08 (1H, m), 2.11-2.24 (1H, m), 2.53-2.71 (2H, m), 2.77-2.89 (1H, m), 2.98-3.20 (2H, m), 3.61-3.77 (2H, m), 3.93-4.03 (1H, m), 4.90 (1H, s), 5.70 (1H, d), 6.74 (1H, d), 7.29 (1H, d), 7.35 (1H, d), 7.93 (1H, dd), 8.48 (1H, s), 8.60 (1H, d). m/z: ES+ [M+H]+ 499.

Preparation of (6S,8R)-7-((1-fluorocyclopropyl)methyl)-6-(5-(2-(3-(fluoromethyl)azetidin-1-yl)ethoxy)pyridin-2-yl)-8-methyl-3-(tetrahydro-2H-pyran-2-yl)-6,7,8,9-tetrahydro-3H-pyrazolo[4,3-f]isoquinoline

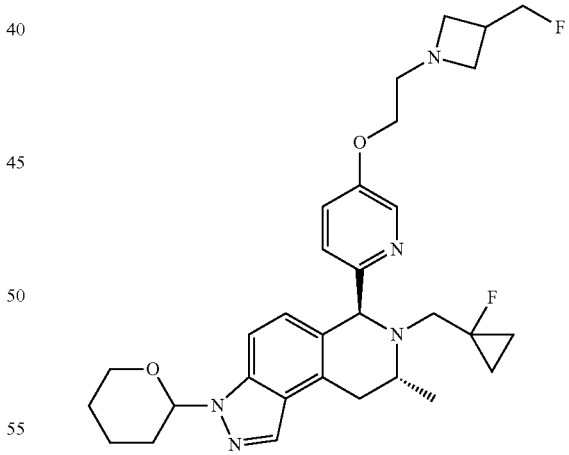

A solution of (6S,8R)-6-(5-bromopyridin-2-yl)-7-((1-fluorocyclopropyl)methyl)-8-methyl-3-(tetrahydro-2H-pyran-2-yl)-6,7,8,9-tetrahydro-3H-pyrazolo[4,3-f]isoquinoline (62 mg, 0.12 mmol) and 2-(3-(fluoromethyl)azetidin-1-yl)ethan-1-ol (33 mg, 0.25 mmol) in toluene (1.0 mL) was degassed and back-filled with nitrogen (3×). Cesium carbonate (101 mg, 0.31 mmol) and RockPhos 3rd Generation Precatalyst (5 mg, 6 μmol) were added sequentially. The suspension was degassed and back-filled with nitrogen (3×) and then heated at 75° C. for 2.5 hours. After cooling to room temperature, the reaction was diluted with EtOAc and washed with saturated aqueous sodium chloride. The aqueous layer was extracted with EtOAc, then the combined organic layers were dried over sodium sulfate, filtered, and concentrated under reduced pressure. The resulting residue was used in the next step without further purification. m/z: ES+ [M+H]+ 552.

Example 9

Preparation of (6S,8R)-6-(4-(2-(3-(fluoromethyl)azetidin-1-yl)ethoxy)-2-methoxyphenyl)-7-isobutyl-8-methyl-6,7,8,9-tetrahydro-3H-pyrazolo[4,3-f]isoquinoline

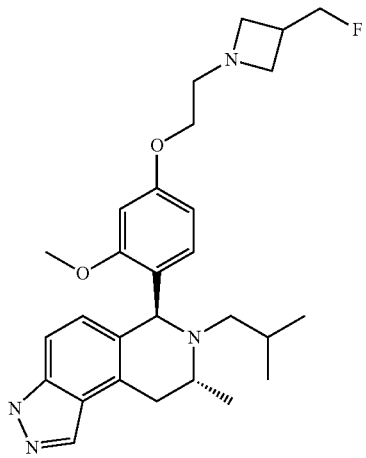 [SMILES: COc1cc(OCCN2CC(CF)C2)ccc1[C@@H]1c2ccc3[nH]ncc3c2C[C@@H](C)N1CC(C)C]

(6S,8R)-6-(4-(2-(3-(Fluoromethyl)azetidin-1-yl)ethoxy)-2-methoxyphenyl)-7-isobutyl-8-methyl-3-(tetrahydro-2H-pyran-2-yl)-6,7,8,9-tetrahydro-3H-pyrazolo[4,3-f]isoquinoline (120 mg, 0.21 mmol) was dissolved in MeOH (2 mL) and treated slowly with HCl in dioxane (4M; 0.53 mL, 2.1 mmol) at room temperature. The reaction was stirred for 30 minutes under these conditions and then concentrated under reduced pressure. The resulting residue was purified by preparative HPLC (Waters Xbridge Phenyl column, 5 μm silica, 19 mm diameter, 100 mm length, 20 mL/min), eluting with 50 to 80% acetonitrile in water containing 0.2% $NH_4OH$ (pH 10) over 6 minutes. Product fractions were concentrated under reduced pressure to afford (6S,8R)-6-(4-(2-(3-(fluoromethyl)azetidin-1-yl)ethoxy)-2-methoxyphenyl)-7-isobutyl-8-methyl-6,7,8,9-tetrahydro-3H-pyrazolo[4,3-f]isoquinoline (38 mg, 37%) as a light yellow solid. $^1$H NMR (300 MHz, DMSO-$d_6$, 27° C.) 0.73 (3H, d), 0.83 (3H, d), 0.97 (3H, d), 1.78-1.91 (1H, m), 1.91-2.04 (1H, m), 2.19-2.30 (1H, m), 2.65-2.75 (3H, m), 2.80 (1H, dd), 3.00 (2 H, t), 3.12 (1H, dd), 3.26-3.35 (2H, m), 3.36-3.46 (1H, m), 3.81-3.90 (5H, m), 4.51 (2H, dd), 5.16 (1H, s), 6.29 (1H, dd), 6.54 (1H, d), 6.65 (2H, app dd), 7.17 (1H, d), 8.03 (1H, s), 12.90 (1H, br. s). m/z: ES+ [M+H]+ 481.

The starting material (6S,8R)-6-(4-(2-(3-(Fluoromethyl)azetidin-1-yl)ethoxy)-2-methoxyphenyl)-7-isobutyl-8-methyl-3-(tetrahydro-2H-pyran-2-yl)-6,7,8,9-tetrahydro-3H-pyrazolo[4,3-f]isoquinoline was prepared as follows;

Preparation of (1S,3R)-1-(4-bromo-2-methoxyphenyl)-2-isobutyl-3,5-dimethyl-1,2,3,4-tetrahydroisoauinolin-6-amine

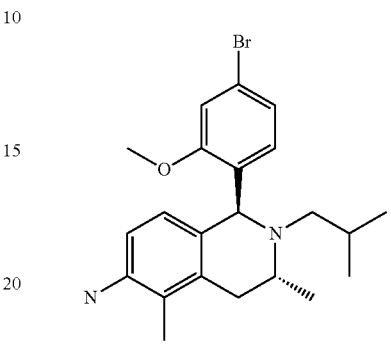

(R)-3-(2-(isobutylamino)propyl)-2-methylaniline, 2trifluoroacetic acid (310 mg, 0.69 mmol) and 4-bromo-2-methoxybenzaldehyde (297 mg, 1.38 mmol) were suspended in acetic acid (4 mL) and water (0.082 mL). The reaction was heated to 80° C. under nitrogen for 18 hours. The reaction was concentrated under reduced pressure (40° C. water bath temperature), and the resulting residue was dissolved in EtOAc (12 mL) and neutralized with saturated aqueous $NaHCO_3$. The aqueous layer was extracted with EtOAc (10 mL), and the combined organic layers were dried over sodium sulfate, filtered, and concentrated under reduced pressure to a yellow residue. This residue was redissolved in EtOAc (11 mL) and treated with aqueous HCl (1N; 7 mL), and the biphasic mixture was stirred vigorously for 20 minutes. The layers were separated, and the organic layer was extracted with aqueous HCl (1N; 2×4 mL). The combined acidic aqueous layers were extracted with DCM (10 mL) and then basified with saturated potassium carbonate and extracted with DCM (3×11 mL). The combined DCM extracts of the basified aqueous layers were dried over sodium sulfate, filtered, and concentrated under reduced pressure. The resulting residue was purified by flash silica chromatography, elution gradient 0 to 80% EtOAc in hexanes. Product fractions were combined and concentrated under reduced pressure to afford (1S,3R)-1-(4-bromo-2-methoxyphenyl)-2-isobutyl-3,5-dimethyl-1,2,3,4-tetrahydroisoquinolin-6-amine (213 mg, 74%) as an off-white foam. $^1$H NMR (300 MHz, DMSO-$d_6$, 27° C.) 0.72 (3H, d), 0.82 (3H, d), 0.91 (3H, d), 1.75-1.92 (2H, m), 1.94 (3H, s), 2.13-2.25 (1H, m), 2.40 (1H, dd), 2.58-2.77 (1H, m), 3.15-3.27 (1H, m), 3.86 (3H, s), 4.51-4.63 (2H, m), 5.01 (1H, s), 6.27 (1H, d), 6.37 (1H, d), 6.71 (1H, d), 6.94 (1 H, dd), 7.15 (1 H). m/z: ES+ [M+H]+ 417.

Preparation of (6S,8R)-6-(4-bromo-2-methoxyphenyl)-7-isobutyl-8-methyl-6,7,8,9-tetrahydro-3H-pyrazolo[4,3-f]isoquinoline

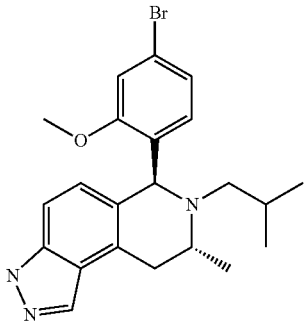 [SMILES: COc1cc(Br)ccc1[C@@H]1c2ccc3[nH]ncc3c2C[C@@H](C)N1CC(C)C]

A solution of sodium nitrite (35 mg, 0.51 mmol) in water (0.20 mL) was added dropwise over 1 minute to a stirred solution of (1S,3R)-1-(4-bromo-2-methoxyphenyl)-2-isobutyl-3,5-dimethyl-1,2,3,4-tetrahydroisoquinolin-6-amine (211 mg, 0.51 mmol) in propionic acid (2 mL) at −20° C. (salt/ice bath) in a 100 mL pear-shaped flask. After 20 minutes the reaction was diluted with ice-cold EtOAc (10 mL). The biphasic mixture was stirred vigorously for 10 minuts and neutralised by slow addition of cold saturated aqueous NaHCO$_3$ (20 mL). The phases were separated, and the organic layer was washed with saturated NaHCO$_3$ (12.5 mL) and saturated aqueous sodium chloride (8 mL), dried over MgSO$_4$, filtered, and concentrated under reduced pressure to a brown residue. This residue was purified by flash silica chromatography, elution gradient 0 to 70% EtOAc in hexanes. Product fractions were concentrated under reduced pressure to give (6S,8R)-6-(4-bromo-2-methoxyphenyl)-7-isobutyl-8-methyl-6,7,8,9-tetrahydro-3H-pyrazolo[4,3 f]isoquinoline (132 mg, 61%) as a yellow-orange film. $^1$H NMR (300 MHz, DMSO-d$_6$, 27° C.) 0.71 (3H, d), 0.82 (3H, d), 0.95 (3H, d), 1.75-1.96 (2H, m) 2.27-2.35 (1H, m) 2.82 (1H, dd) 3.06-3.22 (1H, m) 3.31-3.46 (1H, m) 3.89 (3H, s), 5.18 (1H, s), 6.67 (1H, d), 6.75 (1H, d), 6.93 (1H, dd), 7.12-7.24 (2H, m), 8.03 (1H, s), 12.94 (1H, s). m/z: ES+ [M+H]+ 428.

Preparation of (6S,8R)-6-(4-bromo-2-methoxyphenyl)-7-isobutyl-8-methyl-3-(tetrahydro-2H-pyran-2-yl)-6,7,8,9-tetrahydro-3H-pyrazolo[4,3-f]isoquinoline

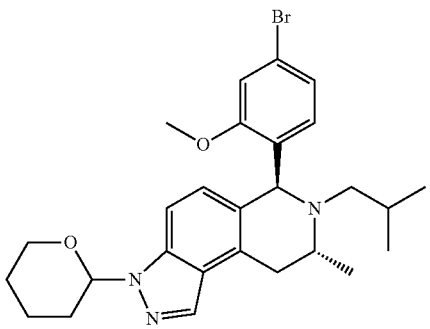 [SMILES: COc1cc(Br)ccc1[C@@H]1c2ccc3c(cnn3C3CCCCO3)c2C[C@@H](C)N1CC(C)C]

3,4-Dihydro-2H-pyran (0.041 mL, 0.45 mmol) and para-toluenesulfonic acid monohydrate (6 mg, 0.03 mmol) were added sequentially to a solution of (6S,8R)-6-(4-bromo-2-methoxyphenyl)-7-isobutyl-8-methyl-6,7,8,9-tetrahydro-3H-pyrazolo[4,3-f]isoquinoline (129 mg, 0.30 mmol) in DCM (1.5 mL) at room temperature. The reaction was stirred at room temperature for 30 minutes and then heated at 40° C. for 3 hours. More para-toluenesulfonic acid monohydrate (6 mg, 0.03 mmol) was added, and the reaction was heated for another 2 hours under these conditions. More 3,4-dihydro-2H-pyran (0.041 mL, 0.45 mmol) was added, and the reaction was transferred to a sealed microwave vessel (behind a blast shield) and heated at 100° C. for 30 minutes. The reaction was diluted with DCM (10 mL) and washed with saturated aqueous NaHCO$_3$ (2 mL). The organic layer was dried over sodium sulfate, filtered, and concentrated under reduced pressure. The resulting residue was purified by flash silica chromatography, elution gradient 0 to 70% EtOAc in hexanes. Product fractions were concentrated under reduced pressure to give (6S,8R)-6-(4-bromo-2-methoxyphenyl)-7-isobutyl-8-methyl-3-(tetrahydro-2H-pyran-2-yl)-6,7,8,9-tetrahydro-3H-pyrazolo[4,3-f]isoquinoline (114 mg, 74%) as a yellow oil. $^1$H NMR (300 MHz, DMSO-d$_6$, 27° C.) 0.72 (3H, d), 0.83 (3 H, d), 0.96 (3H, d), 1.54-1.65 (2H, m), 1.66-2.08 (5H, m), 2.11-2.36 (2H, m), 2.67-2.78 (1H, m), 3.06 (1H, d), 3.33-3.43 (1H, m), 3.66-3.77 (1H, m), 3.91 (3H, s), 3.95-4.02 (1H, m), 5.12 (1H, s), 5.69 (1H, dd), 6.57 (1H, d), 6.80 (1H, dd), 6.96 (1H, dd), 7.21 (1 H, s), 7.26 (1 H, d), 8.45 (1 H, s). m/z: ES+ [M+H]+ 513.

Preparation of (6S,8R)-6-(4-(2-(3-(fluoromethyl)azetidin-1-yl)ethoxy)-2-methoxyphenyl)-7-isobutyl-8-methyl-3-(tetrahydro-2H-pyran-2-yl)-6,7,8,9-tetrahydro-3H-pyrazolo[4,3-f]isoquinoline

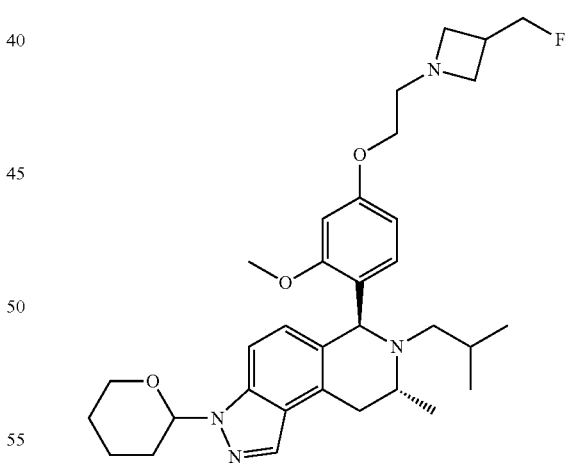

A solution of (6S,8R)-6-(4-bromo-2-methoxyphenyl)-7-isobutyl-8-methyl-3-(tetrahydro-2H-pyran-2-yl)-6,7,8,9-tetrahydro-3H-pyrazolo[4,3-f]isoquinoline (112 mg, 0.22 mmol) and 2-(3-(fluoromethyl)azetidin-1-yl)ethan-1-ol (58 mg, 0.44 mmol) in toluene (1.821 ml) was degassed and back-filled with nitrogen (3×). Cesium carbonate (178 mg, 0.55 mmol) and RockPhos 3rd Generation Precatalyst (10 mg, 11 μmol) were added successively. The suspension was degassed and back-filled with nitrogen (3×) and then heated at 90° C. for 5 hours. After cooling, the reaction was diluted with EtOAc and washed with water. The aqueous layer was extracted with EtOAc, and the combined organic layers were dried over sodium sulfate, filtered, and concentrated under reduced pressure. The resulting crude residue was used without further purification. m/z: ES+ [M+H]+ 565.

Example 10

Preparation of (6S,8R)-7-(2,2-difluoro-3-methoxypropyl)-6-(5-(2-(3-(fluoromethyl)azetidin-1-yl)ethoxy)pyridin-2-yl)-8-methyl-6,7,8,9-tetrahydro-3H-pyrazolo[4,3-f]isoquinoline

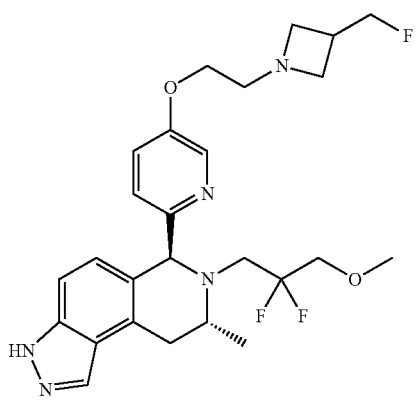 [SMILES: COCC(F)(F)CN1[C@H](c2ccc(OCCN3CC(CF)C3)cn2)c2ccc3[nH]ncc3c2C[C@H]1C]

RockPhos 3$^{rd}$ Generation Precatalyst (12.76 mg, 0.01 mmol) and cesium carbonate (303 mg, 0.93 mmol) were added to a degassed solution of (6S,8R)-6-(5-bromopyridin-2-yl)-7-(2,2-difluoro-3-methoxypropyl)-8-methyl-3-(tetrahydro-2H-pyran-2-yl)-6,7,8,9-tetrahydro-3H-pyrazolo[4,3-f]isoquinoline (200 mg, 0.37 mmol) and 2-(3-(fluoromethyl)azetidin-1-yl)ethan-1-ol (99 mg, 0.75 mmol) in toluene (2988 μL) and the reaction was heated to 90° C. for 5 hours. After cooling, the reaction was diluted with DCM and washed with water. The organic phase was evaporated, then dissolved in DCM (3 mL), before trifluoroacetic acid (1.5 mL) was added. The mixture was stirred at room temperature for 1 hour, then was diluted with DCM and washed with saturated NaHCO$_3$ solution. The layers were separated and the aqueous phase was extracted with DCM. The combined organic phases were dried and evaporated. The crude product was purified by preparative HPLC (Waters XBridge Prep C18 OBD column, 5μ silica, 30 mm diameter, 100 mm length), using decreasingly polar mixtures of water (containing 0.1% NH3) and MeCN as eluents. Fractions containing the desired compound were evaporated to dryness to afford (6S,8R)-7-(2,2-difluoro-3-methoxypropyl)-6-(5-(2-(3-(fluoromethyl)azetidin-1-yl)ethoxy)pyridin-2-yl)-8-methyl-6,7,8,9-tetrahydro-3 H-pyrazolo[4 ,3-f]isoquinoline (102 mg, 54%) as a colourless gummy solid. $^1$H NMR (500 MHz, CDCl$_3$, 27° C.) 1.12 (3H, d), 2.68-2.94 (5H, m), 3.08-3.15 (2H, m), 3.15-3.23 (2H, m), 3.38 (3H, s), 3.46-3.56 (3H, m), 3.61 (1H, q), 3.73 (1H, dt), 3.99 (2H, t), 4.44 (1H, d), 4.54 (1H, d), 5.12 (1H, s), 6.81 (1H, d), 7.05 (1H, d), 7.12 (1H, dd), 7.26-7.32 (1H, m), 7.94 (1H, d), 8.17 (1H, d), 11.60 (1H, s). m/z: ES+ [M+H]+ 504.

Preparation of 2,2-difluoro-3-(trityloxy)propan-1-ol

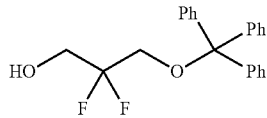

2,2-Difluoropropane-1,3-diol (2.50 g, 22.3 mmol) was dissolved in DCM (61.7 mL) and THF (15.4 mL). DIPEA (3.93 mL, 22.3 mmol) was added, followed by (chloromethanetriyl)tribenzene (6.22 g, 22.3 mmol) and finally DMAP (0.288 g, 2.23 mmol). The reaction was heated to 40° C. for 2 hours. After cooling, the reaction was washed with 1N HCl solution, then dried and evaporated. The crude product was purified by flash silica chromatography, elution gradient 0 to 25% EtOAc in heptane. Pure fractions were evaporated to dryness to afford 2,2-difluoro-3-(trityloxy)propan-1-ol (4.43 g, 56%) as a colourless solid. $^1$H NMR (500 MHz, CDCl$_3$) 3.42 (2H, t), 3.92 (2H, t), 7.23-7.30 (4H, m), 7.30-7.39 (6H, m), 7.39-7.49 (6H, m).

Preparation of ((2,2-difluoro-3-methoxypropoxy)methanetriyl)tribenzene

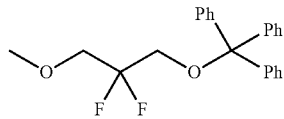 [SMILES: COCC(F)(F)COC(c1ccccc1)(c1ccccc1)c1ccccc1]

Sodium hydride (0.562 g, 14.0 mmol) was added to a solution of 2,2-difluoro-3-(trityloxy)propan-1-ol (4.15 g, 11.7 mmol) in THF (46 mL) and the reaction was stirred for 1 hour, then iodomethane (0.802 mL, 12.9 mmol) was added in THF (5 mL). The reaction was stirred for a further 1 hour. The reaction was quenched with water and brine, then extracted with EtOAc. The organic layer was dried and evaporated to afford ((2,2-difluoro-3-methoxypropoxy)methanetriyl)tribenzene (4.18 g, 97%) as a pale yellow oil. $^1$H NMR (500 MHz, CDCl$_3$) 3.36 (2H, t), 3.40 (3H, s), 3.77 (2H, t), 7.15-7.28 (3H, m), 7.28-7.38 (6H, m), 7.39-7.47 (6H, m).

Preparation of 2,2-difluoro-3-methoxypropyl trifluoromethanesulfonate

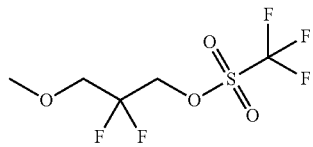

Trifluoromethanesulfonic anhydride (1.918 mL, 11.40 mmol) was added to a solution of ((2,2-difluoro-3-methoxypropoxy)methanetriyl)tribenzene (4.00 g, 10.9 mmol) in DCM (39.6 mL). The reaction was stirred for 30 minutes, then triethylsilane (1.934 mL, 11.94 mmol) was added and the reaction was stirred for a further 30 minutes. The reaction was evaporated and the triflate was used directly in the next stage.

Preparation of (R)-1-(3-bromo-2-methylphenyl)propan-2-amine

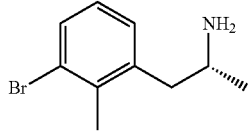

n-BuLi (26.1 mL, 41.8 mmol) was added dropwise to a solution of 1,3-dibromo-2-methylbenzene (9.95 g, 39.8 mmol) in THF (100 mL) at -78° C. After stirring for 30 minutes, (R)-tert-butyl 4-methyl-1,2,3-oxathiazolidine-3-carboxylate 2,2-dioxide (10.39 g, 43.8 mmol) was added in portions and the reaction was stirred for a further 30 minutes before being allowed to warm to 0° C. over 30 minutes. 1N citric acid was added and the mixture was stirred for 5 minutes before it was extracted with EtOAc (×2). The combined organic phases were evaporated. The residue was stirred in 4M HCl in dioxane (69.7 mL, 278.7 mmol) at room temperature for 1 hour, then the volatiles were evaporated. The residue was suspended in diethyl ether, and extracted with water (×2). The combined aqueous phases were basified by addition of 2N $Na_2CO_3$, then extracted with DCM (×3). The combined organics phases were dried over $MgSO_4$ and concentrated to afford (R)-1-(3-bromo-2-methylphenyl)propan-2-amine (7.55 g, 83%) as a yellow oil. $^1$H NMR (400 MHz, $CDCl_3$, 27° C.) 1.13 (3H, d), 1.43 (2H, s), 2.40 (3H, s), 2.61 (1H, dd), 2.77 (1H, dd), 3.14 (1H, dq), 6.97 (1H, t), 7.08 (1H, d), 7.43 (1H, d). m/z (ES+), [M+H]+=228.

Preparation of (R)-N-(1-(3-bromo-2-methylphenyl)propan-2-yl)-2,2-difluoro-3-methoxypropan-1-amine

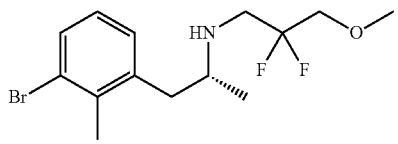 [SMILES: COCC(F)(F)CN[C@H](C)Cc1cccc(Br)c1C]

2,2-Difluoro-3-methoxypropyl trifluoromethanesulfonate (3.03 g, 11.73 mmol) (crude from the previous step) was added to a solution of (R)-1-(3-bromo-2-methylphenyl)propan-2-amine (2.327 g, 10.2 mmol) and DIPEA (2.82 mL, 16.32 mmol) in 1,4-dioxane (34.3 mL) and the reaction was heated to 80° C. overnight. After cooling, the volatiles were evaporated, then the residue was dissolved in DCM and washed with brine. The organic phase was dried and evaporated, then the crude product was purified by flash silica chromatography, elution gradient 0 to 100% EtOAc in heptane. Pure fractions were evaporated to dryness to afford (R)-N-(1-(3-bromo-2-methylphenyl)prop an-2-yl)-2,2-difluoro-3-methoxyprop an-1-amine (2.330 g, 68%) as a pale yellow oil. $^1$H NMR (500 MHz, $CDCl_3$) 1.06 (3H, d), 2.40 (3H, s), 2.63 (1H, dd), 2.82 (1H, dd), 2.86-2.94 (1H, m), 2.95-3.11 (2H, m), 3.38 (3H, s), 3.51-3.63 (2H, m), 6.94-7 (1H, m), 7.07 (1H, dd), 7.4-7.51 (1H, m). m/z: ES+ [M+H]+ 336.

Preparation of (R)-3-(2-((2,2-difluoro-3-methoxypropyl)amino)propyl)-2-methylaniline

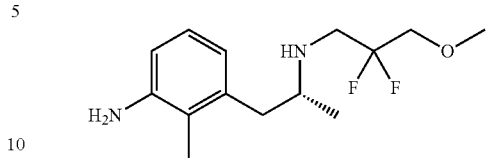

$Pd_2(dba)_3$ (0.184 g, 0.20 mmol) and Rac-BINAP (0.250 g, 0.40 mmol) were added to a suspension of (R)-N-(1-(3-bromo-2-methylphenyl)propan-2-yl)-2,2-difluoro-3-methoxypropan-1-amine (2.25 g, 6.69 mmol), benzophenone imine (1.235 mL, 7.36 mmol) and sodium tert-butoxide (0.965 g, 10.0 mmol) in degassed toluene (28.5 mL) and the reaction was heated to 90° C. for 3 hours. After cooling, the toluene was largely evaporated, then the residue was dissolved in DCM and washed with water. The aqueous phase was extracted with DCM, then the organics were evaporated to ~50 mL volume. 2N HCl solution (50 mL) was added and the biphasic mixture was stirred vigorously for 30 minutes. The layers were separated, then the aqueous was extracted with DCM. The organic phase was back extracted with 1N HCl. The combined aqueous phases were basified by addition of solid $K_2CO_3$ then extracted with DCM (×3), and the combined DCM extracts were dried and evaporated to afford (R)-3-(2-((2,2-difluoro-3-methoxypropyl)amino)propyl)-2-methylaniline (1.780 g, 98%) as a light brown oil. $^1$H NMR (500 MHz, $CDCl_3$) 1.06 (3H, d), 2.11 (3H, s), 2.59 (1H, dd), 2.75 (1H, dd), 2.86-2.94 (1H, m), 2.94-3.12 (2H, m), 3.38 (3H, s), 3.53-3.63 (4H, m), 6.5-6.68 (2H, m), 6.86-7.01 (1H, m). m/z: ES+ [M+H]+ 273.

Preparation of (1S,3R)-1-(5-bromopyridin-2-yl)-2-(2,2-difluoro-3-methoxypropyl)-3,5-dimethyl-1,2,3,4-tetrahydroisoauinolin-6-amine

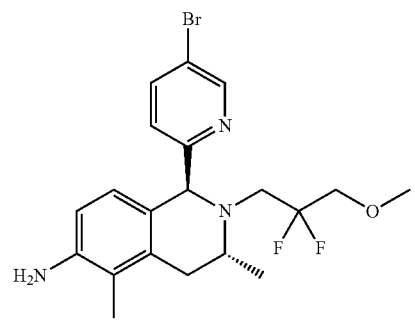 [SMILES: COCC(F)(F)CN1[C@H](c2ccc(Br)cn2)c2ccc(N)c(C)c2C[C@H]1C]

5-Bromopicolinaldehyde (1172 mg, 6.30 mmol) was added to a solution of (R)-3-(2-((2,2-difluoro-3-methoxypropyl)amino)propyl)-2-methylaniline (817 mg, 3.00 mmol) in acetic acid (14.7 mL) and water (270 µL, 15.0 mmol) and the reaction was heated to 80° C. for 2 hours. After cooling, the volatiles were evaporated under vacuum. The residue was dissolved in DCM and washed with saturated $NaHCO_3$ solution. The organic was evaporated to a volume ~20 mL and 2N HCl solution (20 mL) was added. The biphasic mixture was stirred for 15 minutes, then separated. The organic was extracted with water, then the aqueous phase was back-extracted with DCM. The aqueous phase was then basified by addition of solid K₂CO₃, then extracted with DCM. The organic extracts were dried and evaporated. The crude product was purified by flash silica chromatography, elution gradient 0 to 50% EtOAc in heptane. Pure fractions were evaporated to dryness to afford (1S,3R)-1-(5-bromopyridin-2-yl)-2-(2,2-difluoro-3-methoxypropyl)-3,5-dimethyl-1,2,3,4-tetrahydroisoquinolin-6-amine (810 mg, 61%) as a beige solid. $^1$H NMR (500 MHz, CDCl₃) 1.07 (3H, d), 2.05 (3H, s), 2.49 (1H, d), 2.75 (2H, dd), 3.04-3.17 (1H, m), 3.30-3.36 (1H, m), 3.37 (3H, s), 3.58-3.74 (2H, m), 4.96 (1H, s), 6.51 (1H, d), 6.60 (1H, d), 7.22 (1H, d), 7.68 (1H, dd), 8.55 (1H, dd). m/z: ES+ [M+H]+ 440.

Preparation of (6S,8R)-6-(5-bromopyridin-2-yl)-7-(2,2-difluoro-3-methoxypropyl)-8-methyl-6,7,8,9-tetrahydro-3H-pyrazolo[4,3-f]isoquinoline

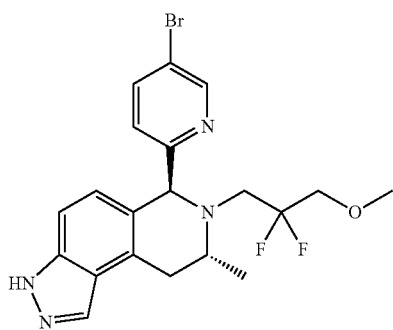 [SMILES: COCC(F)(F)CN1[C@H](c2ccc(Br)cn2)c2ccc3[nH]ncc3c2C[C@H]1C]

Sodium nitrite (133 mg, 1.93 mmol) was added in water (0.5 mL) to a cooled solution of (1S,3R)-1-(5-bromopyridin-2-yl)-2-(2,2-difluoro-3-methoxypropyl)-3,5-dimethyl-1,2,3,4-tetrahydroisoquinolin-6-amine (771 mg, 1.75 mmol) in propionic acid (5833 μL)/water (1167 μL) at −15° C. The reaction was stirred for 30 minutes, then EtOAc (50 mL), which had been cooled in dry-ice was added. The reaction was quenched by addition of 2N Na₂CO₃ until bubbling ceased, then the layers were separated. The aqueous was extracted with EtOAc, then the organic was dried and evaporated. The crude product was purified by flash silica chromatography, elution gradient 0 to 50% EtOAc in heptane. Pure fractions were evaporated to dryness to afford (6S,8R)-6-(5-bromopyridin-2-yl)-7-(2,2-difluoro-3-methoxypropyl)-8-methyl-6,7,8,9-tetrahydro-3H-pyrazolo[4,3-f]isoquinoline (460 mg, 58%) as a pale yellow solid. $^1$H NMR (500 MHz, CDCl₃) 1.14 (3H, d), 2.81 (1H, dd), 2.88 (1H, dd), 3.10-3.26 (2H, m), 3.38 (3H, s), 3.46-3.55 (1H, m), 3.58-3.76 (2H, m), 5.13 (1H, s), 6.94 (1H, d), 7.23 (1H, dd), 7.29 (1H, d), 7.72 (1H, dd), 8.05 (1H, d), 8.57 (1H, dd). m/z: ES+ [M+H]+ 451.

Preparation of (6S,8R)-6-(5-bromopyridin-2-yl)-7-(2,2-difluoro-3-methoxypropyl)-8-methyl-3-(tetrahydro-2H-pyran-2-yl)-6,7,8,9-tetrahydro-3H-pyrazolo[4,3-f]isoquinoline

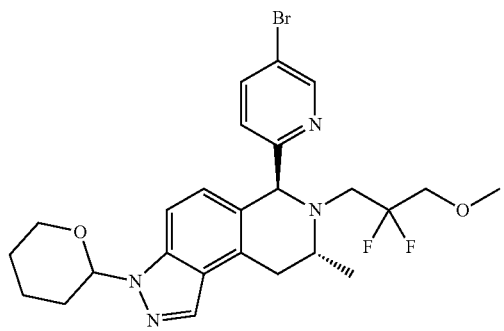 [SMILES: COCC(F)(F)CN1[C@H](c2ccc(Br)cn2)c2ccc3c(cnn3C3CCCCO3)c2C[C@H]1C]

3,4-Dihydro-2H-pyran (0.114 mL, 1.25 mmol) was added to a solution of (6S,8R)-6-(5-bromopyridin-2-yl)-7-(2,2-difluoro-3-methoxypropyl)-8-methyl-6,7,8,9-tetrahydro-3H-pyrazolo[4,3-f]isoquinoline (450 mg, 1.00 mmol) and para-toluenesulfonic acid hydrate (37.9 mg, 0.20 mmol) in DCM (5 mL) and the reaction was heated to 45° C. for 3 hours. After cooling, the reaction was diluted with DCM and washed with saturated NaHCO₃ solution. The organic phase was dried and evaporated, then the crude was passed through a plug of silica (1:1 EtOAc/heptane). The filtrate was evaporated to afford (6S,8R)-6-(5-bromopyridin-2-yl)-7-(2,2-difluoro-3-methoxypropyl)-8-methyl-3-(tetrahydro-2H-pyran-2-yl)-6,7,8,9-tetrahydro-3H-pyrazolo[4,3-f]isoquinoline (510 mg, 9%) as an orange solid (-6.5:1 ratio of THP regioisomers). m/z: ES+ [M+H]+ 535.

Examples 11-48 (Table E below) were similarly prepared using methods analogous to those described above. Further intermediates used in the preparation of Examples 11-48 are described as follows;

Intermediate Used in the Preparation of Examples 25-27

Preparation of 4-bromo-2-fluoro-6-methoxybenzaldehyde

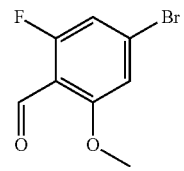

Sodium methanolate (2.90 g, 53.76 mmol) was added to a solution of 4-bromo-2,6-difluorobenzaldehyde (9.90 g, 44.8 mmol) in methanol (90 mL) and the reaction was heated to reflux for 5 hours. After cooling, the volatiles were evaporated. The residue was dissolved in DCM (300 mL) and washed with 1N HCl (300 mL) solution and brine. The organic phase was dried and evaporated, then the crude product was purified by flash silica chromatography, elution gradient 0 to 100% EtOAc in heptane. Pure fractions were evaporated to dryness to afford 4-bromo-2-fluoro-6- methoxybenzaldehyde (6.79 g, 65%) as colourless solid. ¹H NMR (500 MHz, CDCl₃, 27° C.) 3.94 (3H, s), 6.90-7.00 (2H, m), 10.38 (1H, s).

Intermediates Used in the Preparation of Example 42

Preparation of (6-chloro-4-methoxypyridin-3-yl)methanol

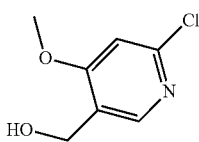

Diisobutylaluminium hydride (1 M in toluene; 7.60 mL, 7.60 mmol) was added dropwise to a cooled solution of methyl 6-chloro-4-methoxynicotinate (958 mg, 4.75 mmol) in THF (11.4 mL) at −60° C. The reaction was maintained under these conditions for 1 hour. An additional portion of diisobutylaluminium hydride (0.5 equiv, 2.5 mL) was then added and the reaction was stirred for a further 1 hour. The reaction was quenched by addition of water and EtOAc. The layers were separated and the aqueous layer was extracted with EtOAc. The combined organic layers were washed with saturated aqueous sodium chloride, dried over sodium sulfate, filtered and concentrated under reduced pressure. The resulting residue was purified by flash silica chromatography, elution gradient 0 to 100% EtOAc in heptane. Product fractions were evaporated to dryness to afford 6-chloro-4-methoxybenzaldehyde as a colourless solid (776 mg, 94%). ¹H NMR (500 MHz, CDCl₃, 27° C.) 2.14 (1H, t), 3.92 (3H, s), 4.67 (2H, d), 6.83 (1H, s), 8.19 (1H, s). m/z: ES+ [M+H]+ 174.

Preparation of 6-chloro-4-methoxynicotinaldehyde

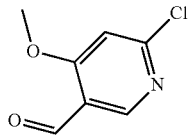

Dess-Martin periodinane (2.08 g, 4.91 mmol) was added to a solution of (6-chloro-4-methoxypyridin-3-yl)methanol (775 mg, 4.46 mmol) in DCM (19.8 mL) and the reaction was stirred at room temperature for 1 hour. A solution of aqueous Na₂CO₃ (2N; 20 mL) was added and the biphasic mixture was stirred at room temperature for 10 minutes. The layers were separated and the aqueous layer was extracted with DCM. The combined organic layers were washed with saturated aqueous sodium chloride, dried over sodium sulfate, filtered and concentrated under reduced pressure. The resulting residue was purified by flash silica chromatography, elution gradient 0 to 50% EtOAc in heptane. Product fractions were evaporated to dryness to afford 6-chloro-4-methoxynicotinaldehyde (665 mg, 87%) as a colourless solid. ¹H NMR (500 MHz, CDCl₃, 27° C.) 4.02 (3H, s), 6.97 (1H, s), 8.68 (1H, s), 10.37 (1H, d). m/z: ES+ [M+H]+ 172.

TABLE E

| Example | Structure | Name | 1H NMR | LCMS [M + H] |
|---|---|---|---|---|
| 11 | 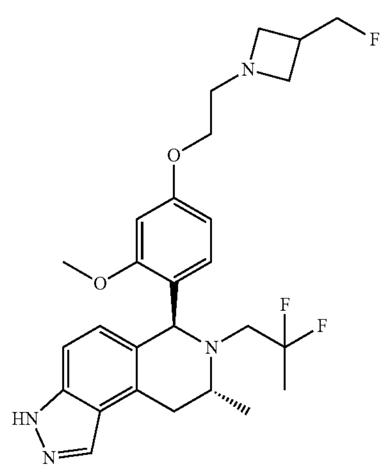 [SMILES: COc1cc(OCCN2CC(CF)C2)ccc1[C@@H]1c2ccc3[nH]ncc3c2C[C@@H](C)N1CC(C)(F)F] | (6S,8R)-7-(2,2-difluoropropyl)-6-(4-(2-(3-(fluoromethyl)azetidin-1-yl)ethoxy)-2-methoxyphenyl)-8-methyl-6,7,8,9-tetrahydro-3H-pyrazolo[4,3-f]isoquinoline | ¹H NMR (500 MHz, CDCl₃, 27° C.) 1.09 (3H, d), 1.51 (3H, t), 2.63 (1H, q), 2.89 (5H, s), 3.23 (3H, dd), 3.51-3.66 (3H, m), 3.86 (3H, s), 3.95 (2H, s), 4.46 (1H, d), 4.56 (1H, d), 5.38 (1H, s), 6.26 (1H, dd), 6.50 (1H, d), 6.69 (1H, d), 6.78 (1H, d), 7.15 (1H, d), 8.05 (1H, s), 10.10 (1H, s). | 503 |

TABLE E-continued

| Example | Structure | Name | 1H NMR | LCMS [M + H] |
|---|---|---|---|---|
| 12 | 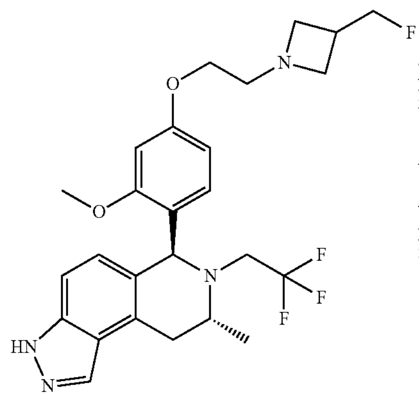 | (6S,8R)-6-(4-(2-(3-(fluoromethyl)azetidin-1-yl)ethoxy)-2-methoxyphenyl)-8-methyl-7-(2,2,2-trifluoroethyl)-6,7,8,9-tetrahydro-3H-pyrazolo[4,3-f]isoquinoline | ¹H NMR (300 MHz, DMSO-d₆, 27° C.) 1.06 (3H, d), 2.70 (3H, t), 2.79-2.95 (2H, m), 2.99 (2H, t), 3.14 (1H, dd), 3.41 (4H, dd), 3.85 (3H, s), 3.86-3.93 (2H, m), 4.42 (1H, d), 4.58 (1H, d), 5.36 (1H, s), 6.30 (1H, dd), 6.52-6.61 (2H, m), 6.66 (1H, d), 7.21 (1H, d), 8.05 (1H, s), 12.97 (1H, s). | 507 |
| 13 | 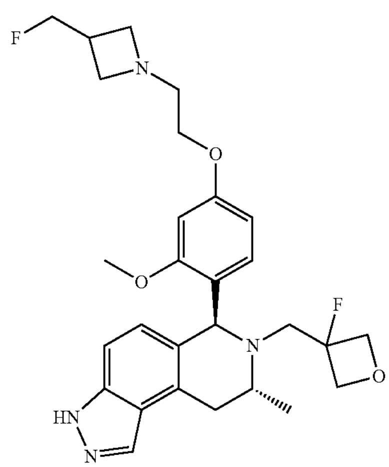 [SMILES: COc1cc(OCCN2CC(CF)C2)ccc1[C@@H]1c2ccc3[nH]ncc3c2C[C@@H](C)N1CC1(F)COC1] | (6S,8R)-6-(4-(2-(3-(fluoromethyl)azetidin-1-yl)ethoxy)-2-methoxyphenyl)-7-((3-fluorooxetan-3-yl)methyl)-8-methyl-6,7,8,9-tetrahydro-3H-pyrazolo[4,3-f]isoquinoline | ¹H NMR (300 MHz, DMSO-d₆, 27° C.) 1.02 (3H, d), 2.62-2.91 (5H, m), 2.98-3.15 (3H, m), 3.17 (1H, d), 3.33-3.5 (3H, m), 3.86 (3H, s), 3.87-3.95 (1H, m), 4.3-4.4 (1H, m), 4.43 (2H, d), 4.44-4.56 (2H, m), 4.59 (2H, d), 5.31 (1H, s), 6.31 (1H, dd), 6.57 (2H, dd), 6.65 (1H, d), 7.20 (1H, d), 8.05 (1H, s), 12.95 (1H, s). | 513 |
| 14 | 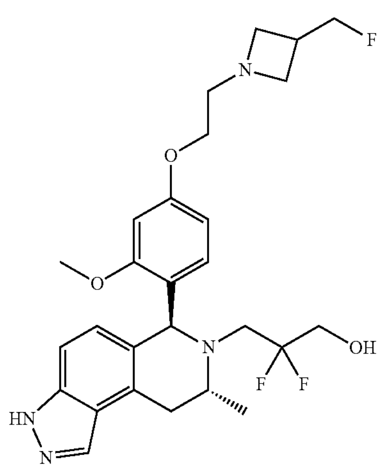 [SMILES: COc1cc(OCCN2CC(CF)C2)ccc1[C@@H]1c2ccc3[nH]ncc3c2C[C@@H](C)N1CC(F)(F)CO] | 2,2-difluoro-3-((6S,8R)-6-(4-(2-(3-(fluoromethyl)azetidin-1-yl)ethoxy)-2-methoxyphenyl)-8-methyl-3,6,8,9-tetrahydro-7H-pyrazolo[4,3-f]isoquinolin-7-yl)propan-1-ol | ¹H NMR (500 MHz, MeOD-d₄, 27° C.) 1.28 (3H, d), 2.88 (1H, tt), 2.99-3.04 (3H, m), 3.04-3.1 (1H, m), 3.23-3.35 (2H, m), 3.35-3.41 (3H, m), 3.70 (2H, t), 3.73-3.9 (2H, m), 4.05 (3H, s), 4.14 (2H, t), 4.60 (1H, d), 4.70 (1H, d), 5.57 (1H, s), 6.50 (1H, dd), 6.66-6.84 (2H, m), 6.91 (1H, d), 7.39 (1H, d), 8.23 (1H, s). | 519 |

TABLE E-continued

| Example | Structure | Name | 1H NMR | LCMS [M + H] |
|---|---|---|---|---|
| 15 | 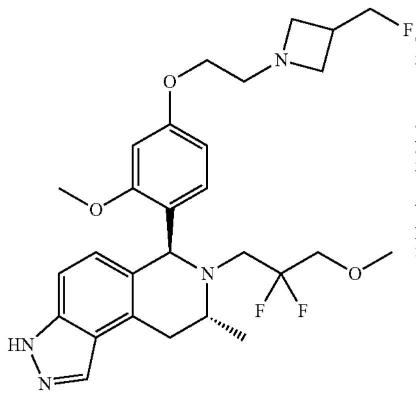 | (6S,8R)-7-(2,2-difluoro-3-methoxypropyl)-6-(4-(2-(3-(fluoromethyl)azetidin-1-yl)ethoxy)-2-methoxyphenyl)-8-methyl-6,7,8,9-tetrahydro-3H-pyrazolo[4,3-f]isoquinoline | $^1$H NMR (500 MHz, CDCl$_3$, 27° C.) 1.09 (3H, d), 2.73 (1H, td), 2.83 (1H, dd), 2.87-2.93 (3H, m), 2.98-3.09 (1H, m), 3.13 (1H, dd), 3.26 (2H, t), 3.37 (3H, s), 3.55 (2H, dt), 3.61 (2H, t), 3.74-3.82 (1H, m), 3.83 (3H, s), 3.95 (2H, t), 4.44 (1H, d), 4.54 (1H, d), 5.40 (1H, s), 6.22 (1H, dd), 6.47 (1H, d), 6.56 (1H, d), 6.75 (1H, d), 7.13 (1H, d), 8.05 (1H, d). | 533 |
| 16 | ISOMER 1 | (6S,8R)-7-(2-fluoro-3-methoxy-2-methylpropyl)-6-(4-(2-(3-(fluoromethyl)azetidin-1-yl)ethoxy)-2-methoxyphenyl)-8-methyl-6,7,8,9-tetrahydro-3H-pyrazolo[4,3-f]isoquinoline | $^1$H NMR (500 MHz, DMSO-d$_6$, 27° C.) 0.97 (3H, d), 1.20 (3H, d), 2.33-2.42 (1H, m), 2.69 (2H, t), 2.77-2.87 (2H, m), 2.99 (2H, t), 3.09-3.21 (2H, m), 3.23 (3H, s), 3.44-3.56 (2H, m), 3.84 (3H, s), 3.86 (2H, t), 4.44 (1H, d), 4.53 (1H, d), 5.23 (1H, s), 6.30 (1H, dd), 6.54 (1H, d), 6.57 (1H, d), 6.61 (1H, d), 7.17 (1H, d), 8.04 (1H, s), 12.93 (1H, s). 3 H obscured by water. | 529 |
| 17 | ISOMER 2 | (6S,8R)-7-(2-fluoro-3-methoxy-2-methylpropyl)-6-(4-(2-(3-(fluoromethyl)azetidin-1-yl)ethoxy)-2-methoxyphenyl)-8-methyl-6,7,8,9-tetrahydro-3H-pyrazolo[4,3-f]isoquinoline | $^1$H NMR (500 MHz, DMSO-d$_6$, 27° C.) 0.97 (3H, d), 1.18 (3H, d), 2.36 (1H, dd), 2.69 (2H, t), 2.7-2.87 (2H, m), 2.96-3.02 (2H, m), 3.07-3.16 (1H, m), 3.25 (3H, s), 3.33-3.4 (1H, m), 3.41-3.55 (2H, m), 3.85 (3H, s), 3.85-3.88 (2H, m), 4.45 (1H, d), 4.54 (1H, d), 5.24 (1H, s), 6.28 (1H, dd), 6.56 (1H, d), 6.63 (1H, d), 7.18 (1H, d), 8.04 (1H, s), 12.93 (1H, s). 3H obscured by solvent. | 529 |

TABLE E-continued

| Example | Structure | Name | 1H NMR | LCMS [M + H] |
|---|---|---|---|---|
| 18 | ISOMER 1 | (6S,8R)-7-(2,3-difluoropropyl)-6-(4-(2-(3-(fluoromethyl)azetidin-1-yl)ethoxy)-2-methoxyphenyl)-8-methyl-6,7,8,9-tetrahydro-3H-pyrazolo[4,3-f]isoquinoline | $^1$H NMR (500 MHz, CDCl$_3$, 27° C.) 1.12 (3H, d), 2.51-2.68 (1H, m), 2.74-2.84 (2H, m), 2.83-3 (3H, m), 3.08-3.17 (2H, m), 3.16-3.22 (1H, m), 3.44-3.56 (3H, m), 3.89 (3H, s), 3.89-3.96 (2H, m), 4.37-4.85 (5H, m), 5.31 (1H, s), 6.27 (1H, dd), 6.51 (1H, d), 6.64 (1H, d), 6.79 (1H, d), 7.16 (1H, d), 8.06 (1H, d), 9.98 (1H, s). | 504 |
| 19 | ISOMER 2 | (6S,8R)-7-(2,3-difluoropropyl)-6-(4-(2-(3-(fluoromethyl)azetidin-1-yl)ethoxy)-2-methoxyphenyl)-8-methyl-6,7,8,9-tetrahydro-3H-pyrazolo[4,3-f]isoquinoline | $^1$H NMR (500 MHz, CDCl$_3$, 27° C.) 1.09 (3H, d), 2.58-2.68 (m, 1H), 2.81 (3H, t), 2.84-2.96 (2H, m), 3.03 (1H, dd), 3.13 (2H, t), 3.41 (1H, s), 3.47 (2H, td), 3.87 (3H, s), 3.90 (2H, t), 4.46 (1H, d), 4.55 (1H, d), 4.62-5.08 (3H, m), 5.33 (1H, s), 6.22 (1H, dd), 6.45-6.54 (2H, m), 6.86 (1H, s), 7.22 (1H, d), 8.07 (1H, d), 10.04 (1H, s). | 504 |
| 20 | ISOMER 1 | (6S,8R)-7-(2,3-difluoro-2-methylpropyl)-6-(4-(2-(3-(fluoromethyl)azetidin-1-yl)ethoxy)-2-methoxyphenyl)-8-methyl-6,7,8,9-tetrahydro-3H-pyrazolo[4,3-f]isoquinoline | $^1$H NMR (300 MHz, CD$_2$Cl$_2$, 27° C.) 1.06 (3H, d), 1.29 (3H, dd), 2.57 (1H, ddd), 2.72-2.93 (5H, m), 3.07-3.19 (3H, m), 3.39-3.48 (2H, m), 3.50-3.59 (1H, m), 3.86 (3H, s), 3.90 (2H, t), 4.48 (3H, ddd), 5.39 (1H, s), 6.22 (1H, dd), 6.48 (1H, d), 6.59 (1H, d), 6.78 (1H, d), 7.19 (1H, dd), 8.04 (1H, d). | 517 |

TABLE E-continued

| Example | Structure | Name | 1H NMR | LCMS [M + H] |
|---|---|---|---|---|
| 21 | ISOMER 2 | (6S,8R)-7-(2,3-difluoro-2-methylpropyl)-6-(4-(2-(3-(fluoromethyl)azetidin-1-yl)ethoxy)-2-methoxyphenyl)-8-methyl-6,7,8,9-tetrahydro-3H-pyrazolo[4,3-f]isoquinoline | $^1$H NMR (300 MHz, $CD_2Cl_2$, 27° C.) 1.05 (3H, d), 1.27 (3H, dd), 2.38-2.58 (1H, m), 2.73-2.86 (3H, m), 2.86-3.04 (2H, m), 3.15 (2H, t), 3.28 (1H, dd), 3.46 (2H, t), 3.64-3.75 (1H, m), 3.85 (3H, s), 3.87-3.94 (2H, m), 3.96-4.25 (1H, m), 4.43 (1H, d), 4.47-4.75 (1H, m), 4.59 (1H, d), 5.26 (1H, s), 6.28 (1H, dd), 6.48 (1H, d), 6.71 (2H, d), 7.14 (1H, d), 8.03 (1H, s). | 517 |
| 22 | 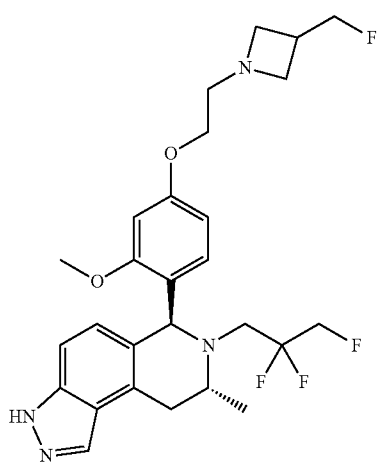 [SMILES: COc1cc(OCCN2CC(CF)C2)ccc1[C@@H]1c2ccc3[nH]ncc3c2C[C@@H](C)N1CC(F)(F)CF] | (6S,8R)-6-(4-(2-(3-(fluoromethyl)azetidin-1-yl)ethoxy)-2-methoxyphenyl)-8-methyl-7-(2,2,3-trifluoropropyl)-6,7,8,9-tetrahydro-3H-pyrazolo[4,3-f]isoquinoline | $^1$H NMR (500 MHz, MeOD-$d_4$, 27° C.) 1.58 (3H, d), 3.34 (2H, dd), 3.53-3.71 (2H, m), 3.82 (2H, d), 3.98 (1H, s), 4.14 (3H, s), 4.25-4.46 (4H, m), 4.46-4.7 (3H, m), 4.7-4.95 (4H, m), 6.26 (1H, s), 6.55-6.71 (1H, m), 6.81 (1H, d), 6.92 (1H, s), 7.02 (1H, d), 7.58 (1H, d), 8.35 (1H, s). | 521 |
| 23 | 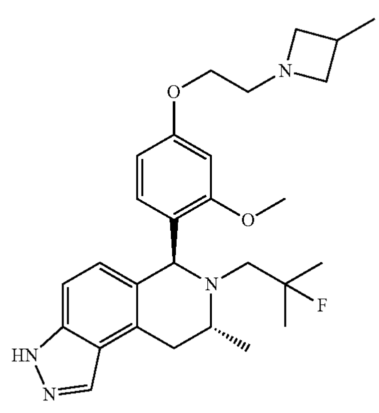 [SMILES: COc1cc(OCCN2CC(C)C2)ccc1[C@@H]1c2ccc3[nH]ncc3c2C[C@@H](C)N1CC(C)(C)F] | (6S,8R)-7-(2-fluoro-2-methylpropyl)-6-(2-methoxy-4-(2-(3-methylazetidin-1-yl)ethoxy)phenyl)-8-methyl-6,7,8,9-tetrahydro-3H-pyrazolo[4,3-f]isoquinoline | $^1$H NMR (500 MHz, $CDCl_3$, 27° C.) 1.05 (3H, d), 1.14 (3H, d), 1.24 (6H, dd), 2.34 (1H, dd), 2.61 (1H, dq), 2.75-2.89 (6H, m), 3.30 (1H, d), 3.54-3.59 (2H, m), 3.69-3.76 (1H, m), 3.85 (3H, s), 3.89 (2H, tq), 5.33 (1H, s), 6.27 (1H, dd), 6.48 (1H, d), 6.77 (1H, d), 6.80 (1H, d), 7.12 (1H, d), 8.05 (1H, d), 10.10 (1H, s). | 481 |

TABLE E-continued

| Example | Name | 1H NMR | LCMS [M + H] |
|---|---|---|---|
| 24 | (6S,8R)-7-(2-fluoro-2-methylpropyl)-6-(2-methoxy-4-(2-(3-methoxyazetidin-1-yl)ethoxy)phenyl)-8-methyl-6,7,8,9-tetrahydro-3H-pyrazolo[4,3-f]isoquinoline | $^1$H NMR (500 MHz, CDCl$_3$, 27° C.) 1.05 (3H, d), 1.25 (6H, dd), 2.34 (1H, dd), 2.75-2.89 (4H, m), 3.00 (2H, td), 3.26 (3H, s), 3.30 (1H, d), 3.72 (3H, td), 3.86 (3H, s), 3.88-3.95 (2H, m), 4.06 (1H, p), 5.33 (1H, s), 6.27 (1H, dd), 6.49 (1H, d), 6.76 (1H, s), 6.80 (1H, d), 7.12 (1H, d), 8.05 (1H, d), 10.01 (1H, s). | 497 |
| 25 | (6S,8R)-7-(2,2-difluoropropyl)-6-(2-fluoro-4-(2-(3-(fluoromethyl)azetidin-1-yl)ethoxy)-6-methoxyphenyl)-8-methyl-6,7,8,9-tetrahydro-3H-pyrazolo[4,3-f]isoquinoline | $^1$H NMR (300 MHz, DMSO-d$_6$, 27° C.): 0.99 (3H, d), 1.33 (3H, t), 2.63-2.79 (3H, m), 2.87-3.07 (4H, m), 3.21-3.35 (3H, m), 3.49-3.59 (1H, m), 3.78 (3H, br s), 3.90 (2H, t), 4.42 (1H, d), 4.58 (1H, d), 5.29 (1H, s), 6.24 (1H, d), 6.44 (1H, s), 6.60 (1H, d), 7.16 (1H, d), 8.03 (1H, s), 12.91 (1H, s). | 521 |
| 26 | 2,2-difluoro-3-((6S,8R)-6-(2-fluoro-4-(2-(3-(fluoromethyl)azetidin-1-yl)ethoxy)-6-methoxyphenyl)-8-methyl-8,9-dihydro-3H-pyrazolo[4,3-f]isoquinolin-7(6H)-yl)propan-1-ol | $^1$H NMR (500 MHz, DMSO-d$_6$, 27° C.) 0.92 (3H, d), 2.47 (1H, s), 2.5-2.59 (1H, m), 2.65 (3H, br s), 2.83 (1H, dd), 2.89-3.05 (3H, m), 3.07-3.22 (3H, m), 3.44-3.63 (3H, m), 3.76 (2H, br s), 3.82 (2H, t), 4.39 (1H, d), 4.49 (1H, d), 5.09 (1H, t), 5.20 (1H, s), 6.15 (1H, d), 6.35 (1H, s), 6.52 (1H, d), 7.08 (1H, d), 7.96 (1H, s), 12.85 (1H, s). | 537 |

TABLE E-continued

| Example | Structure | Name | 1H NMR | LCMS [M + H] |
|---|---|---|---|---|
| 27 | 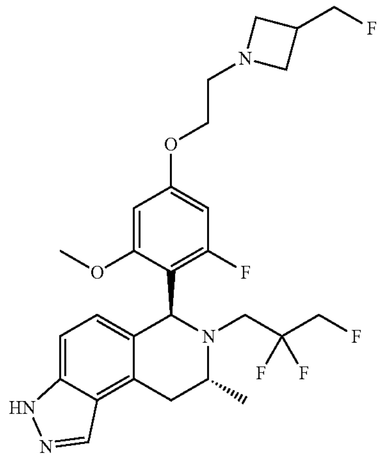 [SMILES: COc1cc(OCCN2CC(CF)C2)cc(F)c1[C@@H]1c2ccc3[nH]ncc3c2C[C@@H](C)N1CC(F)(F)CF] | (6S,8R)-6-(2-fluoro-4-(2-(3-(fluoromethyl)azetidin-1-yl)ethoxy)-6-methoxyphenyl)-8-methyl-7-(2,2,3-trifluoropropyl)-6,7,8,9-tetrahydro-3H-pyrazolo[4,3-f]isoquinoline | $^1$H NMR (500 MHz, DMSO-d$_6$, 27° C.) 1.01 (3H, d), 2.64-2.79 (4H, m), 2.90 (1H, dd), 2.99 (2H, t), 3.15 (1H, q), 3.25 (1H, dd), 3.28-3.31 (2H, m), 3.32 (3H, s), 3.39-3.56 (1H, m), 3.89 (2H, t), 4.25-4.44 (1H, m), 4.45 (1H, d), 4.55 (1H, d), 4.58-4.74 (1H, m), 5.28 (1H, s), 6.23 (1H, d), 6.43 (1H, s), 6.60 (1H, d), 7.16 (1H, d), 8.04 (1H, s), 12.94 (1H, s). Assigned Hs: 31. | 539 |
| 28 | 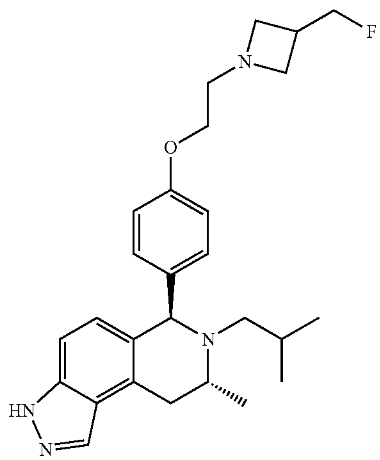 [SMILES: CC(C)CN1[C@H](c2ccc(OCCN3CC(CF)C3)cc2)c2ccc3[nH]ncc3c2C[C@H]1C] | (6R,8R)-6-(4-(2-(3-(fluoromethyl)azetidin-1-yl)ethoxy)phenyl)-7-isobutyl-8-methyl-6,7,8,9-tetrahydro-3H-pyrazolo[4,3-f]isoquinoline | 1H NMR (500 MHz, DMSO-d$_6$, 27° C.) 0.74 (3H, d), 0.87 (3H, d), 0.97 (3H, d), 1.76 (1H, dt), 2.04 (1H, dd), 2.29 (1H, dd), 2.7-2.85 (4H, m), 3-3.12 (3H, m), 3.24-3.43 (3H, m), 3.88 (2H, t), 4.45 (1H, d), 4.55 (1H, d), 4.72 (1H, s), 6.72-6.83 (3H, m), 7.06 (2H, d), 7.21 (1H, d), 8.04 (1H, s), 12.96 (1H, s). | 451 |
| 29 | 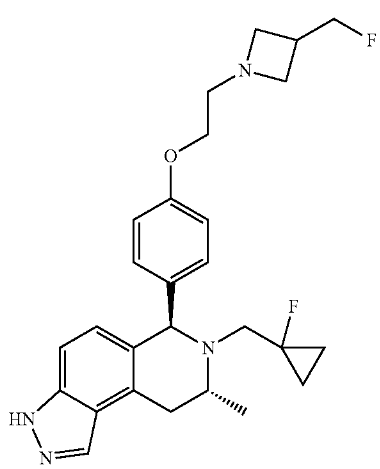 [SMILES: C[C@@H]1Cc2c(ccc3[nH]ncc23)[C@@H](c2ccc(OCCN3CC(CF)C3)cc2)N1CC1(F)CC1] | (6R,8R)-7-((1-fluorocyclopropyl)methyl)-6-(4-(2-(3-(fluoromethyl)azetidin-1-yl)ethoxy)phenyl)-8-methyl-6,7,8,9-tetrahydro-3H-pyrazolo[4,3-f]isoquinoline | $^1$H NMR (300 MHz, MeOD-d$_4$, 27° C.) 0.45-0.66 (2H, m), 0.88-1.09 (4H, m), 1.16 (3H, d), 2.6-2.81 (1H, m), 2.91 (2H, t), 2.98-3.2 (2H, m), 3.26 (2H, t), 3.53-3.63 (2H, m), 3.64-3.81 (1H, m), 4.03 (2H, t), 4.45 (1H, d), 4.61 (1H, d), 5.04 (1H, s), 6.87 (3H, dd), 7.20 (2H, d), 7.28 (1H, d), 8.11 (1H, d). | 467 |

TABLE E-continued

| Example | Structure | Name | 1H NMR | LCMS [M + H] |
|---|---|---|---|---|
| 30 | 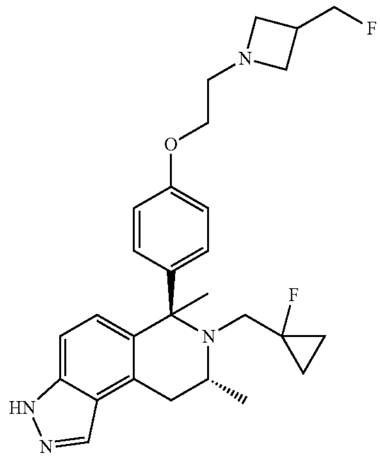 [SMILES: C[C@@H]1Cc2c(ccc3[nH]ncc23)[C@@](C)(c2ccc(OCCN3CC(CF)C3)cc2)N1CC1(F)CC1] | (6R,8R)-7-((1-fluorocyclopropyl)methyl)-6-(4-(2-(3-(fluoromethyl)azetidin-1-yl)ethoxy)phenyl)-6,8-dimethyl-6,7,8,9-tetrahydro-3H-pyrazolo[4,3-f]isoquinoline | $^1$H NMR (600 MHz, MeOD-d$_4$, 27° C.) 0.26-0.45 (2H, m), 0.77-0.98 (2H, m), 1.18 (3H, d), 1.85 (3H, s), 2.75 (1H, dd), 2.85 (3H, t), 3.07 (1H, dd), 3.14-3.24 (4H, m), 3.53 (2H, t), 3.89 (1H, q), 3.96 (2H, t), 4.44 (1H, d), 4.52 (1H, d), 6.75 (2H, d), 6.95 (1H, d), 7.22 (1H, d), 7.28 (2H, d), 8.07 (1H, s). | 481 |
| 31 | 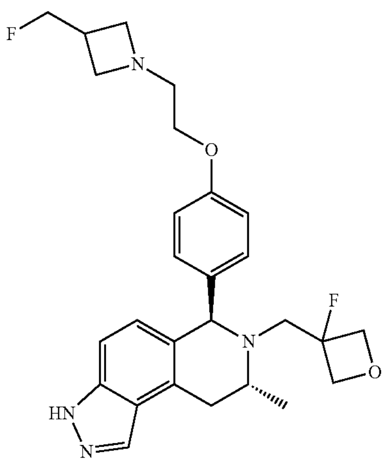 [SMILES: C[C@@H]1Cc2c(ccc3[nH]ncc23)[C@@H](c2ccc(OCCN3CC(CF)C3)cc2)N1CC1(F)COC1] | (6R,8R)-6-(4-(2-(3-(fluoromethyl)azetidin-1-yl)ethoxy)phenyl)-7-((3-fluorooxetan-3-yl)methyl)-8-methyl-6,7,8,9-tetrahydro-3H-pyrazolo[4,3-f]isoquinoline | $^1$H NMR (300 MHz, DMSO-d$_6$, 27° C.) 1.06 (3H, d), 2.65-2.89 (5H, m), 2.95-3.14 (3H, m), 3.17 (2H, d), 3.38 (2H, br s), 3.89 (2H, t), 4.27-4.46 (2H, m), 4.50 (1H, t), 4.54-4.74 (3H, m), 4.94 (1H, s), 6.80 (3H, d), 7.03 (2H, d), 7.27 (1H, d), 8.06 (1H, s), 13.00 (1H, s). | 483 |
| 32 | 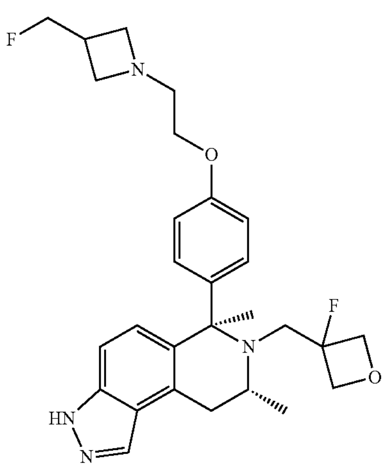 [SMILES: C[C@@H]1Cc2c(ccc3[nH]ncc23)[C@@](C)(c2ccc(OCCN3CC(CF)C3)cc2)N1CC1(F)COC1] | (6R,8R)-6-(4-(2-(3-(fluoromethyl)azetidin-1-yl)ethoxy)phenyl)-7-((3-fluorooxetan-3-yl)methyl)-6,8-dimethyl-6,7,8,9-tetrahydro-3H-pyrazolo[4,3-f]isoquinoline | $^1$H NMR (300 MHz, DMSO-d$_6$, 27° C.) 1.08 (3H, d), 1.78 (3H, s), 2.62-2.77 (3H, m), 2.79-2.92 (1H, m), 2.97 (3H, t), 3-3.04 (1H, m), 3.05-3.23 (2H, m), 3.50 (2H, s), 3.84 (2H, t), 3.93 (1H, dd), 4.26-4.52 (4H, m), 4.56 (1H, d), 6.74 (2H, d), 6.81 (1H, d), 7.20 (3H, d), 8.05 (1H, s). | 497 |

TABLE E-continued

| Example | Structure | Name | 1H NMR | LCMS [M + H] |
|---|---|---|---|---|
| 33 | 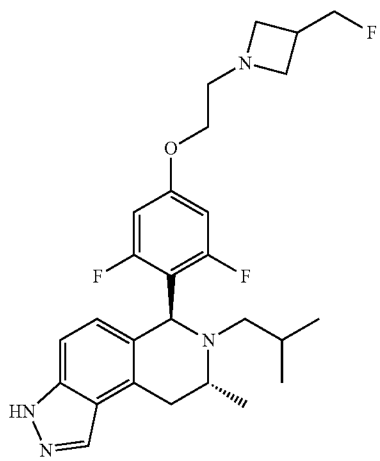 [SMILES: CC(C)CN1[C@H](c2c(F)cc(OCCN3CC(CF)C3)cc2F)c2ccc3[nH]ncc3c2C[C@H]1C] | (6S,8R)-6-(2,6-difluoro-4-(2-(3-(fluoromethyl)azetidin-1-yl)ethoxy)phenyl)-7-isobutyl-8-methyl-6,7,8,9-tetrahydro-3H-pyrazolo[4,3-f]isoquinoline | $^1$H NMR (500 MHz, DMSO-d$_6$, 27° C.) 0.67 (3H d) 0.80 (3H, d) 0.97 (3H, d) 1.26 (1H, s) 1.58-1.73 (1H, m) 1.99 (1H, br dd) 2.43 (1H, br dd) 2.72 (3H, br t) 2.86-3.06 (3H, m) 3.20 (1H, br t) 3.25-3.30 (1H, m) 3.47 (1H, br d) 3.94 (2H, t) 4.44 (1H, d) 4.59 (1H, d) 5.06 (1H, s) 6.49-6.74 (3H, m) 7.22 (1H, d) 8.07 (1H, s) 12.96 (1H, s) | 487 |
| 34 | ISOMER 1 | (6S,8R)-6-(2,6-difluoro-4-(2-(3-(fluoromethyl)azetidin-1-yl)ethoxy)phenyl)-7-(2,3-difluoropropyl)-8-methyl-6,7,8,9-tetrahydro-3H-pyrazolo[4,3-f]isoquinoline | $^1$H NMR (500 MHz, CDCl$_3$, 27° C.) 1.11 (3H, d), 2.66 (1H, td), 2.78-2.91 (3H, m), 2.95 (1H, dd), 2.97-3.04 (1H, m), 3.09-3.18 (2H, m), 3.39 (1H, dd), 3.48 (2H, t), 3.51-3.62 (1H, m), 3.86-3.95 (2H, m), 4.17-4.78 (5H, m), 5.20 (1H, s), 6.38 (2H, d), 6.79 (1H, d), 7.17 (1H, d), 8.06 (1H, d). | 509 |
| 35 | ISOMER 2 | (6S,8R)-6-(2,6-difluoro-4-(2-(3-(fluoromethyl)azetidin-1-yl)ethoxy)phenyl)-7-(2,3-difluoropropyl)-8-methyl-6,7,8,9-tetrahydro-3H-pyrazolo[4,3-f]isoquinoline | $^1$H NMR (500 MHz, CDCl$_3$, 27° C.) 1.10 (3H, d), 2.62-2.78 (1H, m), 2.78-2.95 (4H, m), 3.00-3.12 (1H, m), 3.14 (2H, t), 3.36 (1H, dd), 3.44-3.53 (2H, m), 3.53-3.62 (1H, m), 3.83-3.95 (2H, m), 4.37-4.75 (5H, m), 5.24 (1H, s), 6.39 (2H, t), 6.81 (1H, d), 7.19 (1H, d), 8.06 (1H, d). | 509 |

TABLE E-continued

| Example | Structure | Name | 1H NMR | LCMS [M + H] |
|---|---|---|---|---|
| 36 | 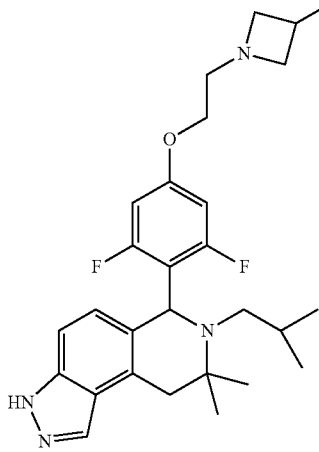 ISOMER 2 | 6-(2,6-difluoro-4-(2-(3-(fluoromethyl)azetidin-1-yl)ethoxy)phenyl)-7-isobutyl-8,8-dimethyl-6,7,8,9-tetrahydro-3H-pyrazolo[4,3-f]isoquinoline | $^1$H NMR (400 MHz, CDCl$_3$, 27° C.) 0.50 (3H, d), 0.73 (3H, d), 1.00 (3H, s), 1.16 (1H, dt), 1.37 (3H, s), 2.08 (1H, dd), 2.74 (1H, dd), 2.81-2.95 (4H, m), 3.16 (2H, t), 3.31 (1H, d), 3.41-3.57 (2H, m), 3.91 (2H, t), 4.46 (1H, d), 4.58 (1H, d), 5.14 (1H, s), 6.36 (2H, d), 6.79 (1H, d), 7.15 (1H, d), 8.06 (1H, s). | 501 |
| 37 | 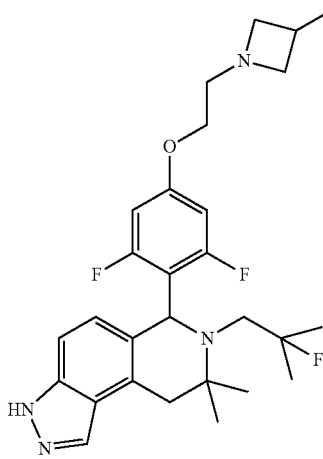 ISOMER 2 | 6-(2,6-difluoro-4-(2-(3-(fluoromethyl)azetidin-1-yl)ethoxy)phenyl)-7-(2-fluoro-2-methylpropyl)-8,8-dimethyl-6,7,8,9-tetrahydro-3H-pyrazolo[4,3-f]isoquinoline | $^1$H NMR (500 MHz, DMSO-d$_6$, 27° C.) 0.82 (3H, d), 0.86 (3H, s), 1.01 (3H, d), 1.23 (3H, s), 2.24-2.39 (1H, m), 2.55-2.69 (3H, m), 2.82-2.96 (3H, m), 3.06 (1H, d), 3.22 (3H, d), 3.82 (2H, t), 4.38 (1H, d), 4.48 (1H, d), 5.01 (1H, s), 6.50 (2H, d), 6.55 (1H, d), 7.12 (1H, d), 8.00 (1H, s), 12.89 (1H, s). | 519 |
| 38 | 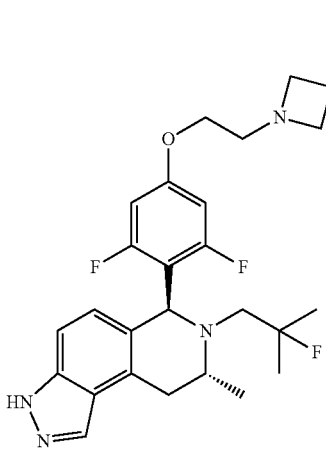 | (6S,8R)-6-(4-(2-(3-(difluoromethyl)azetidin-1-yl)ethoxy)-2,6-difluorophenyl)-7-(2-fluoro-2-methylpropyl)-8-methyl-6,7,8,9-tetrahydro-3H-pyrazolo[4,3-f]isoquinoline | $^1$H NMR (500 MHz, CDCl$_3$, 27° C.) 1.04 (3H, d), 1.16 (3H, d), 1.20 (3H, d), 2.33 (1H, dd), 2.78-2.84 (2H, m), 2.85-2.98 (3H, m), 3.29 (2H, dd), 3.40-3.57 (3H, m), 3.76 (1H, dq), 3.89 (2H, ddd), 5.21 (1H, s), 5.96 (1H, td), 6.33 (2H, d), 6.75 (1H, d), 7.13 (1H, d), 8.07 (1H, d), 10.75 (1H, s). | 523 |

TABLE E-continued

| Example | Structure | Name | 1H NMR | LCMS [M + H] |
|---|---|---|---|---|
| 39 | 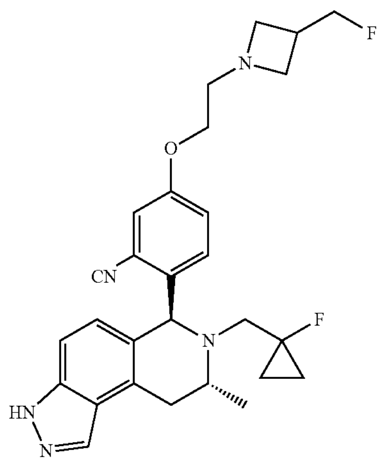 [SMILES: C[C@@H]1Cc2c(ccc3[nH]ncc23)[C@@H](c2ccc(OCCN3CC(CF)C3)cc2C#N)N1CC1(F)CC1] | 2-((6S,8R)-7-((1-fluorocyclo-propyl)methyl)-8-methyl-6,7,8,9-tetrahydro-3H-pyrazolo[4,3-f]isoquinolin-6-yl)-5-(2-(3-(fluoromethyl)azetidin-1-yl)ethoxy)benzonitrile | $^1$H NMR (500 MHz, CDCl$_3$, 27° C.) 0.29-0.6 (2H, m), 0.85-1.05 (2H, m), 1.09 (3H, d), 2.60 (1H, dd), 2.86 (2H, br s), 2.94-3.04 (2H, m), 3.05-3.13 (1H, m), 3.17 (2H, br s), 3.49 (1H, br s), 3.59 (2H, dd), 3.84-4.08 (3H, m), 4.46 (1H, d), 4.55 (1H, d), 5.12 (1H, s), 6.69 (1H, d), 6.98 (1H, dd), 7.09 (1H, d), 7.15 (1H, d), 7.24 (1H, s), 8.09 (1H, s), 10.03 (1H, s). | 492 |
| 40 | 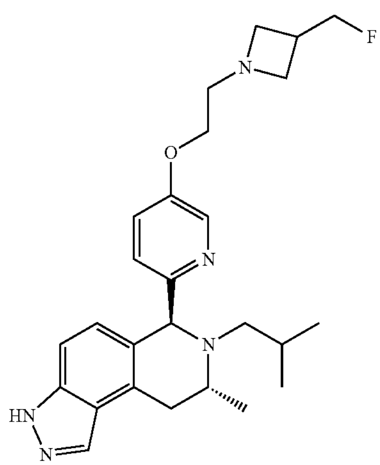 [SMILES: CC(C)CN1[C@H](c2ccc(OCCN3CC(CF)C3)cn2)c2ccc3[nH]ncc3c2C[C@H]1C] | (6S,8R)-6-(5-(2-(3-(fluoromethyl)azetidin-1-yl)ethoxy)pyridin-2-yl)-7-isobutyl-8-methyl-6,7,8,9-tetrahydro-3H-pyrazolo[4,3-f]isoquinoline | $^1$H NMR (300 MHz, MeOH-d$_4$, 27° C.) 0.74 (3H, br d) 0.83 (3H, br d) 1.05 (3H br d) 1.30 (1H, br s,) 1.58-1.77 (1H, m) 1.90-2.06 (1H, m) 2.41-2.56 (1H,) 2.41-2.56 (1H, m) 2.77-3.05 (4H, m) 3.18-3.28 (2H, m) 3.36-3.48 (1H, m) 3.57 (3H, br t) 3.98-4.17 (2H, m) 4.32-4.46 (1H, m) 4.51-4.63 (1H, m) 6.76 (1H, br d) 7.10-7.24 (1H, m) 7.25-7.39 (2H, m) 7.98-8.19 (2H, m). | 452 |
| 41 | 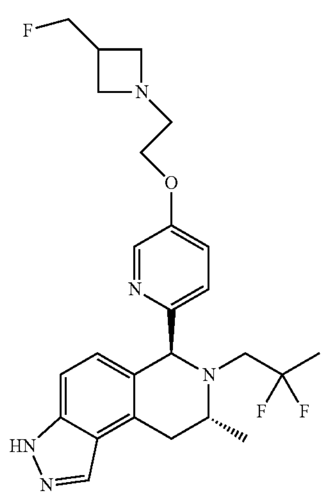 [SMILES: C[C@@H]1Cc2c(ccc3[nH]ncc23)[C@@H](c2ccc(OCCN3CC(CF)C3)cn2)N1CC(C)(F)F] | (6S,8R)-7-(2,2-difluoropropyl)-6-(5-(2-(3-(fluoromethyl)azetidin-1-yl)ethoxy)pyridin-2-yl)-8-methyl-6,7,8,9-tetrahydro-3H-pyrazolo[4,3-f]isoquinoline | 1H NMR (300 MHz, DMSO-d6) 1.05 (3H, d) 1.56 (3H, t) 2.60-2.89 (5H, m) 2.94-3.01 (2H, m) 3.03-3.14 (2H, m,) 3.24-3.28 (2H, m) 3.38-3.49 (1H, m) 3.94 (2H, t) 4.40 (1H, d,) 4.56 (1H, d) 4.98 (1H, s) 6.79 (1H, d) 7.10-7.33 (3H, m) 8.04 (1H, s) 8.12 (1H, d) 12.96 (1H, br s). | 474 |

TABLE E-continued

| Example | Structure | Name | 1H NMR | LCMS [M + H] |
|---|---|---|---|---|
| 42 | 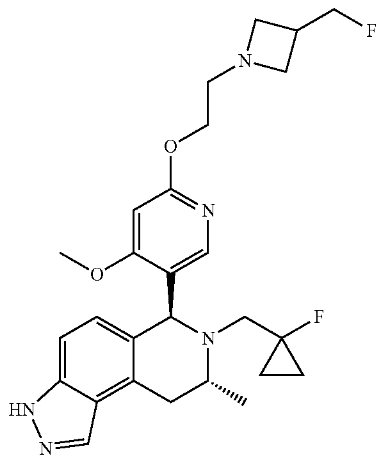 [SMILES: COc1cc(OCCN2CC(CF)C2)ncc1[C@@H]1c2ccc3[nH]ncc3c2C[C@@H](C)N1CC1(F)CC1] | (6S,8R)-7-((1-fluorocyclo-propyl)methyl)-6-(6-(2-(3-(fluoromethyl) azetidin-1-yl)ethoxy)-4-methoxypyridin-3-yl)-8-methyl-6,7,8,9-tetrahydro-3H-pyrazolo[4,3-f]isoquinoline | $^1$H NMR (500 MHz, CDCl$_3$) 0.39-0.73 (2H, m), 0.87-1.08 (2H, m), 1.11 (3H, d), 2.57 (1H, dd), 2.79 (2H, t), 2.86 (2H, dd), 3.10 (2H, t), 3.12-3.25 (2H, m), 3.48 (2H, br s), 3.63-3.73 (1H, m), 3.85 (3H, s), 4.22 (2H, q), 4.43 (1H, d), 4.53 (1H, d), 5.37 (1H, s), 6.24 (1H, s), 6.79 (1H, d), 7.10 (1H, d), 7.44 (1H, s), 8.03 (1H, s), 10.67 (1H, s). | 498 |
| 43 | 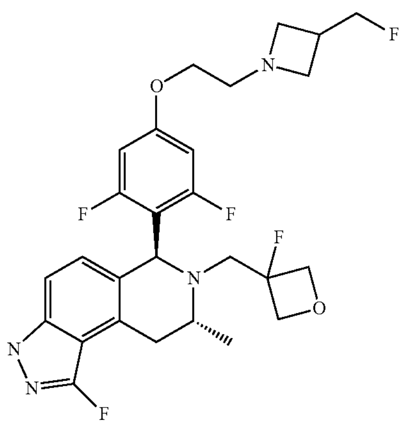 [SMILES: C[C@@H]1Cc2c(ccc3[nH]nc(F)c23)[C@@H](c2c(F)cc(OCCN3CC(CF)C3)cc2F)N1CC1(F)COC1] | (6S,8R)-6-(2,6-difluoro-4-(2-(3-(fluoromethyl) azetidin-1-yl)ethoxy) phenyl)-1-fluoro-7-((3-fluorooxetan-3-yl)methyl)-8-methyl-6,7,8,9-tetrahydro-3H-pyrazolo[4,3-f]isoquinoline | $^1$H NMR (500 MHz, CDCl$_3$, 27° C.) 1.09 (3H, d), 2.86 (1H, dd), 2.92-3.06 (3H, m), 3.16 (1H, dd), 3.27-3.44 (3H, m), 3.53-3.65 (1H, m), 3.72 (2H, t), 3.94-4.05 (2H, m), 4.31 (1H, dd), 4.37-4.43 (2H, m), 4.44 (1H, d), 4.54 (1H, d), 4.60-4.74 (2H, m), 5.25 (1H, s), 6.38 (2H, d), 6.83 (1H, d), 6.96-7.07 (1H, m), 9.06 (1H, s). | 537 |
| 44 | 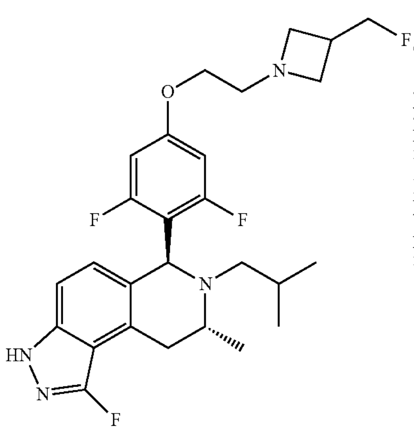 [SMILES: CC(C)CN1[C@H](c2c(F)cc(OCCN3CC(CF)C3)cc2F)c2ccc3[nH]nc(F)c3c2C[C@H]1C] | (6S,8R)-6-(2,6-difluoro-4-(2-(3-(fluoromethyl) azetidin-1-yl)ethoxy) phenyl)-1-fluoro-7-isobutyl-8-methyl-6,7,8,9-tetrahydro-3H-pyrazolo[4,3-f]isoquinoline | $^1$H NMR (500 MHz, CDCl$_3$, 27° C.) 0.68 (3H, d), 0.81 (3H, d), 1.01 (3H, d), 1.62-1.76 (1H, m), 2.01 (1H, dd), 2.41 (1H, dd), 2.82 (2H, t), 2.84-2.96 (1H, m), 3.02 (1H, d), 3.15 (2H, t), 3.40 (1H, dd), 3.46-3.50 (3H, m), 3.90 (2H, t), 4.45 (1H, d), 4.55 (1H, d), 5.10 (1H, s), 6.34 (2H, d), 6.82 (1H, d), 6.99 (1H, d), 9.22 (1H, s). | 505 |

TABLE E-continued

| Example | Structure | Name | 1H NMR | LCMS [M + H] |
|---|---|---|---|---|
| 45 | 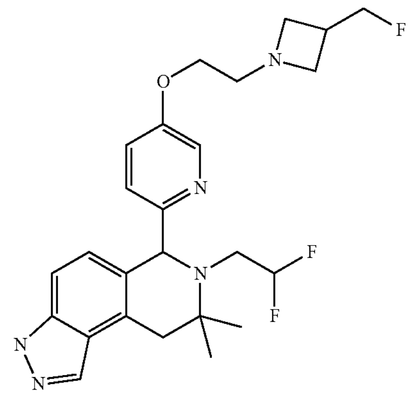 [SMILES: CC1(C)Cc2c(ccc3[nH]ncc23)C(c2ccc(OCCN3CC(CF)C3)cn2)N1CC(F)F] | 7-(2,2-difluoroethyl)-6-(5-(2-(3-(fluoromethyl)azetidin-1-yl)ethoxy)pyridin-2-yl)-8,8-dimethyl-6,7,8,9-tetrahydro-3H-pyrazolo[4,3-f]isoquinoline | $^1$H NMR (500 MHz, CDCl$_3$, 27° C.) 1.04 (3H, s), 1.41 (3H, s), 2.76-2.91 (4H, m), 2.93 (1H, d), 3.20 (2H, t), 3.28 (2H, d), 3.53 (2H, td), 3.98-4.04 (2H, m), 4.44 (1H, d), 4.54 (1H, d), 4.83 (1H, tdd), 4.95 (1H, s), 6.68 (1H, d), 7.05 (1H, dd), 7.08 (1H, d), 7.12 (1H, d), 8.04 (1H, d), 8.15-8.19 (1H, m). | 474 |
| 46 | 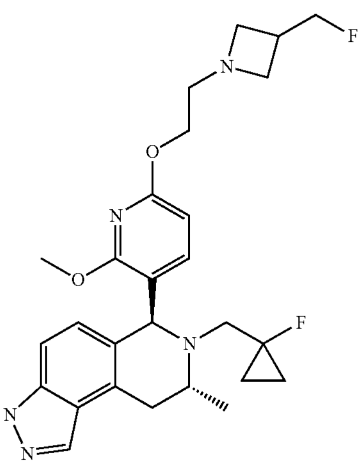 [SMILES: COc1nc(OCCN2CC(CF)C2)ccc1[C@@H]1c2ccc3[nH]ncc3c2C[C@@H](C)N1CC1(F)CC1] | (6S,8R)-7-((1-fluorocyclopropyl)methyl)-6-(6-(2-(3-(fluoromethyl)azetidin-1-yl)ethoxy)-2-methoxypyridin-3-yl)-8-methyl-6,7,8,9-tetrahydro-3H-pyrazolo[4,3-f]isoquinoline | $^1$H NMR (300 MHz, CDCl$_3$, 27° C.) 0.43-0.57 (2H, m), 0.95 (2H, d), 1.07 (3H, d), 2.59 (1H, dd), 2.78-2.94 (4H, m), 3.05 (1H, br dd), 3.10-3.26 (2H, m), 3.33 (1H, br dd), 3.42-3.62 (2H, m), 3.70-3.81 (1H, m), 3.98 (3H, s), 4.31 (2H, br s), 4.43 (1H, d), 4.54 (1H, d), 5.24 (1H, s), 6.13 (1H, d), 6.79 (1H, d), 7.13 (1H, d), 7.18 (1H, d), 8.03 (1H, d), 9.99 (1H, br s) | 498 |
| 47 | 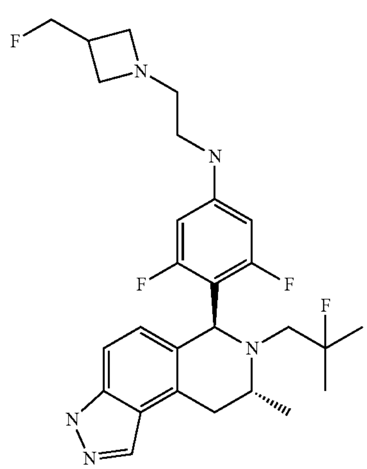 [SMILES: C[C@@H]1Cc2c(ccc3[nH]ncc23)[C@@H](c2c(F)cc(NCCN3CC(CF)C3)cc2F)N1CC(C)(C)F] | 3,5-difluoro-4-((6S,8R)-7-(2-fluoro-2-methylpropyl)-8-methyl-6,7,8,9-tetrahydro-3H-pyrazolo[4,3-f]isoquinolin-6-yl)-N-(2-(3-(fluoromethyl)azetidin-1-yl)ethyl)aniline | $^1$H NMR (500 MHz, CDCl$_3$, 27° C.) 1.01 (3H, d), 1.16 (3H, d), 1.20 (3H, d), 2.35 (1H, dd), 2.64 (2H, t), 2.72-2.84 (1H, m), 2.84-2.90 (2H, m), 2.93-2.98 (2H, m), 3.04 (2H, t), 3.36 (2H, t), 3.43 (1H, dd), 3.71-3.79 (1H, m), 4.34-4.40 (1H, m), 4.48 (2H, dd), 5.13 (1H, s), 6.00 (2H, d), 6.81 (1H, d), 7.12 (1H, d), 8.04 (1H, s), 10.13 (1H, br s) | 504 |

TABLE E-continued

| Example | Structure | Name | 1H NMR | LCMS [M + H] |
|---|---|---|---|---|
| 48 | 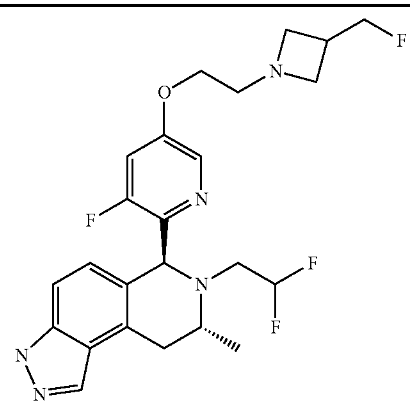 | (6S,8R)-7-(2,2-difluoroethyl)-6-(3-fluoro-5-(2-(3-(fluoromethyl)azetidin-1-yl)ethoxy)pyridin-2-yl)-8-methyl-6,7,8,9-tetrahydro-3H-pyrazolo[4,3-f]isoquinoline | $^1$H NMR (500 MHz, CDCl$_3$, 27° C.) 1.14 (3H, d), 2.71-2.90 (5H, m), 3.06 (1H, qd), 3.15 (2H, dd), 3.21 (1H, dd), 3.49 (2H, s), 3.60-3.70 (1H, m), 3.98 (2H, tt), 4.45 (1H, d), 4.54 (1H, d), 5.34 (1H, s), 5.77 (1H, tt), 6.77 (1H, d), 6.97 (1H, dd), 7.12 (1H, d), 7.99-8.03 (2H, m), 10.53 (1H, s). | 478 |

Example 49

Preparation of (6S,8R)-6-(5-(2-(3-(fluoromethyl)azetidin-1-yl)ethoxy)pyridin-2-yl)-8-methyl-7-(2,2,2-trifluoroethyl)-6,7,8,9-tetrahydro-3H-pyrazolo[4,3-f]isoquinoline

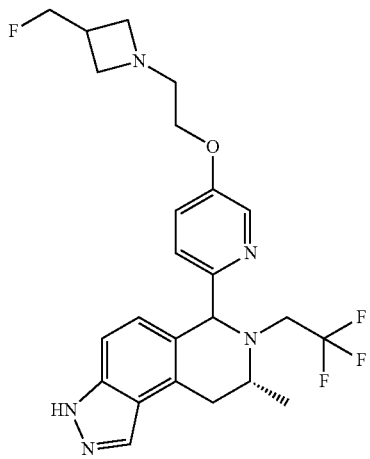 [SMILES: C[C@@H]1Cc2c(ccc3[nH]ncc23)C(c2ccc(OCCN3CC(CF)C3)cn2)N1CC(F)(F)F]

4M HCl-dioxane (7.39 mL, 29.6 mmol) was added to a stirred solution of (6S,8R)-6-(5-(2-(3-(fluoromethyl)azetidin-1-yl)ethoxy)pyridin-2-yl)-8-methyl-2-(tetrahydro-2H-pyran-2-yl)-7-(2,2,2-trifluoroethyl)-6,7,8,9-tetrahydro -3H-pyrazolo [4,3-f]isoquinoline with (6S,8R)-6-(5-(2-(3-(fluoromethyl)azetidin-1-yl)ethoxy)pyridin-2-yl)-8-methyl-3-(tetrahydro-2H-pyran-2-yl)-7-(2,2,2-trifluoroethyl)-6,7,8,9-tetrahydro-3H-pyrazolo [4,3-f]isoquinoline (1.66 g, 2.96 mmol) in methanol (5 mL) and the reaction mixture was stirred at room temperature for 16 hours. The mixture was concentrated under reduced pressure and the residue was dissolved in EtOAc (50 mL) and saturated NaHCO$_3$ solution (50 mL). The layers were separated and the aqueous layer was extracted with EtOAc (3×50 mL). The combined organic layers were dried (Na$_2$SO$_4$), filtered and concentrated under reduced pressure to give the crude product as a light brown oil. The crude product was purified by flash silica chromatography, elution gradient 0 to 10% 1M NH3/ MeOH in DCM, and then by chiral by SFC (Phenomonex Lux Cl, 30×250 mm, 5 micron) eluting with 30% MeOH +0.1% NH3/70% supercritical CO$_2$ to afford (6S,8R)-6-(5-(2-(3-(fluoromethyl)azetidin-1-yl)ethoxy)pyridin-2-yl)-8-methyl-7-(2,2,2-trifluoroethyl)-6,7 ,8,9-tetrahydro-3H-pyrazolo [4,34] isoquinoline (0.989 g, 70%) as a pale yellow foam. $^1$H NMR (500 MHz, CDCl$_3$, 27° C.) 1.15 (3H, d), 2.80-2.93 (4H, m), 3.01 (1H, dq), 3.15 (2H, t), 3.20-3.38 (2H, m), 3.49 (2H, t), 3.55-3.64 (1H, m), 3.98 (2H, t), 4.50 (2H, dd), 5.08 (1H, s), 6.90 (1H, d), 7.14 (1H, dd), 7.19 (1H, d), 7.32 (1H, d), 8.04 (1H, d), 8.13-8.20 (1H, m), 10.16 (1H, s). m/z: ES+ [M+H]+ 478.

The ((6S,8R)-6-(5-(2-(3-(fluoromethyl)azetidin-1-yl) ethoxy)pyridin-2-yl)-8-methyl-2-(tetrahydro-2H-pyran-2-yl)-7-(2,2,2-trifluoroethyl)-6,7 ,8,9-tetrahydro-3H-pyrazolo [4,3-f]isoquinoline with (6S,8R)-6-(5-(2-(3-(fluoromethyl) azetidin-1-yl)ethoxy)pyridin-2-yl)-8-methyl-3-(tetrahydro-2H-pyran-2-yl)-7-(2,2,2-trifluoroethyl)-6,7 ,8,9-tetrahydro -3H-pyrazolo [4,3-f]isoquinoline was prepared as follows;

Preparation of (R)-1-(1H-indazol-4-yl)propan-2-amine n-BuLi (46.9 mL, 75.00 mmol) was added to a solution of 4-bromo-1H-indazole (5.91 g, 30 mmol) in THF (73.1 mL) at −78° C. After stirring for 10 minutes, the reaction was warmed to −50° C. for 30 min, then cooled back to −78° C. (R)-tert-butyl 4-methyl-1,2,3-oxathiazolidine-3-carboxylate 2,2-dioxide (9.97 g, 42.0 mmol) was added in portions and the reaction was stirred for 1 hour before being allowed to warm to 0° C. Water (100 mL) and diethyl ether (100 mL) were added and the mixture was stirred for 5 minutes. The layers were separated and the aqueous was extracted with EtOAc. The combined organics were extracted with water, then to the combined aqueous was added to 2N HCl (100 mL). The solution was extracted with DCM (×2) and the combined organics were dried over MgSO₄, filtered and concentrated to afford (R)-tert-butyl (1-(1H-indazol-4-yl)propan-2-yl)carbamate (6.45 g, 78%) as an off-white solid. ¹H NMR (400 MHz, CDCl₃, 27° C.) 1.11 (3H, d), 1.43 (9H, s), 2.95 (1H, dd), 3.24 (1H, d), 3.98-4.25 (1H, m), 4.51-4.61 (1H, m), 6.95 (1H, d), 7.30 (1H, dd), 7.39 (1H, d), 8.23 (1H, s). m/z (ES+), [M+H]+=276.

Preparation of (R)-1-(1H-indazol-4-yl)propan-2-amine

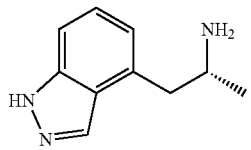

Hydrogen chloride 4M in dioxane (21.25 mL, 84.98 mmol) was added to tert-butyl (R)-(1-(1H-indazol-4-yl)propan-2-yl)carbamate (2.34 g, 8.50 mmol) and the resulting suspension stirred overnight. The reaction was concentrated and taken up in methanol. The solution was applied to a pre-wetted (methanol) SCX-2 cartridge. The cartridge was washed with methanol and eluted with 1M ammonia in methanol solution. The eluent was concentrated to give (R)-1-(1H-indazol-4-yl)propan-2-amine (1.20 g, 81%) as a golden gum. ¹H NMR (400 MHz, CDCl₃, 27 ° C.) 1.20 (3H, d), 1.79 (2H, s), 2.87 (1H, dd), 3.06 (1H, dd), 3.34-3.45 (1H, m), 6.91-7.04 (1H, m), 7.28-7.42 (2H, m), 8.12 (1H, d). m/z: ES+ [M+H]+ 176.

Preparation of (R)-1-(1H-indazol-4-yl)-N-(2,2,2-trifluoroethyl)propan-2-amine

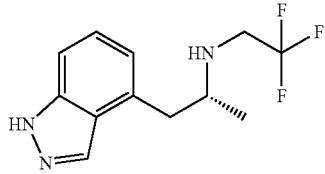 [SMILES: C[C@H](Cc1cccc2[nH]ncc12)NCC(F)(F)F]

Trifluoromethanesulfonic anhydride (1.39 mL, 8.27 mmol) was added to a cooled solution of 2,2,2-trifluoroethan-1-ol (0.57 mL, 7.88 mmol) in DCM (16.6 mL) followed by 2,6-dimethylpyridine (1.10 mL, 9.46 mmol). The reaction was allowed to warm to room temperature and stirred for 1 hour. The reaction was washed with 2N HCl (20 mL). The organic phase was dried over MgSO₄ and filtered to give a solution of 2,2,2-trifluoroethyl trifluoromethanesulfonate which was used directly. To this solution was added to a solution of (R) -1-(1H-indazol-4-yl)propan-2-amine (1.20 g, 6.85 mmol) and N-ethyl-N-isopropylpropan-2-amine (1.67 mL, 9.59 mmol) in 1,4-dioxane (5 mL). The reaction was stirred at 50° C. overnight. After cooling, the reaction was diluted with DCM and washed with water. The aqueous was extracted with DCM, then the combined organics were dried (Na₂SO₄) and concentrated. The crude product was purified by flash silica chromatography, elution gradient 0-50% ethyl acetate in heptane. Pure fractions were evaporated to dryness to afford (R)-1-(1H-indazol-4-yl)-N-(2,2,2-trifluoroethyl)propan-2-amine (0.890 g, 50%) as a colourless oil. ¹H NMR (500 MHz, CDCl₃, 27° C.) 1.12 (3H, d), 2.96 (1H, dd), 3.08 (1H, dd), 3.13-3.30 (3H, m), 6.98 (1H, dd), 7.33 (1H, dd), 7.39 (1H, d), 8.12 (1H, d), 10.26 (1H, s). ¹⁹F NMR (471 MHz, CDCl₃, 27° C.) -71.85 (J=9.4). m/z: ES+ [M+H]+ 258.

Preparation of (6S,8R)-6-(5-bromopyridin-2-yl)-8-methyl-7-(2,2,2-trifluoroethyl)-6,7,8,9-tetrahydro-3H-pyrazolo[4,3-f]isoquinoline

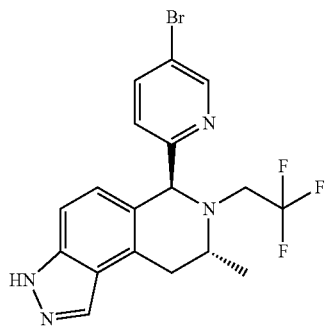 [SMILES: C[C@@H]1Cc2c(ccc3[nH]ncc23)[C@@H](c2ccc(Br)cn2)N1CC(F)(F)F]

Trifluoroacetic acid (4.89 mL) was added to a solution of (R)-1-(1H-indazol-4-yl)-N-(2,2,2-trifluoroethyl)propan-2-amine (5.28 g, 20.5 mmol) and 5-bromopicolinaldehyde (4.20 g, 22.6 mmol) in toluene (98 mL) under nitrogen and the resulting mixture was heated to 90° C. and stirred at 90° C. for 4 hours. The reaction mixture was diluted with EtOAc (100 mL) and washed with saturated aqueous NaHCO₃ (50 mL), saturated aqueous sodium chloride (50 mL), dried (MgSO₄), filtered and concentrated under reduced pressure to give the crude product as a brown gum. The crude product was purified by flash silica chromatography, elution gradient 0 to 50% EtOAc in heptane. Fractions were evaporated to dryness to afford (6S,8R)-6-(5-bromopyridin-2-yl)-8-methyl-7-(2,2,2-trifluoroethyl)-6,7 ,8,9-tetrahydro-3H-pyrazolo [4,3-f]isoquinoline (7.69 g, 88%) as a beige solid. 12.5:1 cis to trans ratio. ¹H NMR (500 MHz, CDCl₃, 27° C.) 1.16 (3H, d), 2.90 (1H, dd), 2.93-3.03 (1H, m), 3.23-3.36 (2H, m), 3.51-3.59 (1H, m), 5.10 (1H, s), 6.94 (1H, d), 7.22-7.25 (1H, m), 7.39 (1H, d), 7.75 (1H, d), 8.06 (1H, d), 8.56 (1H, dd), 10.11 (1H, s). m/z: ES+ [M+H]+ 425.

151

Preparation of (6S,8R)-6-(5-bromopyridin-2-yl)-8-methyl-2-(tetrahydro-2H-pyran-2-yl)-7-(2,2,2-trifluoroethyl)-6,7,8,9-tetrahydro-2H-pyrazolo[4,3-f]isoquinoline compound and (6S,8R)-6-(5-bromopyridin-2-yl)-8-methyl-3-(tetrahydro-2H-pyran-2-yl)-7-(2,2,2-trifluoroethyl)-6,7,8,9-tetrahydro-3H-pyrazolo[4,3-f]isoquinoline

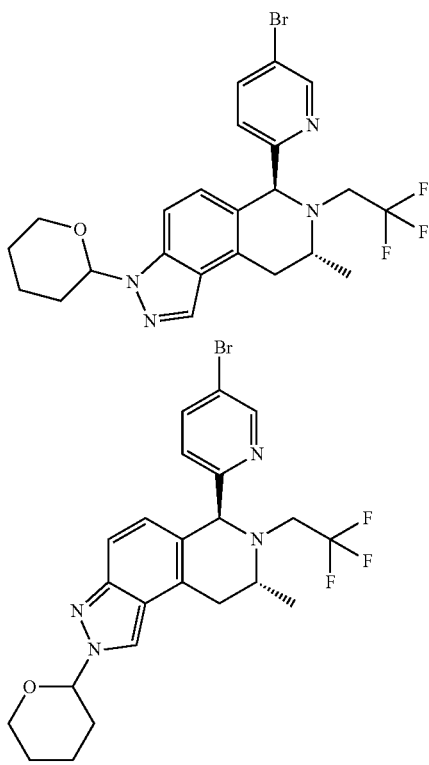

3,4-Dihydro-2H-pyran (0.64 mL, 7.05 mmol) was added to a stirred solution of (6S,8R)-6-(5-bromopyridin-2-yl)-8-methyl-7-(2,2,2-trifluoroethyl)-6,7,8,9-tetrahydro-3H-pyrazolo [4,3-f]isoquinoline (2.00 g, 4.70 mmol) and p-toluenesulfonic acid monohydrate (0.18 g, 0.94 mmol) in DCM (7.2 mL) and the reaction mixture was heated to reflux and stirred at reflux for 3 hours. After cooling, the reaction was diluted with DCM (25 mL) washed with saturated aqueous NaHCO₃ (10 mL), dried (Na₂SO₄), filtered and concentrated under reduced pressure. The crude product was purified by flash silica chromatography, elution gradient 0 to 50% EtOAc in heptane. Product containing fractions were evaporated to dryness to afford a mixture of (6S,8R)-6-(5-bromopyridin-2-yl)-8-methyl-2-(tetrahydro-2H-pyran-2-yl)-7-(2,2,2-trifluoroethyl)-6,7,8,9-tetrahydro -2H-pyrazolo [4,3-f]isoquinoline compound with (6S,8R)-6-(5-bromopyridin-2-yl)-8-methyl-3-(tetrahydro-2H-pyran-2-yl)-7-(2,2,2-trifluoroethyl)-6,7 ,8,9-tetrahydro-3H-pyrazolo[4,3-f] isoquinoline (2.11 g, 88%), as a yellow gum. ¹H NMR (500 MHz, CDCl₃, 27° C.) 1.14 (3H, d), 1.55 (1H, s), 1.60-1.88 (2H, m), 2.00-2.19 (2H, m), 2.51-2.63 (1H, m), 2.88 (1H, dd), 2.92-3.05 (1H, m), 3.29 (2H, ddd), 3.47-3.59 (1H, m), 3.67-3.79 (1H, m), 4.02 (1H, d), 5.08 (1H, s), 5.67 (1H, dt), 6.92 (1H, t), 7.28-7.38 (2H, m), 7.72 (1H, ddd), 8.01 (1H, t), 8.52-8.58 (1H, m). m/z: ES+ [M+H]+ 509.

152

Preparation of (6S,8R)-6-(5-(2-(3-(fluoromethyl)azetidin-1-yl)ethoxy)pyridin-2-yl)-8-methyl-2-(tetrahydro-2H-pyran-2-yl)-7-(2,2,2-trifluoroethyl)-6,7,8,9-tetrahydro-3H-pyrazolo[4,3-f]isoquinoline and (6S,8R)-6-(5-(2-(3-(fluoromethyl)azetidin-1-yl)ethoxy)pyridin-2-yl)-8-methyl-3-(tetrahydro-2H-pyran-2-yl)-7-(2,2,2-trifluoroethyl)-6,7,8,9-tetrahydro-3H-pyrazolo[4,3-f]isoquinoline

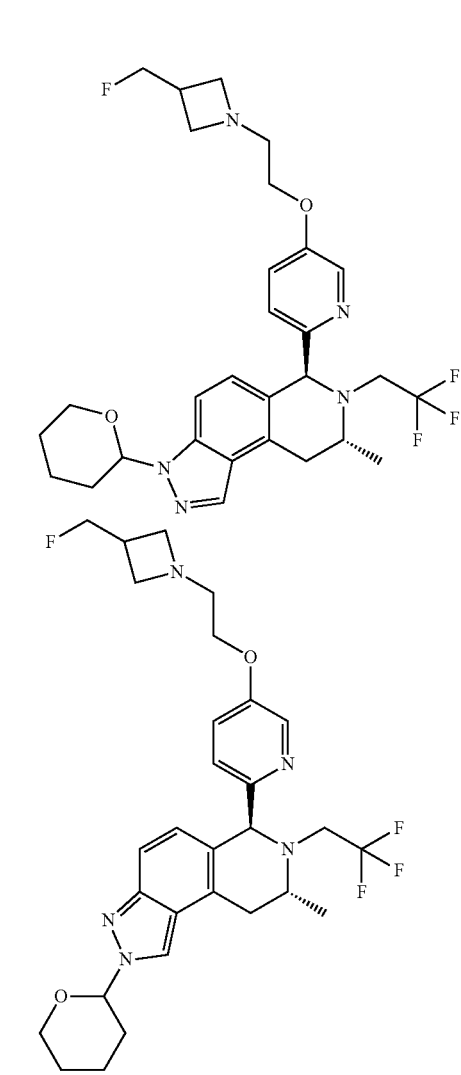

RockPhos 3rd generation (0.35 g, 0.41 mmol) was added to a degassed mixture of 6-(5-bromopyridin-2-yl)-8-methyl-2-(tetrahydro-2H-pyran-2-yl)-7-(2,2,2-trifluoroethyl)-6,7,8,9-tetrahydro-2H-pyrazolo [4,3-f]isoquinoline compound with (6S,8R)-6-(5-bromopyridin-2-yl)-8-methyl-3-(tetrahydro-2H-pyran-2-yl)-7-(2,2,2-trifluoroethyl)-6,7 ,8,9-tetrahydro -3H-pyrazolo [4,3-f]isoquinoline (2.11 g, 4.14 mmol), 2-(3-(fluoromethyl)azetidin-1-yl)ethan-1-ol (1.10 g, 8.28 mmol) and cesium carbonate (3.37 g, 10.36 mmol) in toluene (41 mL) under nitrogen. The resulting mixture was heated to 90° C. and stirred at 90° C. for 16 hours. The reaction mixture was allowed to cool to room temperature and the solids were filtered off through Celite™, washing with EtOAc (10 mL). The filtrate was concetrated under reduced pressure to give the crude product as a brown gum which was purified by flash silica chromatography, elution gradient 0 to 5% 1M NH3/MeOH in DCM. Fractions containing the product were combined to afford (6S,8R)-6-(5-(2-(3-(fluoromethyl)azetidin-1-yl)ethoxy)pyridin-2-yl)-8-methyl-2-(tetrahydro-2H-pyran-2-yl)-7-(2,2,2-trifluoroethyl)-6,7,8,9-tetrahydro -3H-pyrazolo [4,3-f]isoquinoline with (6S,8R)-6-(5-(2-(3-(fluoromethyl)azetidin-1-yl)ethoxy)pyridin-2-yl)-8-methyl-3-(tetrahydro-2H-pyran-2-yl)-7-(2,2,2-trifluoroethyl)-6,7 ,8,9-tetrahydro -3H-pyrazolo [4,3-f]isoquinoline (1.66 g, 71%) as a yellow gum. $^1$H NMR (500 MHz, CDCl$_3$, 27° C.) 1.12 (3H, d), 1.60-1.69 (1H, m), 1.69-1.79 (2H, m), 2.00-2.09 (1H, m), 2.10-2.19 (1H, m), 2.50-2.62 (1H, m), 2.81-2.91 (4H, m), 2.94 -3.05 (1H, m), 3.14 (2H, t), 3.19-3.39 (2H, m), 3.46-3.50 (2H, m), 3.54-3.64 (1H, m), 3.66 -3.77 (1H, m), 3.95-4.05 (3H, m), 4.51 (2H, ddd), 5.06 (1H, s), 5.66 (1H, dt), 6.89 (1H, dd), 7.10-7.15 (1H, m), 7.23-7.31 (2H, m), 8.00 (1H, d), 8.14-8.20 (1H, m). m/z: ES+ [M+H]+ 562.

Example 50

Preparation of (6S,8R)-6-(3-fluoro-5-(2-(3-(fluoromethyl)azetidin-1-yl)ethoxy)pyridin-2-yl)-8-methyl-7-(2,2,2-trifluoroethyl)-6,7,8,9-tetrahydro-3H-pyrazolo[4,3-f]isoquinoline

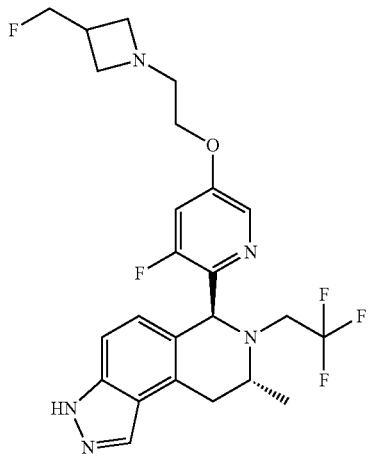 [SMILES: C[C@@H]1Cc2c(ccc3[nH]ncc23)[C@@H](c2ncc(OCCN3CC(CF)C3)cc2F)N1CC(F)(F)F]

A solution of 2-(3-(fluoromethyl)azetidin-1-yl)ethan-1-ol (106 mg, 0.80 mmol) in toluene (3.30 mL) was added to a flask containing (6S,8R)-6-(5-bromo-3-fluoropyridin-2-yl)-8-methyl-3-(tetrahydro-2H-pyran-2-yl)-7-(2,2,2-trifluoroethyl)-6,7,8,9-tetrahydro-3H-pyrazolo[4,3-f]isoquinoline (210 mg, 0.40 mmol) and cesium carbonate (324 mg, 1.00 mmol). The reaction was degassed by infusion with a stream of nitrogen for 5 minutes, followed by addition of RockPhos 3rd generation catalyst (16.70 mg, 0.02 mmol) to the reaction mixture. The reaction mixture was heated to 90° C. for 4 hours. After cooling, the reaction was diluted with EtOAc (5 mL) and washed with water (5 mL). The aqueous layer was extracted with EtOAc (3×5 mL), then the combined organics were dried over MgSO$_4$, filtered and evaporated. The crude residue was dissolved in MeOH (4 mL) and 4.0M HCl in dioxane (1 mL) was added. The reaction was stirred at room temperature for 16 hours. The reaction was diluted with DCM (5 mL) and basified by addition of saturated aqueous solution of NaHCO$_3$ (10 mL). The layers were separated and the aqueous was extracted with DCM (3×10 mL). The combined organics were dried over MgSO$_4$, filtered and evaporated. The crude product was purified by preparative HPLC (Waters XSelect CSH C18 column, 5 μ silica, 30 mm diameter, 100 mm length), using decreasingly polar mixtures of water (containing 1% NH$_3$) and MeCN as eluents. Fractions containing the desired compound were evaporated to dryness to afford (6S,8R)-6-(3-fluoro-5-(2-(3-(fluoromethyl)azetidin-1-yl)ethoxy)pyridin-2-yl)-8-methyl-7-(2,2,2-trifluoroethyl)-6,7,8,9-tetrahydro-3H-pyrazolo[4,3-f]isoquinoline (73.0 mg, 37%) as a yellow gum. $^1$H NMR (500 MHz, CDCl$_3$, 27° C.) 1.15 (d, 3H), 2.62 (s, 2H), 2.80-2.92 (m, 2H), 2.95-3.06 (m, 1H), 3.14 (dd, 2H), 3.22-3.30 (m, 2H), 3.48 (td, 2H), 3.70-3.80 (m, 1H), 3.92-4.02 (m, 2H), 4.45 (d, 1H), 4.54 (d, 1H), 5.38 (s, 1H), 6.80 (d, 1H), 6.94 (dd, 1H), 7.15-7.20 (m, 1H), 8.00 (d, 1H), 8.05 (d, 1H), 10.21 (s, 1H). m/z: ES+ [M+H]+ 496.

The (6S,8R)-6-(5-bromo-3-fluoropyridin-2-yl)-8-methyl-3-(tetrahydro-2H-pyran-2-yl)-7-(2,2,2-trifluoroethyl)-6,7,8,9-tetrahydro-3H-pyrazolo[4,3-f]isoquinoline was prepared as follows;

Preparation of (6S,8R)-6-(5-bromo-3-fluoropyridin-2-yl)-8-methyl-7-(2,2,2-trifluoroethyl)-6,7,8,9-tetrahydro-3H-pyrazolo[4,3-f]isoquinoline

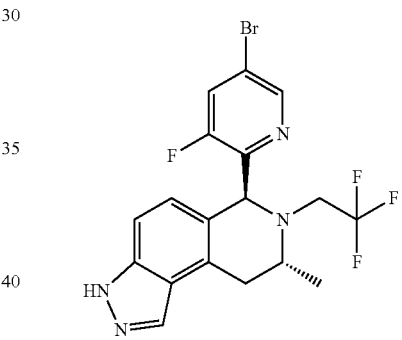

Trifluoroacetic acid (2.13 mL) was added to a solution of (R)-1-(1H-indazol-4-yl)-N-(2,2,2-trifluoroethyl)propan-2-amine (1.15 g, 4.47 mmol) and 5-bromo-3-fluoropicolinaldehyde (912 mg, 4.47 mmol) in toluene (43 mL) and the resulting mixture stirred at 100° C. for 30 minutes. The reaction was cooled to room temperature and evaporated then the residue was partitioned between DCM (20 mL) and aqueous 2M NaOH (20 mL). The layers were seperated and the organic layer was dried over MgSO$_4$, filtered and evapourated. The crude product was purified by flash silica chromatography, elution gradient 0 to 40% EtOAc in heptane. Fractions containing product were combined and concentrated to dryness to afford (6S,8R)-6-(5-bromo-3-fluoropyridin-2-yl)-8-methyl-7-(2,2,2-trifluoroethyl)-6,7,8,9-tetrahydro-3H-pyrazolo [4,3-f]isoquinoline (1149 mg, 58%) as a yellow solid. $^1$H NMR (500 MHz, CDCl$_3$, 27° C.) 1.16 (d, 3H), 2.86 (dd, 1H), 3.01 (dq, 1H), 3.19-3.35 (m, 2H), 3.68-3.78 (m, 1H), 5.42 (s, 1H), 6.80 (d, 1H), 7.20 (d, 1H), 7.59 (dd, 1H), 8.05 (d, 1H), 8.27-8.50 (m, 1H). m/z: ES+ [M+H]+ 443.

155

Preparation of (6S,8R)-6-(5-bromo-3-fluoropyridin-2-yl)-8-methyl-3-(tetrahydro-2H-pyran-2-yl)-7-(2,2,2-trifluoroethyl)-6,7,8,9-tetrahydro-3H-pyrazolo[4,3-f]isoquinoline

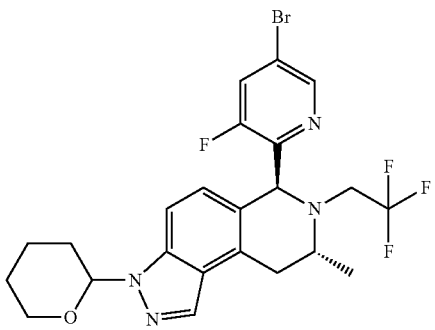 [SMILES: C[C@@H]1Cc2c(ccc3c2cnn3C2CCCCO2)[C@@H](c2ncc(Br)cc2F)N1CC(F)(F)F]

4-Methylbenzenesulfonic acid hydrate (9.87 mg, 0.05 mmol) was added to a solution of (6S,8R)-6-(5-bromo-3-fluoropyridin-2-yl)-8-methyl-7-(2,2,2-trifluoroethyl)-6,7,8,9-tetrahydro-3H-pyrazolo[4,3-f]isoquinoline (230 mg, 0.52 mmol) and 3,4-dihydro-2H-pyran (0.142 mL, 1.56 mmol) in DCM (10 mL) and the mixture heated at 40° C. for 2 hours. The reaction mixture was diluted with DCM (20 mL) and washed with aqueous 2 M NaOH (30 mL). The organic phase was evaporated to a dark brown oil that was purified by flash silica chromatography, elution gradient 0 to 40% EtOAc in heptane. Pure fractions were evaporated to dryness to afford (6S,8R)-6-(5-bromo-3-fluorop yridin-2-yl)-8-methyl-3-(tetrahydro-2H-p yran-2-yl)-7-(2,2,2-trifluoroethyl)-6,7 ,8,9-tetrahydro-3H-pyrazolo[4,3-f]isoquinoline (212 mg, 77%) as a yellow gum. $^1$H NMR (500 MHz, CDCl$_3$, 27° C.) 1.13 (d, 3H), 1.59-1.84 (m, 3H), 1.97-2.09 (m, 1H), 2.14 (dd, 1H), 2.44-2.65 (m, 1H), 2.78-2.91 (m, 1H), 2.91-3.08 (m, 1H), 3.15-3.39 (m, 2H), 3.62-3.82 (m, 2H), 4.02 (d, 1H), 5.39 (s, 1H), 5.67 (ddd, 1H), 6.81 (dd, 1H), 7.33 (dd, 1H), 7.56 (ddd, 1H), 8.03 (dd, 1H), 8.34 (d, 1H). m/z: ES+ [M+H]+ 527.

Example 51

Preparation of (6S,8R)-7-(2,2-difluoroethyl)-6-(5-(2-(3-(fluoromethyl)azetidin-1-yl)ethoxy)pyridin-2-yl)-8-methyl-6,7,8,9-tetrahydro-3H-pyrazolo[4,3-f]isoquinoline

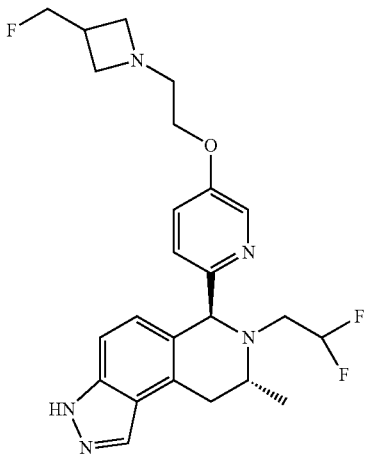 [SMILES: C[C@@H]1Cc2c(ccc3[nH]ncc23)[C@@H](c2ccc(OCCN3CC(CF)C3)cn2)N1CC(F)F]

A solution of (6S,8R)-6-(5-bromopyridin-2-yl)-7-(2,2-difluoroethyl)-8-methyl-3-(tetrahydro-2H-pyran-2-yl)-6,7,8,9-tetrahydro-3H-pyrazolo[4,3-f]isoquinoline (120 mg, 0.24 mmol) in toluene (5 mL) was dried azeotropically under reduced pressure and then redissolved in toluene (5 mL) containing 2-(3-(fluoromethyl)azetidin-1-yl)ethan-1-ol (65 mg, 0.49 mmol). The solution was degassed by infusion with a stream of nitrogen for 5 minutes. Cesium carbonate (199 mg, 0.61 mmol) and RockPhos 3rd Generation Precatalyst (10 mg, 0.01 mmol) were added sequentially, and the reaction mixture was heated at 90° C. for 2 hours. The reaction mixture was then diluted with water and extracted with ethyl acetate. The organic layer was dried over sodium sulfate, filtered and concentrated under reduced pressure. HCl in dioxane (4 M; 0.20 mL, 0.78 mmol) was added to a solution of the resulting residue in MeOH (2 mL), and this new solution was stirred for 5 hours at room temperature. The reaction was concentrated under reduced pressure, and the new residue was purified by reversed phase HPLC (Teledyne ISCO C18 RediSep® Rf Gold® 40 g column), eluting with 0 to 80% acetonitrile in water containing 0.1% ammonium hydroxide (pH 10). Product fractions were concentrated under reduced pressure to afford (6S,8R)-7-(2,2-difluoroethyl)-6-(5-(2-(3-(fluoromethyl)azetidin-1-yl) ethoxy)p yridin-2-yl)-8-methyl-6,7 ,8,9-tetrahydro -3H-pyrazolo [4,3-f]isoquinoline (46 mg, 64%) as a light yellow solid. $^1$H NMR (DMSO-d$_6$, 27° C.) 1.06 (3H, d), 2.57-2.78 (4H, m), 2.87 (1H, dd), 2.99 (2H, t), 3.04-3.22 (2H, m), 3.26-3.30 (2H, m, obscured), 3.41-3.57 (1H, m), 3.96 (2H, t), 4.49 (2H, dd), 4.99 (1H, s), 5.90 (1H, tt), 6.77 (1H, d), 7.21 (2H, d), 7.26-7.35 (1H, m), 8.06 (1H, s), 8.14 (1H, d), 12.97 (1H, s). m/z: ES+ [M+H]+ 460.

Procedures used to prepare the starting material (6S,8R)-6-(5-bromopyridin-2-yl)-7-(2,2-difluoroethyl)-8-methyl-3-(tetrahydro-2H-pyran-2-yl)-6,7,8,9-tetrahydro-3H-pyrazolo[4,3-f]isoquinoline uinoline are described below.

Preparation of (1S,3R)-1-(5-bromopyridin-2-yl)-2-(2,2-difluoroethyl)-3,5-dimethyl-1,2,3,4-tetrahydroisoauinolin-6-amine

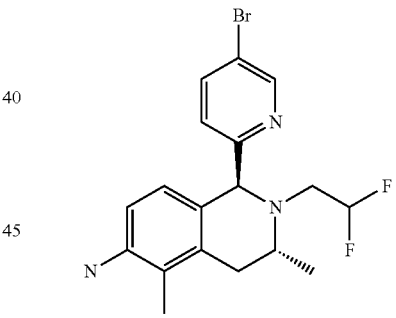

5-Bromopicolinaldehyde (2.74 g, 14.72 mmol) was added to a solution of (R)-3-(2-((2,2-difluoroethyl)amino)propyl)-2-methylaniline (1.6 g, 7.01 mmol) in acetic acid (34.4 mL) and water (0.631 mL, 35.04 mmol), and the reaction was heated at 80° C. for 3 hours. Solvent was removed under vaccum, and the resulting residue was dissolved in methanol. Sodium acetate (1.15 g, 14.0 mmol) and hydroxylamine hydrochloride (0.73 g, 11 mmol) were added, and the reaction was stirred at room temperature for 3 hours. Methanol was removed under vaccum, and the resulting residue was taken up in water. Saturated aqueous NaHCO$_3$ was added, and the mixture was extracted with ethyl acetate. The organic layer was dried over Na$_2$SO$_4$, filtered, and concentrated under reduced pressure. The resulting residue was purified by flash silica chromatography, elution gradient 0 to 95% EtOAc in hexanes. Product fractions were concentrated under reduced pressure to afford (1S,3R)-1-(5-bromopyridin-2-yl)-2-(2,2-difluoroethyl)-3 ,5-dimethyl-1,2,3 ,4-tetrahydroisoquinolin-6-amine (1.35 g, 49%) as a colourless gum. ¹H NMR (DMSO-d₆, 27° C.) 1.01 (3H, d), 1.94 (3H, s), 2.39-2.64 (2H, m, obscured), 2.74 (1H, dd), 2.91-3.14 (1H, m), 3.23-3.33 (1H, m, obscured), 4.66 (2H, s), 4.81 (1H, s), 5.93 (1H, tt), 6.40 (2H, s), 7.23 (1H, d), 7.92 (1H, dd), 8.57 (1H, d). m/z: ES+ [M+H]+ 396.

Preparation of (6S,8R)-6-(5-bromopyridin-2-yl)-7-(2,2-difluoroethyl)-8-methyl-6,7,8,9-tetrahydro-3H-pyrazolo[4,3-f]isoquinoline

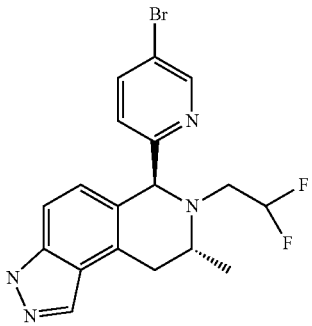 [SMILES: C[C@@H]1Cc2c(ccc3[nH]ncc23)[C@@H](c2ccc(Br)cn2)N1CC(F)F]

A solution of sodium nitrite (87 mg, 1.3 mmol) in water (0.43 mL) was added dropwise to a cooled solution of (1S,3R)-1-(5-bromopyridin-2-yl)-2-(2,2-difluoroethyl)-3,5-dimethyl-1,2,3,4-tetrahydroisoquinolin-6-amine (500 mg, 1.26 mmol) in propionic acid (4.3 mL) at −10° C. (ice/salt bath) with vigorous stirring. After 20 minutes, the reaction was diluted with cold (0° C.) ethyl acetate (10 mL) and quenched with slow addition of ice-cold saturated aqueous NaHCO₃ (10 mL) over 15 minutes while maintaining a reaction temperature of 0° C. The reaction mixture was then allowed to warm to room temperature over 2 hours with stirring. The layers were separated, and the aqueous layer was extracted with ethyl acetate. The combined organic layers were dried over Na₂SO₄, filtered, and concentrated under reduced pressure. The resulting residue was purified by flash silica chromatography, elution gradient 0 to 60% EtOAc in hexanes. Product fractions were concentrated under reduced pressure to afford (6S,8R)-6-(5-bromopyridin-2-yl)-7-(2,2-difluoroethyl)-8-methyl-6,7,8,9-tetrahydro-3H-pyrazolo [4,3-f]isoquinoline (253 mg, 49%) as a brown foam. ¹H NMR (DMSO-d₆, 27° C.) 1.08 (3H, d), 2.54 -2.77 (1H, m), 2.89 (1H, dd), 3.04-3.24 (2H, m), 3.36-3.53 (1H, m), 5.05 (1H, s), 6.00 (1H, tt), 6.83 (1H, d), 7.25 (1H, d), 7.35 (1H, d), 7.97 (1H, dd), 8.08 (1H, s), 8.59 (1H, d), 12.99 (1H, s). m/z: ES+ [M+H]+ 407

Preparation of (6S,8R)-6-(5-bromopyridin-2-yl)-7-(2,2-difluoroethyl)-8-methyl-3-(tetrahydro-2H-pyran-2-yl)-6,7,8,9-tetrahydro-3H-pyrazolo[4,3-f]isoquinoline

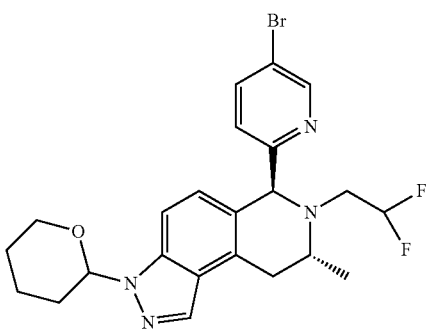 [SMILES: C[C@@H]1Cc2c(ccc3c2cnn3C2CCCCO2)[C@@H](c2ccc(Br)cn2)N1CC(F)F]

4-Methylbenzenesulfonic acid hydrate (12 mg, 0.060 mmol) was added to a stirred solution of (6S,8R)-6-(5-bromopyridin-2-yl)-7-(2,2-difluoroethyl)-8-methyl-6,7,8,9-tetrahydro-3H-pyrazolo[4,3-f]isoquinoline (260 mg, 0.64 mmol) and 3,4-dihydro-2H-pyran (0.284 mL, 3.19 mmol) in DCM (5 mL). The reaction was warmed to 50° C. and maintained under these conditions for 24 h. The reaction was diluted with water and saturated aqueous NaHCO₃. The mixture was extracted with ethyl acetate. The organic layer was dried over Na₂SO₄, filtered, and concentrated under reduced pressure. The resulting residue was purified by flash silica chromatography, elution gradient 0 to 80% EtOAc in hexanes. Product fractions were concentrated under reduced pressure to afford (6S,8R)-6-(5-bromopyridin-2-yl)-7-(2,2-difluoroethyl)-8-methyl-3-(tetrahydro-2H-pyran-2-yl)-6,7,8,9-tetrahydro-3H-pyrazolo[4,3-f]isoquinoline (243 mg, 77%) as an orange foam. m/z: ES+ [M+H]+ 491.

The invention claimed is:

1. A compound, or a pharmaceutically acceptable salt thereof, wherein the compound is (6S,8R)-6-(5-(2-(3-(fluoromethyl)azetidin-1-yl)ethoxy)pyridin-2-yl)-8-methyl-7-(2,2,2-trifluoroethyl)-6,7,8,9-tetrahydro-3H-pyrazolo[4,3-f] isoquinoline, which compound has the following structure:

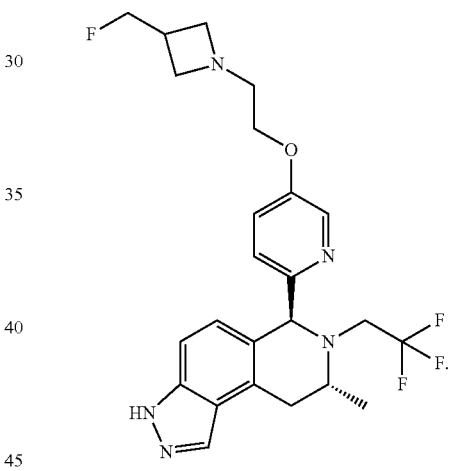

2. A pharmaceutical composition, which comprises the compound according to claim 1, or a pharmaceutically acceptable salt thereof, in association with a pharmaceutically-acceptable excipient.

3. A compound, wherein the compound is (6S,8R)-6-(5-(2-(3-(fluoromethyl)azetidin-1-yl)ethoxy)pyridin-2-yl)-8-methyl-7-(2,2,2-trifluoroethyl)-6,7,8,9-tetrahydro-3H-pyrazolo [4,3-f] isoquinoline.

4. A pharmaceutical composition, which comprises the compound according to claim 3, in association with a pharmaceutically-acceptable excipient.

5. A pharmaceutically acceptable salt of (6S,8R)-6-(5-(2-(3-(fluoromethyl)azetidin-1-yl)ethoxy)pyridin-2-yl)-8-methyl-7-(2,2,2-trifluoroethyl)-6,7,8,9-tetrahydro-3H-pyrazolo [4,3-f] isoquinoline.

6. A pharmaceutical composition, which comprises the salt according to claim 5, in association with a pharmaceutically-acceptable excipient.

7. A compound, or a pharmaceutically acceptable salt thereof, wherein the compound is (6S,8R)-7-(2,2-difluoroethyl)-6-(5-(2-(3-(fluoromethyl)azetidin-1-yl)ethoxy)pyridin-2-yl)-8-methyl-6,7,8,9-tetrahydro-3H-pyrazolo[4,3-f]lisoquinoline, which compound has the following structure:

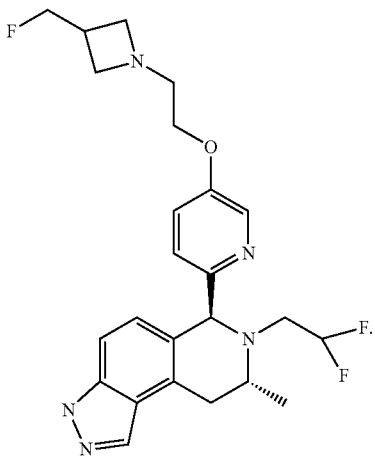 [SMILES: C[C@@H]1Cc2c(ccc3[nH]ncc23)[C@@H](c2ccc(OCCN3CC(CF)C3)cn2)N1CC(F)F]

8. A pharmaceutical composition, which comprises the compound according to claim 7, or a pharmaceutically acceptable salt thereof, in association with a pharmaceutically-acceptable excipient.

9. A compound, wherein the compound is (6S,8R)-7-(2,2-difluoroethyl)-6-(5-(2-(3-(fluoromethyl)azetidin- 1-yl)ethoxy)pyridin-2-yl)-8 -methyl-6,7,8,9-tetrahydro-3H-pyrazolo [4,3-f] isoquinoline.

10. A pharmaceutical composition, which comprises the compound according to claim 9, in association with a pharmaceutically-acceptable excipient.

11. A pharmaceutically acceptable salt of (6S,8R)-7-(2,2-difluoroethyl)-6-(5-(2-(3-(fluoromethyl)azetidin- 1 -yl)ethoxy)pyridin-2-yl)-8 -methyl-6,7,8 ,9-tetrahydro-3H-pyrazolo [4,3 -f] isoquinoline.

12. A pharmaceutical composition, which comprises the salt according to claim 11, in association with a pharmaceutically-acceptable excipient.

* * * * *